(12) United States Patent
Lotta et al.

(10) Patent No.: US 12,049,670 B2
(45) Date of Patent: Jul. 30, 2024

(54) PROPROTEIN CONVERTASE SUBTILISIN/KEXIN TYPE 1 (PCSK1) VARIANTS AND USES THEREOF

(71) Applicant: Regeneron Pharmaceuticals, Inc., Tarrytown, NY (US)

(72) Inventors: Luca Andrea Lotta, Tarrytown, NY (US); Manuel Allen Revez Ferreira, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 250 days.

(21) Appl. No.: 17/306,699

(22) Filed: May 3, 2021

(65) Prior Publication Data
US 2021/0353709 A1    Nov. 18, 2021

Related U.S. Application Data

(60) Provisional application No. 63/019,589, filed on May 4, 2020.

(51) Int. Cl.
*C12Q 1/6883* (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS

2018/0311309 A1* 11/2018 Ploeg ................. A61P 3/10

FOREIGN PATENT DOCUMENTS

| WO | 2010072608 | 7/2010 |
|----|-----------|--------|
| WO | 2019162312 | 8/2019 |

OTHER PUBLICATIONS

Bouhours-Nouet et al. Oct. 2015. ESPE Abstracts, ePoster. 84 P-2-353, available via URL: < abstracts.eurospe.org/hrp/0084/hrp0084p2-353>. (Year: 2015).*
NCBI Database Reference SNP (rs) Report for rs1480597482, available via URL: <ncbi.nlm.nih.gov/snp/rs1480597482#variant_details>, printed on Nov. 2, 2023 (Year: 2023).*
Kuhnen et al., "Proopiomelanocortin Deficiency Treated with a Melanocortin-4 Receptor Agonist", New England Journal of Medicine, 2016, 375(3), pp. 240-246.
Von Schnurbein et al., "Monogenic obesity", Monatsschrift Fuer Kinderheilkunde, 2018, 166(5), pp. 388-394.
Anonymous, "NCT02311673 on Aug. 3, 2015: ClinicalTrials.gov Archive", 2015, pp. 1-5.
Chen et al., "RM-493, a Melanocortin-4 Receptor (MC4R) Agonist, Increases Resting Energy Expenditure in Obese Individuals", Journal of Clinical Endocrinology and Metabolism, 2015, 100(4), pp. 1639-1645.
Proenca da Fonseca et al., "Genetics of non-syndromic childhood obesity and the use of high-throughput DNA sequencing technologies", Journal of Diabetes and its Complications, 2017, 31(10), pp. 1549-1561.
Rohde et al., "Genetics and epigenetics in obesity", Metabolism Clinical and Experimental, 2018, 92, pp. 37-50.
Philippe et al., "A nonsense loss-of-function mutation incontributes to dominantly inherited human obesity", International Journal of Obesity, 2014, 39(2), pp. 295-302.
Nead et al., "Contribution of common non-synonymous variants in PCSK1 to body mass index variation and risk of obesity: a systematic review and meta-analysis with evidence from up to 331, 175 individuals", Human Molecular Genetics, 2015, 24(12), pp. 3528-3594.
Stahel et al., "Phenotypic and genetic analysis of an adult cohort with extreme obesity", International Journal of Obesity, 2018, 43(10), pp. 2057-2065.
Ayers et al., "Melanocortin-4 receptor pathway dysfunction in obese patients: Prevalence estimates of LEPR, POMC, and PCSK1 variants", Endocrine Reviews, 2018, 39(2), Supplement 1.
Benzinou et al., "Common nonsynonymous variants in PCSK1 confer risk of obesity", Nature Genetics, 2008, 40(8), pp. 943-945.
Benzinou et al., "Common nonsynonymous variants in PCSK1 confer risk of obesity", Nature Genetics, 2008, 40(8), supplementary, pp. 1-13.
Blanco et al., "Biochemical and Cell Biological Properties of the Human Prohormone Convertase 1/3 Ser357Gly Mutation: A PC1/3 Hypermorph", Endocrinology, 2014, 155(9), pp. 3434-3447.
Blanco et al., "Revisiting PC1/3 Mutants: Dominant-Negative Effect of Endoplasmic Reticulum-Retained Mutants", Endrocrinology, 2015, 156(10), pp. 3625-3637.
Bouhours-Nouet et al., "A New Mutation of PCSK1 Revealed by Neonatal Malabsorptive Diarrhoea, Panhypopituitarism, and Major Obesity", EXPE Poster at Barcelona, 2015, pp. 1.
Creemers et al., "Heterozygous Mutations Causing Partial Prohormone Convertase 1 Deficiency Contribute to Human Obesity", Diabetes, 2012, 61(2), pp. 383-390.
Creemers et al., "Heterozygous Mutations Causing Partial Prohormone Convertase 1 Deficiency Contribute to Human Obesity", Diabetes, 2012, 61(2), supplementary, pp. 1-2.
Farooqi et al., "Hyperphagia and early-onset obesity due to a novel homozygous missense mutation in prohormone convertase 1/3", J Clin Endocrinol Metab, 2007, 92(9), pp. 3369-3373.
Frank et al., "Severe obesity and diabetes insipidus in a patient with PCSK1 deficiency", Mol Genet Metab, 2013, 110 (1-2), pp. 191-194.
Harter et al., "Early Clinical Diagnosis of PC1/3 Deficiency in a Patient With a Novel Homozygous PCSK1 Splice-Site Mutation", J Pediatr Gastroentrol Nutr, 2016, 62(4), pp. 577-580.
Jackson et al., "Obesity and impaired prohormone processing associated with mutations in the human prohormone convertase 1 gene", Nature Genetics, 1997, 16(3), pp. 303-306.
Jackson et al., "Small-intestinal dysfunction accompanies the complex endocrinopathy of human proprotein convertase 1 deficiency", J. Clin. Investigation, 2003, 112(10), pp. 1550-1560.

(Continued)

*Primary Examiner* — Carla J Myers
(74) *Attorney, Agent, or Firm* — Armstrong Teasdale LLP

(57) ABSTRACT

Methods of treating obesity and methods of identifying susceptibility of an obese subject to treatment with an agonist of the leptin-melanocortin signaling pathway are provided herein.

7 Claims, 1 Drawing Sheet
Specification includes a Sequence Listing.

(56) References Cited

OTHER PUBLICATIONS

Martin et al., "Congenital proprotein convertase 1/3 deficiency causes malabsorptive diarrhea and other endocrinopathies in a pediatric cohort", Gastroenterology, 2013, 145(1), pp. 138-148.

Martin et al., "Congenital proprotein convertase 1/3 deficiency causes malabsorptive diarrhea and other endocrinopathies in a pediatric cohort", Gastroenterology, 2013, 145(1), supplementary, pp. 1-4.

O'Rahilly et al., "Impaired Processing of Prohormones Associated with Abnormalities of Glucose Homeostasis and Adrenal Function", N Engl J Med, 1995, 333, pp. 1386-1391.

Philippe et al., "A nonsense loss-of-function mutation in PCSK1 contributes to dominantly inherited human obesity", Intl J Obesity, 2015, 39(2), pp. 295-302.

Philippe et al., "A nonsense loss-of-function mutation in PCSK1 contributes to dominantly inherited human obesity", Intl J Obesity, 2015, 39(2), supplementary, pp. 1-3.

Pickett et al., "Functional Consequences of a Novel Variant of PCSK1", PLOS One, 2013, 8(1), e55065, pp. 1-8.

Wilschanski et al., "A Novel Familial Mutation in the PCSK1 Gene That Alters the Oxyanion Hole Residue of Proprotein Convertase 1/3 and Impairs Its Enzymatic Activity", PLOS One, 2014, 9(10), e108878, pp. 1-7.

Yourshaw et al., "Exome sequencing finds a novel PCSK1 mutation in a child with generalized malabsorptive diarrhea and diabetes insipidus", J Pediatr Gastroenterol Nutr, 2013, 57(6), pp. 759-767.

Yourshaw et al., "Exome sequencing finds a novel PCSK1 mutation in a child with generalized malabsorptive diarrhea and diabetes insipidus", J Pediatr Gastroenterol Nutr, 2013, 57(6), supplementary, pp. 1.

\* cited by examiner

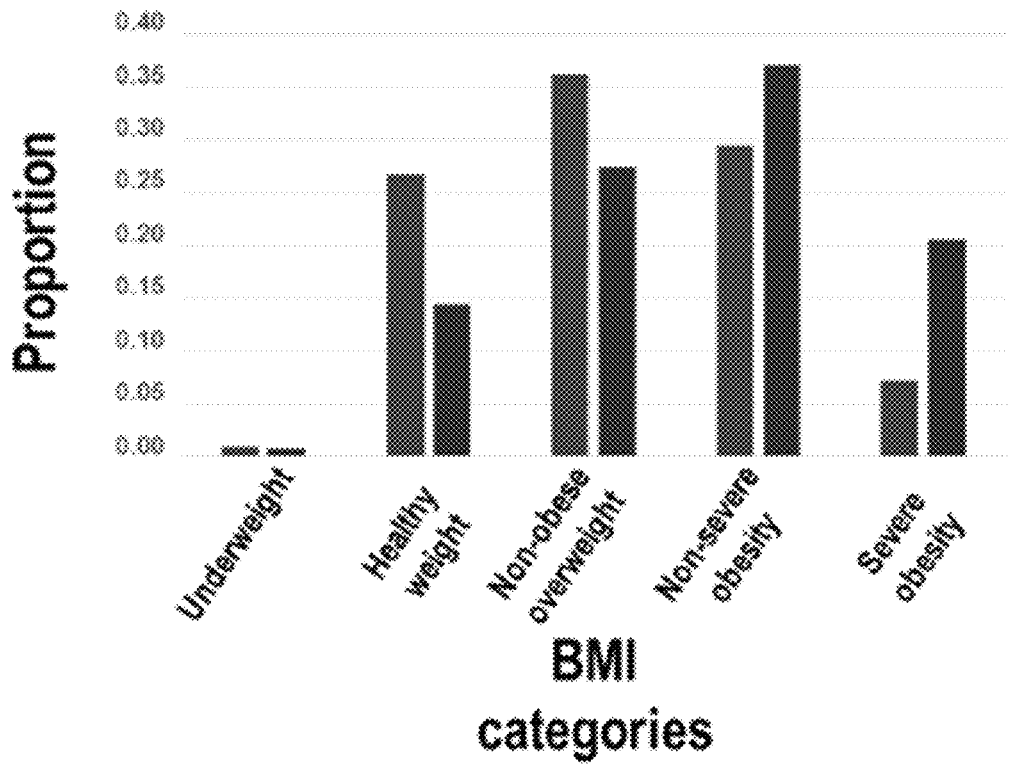
Non-carriers (left bar)
pLOF carriers (right bar)
| Category | BMI range, kg/m² |
|---|---|
| Underweight | <18.5 |
| Healthy weight | 18.5-24.9 |
| Non-obese overweight | 25-29.9 |
| Non-severe obesity | 30-39.9 |
| Severe obesity | ≥40 |

PROPROTEIN CONVERTASE SUBTILISIN/KEXIN TYPE 1 (PCSK1) VARIANTS AND USES THEREOF

REFERENCE TO A SEQUENCE LISTING

This application includes a Sequence Listing submitted electronically as a text file named 18923804101SEQ, created on May 1, 2021, with a size of 189 kilobytes. The Sequence Listing is incorporated herein by reference.

FIELD

The present disclosure provides methods of treating subjects having obesity, methods of identifying subjects having an increased risk of developing obesity, and methods of identifying susceptibility of an obese subject to treatment with an agonist of the leptin-melanocortin signaling pathway.

BACKGROUND

Obesity and its cardio-metabolic complications, in particular type 2 diabetes and coronary artery disease, account for significant morbidity and mortality globally. There is a substantial unmet medical need for safe and effective weight loss approaches.

Lifestyle interventions on diet and physical activity are the first option for the management of obesity and overweight, but efficacy can be limited, and weight regain is common. Bariatric surgery can be highly effective for weight loss in severely obese or high-risk patients, but its use is limited by its invasive nature, cost, risk of perioperative adverse events including perioperative death. While a few drugs have demonstrated efficacy in weight-reduction, pharmacotherapy for the treatment of obesity is limited by the modest weight loss induced by most drugs, side effect profile of some agents, contraindications, low compliance, and barriers to treatment including underprescription.

PCSK1 is a member of the subtilisin-like proprotein convertase family, which includes proteases that process protein and peptide precursors trafficking through regulated or constitutive branches of the secretory pathway. PCSK1 is one of the seven basic amino acid-specific enzymes which cleave their substrates at single or paired basic residues. PCSK1 is packaged into and activated in dense core secretory granules and expressed in the neuroendocrine system and brain. PCSK1 is Involved in the processing of hormone and other protein precursors at sites comprised of pairs of basic amino acid residues. Substrates include proopiomelanocortin (POMC), renin, enkephalin, dynorphin, somatostatin, insulin and AGRP. PCSK1 activity is essential for the activating cleavage of many peptide hormone precursors implicated in the regulation of food ingestion, glucose homeostasis, and energy homeostasis, for example, proopiomelanocortin, proinsulin, proglucagon, and proghrelin.

SUMMARY

The present disclosure provides methods of treating a subject having obesity comprising administering to the subject an agonist of the leptin-melanocortin signaling pathway.

The present disclosure also provides methods of treating a subject having elevated body mass index (BMI) comprising administering to the subject an agonist of the leptin-melanocortin signaling pathway.

The present disclosure also provides in such methods the detection of the presence in heterozygous state or absence of a PCSK1 variant nucleic acid molecule or PCSK1 variant polypeptide associated with an increased risk of developing obesity and/or elevated BMI in a biological sample from the subject.

The present disclosure also provides methods of identifying susceptibility of an obese subject to treatment with an agonist of the leptin-melanocortin signaling pathway comprising detecting the presence or absence of one copy of a PCSK1 genetic variant associated with an increased risk of developing obesity and/or elevated BMI in a biological sample from the subject, wherein when one copy of a PCSK1 genetic variant is detected, the subject is susceptible to treatment with an agonist of the leptin-melanocortin signaling pathway.

The present disclosure also provides methods of identifying susceptibility of a subject having elevated BMI to treatment with an agonist of the leptin-melanocortin signaling pathway comprising detecting the presence or absence of one copy of a PCSK1 genetic variant associated with an increased risk of developing obesity and/or elevated BMI in a biological sample from the subject, wherein when one copy of a PCSK1 genetic variant is detected, the subject is susceptible to treatment with an agonist of the leptin-melanocortin signaling pathway.

BRIEF DESCRIPTION OF THE FIGURES

The accompanying FIGURES, which are incorporated in and constitute a part of this specification, illustrate several aspects and together with the description serve to explain some principles of the present disclosure.

The patent or application file contains at least one drawing executed in color. Copies of this patent or patent application publication with color drawings will be provided by the Office upon request and payment of the necessary fee.

FIG. 1 shows the proportion of PCSK1 pLoF carriers among individuals having different categories of BMI from the UK Biobank (UKB) population-based cohort and the MyCode Community Health Initiative cohort from the Geisinger Health System (GHS) healthcare-system-based cohort.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

As used herein, the phrase "corresponding to", or grammatical variations thereof, when used in the context of the numbering of a particular amino acid or nucleotide sequence or position refers to the numbering of a specified reference sequence when the particular amino acid or nucleotide sequence is compared to the reference sequence (e.g., with the reference sequence herein being the nucleic acid molecule or polypeptide of (wild type) PCSK1). In other words, the residue (e.g., amino acid or nucleotide) number or residue (e.g., amino acid or nucleotide) position of a particular polymer is designated with respect to the reference sequence rather than by the actual numerical position of the residue within the particular amino acid or nucleotide sequence. For example, a particular amino acid sequence or nucleotide sequence can be aligned to a reference sequence by introducing gaps to optimize residue matches between the two sequences. In these cases, although the gaps are present, the numbering of the residue in the particular amino acid or nucleotide sequence is made with respect to the reference sequence to which it has been aligned. A variety of computational algorithms exist that can be used for performing a sequence alignment to identify a nucleotide or amino acid position in one polymeric molecule that corresponds to a nucleotide or amino acid position in another polymeric molecule. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

It has been observed in accordance with the present disclosure that predicted loss of function variants in PCSK1 in the heterozygous state associate with a risk of developing obesity or elevated BMI. Homozygous carrier status for loss of function variants in PCSK1 is a known cause of severe obesity with hormonal disturbances, but the heterozygous carrier state has not been associated with higher BMI or increased risk of obesity before, such that the obese phenotype conferred by LOF variants in PCSK1 is considered an autosomal recessive trait. Because the allele frequency for PCSK1 LOF mutations in European ancestry participants in the UKB and GHS studies is 0.027%, the heterozygous carriers in PCSK1 are over 7000 times more common than homozygous carriers (1 every ~1,800 people for heterozygous carriers vs 1 every ~13,500,000 people for homozygous carriers). Hence, the finding of an association between heterozygous carrier state and higher BMI and obesity risk means that the etiologic contribution of PCSK1 LOF variants to obesity is greater than currently thought. Therefore, humans that are heterozygous for PCSK1 alterations that associate with obesity or elevated BMI may be treated such that obesity or elevated BMI is inhibited, the symptoms thereof are reduced, and/or development of symptoms is repressed. In addition, humans that are heterozygous for PCSK1 alterations that associate with obesity or elevated BMI may be treated to prevent obesity by specific interventions, such as any of those disclosed herein. It is also believed that humans having obesity or elevated BMI may be treated with molecules that promote MC4R signaling, which is defective in people with PCSK1 LOF.

For purposes of the present disclosure, any particular human can be categorized as having one of three PCSK1 genotypes: i) PCSK1 reference; ii) heterozygous for a PCSK1 variant nucleic acid molecule associated with an increased risk of developing obesity and/or elevated BMI as discovered herein, and iii) homozygous for a PCSK1 variant nucleic acid molecule associated with an increased risk of developing obesity and/or elevated BMI. A human is PCSK1 reference when the human does not have a copy of a PCSK1 variant nucleic acid molecule associated with an increased risk of developing obesity and/or elevated BMI. A human is heterozygous for a PCSK1 variant nucleic acid molecule associated with an increased risk of developing obesity and/or elevated BMI when the human has a single copy of a PCSK1 variant nucleic acid molecule associated with an increased risk of developing obesity and/or elevated BMI. A subject who has a PCSK1 polypeptide having a partial loss-of-function (or predicted partial loss-of-function) is hypomorphic for PCSK1. A human is homozygous for a PCSK1 variant nucleic acid molecule associated with an increased risk of developing obesity and/or elevated BMI when the human has two copies of any of the PCSK1 variant nucleic acid molecule associated with an increased risk of developing obesity and/or elevated BMI.

For subjects that are genotyped or determined to be heterozygous for a PCSK1 variant nucleic acid molecule associated with an increased risk of developing obesity and/or elevated BMI, such subjects are associated with having increased odds of developing obesity and/or elevated BMI. For subjects that are genotyped or determined to be heterozygous for a PCSK1 variant nucleic acid molecule, such subjects can be treated with an agent effective to treat obesity, such as type 1 obesity, type 2 obesity, or type 3 obesity, and/or with an agent effective to treat increased BMI.

In any of the embodiments described herein, the PCSK1 variant nucleic acid molecule associated with an increased risk of developing obesity and/or elevated BMI can be any PCSK1 nucleic acid molecule (such as, for example, genomic nucleic acid molecule, mRNA molecule, or cDNA molecule produced from the mRNA molecule) encoding a PCSK1 polypeptide having a partial loss-of-function, a complete loss-of-function, a predicted partial loss-of-function, or a predicted complete loss-of-function. In any of the embodiments described herein, the PCSK1 variant nucleic acid molecule associated with an increased risk of developing obesity and/or elevated BMI can also be any PCSK1 variant nucleic acid molecule (such as, for example, genomic nucleic acid molecule, mRNA molecule, or cDNA molecule produced from the mRNA molecule) predicted or shown to be associated with higher BMI, obesity risk, or to result in PCSK1 loss of function in vitro or in vivo. In any of the embodiments described herein, the PCSK1 variant nucleic acid molecule associated with an increased risk of developing obesity and/or elevated BMI can also be any PCSK1 protein truncating variant.

In any of the embodiments described herein, the variant PCSK1 polypeptide can be any PCSK1 polypeptide having a partial loss-of-function, a complete loss-of-function, a predicted partial loss-of-function, or a predicted complete loss-of-function.

The PCSK1 predicted loss-of-function variant nucleic acid molecule can be any one or more of the variant nucleic acid molecules described herein. In some embodiments, the PCSK1 variant nucleic acid molecule associated with an increased risk of developing obesity and/or elevated BMI is a protein truncating variant. A PCSK1 variant nucleic acid molecule associated with an increased risk of developing obesity and/or elevated BMI is also any PCSK1 deleterious missense variant nucleic acid molecule. The PCSK1 deleterious variant nucleic acid molecule can be any one or more of the variant nucleic acid molecules described herein. In some embodiments, the subject has one or two of the following loss-of-function variant PCSK1 nucleic acid molecules: 5:96393172:A:C, 5:96393258:G:A, 5:96393366:G:A, 5:96394941:G:A, 5:96394988:C:T, 5:96397351:CAA:C, 5:96397358:C:T, 5:96397377:C:A, 5:96397382:C:T, 5:96397390:AAC:A, 5:96397440:C:A, 5:96398877:A:G, 5:96398887:GAAGT:G, 5:96398922:A:C, 5:96399952:C:A, 5:96399993:T:A, 5:96400071:G:A, 5:96400106:C:T, 5:96400170:G:A, 5:96408221:A:C, 5:96408288:C:CA, 5:96408299:A:AG, 5:96408310:A:AG, 5:96408324:C:G, 5:96410771:T:TA, 5:96410773:C:T, 5:96410797:C:A, 5:96410840:G:C, 5:96410840:G:T, 5:96410844:CAGGGG-GAT:C, 5:96410910:T:TC, 5:96410935:G:GC, 5:96410974:TC:T, 5:96410983:T:TC, 5:96412437:C:CA, 5:96412452:C:A, 5:96412454:A:AT, 5:96416067:G:T, 5:96416072:T:A, 5:96421879:CT:C, 5:96421881:T:A, 5:96421893:TG:T, 5:96421905:G:A, 5:96421940:TA:T, 5:96421951:TG:T, 5:96421954:AT:A, 5:96423354:CA:C, 5:96423401:CAA:C, 5:96425819:C:G, 5:96425827:C:T, 5:96425843:TG:T, 5:96425891:T:A, 5:96425892:AC:A, 5:96429256:CT:C, 5:96429260:G:A, 5:96429269:TG:T, 5:96429310:G:T, 5:96429319:T:C, 5:96432082:C:T, 5:96432861:A:C, 5:96432869:CA:C, 5:96432913:C:A, 5:96432957:CT:C, 5:96432971:AC:A, 5:96432981:G:GCA, 5:96432993:CAA:C, 5:96433040:C:T, 5:96433041:A:G.

In any of the embodiments described herein, the obesity is type 1 obesity, type 2 obesity, or type 3 obesity. In any of the embodiments described herein, the obesity is type 1 obesity. In any of the embodiments described herein, the obesity is type 2 obesity. In any of the embodiments described herein, the obesity is type 3 obesity. In any of the embodiments described herein, the subject has increased BMI.

Symptoms of obesity include, but are not limited to, excess body fat accumulation (particularly around the waist), breathlessness, increased sweating, snoring, inability to cope with sudden physical activity, feeling very tired every day, back and joint pains, skin problems (from moisture accumulating in the folds of skin).

The nucleotide sequence of a PCSK1 reference genomic nucleic acid molecule is set forth in SEQ ID NO:1 (ENST00000311106.8 encompassing chr5:96,390,333-96,433,248 in the GRCh38/hg38 human genome assembly; ENSG00000175426.11), which is 42,916 nucleotides in length. The first nucleotide recited in SEQ ID NO:1 corresponds to the nucleotide at position 96,390,333 of chromosome 5.

The nucleotide sequences of PCSK1 reference mRNA molecules produced through alternative splicing are set forth in SEQ ID NOs:2-12. The variant nucleotides at their respective variant positions for the variant genomic nucleic acid molecules described herein also have corresponding variant nucleotides at their respective variant positions for the variant mRNA molecules based upon the PCSK1 reference mRNA sequences according to SEQ ID NOs:2-12. Any of these PCSK1 variant mRNA molecules can be detected in any of the methods described herein.

The nucleotide sequences of PCSK1 reference cDNA molecules are set forth in SEQ ID NOs:13-23. The variant nucleotides at their respective variant positions for the variant genomic nucleic acid molecules described herein also have corresponding variant nucleotides at their respective variant positions for the variant cDNA molecules based upon the PCSK1 reference cDNA sequence according to SEQ ID NOs:13-23. Any of these PCSK1 variant cDNA molecules can be detected in any of the methods described herein.

The amino acid sequences of PCSK1 reference polypeptide isoforms are set forth in SEQ ID NOs:24-31. Using the translated nucleotide sequence of either the PCSK1 mRNA or cDNA molecules, the PCSK1 variant polypeptides have corresponding translated variant amino acids at variant positions (codons). Any of these PCSK1 variant polypeptides can be detected in any of the methods described herein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure provides methods of treating a subject having obesity and/or increased BMI comprising administering to the subject an agonist of the leptin-melanocortin signaling pathway. In any of the embodiments described herein, the obesity is type 1 obesity, type 2 obesity, or type 3 obesity.

In any of the embodiments described herein, the agonist of the leptin-melanocortin signaling pathway is an MC4R agonist or a PCSK1 agonist. In some embodiments, the agonist of the leptin-melanocortin signaling pathway is an MC4R agonist. In some embodiments, the agonist of the leptin-melanocortin signaling pathway is a PCSK1 agonist. In some embodiments, the leptin-melanocortin signaling pathway agonist comprises a protein, a peptide, a nucleic acid molecule, or a small molecule.

In some embodiments, the MC4R agonist is a protein, such as recombinant MC4R. In some embodiments, the MC4R agonist is a peptide. In some embodiments, the peptide MC4R agonist is setmelanotide. In some embodiments, the peptide MC4R agonist is a peptide having the amino acid sequence His-Phe-Arg-Trp (SEQ ID NO:32). In some embodiments, the MC4R agonist is a peptide mimetic, such as (1,2,3R,4-tetrahydroisoquinoline-3-carboxylic acid). In some embodiments, the MC4R agonist is a small molecule, such as ALB-127158(a).

In some embodiments, the PCSK1 agonist is a protein, such as recombinant PCSK1. In some embodiments, the PCSK1 agonist is a peptide analog of PCSK1. In some embodiments, the PCSK1 agonist is a peptide.

In any of the embodiments described herein, the subject having obesity and/or elevated BMI can be treated with additional therapeutic agents. Examples of therapeutic agents that treat or inhibit obesity include, but are not limited to, sibutramine, orlistat, phentermine plus topiramate, lorcaserin, bupropion plus naltrexone, liraglutide, phentermine plus diethylpropion, bupropion, metformin, pramlintide, topiramate, and zonisamide, or any combination thereof. In some embodiments, the therapeutic agent that treats or inhibits obesity and/or reduces BMI is a combination of setmelanotide and one or more of sibutramine, orlistat, phentermine, lorcaserin, naltrexone, liraglutide, diethylpropion, bupropion, metformin, pramlintide, topiramate, and zonisamide.

Administration of the therapeutic agents that treat or inhibit obesity or elevated BMI can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit obesity or elevated BMI can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in obesity, decreased BMI, or both, a decrease/reduction in the severity of obesity, a decrease/reduction in symptoms and obesity-related effects, elevated BMI-related effects, or both, delaying the onset of symptoms and obesity-related effects, elevated BMI-related effects, or both, reducing the severity of symptoms of obesity-related effects, or of elevated BMI-related effects, or both, reducing the number of symptoms and obesity-related effects, or of elevated BMI-related effects, or both, reducing the latency of symptoms and obesity-related effects, or of elevated BMI-related effects, or both, an amelioration of symptoms and obesity-related effects, or of elevated BMI-related effects, or both, reducing secondary symptoms, reducing secondary infections, preventing relapse to obesity, or to elevated BMI, or both, decreasing the number or frequency of relapse episodes, increasing latency between symptomatic episodes, increasing time to sustained progression, speeding recovery, and/or increasing efficacy of or decreasing resistance to alternative therapeutics, following administration of the agent or composition comprising the agent. A prophylactic effect may comprise a complete or partial avoidance/inhibition or a delay of obesity, or of elevated BMI, or both development/progression (such as, for example, a complete or partial avoidance/inhibition or a delay) following administration of a therapeutic protocol. Treatment of obesity, elevated BMI, or both encompasses the treatment of subjects already diagnosed as having any form of obesity, or of elevated BMI, or both at any clinical stage or manifestation, the delay of the onset or evolution or aggravation or deterioration of the symptoms or signs of obesity, or of elevated BMI, or both, and/or preventing and/or reducing the severity of obesity, or of elevated BMI, or both.

In any of the embodiments described herein, the methods can further comprise detecting the presence or absence of a PCSK1 variant nucleic acid molecule or variant polypeptide associated with an increased risk of developing obesity and/or elevated BMI in a biological sample from the subject. It is understood that gene sequences within a population and mRNA molecules encoded by such genes can vary due to polymorphisms such as single-nucleotide polymorphisms. The sequences provided herein for the PCSK1 variant nucleic acid molecules disclosed herein are only exemplary sequences. Other sequences for the PCSK1 variant nucleic acid molecules are also possible. The PCSK1 variant nucleic acid molecule or variant polypeptide associated with an increased risk of developing obesity and/or elevated BMI can be any PCSK1 loss-of-function variant or PCSK1 missense variant, such as any of those described herein.

In some embodiments, detecting the presence or absence of the PCSK1 variant nucleic acid molecule or variant polypeptide associated with an increased risk of developing obesity and/or elevated BMI comprises determining whether the subject has a PCSK1 variant genomic nucleic acid molecule associated with an increased risk of developing obesity and/or elevated BMI, a PCSK1 variant mRNA molecule associated with an increased risk of developing obesity and/or elevated BMI, a PCSK1 variant cDNA molecule produced from the mRNA molecule, and/or a PCSK1 variant polypeptide associated with an increased risk of developing obesity and/or elevated BMI. In some embodiments, such determination is carried out by obtaining or having obtained a biological sample from the subject, and performing or having performed an assay on the biological sample to determine whether the subject has a PCSK1 variant nucleic acid molecule or variant polypeptide associated with an increased risk of developing obesity and/or elevated BMI.

Determining whether a subject has a PCSK1 variant nucleic acid molecule or a PCSK1 variant polypeptide associated with an increased risk of developing obesity and/or elevated BMI in a biological sample can be carried out by any of the methods described herein. In some embodiments, the detecting step, determining step, or assay is carried out in vitro. In some embodiments, these methods can be carried out in situ. In some embodiments, these methods can be carried out in vivo. In any of these embodiments, the nucleic acid molecule can be present within a cell obtained from the subject. In some embodiments, the assay is a sequence analysis or genotyping assay for nucleic acid molecules. In some embodiments, the assay is an immunoassay for polypeptides.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. In some embodiments, the biological sample comprises a cell lysate. Such methods can further comprise obtaining a biological sample from the subject. The sample used in the methods disclosed herein will vary based on the assay format, nature of the detection method, and the tissues, cells, or extracts that are used as the sample. A biological sample can be processed differently depending on the assay being employed. For example, when detecting any PCSK1 variant nucleic acid molecule, preliminary processing designed to isolate or enrich the sample for the genomic DNA can be employed. A variety of known techniques may be used for this purpose. When detecting the level of any PCSK1 variant mRNA, different techniques can be used enrich the biological sample with mRNA. Various methods to detect the presence or level of a mRNA or the presence of a particular variant genomic DNA locus can be used.

In some embodiments, the methods can further comprise determining the subject's aggregate burden of having one copy of a PCSK1 variant genomic nucleic acid molecule associated with an increased risk of developing obesity and/or elevated BMI, PCSK1 variant mRNA molecules associated with an increased risk of developing obesity and/or elevated BMI, PCSK1 variant cDNA molecules produced from the mRNA molecules, and/or PCSK1 variant polypeptides associated with an increased risk of developing obesity and/or elevated BMI. The aggregate burden is the sum of all rare variants in the heterozygous state for the PCSK1 gene, which can be carried out in an association analysis with obesity. In some embodiments, the subject is heterozygous for one copy of any of the PCSK1 variants associated with an increased risk of developing obesity and/or elevated BMI. The result of the association analysis suggests that a heterozygous state of rare loss-of-function and missense variants of PCSK1 are associated with increased risk of obesity.

In some embodiments, the detecting step, determining step, or assay comprises sequencing at least a portion of the nucleotide sequence of the PCSK1 nucleic acid molecule in the biological sample. The sequenced portion comprises a position corresponding to a loss-of-function variant position. When a variant nucleotide at the loss-of-function variant position is detected, the PCSK1 nucleic acid molecule in the biological sample is a PCSK1 loss-of-function variant nucleic acid molecule. The loss-of-function variant position within any particular PCSK1 nucleic acid molecule is the one or more positions of the variant nucleotide sequence that are different compared to the nucleotide sequence of the corresponding reference nucleic acid molecule.

In some embodiments, the detecting step, determining step, or assay comprises: contacting the biological sample with a primer hybridizing to a portion of the nucleotide sequence of the PCSK1 nucleic acid molecule that is proximate to a loss-of-function variant position, extending the primer at least through the loss-of-function variant position, and determining whether the extension product of the primer comprises a variant nucleotide at the loss-of-function variant position. In some embodiments, the detecting step, determining step, or assay comprises sequencing the entire nucleic acid molecule.

In some embodiments, the detecting step, determining step, or assay comprises sequencing at least a portion of the nucleotide sequence of the PCSK1 nucleic acid molecule in the biological sample. The sequenced portion comprises a position corresponding to a missense variant position. When a variant nucleotide at the missense variant position is detected, the PCSK1 nucleic acid molecule in the biological sample is a PCSK1 missense variant nucleic acid molecule. The missense variant position within any particular PCSK1 nucleic acid molecule is the one or more positions of the variant nucleotide sequence that are different compared to the nucleotide sequence of the corresponding reference nucleic acid molecule.

In some embodiments, the detecting step, determining step, or assay comprises contacting the biological sample with a primer hybridizing to a portion of the nucleotide sequence of the PCSK1 nucleic acid molecule that is proximate to a missense variant position, extending the primer at least through the missense variant position, and determining whether the extension product of the primer comprises a variant nucleotide at the missense variant position. In some embodiments, the detecting step, determining step, or assay comprises sequencing the entire nucleic acid molecule.

In some embodiments, the assay comprises contacting the biological sample with a primer, such as an alteration-specific primer, that specifically hybridizes to a PCSK1 variant genomic sequence, variant mRNA sequence, or variant cDNA sequence and not the corresponding PCSK1 reference sequence under stringent conditions.

In some embodiments, only a PCSK1 genomic nucleic acid molecule is analyzed. In some embodiments, only a PCSK1 mRNA is analyzed. In some embodiments, only a PCSK1 cDNA obtained from PCSK1 mRNA is analyzed.

Illustrative examples of nucleic acid sequencing techniques include, but are not limited to, chain terminator (Sanger) sequencing and dye terminator sequencing. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the detecting step, determining step, or assay comprises amplifying at least a portion of the PCSK1 nucleic acid molecule, wherein the portion comprises a loss-of-function variant position, labeling the amplified nucleic acid molecule with a detectable label, contacting the labeled nucleic acid molecule with a support comprising an alteration-specific probe, wherein the alteration-specific probe comprises a nucleotide sequence which hybridizes under stringent conditions to the loss-of-function variant position, and detecting the detectable label. In some embodiments, the nucleic acid molecule in the sample is mRNA and the mRNA is reverse-transcribed into a cDNA prior to the amplifying step.

In some embodiments, the detecting step, determining step, or assay comprises contacting the nucleic acid molecule in the biological sample with an alteration-specific probe comprising a detectable label, wherein the alteration-specific probe comprises a nucleotide sequence which hybridizes under stringent conditions to a loss-of-function variant position, and detecting the detectable label.

In some embodiments, the detecting step, determining step, or assay comprises amplifying at least a portion of the PCSK1 nucleic acid molecule, wherein the portion comprises a missense variant position, labeling the amplified nucleic acid molecule with a detectable label, contacting the labeled nucleic acid molecule with a support comprising an alteration-specific probe, wherein the alteration-specific probe comprises a nucleotide sequence which hybridizes under stringent conditions to the missense variant position, and detecting the detectable label. In some embodiments, the nucleic acid molecule in the sample is mRNA and the mRNA is reverse-transcribed into a cDNA prior to the amplifying step.

In some embodiments, the detecting step, determining step, or assay comprises contacting the nucleic acid molecule in the biological sample with an alteration-specific probe comprising a detectable label, wherein the alteration-specific probe comprises a nucleotide sequence which hybridizes under stringent conditions to a missense variant position, and detecting the detectable label.

The alteration-specific probes or alteration-specific primers described herein comprise a nucleic acid sequence which is complementary to and/or hybridizes, or specifically hybridizes, to a PCSK1 loss-of-function variant nucleic acid molecule, or a PCSK1 missense variant nucleic acid molecule, or the complement thereof. In some embodiments, the alteration-specific probes or alteration-specific primers comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to PCSK1 loss-of-function variant genomic nucleic acid molecules, PCSK1 loss-of-function variant mRNA molecules, and/or PCSK1 loss-of-function variant cDNA molecules under stringent conditions. In some embodiments, alteration-specific probes or alteration-specific primers hybridize to PCSK1 missense variant genomic nucleic acid molecules, PCSK1 missense variant mRNA molecules, and/or PCSK1 missense variant cDNA molecules under stringent conditions.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the assay comprises contacting the biological sample with a probe, such as an alteration-specific probe, that specifically hybridizes to a PCSK1 variant genomic sequence, variant mRNA sequence, or variant cDNA sequence and not the corresponding PCSK1 reference sequence under stringent conditions, and determining whether hybridization has occurred.

In some embodiments, the methods utilize probes and primers of sufficient nucleotide length to bind to the target nucleotide sequence and specifically detect and/or identify a polynucleotide comprising a PCSK1 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, labeled primers or probes directed against purified DNA, amplified DNA, and fixed cell preparations (fluorescence in situ hybridization (FISH)) can be used for detection. In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence-based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, detecting the presence of a human PCSK1 variant polypeptide comprises performing an assay on a sample obtained from a subject to determine whether a PCSK1 polypeptide in the subject contains one copy of a variation that causes the polypeptide to have a loss-of-function (partial or complete) or predicted loss-of-function (partial or complete), or be produced from a missense variant nucleic acid molecule, or be a truncated variant polypeptide. In some embodiments, the assay comprises sequencing at least a portion of the PCSK1 polypeptide that comprises a variant position. In some embodiments, the detecting step comprises sequencing the entire polypeptide.

Identification of a variant amino acid at the variant position of the PCSK1 polypeptide indicates that the PCSK1 polypeptide is a PCSK1 loss-of-function polypeptide, or is produced from a missense variant nucleic acid molecule. In some embodiments, the assay comprises an immunoassay for detecting the presence of a variant polypeptide. Detection of a variant amino acid at the variant position of the PCSK1 polypeptide indicates that the PCSK1 polypeptide is a variant PCSK1 polypeptide.

The probes and/or primers (including alteration-specific probes and alteration-specific primers) described herein comprise or consist of from about 15 to about 100, from about 15 to about 35 nucleotides. In some embodiments, the alteration-specific probes and alteration-specific primers comprise DNA. In some embodiments, the alteration-specific probes and alteration-specific primers comprise RNA. In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers (including alteration-specific probes and alteration-specific primers) specifically hybridize to any of the nucleic acid molecules disclosed herein under stringent conditions. In the context of the disclosure "specifically hybridizes" means that the probe or primer (including alteration-specific probes and alteration-specific primers) does not hybridize to a nucleic acid sequence encoding a PCSK1 reference genomic nucleic acid molecule, a PCSK1 reference mRNA molecule, and/or a PCSK1 reference cDNA molecule. In some embodiments, the probes (such as, for example, an alteration-specific probe) comprise a label. In some embodiments, the label is a fluorescent label, a radiolabel, or biotin.

The present disclosure also provides methods of identifying a subject having an increased risk of developing obesity. The methods comprise determining or having determined whether the subject has any one copy of the PCSK1 loss-of-function variant nucleic acid molecule or polypeptide produced therefrom described herein. The methods can also comprise determining or having determined whether the subject has any one copy of the PCSK1 missense variant nucleic acid molecule or polypeptide produced therefrom described herein. When the subject has one copy of a PCSK1 loss-of-function variant nucleic acid molecule, or a PCSK1 missense variant nucleic acid molecule, or polypeptide produced therefrom, the subject has an increased risk of developing obesity. In some embodiments, the subject is heterozygous for a PCSK1 loss-of-function variant or PCSK1 missense variant. In some embodiments, when a subject is identified as having an increased risk of developing obesity (such as being heterozygous for a PCSK1 loss-of-function variant or PCSK1 missense variant), the subject is further treated with a therapeutic agent that treats or inhibits obesity and/or a leptin-melanocortin signaling pathway agonist (for example, an MC4R agonist), as described herein. Any of the leptin-melanocortin signaling pathway agonists described herein can be administered to the subject.

The present disclosure also provides methods of identifying a subject having an increased risk of developing elevated BMI. The methods comprise determining or having determined whether the subject has any one copy of the PCSK1 loss-of-function variant nucleic acid molecule or polypeptide produced therefrom described herein. The methods can also comprise determining or having determined whether the subject has any one copy of the PCSK1 missense variant nucleic acid molecule or polypeptide produced therefrom described herein. When the subject has one copy of a PCSK1 loss-of-function variant nucleic acid molecule, or a PCSK1 missense variant nucleic acid molecule, or polypeptide produced therefrom, the subject has an increased risk of developing elevated BMI. In some embodiments, the subject is heterozygous for a PCSK1 loss-of-function variant or PCSK1 missense variant. In some embodiments, when a subject is identified as having an increased risk of developing elevated BMI (such as being heterozygous for a PCSK1 loss-of-function variant or PCSK1 missense variant), the subject is further treated with a therapeutic agent that treats or inhibits elevated BMI and/or a leptin-melanocortin signaling pathway agonist (for example, an MC4R agonist), as described herein. Any of the leptin-melanocortin signaling pathway agonists described herein can be administered to the subject.

The present disclosure also provides methods of diagnosing obesity in a subject. The methods comprise determining or having determined whether the subject has any one copy of the PCSK1 loss-of-function variant nucleic acid molecule or polypeptide produced therefrom described herein. The methods can also comprise determining or having determined whether the subject has any one copy of the PCSK1 missense variant nucleic acid molecule or polypeptide produced therefrom described herein. When the subject has one copy of a PCSK1 loss-of-function variant nucleic acid molecule, or a PCSK1 missense variant nucleic acid molecule, or polypeptide produced therefrom, and has one or more symptoms of obesity, the subject is diagnosed as having obesity. In some embodiments, the subject is heterozygous for a PCSK1 loss-of-function variant or PCSK1 missense variant. In some embodiments, when a subject is identified as having obesity (such as having one or more symptoms of obesity and being heterozygous for a PCSK1 loss-of-function variant or PCSK1 missense variant), the subject is further treated with a therapeutic agent that treats or inhibits obesity and/or a leptin-melanocortin signaling pathway agonist (for example, an MC4R agonist), as described herein. Any of the leptin-melanocortin signaling pathway agonists described herein can be administered to the subject.

The present disclosure also provides methods of diagnosing elevated BMI in a subject. The methods comprise determining or having determined whether the subject has any one copy of a PCSK1 loss-of-function variant nucleic acid molecule or polypeptide produced therefrom described herein. The methods can also comprise determining or having determined whether the subject has any one copy of a PCSK1 missense variant nucleic acid molecule or polypeptide produced therefrom described herein. When the subject has one copy of a PCSK1 loss-of-function variant nucleic acid molecule, or a PCSK1 missense variant nucleic acid molecule, or polypeptide produced therefrom, and has one or more symptoms of obesity, the subject is diagnosed as having elevated BMI. In some embodiments, the subject is heterozygous for PCSK1 loss-of-function variant or PCSK1 missense variant. In some embodiments, when a subject is identified as having elevated BMI (such as having one or more symptoms of obesity and being heterozygous for a PCSK1 loss-of-function variant or PCSK1 missense variant), the subject is further treated with a therapeutic agent that treats or inhibits elevated BMI and/or a leptin-melanocortin signaling pathway agonist (for example, an MC4R agonist), as described herein. Any of the leptin-melanocortin signaling pathway agonists described herein can be administered to the subject.

The present disclosure also provides methods of identifying susceptibility of obese subjects to treatment with a leptin-melanocortin signaling pathway agonist (for example, an MC4R agonist). The methods comprise determining or having determined whether the subject has any one copy of a PCSK1 loss-of-function variant nucleic acid molecules or polypeptides produced therefrom as described herein. The methods can also comprise determining or having determined whether the subject has any one copy of a PCSK1 missense variant nucleic acid molecules or polypeptides produced therefrom as described herein. When the subject is heterozygous for a PCSK1 loss-of-function variant nucleic acid molecule, or a PCSK1 missense variant nucleic acid molecule, or a polypeptide produced therefrom, the subject is susceptible to treatment with a leptin-melanocortin signaling pathway agonist (for example, an MC4R agonist). In some embodiments, when a subject is identified as susceptible to treatment (such as being heterozygous for a PCSK1 loss-of-function variant or PCSK1 missense variant), the subject is further treated with a leptin-melanocortin signaling pathway agonist (for example, an MC4R agonist), as described herein. Any of the leptin-melanocortin signaling pathway agonists described herein can be administered to the subject.

The present disclosure also provides methods of identifying susceptibility of subjects having elevated BMI to treatment with a leptin-melanocortin signaling pathway agonist (for example, an MC4R agonist). The methods comprise determining or having determined whether the subject has any one copy of a PCSK1 loss-of-function variant nucleic acid molecule or polypeptide produced therefrom described herein. The methods can also comprise determining or having determined whether the subject has any one copy of a PCSK1 missense variant nucleic acid molecule or polypeptide produced therefrom described herein. When the subject is heterozygous for a PCSK1 loss-of-function variant nucleic acid molecule, or a PCSK1 missense variant nucleic acid molecule, or a polypeptide produced therefrom, the subject is susceptible to treatment with a leptin-melanocortin signaling pathway agonist (for example, an MC4R agonist). In some embodiments, when a subject is identified as susceptible to treatment (such as being heterozygous for a PCSK1 loss of function variant or PCSK1 missense variant), the subject is further treated with a leptin-melanocortin signaling pathway agonist (for example, an MC4R agonist), as described herein. Any of the leptin-melanocortin signaling pathway agonists described herein can be administered to the subject.

The present disclosure also provides molecular complexes comprising any of the PCSK1 variant nucleic acid molecules (genomic nucleic acid molecules, mRNA molecules, or cDNA molecules), or complement thereof, described herein and any of the alteration-specific primers or alteration-specific probes described herein. In some embodiments, the PCSK1 variant nucleic acid molecules (genomic nucleic acid molecules, mRNA molecules, or cDNA molecules), or complement thereof, in the molecular complexes are single-stranded. In some embodiments, the PCSK1 variant nucleic acid molecule is any of the variant genomic nucleic acid molecules described herein. In some embodiments, the PCSK1 variant nucleic acid molecule is any of the variant mRNA molecules described herein. In some embodiments, the PCSK1 variant nucleic acid molecule is any of the variant cDNA molecules described herein. In some embodiments, the molecular complex comprises any of the PCSK1 variant nucleic acid molecules (genomic nucleic acid molecules, mRNA molecules, or cDNA molecules), or complement thereof, described herein and any of the alteration-specific primers described herein. In some embodiments, the molecular complex comprises any of the PCSK1 variant nucleic acid molecules (genomic nucleic acid molecules, mRNA molecules, or cDNA molecules), or complement thereof, described herein and any of the alteration-specific probes described herein. In some embodiments, the molecular complex comprises a non-human polymerase.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1

Aggregate Burden

Experimental Design

Overview: Genetic association studies were performed in the United Kingdom (UK) Biobank (UKB) cohort (Sudlow et al., PLoS Med., 2015, 12, e1001779) and in the MyCode Community Health Initiative cohort from the Geisinger Health System (GHS) (Carey et al., Genet. Med., 2016, 18, 906-913). The UKB is a population-based cohort study of people aged between 40 and 69 from 22 testing centers in the UK. Recruitment took place between 2006 and 2010 (Sudlow et al., PLoS Med., 2015, 12, e1001779). A total of 142,720 European ancestry participants with available whole-exome sequencing and clinical phenotype data were included in this study. The GHS MyCode study is a hospital-based cohort of patients of the GHS (Carey et al., Genet. Med., 2016, 18, 906-913). Recruitment took place between 2007 and 2019. A total of 132,634 European ancestry participants with available whole-exome sequencing and clinical phenotype data were included in this study.

Definition of BMI (UKB and GHS Studies): In both UKB and GHS, body mass index (BMI) was calculated as weight in kilograms divided by height in meters squared on the basis of anthropometric measurements taken at one of the study visits. BMI categories were defined on the basis of the World Health Organization classification.

Sample Preparation and Sequencing

A high-throughput automated approach was used to prepare 100 ng of high-quality genomic DNA for exome capture. The exome was captured using NimbleGen probes (SeqCap VCRome) for a subset of the GHS study (called GHS-VCRome herein) or a slightly modified version of the xGen design available from Integrated DNA Technologies (IDT) for a second subset of GHS (called GHS-IDT herein) or UKB.

A unique 6 base pair (bp) barcode (VCRome) or 10 bp barcode (IDT) was added to each DNA fragment during library preparation to facilitate multiplexed exome capture and sequencing. Equal amounts of sample were pooled prior to exome capture. The captured DNA was amplified by polymerase chain reaction. The multiplexed samples were sequenced using 75 bp paired-end sequencing on an Illumina v4 HiSeq 2500 (GHS-VCRome subset and part of the GHS-IDT subset) or NovaSeq (part of the GHS-IDT subset and UKB). Sequencing had a coverage depth (i.e., number of sequence-reads covering each nucleotide in the target areas of the genome) sufficient to provide greater than 20× coverage over 85% of targeted bases in 96% of VCRome samples and 20× coverage over 90% of targeted bases in 99% of IDT samples.

Sequence Alignment: Raw sequence data from the Illumina sequencers were uploaded to the DNAnexus platform. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations), and single nucleotide variants and intra-read insertion-deletion calling with genotyping software. Sequencing and data quality metric statistics were captured for each sample to evaluate capture, alignment, and variant calling performance.

Sample- and project-level variant calls files (VCFs) were generated. Project-level VCFs contained genotype and the associated metric information for all samples at any site where any sample in the cohort carried a variant from the reference genome.

Variant Annotation and Definition of LOF and Predicted Deleterious Genetic Variants: Single nucleotide variants and insertion-deletions were annotated with the snpEff software using the Ensembl v85 gene definitions to determine their functional impact on transcripts and genes. The functional annotations were then further processed to get a single effect prediction (Regeneron Effect Prediction; REP) for each variant.

To reduce the number of false-positive LOF genetic variant calls, restrictions were imposed on the transcripts in the annotation set. A subset of 54,214 protein-coding transcripts with annotated start and stop transcription sites were considered out of the total 198,002 transcripts in Ensembl v85.

The snpEff predictions that involve protein-coding transcripts with an annotated start and stop were then combined into a single functional impact prediction (i.e., REP) by selecting the most deleterious functional effect class for each gene. The hierarchy used to determine the deleteriousness of a functional effect class is set forth in Table 1.

LOF genetic variants were defined as variants that are predicted to disrupt gene function, by resulting in the likely loss of a copy of the functional gene product. These included insertions or deletions resulting in a frameshift, insertions or deletions or single nucleotide variants resulting in the introduction of a premature stop codon or in the loss of the transcription start site or stop site of the transcript, and variants in donor or acceptor splice sites (see, Table 1 for a full list of variant definitions and effect priority).

TABLE 1

Variant Definitions and Effect Priority

| Effect | Description | Effect Priority | Is a Predicted LOF Variant |
|---|---|---|---|
| Frameshift | Variant causes a frameshift (eg, insertion or deletion (Indel) size that is not a multiple of 3) | 1 | Yes |
| Stop_gained | Variant causes a STOP codon (eg, Cag/Tag, Q/*) | 2 | Yes |
| Start_lost | Variant causes start codon to be mutated into a non-start codon (eg, aTg/aGg, M/R) | 3 | Yes |
| Splice_acceptor | Variant hits a splice acceptor site (defined as 2 bases before exon start, except for the first exon) | 4 | Yes |
| Splice_donor | Variant hits a splice donor site (defined as 2 bases after coding exon end, except for the last exon) | 5 | Yes |
| Stop_lost | Variant causes stop codon to be mutated into a non-stop codon (eg, Tga/Cga, */R) | 6 | Yes |
| Inframe_indel | Variant inserts or deletes 1 or many codons (ie, a multiple of 3) | 7 | No |
| Missense | Variant causes a codon that produces a different amino acid (eg, Tgg/Cgg, W/R) | 8 | No |
| Splice_region | Variant occurs within the region of the splice site, either within 1-3 bases of the exon or 3-8 bases of the intron | 9 | No |
| Synonymous | Variant causes a codon that produces the same amino acid (eg, Ttg/Ctg, L/L) | 10 | No |
| Regulatory_region | Variant hits a known regulatory feature (non-coding) | 11 | No |
| 5_prime_UTR | Variant hits 5'UTR region | 12 | No |
| 3_prime_UTR | Variant hits 3'UTR region | 13 | No |
| Upstream | Variant is upstream of a gene (default length: 5K bases) | 14 | No |
| Downstream | Variant is downstream of a gene (default length: 5K bases) | 15 | No |
| Intronic | Variant hits and intron | 16 | No |
| Intragenic | Variant hits a gene, but no transcripts within the gene | 17 | No |

Missense variants were classified into three groups based on their predicted effect on the PCSK1 protein: predicted to be deleterious by (1) 5/5 in silico prediction algorithms (M3 missense variants), (2) 1/5 algorithms (M4 missense variants), or (3) 0/5 algorithms (M2 missense variants). The prediction algorithms used were: 1) SIFT (available at the world wide web at "ncbi.nlm.nih.gov/pubmed/19561590"); 2) Polyphen2_HDIV and Polyphen2_HVAR (available at the world wide web at "ncbi.nlm.nih.gov/pubmed/

20354512"); 3) LRT (available at the world wide web at "ncbi.nlm.nih.gov/pubmed/19602639"); and 4) Mutation-Taster (available at the world wide web at "ncbi.nlm.nih.gov/pubmed/20676075").

Statistical Analysis

Genes and Genetic Variants of Interest: This study focused on the association with clinical outcomes of LOF genetic variants in the PCSK1 and MC4R genes.

Frequency of variants in the genes of interest: For each individual of European ancestry with whole-exome sequence data, genotype information from all rare (minor allele frequency (MAF)<1%) LOF or LOF plus missense (M2, M3 or M4) variants in PCSK1 or MC4R was collapsed into a single composite genotype, such that: 1) individuals who were homozygous for the human genome reference allele (R) for all LOF variants in the gene of interest were considered homozygous for the reference allele ("RR" composite genotype), 2) individuals who were heterozygous for at least 1 LOF variant in the gene of interest were considered heterozygous ("RA" composite genotype), and 3) individuals with 2 copies of the alternative allele (A) for the same LOF variant were considered homozygous for the alternative allele ("AA" composite genotype). Variants were not phased, thus any individuals who were heterozygotes for 2 or more LOF variants (i.e., compound heterozygotes) was considered heterozygous ("RA" composite genotype). Given the rarity of compound heterozygous carriers of LOF variants, this is highly unlikely to affect any association results.

The frequency of LOF variants in a gene for a given study (GHS-VCRome, GHS-IDT, and UKB) was then estimated as (N_RA+2*N_AA)/(2*N), where N_RA is the number of individuals with a "RA" composite genotype, N_AA is the number of individuals with a "AA" composite genotype, and N is the total number of individuals with a non-missing composite genotype.

Association Between Genetic Variants and Clinical Outcomes of Interest: Given the rarity of each individual LOF or missense variant, the association analyses was restricted to the composite genotype combining all LOF missense variants in a given gene (as described above), instead of testing the association for individual LOF or missense variants, one at a time.

For quantitative traits, association analyses were performed by fitting the linear mixed model implemented in BOLT-LMM v2.3.4 (Loh et al., Nat. Genet., 2018, 50, 906-908). For the model-fitting step of BOLT-LMM, variants with a MAF>0.5% from the exome sequencing data were used. Age, age$^2$, sex, age-by-sex, and 10 ancestry-informative principal components were included as covariates. All quantitative traits were normalized using a rank-based inverse-normal transformation within each sex prior to the BOLT-LMM association analysis. Analyses were performed separately for GHS-VCRome, GHS-IDT, and UKB. Association results were combined across the GHS-VCRome and GHS-IDT sub-studies with METAL using an inverse-variance weighted meta-analysis approach.

Table 2 summarizes the association with body mass index of the burden of predicted loss of function (pLOF) variants or pLOF plus missense variants in PCSK1. The results are from a meta-analysis including 263,183 participants in the UKB or GHS studies.

TABLE 2

| Exposure | Alternative allele frequency, % | Per allele beta (95% CI) in SDs of body mass index | p-value | Number of participants by genotype (RR\|RA\|AA) |
|---|---|---|---|---|
| pLOF-M1.1 | 0.03% | 0.46 (0.30, 0.62) | $1.2 \times 10^{-08}$ | 263,040\|143\|0 |
| pLOF or predicted-deleterious missense variants-M2.1 | 0.72% | 0.07 (0.04, 0.10) | $4.3 \times 10^{-06}$ | 259,405\|3,777\|1 |
| pLOF or predicted deleterious missense variants-M3.1 | 0.24% | 0.10 (0.04, 0.15) | $4.5 \times 10^{-04}$ | 261,927\|1,256\|0 |
| pLOF or predicted-deleterious missense variants-M4.1 | 0.40% | 0.07 (0.03, 0.11) | $5.8 \times 10^{-04}$ | 261,078\|2,105\|0 |

FIG. 1 shows the proportion individuals in different categories of BMI for carriers vs non-carriers of PCSK1 pLOF genetic variants.

Tables 3-6 (M1-M4) list PCSK1 variants included in the association analyses reported in Table 1 (ENST00000311106.8 encompassing chr5:96,390,333-96,433,248 in GRCh38/hg38 human genome assembly; ENSG00000175426.11).

TABLE 3

| VARIANT | AAF | M1 | M2 | M3 | M4 | ANNOTATION | IS_LOF |
|---|---|---|---|---|---|---|---|
| 5:96393172:A:C | 0.0000085 | TRUE | TRUE | TRUE | TRUE | STOP_GAINED | TRUE |
| 5:96393258:G:A | 0.000007 | TRUE | TRUE | TRUE | TRUE | STOP_GAINED | TRUE |
| 5:96393366:G:A | 0.0000194 | TRUE | TRUE | TRUE | TRUE | STOP_GAINED | TRUE |
| 5:96394941:G:A | 0.0000035 | TRUE | TRUE | TRUE | TRUE | STOP_GAINED | TRUE |
| 5:96394988:C:T | 0.0000065 | TRUE | TRUE | TRUE | TRUE | STOP_GAINED | TRUE |
| 5:96397351:CAA:C | 0.0000194 | TRUE | TRUE | TRUE | TRUE | FRAMESHIFT | TRUE |
| 5:96397358:C:T | 0.0000085 | TRUE | TRUE | TRUE | TRUE | STOP_GAINED | TRUE |

TABLE 3-continued

| VARIANT | AAF | M1 | M2 | M3 | M4 | ANNOTATION | IS_LOF |
|---|---|---|---|---|---|---|---|
| 5:96397377:C:A | 0.0000065 | TRUE | TRUE | TRUE | TRUE | STOP_GAINED | TRUE |
| 5:96397382:C:T | 0.0000035 | TRUE | TRUE | TRUE | TRUE | STOP_GAINED | TRUE |
| 5:96397390:AAC:A | 0.0000065 | TRUE | TRUE | TRUE | TRUE | FRAMESHIFT | TRUE |
| 5:96397440:C:A | 0.0000065 | TRUE | TRUE | TRUE | TRUE | STOP_GAINED | TRUE |
| 5:96398877:A:G | 0.0000065 | TRUE | TRUE | TRUE | TRUE | SPLICE_DONOR | TRUE |
| 5:96398887:GAAGT:G | 0.0000085 | TRUE | TRUE | TRUE | TRUE | FRAMESHIFT | TRUE |
| 5:96398922:A:C | 0.0000035 | TRUE | TRUE | TRUE | TRUE | STOP_GAINED | TRUE |
| 5:96399952:C:A | 0.0000065 | TRUE | TRUE | TRUE | TRUE | SPLICE_DONOR | TRUE |
| 5:96399993:T:A | 0.0000105 | TRUE | TRUE | TRUE | TRUE | STOP_GAINED | TRUE |
| 5:96400071:G:A | 0.000007 | TRUE | TRUE | TRUE | TRUE | STOP_GAINED | TRUE |
| 5:96400106:C:T | 0.000013 | TRUE | TRUE | TRUE | TRUE | STOP_GAINED | TRUE |
| 5:96400170:G:A | 0.0000175 | TRUE | TRUE | TRUE | TRUE | STOP_GAINED | TRUE |
| 5:96408221:A:C | 0.0000035 | TRUE | TRUE | TRUE | TRUE | SPLICE_DONOR | TRUE |
| 5:96408288:C:CA | 0.0000065 | TRUE | TRUE | TRUE | TRUE | FRAMESHIFT | TRUE |
| 5:96408299:A:AG | 0.0000065 | TRUE | TRUE | TRUE | TRUE | FRAMESHIFT | TRUE |
| 5:96408310:A:AG | 0.0000035 | TRUE | TRUE | TRUE | TRUE | FRAMESHIFT | TRUE |
| 5:96408324:C:G | 0.0000035 | TRUE | TRUE | TRUE | TRUE | SPLICE_ACCEPTOR | TRUE |
| 5:96410771:T:TA | 0.0000105 | TRUE | TRUE | TRUE | TRUE | SPLICE_DONOR | TRUE |
| 5:96410773:C:T | 0.0000065 | TRUE | TRUE | TRUE | TRUE | SPLICE_DONOR | TRUE |
| 5:96410797:C:A | 0.000007 | TRUE | TRUE | TRUE | TRUE | STOP_GAINED | TRUE |
| 5:96410840:G:C | 0.000028 | TRUE | TRUE | TRUE | TRUE | STOP_GAINED | TRUE |
| 5:96410840:G:T | 0.0000065 | TRUE | TRUE | TRUE | TRUE | STOP_GAINED | TRUE |
| 5:96410844:CAGGGGGAT:C | 0.000007 | TRUE | TRUE | TRUE | TRUE | FRAMESHIFT | TRUE |
| 5:96410910:T:TC | 0.000013 | TRUE | TRUE | TRUE | TRUE | FRAMESHIFT | TRUE |
| 5:96410935:G:GC | 0.0000035 | TRUE | TRUE | TRUE | TRUE | FRAMESHIFT | TRUE |
| 5:96410974:TC:T | 0.0000712 | TRUE | TRUE | TRUE | TRUE | FRAMESHIFT | TRUE |
| 5:96410983:T:TC | 0.0000035 | TRUE | TRUE | TRUE | TRUE | FRAMESHIFT | TRUE |
| 5:96412437:C:CA | 0.0000065 | TRUE | TRUE | TRUE | TRUE | FRAMESHIFT | TRUE |
| 5:96412452:C:A | 0.0000105 | TRUE | TRUE | TRUE | TRUE | STOP_GAINED | TRUE |
| 5:96412454:A:AT | 0.0000065 | TRUE | TRUE | TRUE | TRUE | FRAMESHIFT | TRUE |
| 5:96416067:G:T | 0.0000035 | TRUE | TRUE | TRUE | TRUE | STOP_GAINED | TRUE |
| 5:96416072:T:A | 0.0000035 | TRUE | TRUE | TRUE | TRUE | STOP_GAINED | TRUE |
| 5:96421879:CT:C | 0.0000035 | TRUE | TRUE | TRUE | TRUE | FRAMESHIFT | TRUE |
| 5:96421881:T:A | 0.0000035 | TRUE | TRUE | TRUE | TRUE | STOP_GAINED | TRUE |
| 5:96421893:TG:T | 0.0000065 | TRUE | TRUE | TRUE | TRUE | FRAMESHIFT | TRUE |
| 5:96421905:G:A | 0.0000194 | TRUE | TRUE | TRUE | TRUE | STOP_GAINED | TRUE |
| 5:96421940:TA:T | 0.0000065 | TRUE | TRUE | TRUE | TRUE | FRAMESHIFT | TRUE |
| 5:96421951:TG:T | 0.0000065 | TRUE | TRUE | TRUE | TRUE | FRAMESHIFT | TRUE |
| 5:96421954:AT:A | 0.0000065 | TRUE | TRUE | TRUE | TRUE | FRAMESHIFT | TRUE |
| 5:96423354:CA:C | 0.0000065 | TRUE | TRUE | TRUE | TRUE | FRAMESHIFT | TRUE |
| 5:96423401:CAA:C | 0.0000035 | TRUE | TRUE | TRUE | TRUE | FRAMESHIFT | TRUE |
| 5:96425819:C:G | 0.0000035 | TRUE | TRUE | TRUE | TRUE | SPLICE_DONOR | TRUE |
| 5:96425827:C:T | 0.0000105 | TRUE | TRUE | TRUE | TRUE | STOP_GAINED | TRUE |
| 5:96425843:TG:T | 0.000013 | TRUE | TRUE | TRUE | TRUE | FRAMESHIFT | TRUE |
| 5:96425891:T:A | 0.0000035 | TRUE | TRUE | TRUE | TRUE | STOP_GAINED | TRUE |
| 5:96425892:AC:A | 0.000007 | TRUE | TRUE | TRUE | TRUE | FRAMESHIFT | TRUE |
| 5:96429256:CT:C | 0.0000065 | TRUE | TRUE | TRUE | TRUE | FRAMESHIFT | TRUE |
| 5:96429260:G:A | 0.0000065 | TRUE | TRUE | TRUE | TRUE | STOP_GAINED | TRUE |
| 5:96429269:TG:T | 0.000013 | TRUE | TRUE | TRUE | TRUE | FRAMESHIFT | TRUE |
| 5:96429310:G:T | 0.000007 | TRUE | TRUE | TRUE | TRUE | STOP_GAINED | TRUE |
| 5:96429319:T:C | 0.000007 | TRUE | TRUE | TRUE | TRUE | SPLICE_ACCEPTOR | TRUE |
| 5:96432082:C:T | 0.0000035 | TRUE | TRUE | TRUE | TRUE | SPLICE_DONOR | TRUE |
| 5:96432861:A:C | 0.0000065 | TRUE | TRUE | TRUE | TRUE | SPLICE_DONOR | TRUE |
| 5:96432869:CA:C | 0.0000085 | TRUE | TRUE | TRUE | TRUE | FRAMESHIFT | TRUE |
| 5:96432913:C:A | 0.0000035 | TRUE | TRUE | TRUE | TRUE | STOP_GAINED | TRUE |
| 5:96432957:CT:C | 0.0000065 | TRUE | TRUE | TRUE | TRUE | FRAMESHIFT | TRUE |
| 5:96432971:AC:A | 0.0000259 | TRUE | TRUE | TRUE | TRUE | FRAMESHIFT | TRUE |
| 5:96432981:G:GCA | 0.0000035 | TRUE | TRUE | TRUE | TRUE | FRAMESHIFT | TRUE |
| 5:96432993:CAA:C | 0.0000065 | TRUE | TRUE | TRUE | TRUE | FRAMESHIFT | TRUE |
| 5:96433040:C:T | 0.0000065 | TRUE | TRUE | TRUE | TRUE | START_LOST | TRUE |
| 5:96433041:A:G | 0.0000035 | TRUE | TRUE | TRUE | TRUE | START_LOST | TRUE |

TABLE 4

| VARIANT | AAF | M1 | M2 | M3 | M4 | ANNOTATION | IS_LOF |
|---|---|---|---|---|---|---|---|
| 5:96393012:C:T | 0.0000175 | FALSE | TRUE | FALSE | TRUE | MISSENSE | FALSE |
| 5:96393013:A:T | 0.0000035 | FALSE | TRUE | FALSE | FALSE | MISSENSE | FALSE |
| 5:96393014:T:C | 0.0000035 | FALSE | TRUE | FALSE | FALSE | MISSENSE | FALSE |
| 5:96393026:A:C | 0.0000035 | FALSE | TRUE | FALSE | TRUE | MISSENSE | FALSE |
| 5:96393027:C:T | 0.0000175 | FALSE | TRUE | FALSE | TRUE | MISSENSE | FALSE |
| 5:96393044:C:T | 0.0000245 | FALSE | TRUE | TRUE | TRUE | MISSENSE | FALSE |
| 5:96393045:G:A | 0.0002452 | FALSE | TRUE | TRUE | TRUE | MISSENSE | FALSE |
| 5:96393048:C:T | 0.0000420 | FALSE | TRUE | TRUE | TRUE | MISSENSE | FALSE |
| 5:96393050:T:C | 0.0000070 | FALSE | TRUE | TRUE | TRUE | MISSENSE | FALSE |

TABLE 4-continued

| VARIANT | AAF | M1 | M2 | M3 | M4 | ANNOTATION | IS_LOF |
|---|---|---|---|---|---|---|---|
| 5:96393053:C:T | 0.0000035 | FALSE | TRUE | TRUE | TRUE | MISSENSE | FALSE |
| 5:96393057:G:T | 0.0000065 | FALSE | TRUE | TRUE | TRUE | MISSENSE | FALSE |
| 5:96393065:G:A | 0.0000194 | FALSE | TRUE | TRUE | TRUE | MISSENSE | FALSE |
| 5:96393077:T:C | 0.0000035 | FALSE | TRUE | TRUE | TRUE | MISSENSE | FALSE |
| 5:96393078:A:G | 0.0000035 | FALSE | TRUE | TRUE | TRUE | MISSENSE | FALSE |
| 5:96393083:A:C | 0.0000035 | FALSE | TRUE | FALSE | TRUE | MISSENSE | FALSE |
| 5:96393084:C:T | 0.0000065 | FALSE | TRUE | FALSE | FALSE | MISSENSE | FALSE |
| 5:96393101:T:C | 0.0000070 | FALSE | TRUE | TRUE | TRUE | MISSENSE | FALSE |
| 5:96393104:A:C | 0.0000035 | FALSE | TRUE | TRUE | TRUE | MISSENSE | FALSE |
| 5:96393105:G:C | 0.0000035 | FALSE | TRUE | FALSE | TRUE | MISSENSE | FALSE |
| 5:96393105:G:T | 0.0000035 | FALSE | TRUE | TRUE | TRUE | MISSENSE | FALSE |
| 5:96393119:T:C | 0.0000280 | FALSE | TRUE | FALSE | FALSE | MISSENSE | FALSE |
| 5:96393134:G:C | 0.0000085 | FALSE | TRUE | FALSE | TRUE | MISSENSE | FALSE |
| 5:96393155:G:A | 0.0000035 | FALSE | TRUE | TRUE | TRUE | MISSENSE | FALSE |
| 5:96393156:C:T | 0.0000035 | FALSE | TRUE | TRUE | TRUE | MISSENSE | FALSE |
| 5:96393159:C:T | 0.0000140 | FALSE | TRUE | FALSE | TRUE | MISSENSE | FALSE |
| 5:96393168:T:C | 0.0000070 | FALSE | TRUE | FALSE | FALSE | MISSENSE | FALSE |
| 5:96393169:T:G | 0.0000035 | FALSE | TRUE | FALSE | TRUE | MISSENSE | FALSE |
| 5:96393171:C:G | 0.0000035 | FALSE | TRUE | FALSE | FALSE | MISSENSE | FALSE |
| 5:96393172:A:C | 0.0000085 | TRUE | TRUE | TRUE | TRUE | STOP_GAINED | TRUE |
| 5:96393179:A:C | 0.0000105 | FALSE | TRUE | FALSE | TRUE | MISSENSE | FALSE |
| 5:96393181:G:T | 0.0000035 | FALSE | TRUE | FALSE | FALSE | MISSENSE | FALSE |
| 5:96393183:T:C | 0.0000085 | FALSE | TRUE | FALSE | FALSE | MISSENSE | FALSE |
| 5:96393183:T:G | 0.0000065 | FALSE | TRUE | FALSE | FALSE | MISSENSE | FALSE |
| 5:96393186:G:A | 0.0000085 | FALSE | TRUE | FALSE | TRUE | MISSENSE | FALSE |
| 5:96393187:C:G | 0.0000035 | FALSE | TRUE | FALSE | TRUE | MISSENSE | FALSE |
| 5:96393192:C:A | 0.0000085 | FALSE | TRUE | FALSE | FALSE | MISSENSE | FALSE |
| 5:96393198:G:A | 0.0000130 | FALSE | TRUE | FALSE | FALSE | MISSENSE | FALSE |
| 5:96393210:G:A | 0.0000035 | FALSE | TRUE | FALSE | TRUE | MISSENSE | FALSE |
| 5:96393212:G:A | 0.0000175 | FALSE | TRUE | FALSE | FALSE | MISSENSE | FALSE |
| 5:96393224:G:A | 0.0000070 | FALSE | TRUE | FALSE | FALSE | MISSENSE | FALSE |
| 5:96393225:G:T | 0.0000140 | FALSE | TRUE | FALSE | FALSE | MISSENSE | FALSE |
| 5:96393236:C:T | 0.0000194 | FALSE | TRUE | FALSE | FALSE | MISSENSE | FALSE |
| 5:96393239:A:G | 0.0000140 | FALSE | TRUE | TRUE | TRUE | MISSENSE | FALSE |
| 5:96393257:C:A | 0.0000065 | FALSE | TRUE | FALSE | TRUE | MISSENSE | FALSE |
| 5:96393257:C:T | 0.0000140 | FALSE | TRUE | FALSE | TRUE | MISSENSE | FALSE |
| 5:96393258:G:A | 0.0000070 | TRUE | TRUE | TRUE | TRUE | STOP_GAINED | TRUE |
| 5:96393269:T:C | 0.0000035 | FALSE | TRUE | FALSE | FALSE | MISSENSE | FALSE |
| 5:96393272:G:A | 0.0000035 | FALSE | TRUE | FALSE | TRUE | MISSENSE | FALSE |
| 5:96393281:C:G | 0.0000065 | FALSE | TRUE | FALSE | FALSE | MISSENSE | FALSE |
| 5:96393281:C:T | 0.0000035 | FALSE | TRUE | FALSE | FALSE | MISSENSE | FALSE |
| 5:96393284:T:C | 0.0000065 | FALSE | TRUE | FALSE | TRUE | MISSENSE | FALSE |
| 5:96393285:C:T | 0.0000130 | FALSE | TRUE | FALSE | TRUE | MISSENSE | FALSE |
| 5:96393300:T:A | 0.0000065 | FALSE | TRUE | FALSE | TRUE | MISSENSE | FALSE |
| 5:96393302:C:T | 0.0000771 | FALSE | TRUE | FALSE | FALSE | MISSENSE | FALSE |
| 5:96393303:G:A | 0.0000140 | FALSE | TRUE | FALSE | TRUE | MISSENSE | FALSE |
| 5:96393305:C:A | 0.0000210 | FALSE | TRUE | FALSE | FALSE | MISSENSE | FALSE |
| 5:96393308:C:A | 0.0000453 | FALSE | TRUE | FALSE | TRUE | MISSENSE | FALSE |
| 5:96393312:C:T | 0.0000350 | FALSE | TRUE | FALSE | FALSE | MISSENSE | FALSE |
| 5:96393324:T:G | 0.0000035 | FALSE | TRUE | FALSE | FALSE | MISSENSE | FALSE |
| 5:96393328:G:T | 0.0000389 | FALSE | TRUE | FALSE | FALSE | MISSENSE | FALSE |
| 5:96393342:G:T | 0.0000085 | FALSE | TRUE | FALSE | FALSE | MISSENSE | FALSE |
| 5:96393344:G:T | 0.0000065 | FALSE | TRUE | FALSE | FALSE | MISSENSE | FALSE |
| 5:96393345:T:C | 0.0030547 | FALSE | TRUE | FALSE | FALSE | MISSENSE | FALSE |
| 5:96393347:T:C | 0.0000065 | FALSE | TRUE | FALSE | FALSE | MISSENSE | FALSE |
| 5:96393363:C:T | 0.0000065 | FALSE | TRUE | FALSE | FALSE | MISSENSE | FALSE |
| 5:96393365:T:C | 0.0000035 | FALSE | TRUE | FALSE | FALSE | MISSENSE | FALSE |
| 5:96393366:G:A | 0.0000194 | TRUE | TRUE | TRUE | TRUE | STOP_GAINED | TRUE |
| 5:96393378:C:G | 0.0000035 | FALSE | TRUE | FALSE | TRUE | MISSENSE | FALSE |
| 5:96394878:C:A | 0.0000070 | FALSE | TRUE | FALSE | TRUE | MISSENSE | FALSE |
| 5:96394882:C:G | 0.0000035 | FALSE | TRUE | FALSE | TRUE | MISSENSE | FALSE |
| 5:96394890:C:A | 0.0000035 | FALSE | TRUE | FALSE | TRUE | MISSENSE | FALSE |
| 5:96394893:C:T | 0.0000035 | FALSE | TRUE | FALSE | TRUE | MISSENSE | FALSE |
| 5:96394901:T:G | 0.0000035 | FALSE | TRUE | FALSE | TRUE | MISSENSE | FALSE |
| 5:96394911:C:T | 0.0000175 | FALSE | TRUE | FALSE | TRUE | MISSENSE | FALSE |
| 5:96394925:G:A | 0.0000175 | FALSE | TRUE | TRUE | TRUE | MISSENSE | FALSE |
| 5:96394934:C:T | 0.0000175 | FALSE | TRUE | TRUE | TRUE | MISSENSE | FALSE |
| 5:96394935:G:A | 0.0000035 | FALSE | TRUE | TRUE | TRUE | MISSENSE | FALSE |
| 5:96394941:G:A | 0.0000035 | TRUE | TRUE | TRUE | TRUE | STOP_GAINED | TRUE |
| 5:96394947:T:C | 0.0000065 | FALSE | TRUE | FALSE | TRUE | MISSENSE | FALSE |
| 5:96394964:G:T | 0.0000065 | FALSE | TRUE | FALSE | TRUE | MISSENSE | FALSE |
| 5:96394973:T:C | 0.0000035 | FALSE | TRUE | TRUE | TRUE | MISSENSE | FALSE |
| 5:96394988:C:T | 0.0000065 | TRUE | TRUE | TRUE | TRUE | STOP_GAINED | TRUE |
| 5:96394997:A:G | 0.0000035 | FALSE | TRUE | TRUE | TRUE | MISSENSE | FALSE |
| 5:96395003:C:T | 0.0000065 | FALSE | TRUE | TRUE | TRUE | MISSENSE | FALSE |
| 5:96395024:G:C | 0.0000065 | FALSE | TRUE | TRUE | TRUE | MISSENSE | FALSE |
| 5:96397344:T:C | 0.0000085 | FALSE | TRUE | FALSE | TRUE | MISSENSE | FALSE |
| 5:96397346:A:T | 0.0000105 | FALSE | TRUE | TRUE | TRUE | MISSENSE | FALSE |

TABLE 4-continued

| VARIANT | AAF | M1 | M2 | M3 | M4 | ANNOTATION | IS_LOF |
|---|---|---|---|---|---|---|---|
| 5:96397347:T:A | 0.0000455 | FALSE | TRUE | FALSE | TRUE | MISSENSE | FALSE |
| 5:96397351:CAA:C | 0.0000194 | TRUE | TRUE | TRUE | TRUE | FRAMESHIFT | TRUE |
| 5:96397351:C:G | 0.0000254 | FALSE | TRUE | TRUE | TRUE | MISSENSE | FALSE |
| 5:96397357:C:G | 0.0000065 | FALSE | TRUE | TRUE | TRUE | MISSENSE | FALSE |
| 5:96397358:C:T | 0.0000085 | TRUE | TRUE | TRUE | TRUE | STOP_GAINED | TRUE |
| 5:96397362:T:C | 0.0000035 | FALSE | TRUE | FALSE | TRUE | MISSENSE | FALSE |
| 5:96397364:C:A | 0.0000065 | FALSE | TRUE | TRUE | TRUE | MISSENSE | FALSE |
| 5:96397366:T:C | 0.0000130 | FALSE | TRUE | FALSE | FALSE | MISSENSE | FALSE |
| 5:96397367:A:G | 0.0000280 | FALSE | TRUE | FALSE | FALSE | MISSENSE | FALSE |
| 5:96397372:G:T | 0.0000035 | FALSE | TRUE | FALSE | TRUE | MISSENSE | FALSE |
| 5:96397377:C:A | 0.0000065 | TRUE | TRUE | TRUE | TRUE | STOP_GAINED | TRUE |
| 5:96397380:C:T | 0.0000065 | FALSE | TRUE | TRUE | TRUE | MISSENSE | FALSE |
| 5:96397382:C:T | 0.0000035 | TRUE | TRUE | TRUE | TRUE | STOP_GAINED | TRUE |
| 5:96397390:AAC:A | 0.0000065 | TRUE | TRUE | TRUE | TRUE | FRAMESHIFT | TRUE |
| 5:96397392:C:T | 0.0000701 | FALSE | TRUE | FALSE | TRUE | MISSENSE | FALSE |
| 5:96397397:A:G | 0.0000065 | FALSE | TRUE | TRUE | TRUE | MISSENSE | FALSE |
| 5:96397424:G:C | 0.0000210 | FALSE | TRUE | FALSE | TRUE | MISSENSE | FALSE |
| 5:96397431:T:A | 0.0000035 | FALSE | TRUE | FALSE | TRUE | MISSENSE | FALSE |
| 5:96397432:A:T | 0.0000035 | FALSE | TRUE | TRUE | TRUE | MISSENSE | FALSE |
| 5:96397433:T:C | 0.0000070 | FALSE | TRUE | TRUE | TRUE | MISSENSE | FALSE |
| 5:96397436:C:G | 0.0000194 | FALSE | TRUE | FALSE | TRUE | MISSENSE | FALSE |
| 5:96397437:G:A | 0.0000315 | FALSE | TRUE | FALSE | TRUE | MISSENSE | FALSE |
| 5:96397439:T:C | 0.0000035 | FALSE | TRUE | FALSE | TRUE | MISSENSE | FALSE |
| 5:96397440:C:A | 0.0000065 | TRUE | TRUE | TRUE | TRUE | STOP_GAINED | TRUE |
| 5:96397451:A:G | 0.0000035 | FALSE | TRUE | TRUE | TRUE | MISSENSE | FALSE |
| 5:96397461:T:C | 0.0000035 | FALSE | TRUE | FALSE | TRUE | MISSENSE | FALSE |
| 5:96397463:C:T | 0.0000035 | FALSE | TRUE | FALSE | TRUE | MISSENSE | FALSE |
| 5:96398877:A:G | 0.0000065 | TRUE | TRUE | TRUE | TRUE | SPLICE_DONOR | TRUE |
| 5:96398887:GAAGT:G | 0.0000085 | TRUE | TRUE | TRUE | TRUE | FRAMESHIFT | TRUE |
| 5:96398897:T:C | 0.0000035 | FALSE | TRUE | FALSE | TRUE | MISSENSE | FALSE |
| 5:96398902:T:C | 0.0000035 | FALSE | TRUE | FALSE | TRUE | MISSENSE | FALSE |
| 5:96398911:C:A | 0.0000130 | FALSE | TRUE | TRUE | TRUE | MISSENSE | FALSE |
| 5:96398917:C:T | 0.0002172 | FALSE | TRUE | TRUE | TRUE | MISSENSE | FALSE |
| 5:96398920:G:A | 0.0000035 | FALSE | TRUE | FALSE | TRUE | MISSENSE | FALSE |
| 5:96398922:A:C | 0.0000035 | TRUE | TRUE | TRUE | TRUE | STOP_GAINED | TRUE |
| 5:96398929:A:G | 0.0000035 | FALSE | TRUE | TRUE | TRUE | MISSENSE | FALSE |
| 5:96398945:G:T | 0.0000085 | FALSE | TRUE | FALSE | TRUE | MISSENSE | FALSE |
| 5:96398966:T:G | 0.0000070 | FALSE | TRUE | FALSE | TRUE | MISSENSE | FALSE |
| 5:96398969:C:A | 0.0000245 | FALSE | TRUE | FALSE | FALSE | MISSENSE | FALSE |
| 5:96398980:C:T | 0.0000035 | FALSE | TRUE | FALSE | TRUE | MISSENSE | FALSE |
| 5:96398983:T:A | 0.0000085 | FALSE | TRUE | FALSE | TRUE | MISSENSE | FALSE |
| 5:96398992:C:T | 0.0000065 | FALSE | TRUE | FALSE | FALSE | MISSENSE | FALSE |
| 5:96399007:A:G | 0.0000035 | FALSE | TRUE | FALSE | TRUE | MISSENSE | FALSE |
| 5:96399008:T:C | 0.0000065 | FALSE | TRUE | FALSE | TRUE | MISSENSE | FALSE |
| 5:96399952:C:A | 0.0000065 | TRUE | TRUE | TRUE | TRUE | SPLICE_DONOR | TRUE |
| 5:96399958:C:G | 0.0000070 | FALSE | TRUE | FALSE | TRUE | MISSENSE | FALSE |
| 5:96399969:T:C | 0.0000035 | FALSE | TRUE | FALSE | TRUE | MISSENSE | FALSE |
| 5:96399978:C:T | 0.0000245 | FALSE | TRUE | FALSE | TRUE | MISSENSE | FALSE |
| 5:96399980:A:G | 0.0000453 | FALSE | TRUE | FALSE | TRUE | MISSENSE | FALSE |
| 5:96399993:T:A | 0.0000105 | TRUE | TRUE | TRUE | TRUE | STOP_GAINED | TRUE |
| 5:96399994:C:G | 0.0000070 | FALSE | TRUE | FALSE | TRUE | MISSENSE | FALSE |
| 5:96399996:C:T | 0.0000070 | FALSE | TRUE | FALSE | TRUE | MISSENSE | FALSE |
| 5:96399999:G:T | 0.0000175 | FALSE | TRUE | TRUE | TRUE | MISSENSE | FALSE |
| 5:96400002:C:G | 0.0000070 | FALSE | TRUE | FALSE | TRUE | MISSENSE | FALSE |
| 5:96400002:C:T | 0.0000596 | FALSE | TRUE | TRUE | TRUE | MISSENSE | FALSE |
| 5:96400003:G:T | 0.0000070 | FALSE | TRUE | FALSE | FALSE | MISSENSE | FALSE |
| 5:96400004:C:T | 0.0000105 | FALSE | TRUE | FALSE | FALSE | MISSENSE | FALSE |
| 5:96400010:C:G | 0.0000085 | FALSE | TRUE | TRUE | TRUE | MISSENSE | FALSE |
| 5:96400028:A:G | 0.0000065 | FALSE | TRUE | TRUE | TRUE | MISSENSE | FALSE |
| 5:96400032:C:T | 0.0000035 | FALSE | TRUE | FALSE | TRUE | MISSENSE | FALSE |
| 5:96400038:G:C | 0.0000070 | FALSE | TRUE | TRUE | TRUE | MISSENSE | FALSE |
| 5:96400047:C:A | 0.0000035 | FALSE | TRUE | TRUE | TRUE | MISSENSE | FALSE |
| 5:96400049:T:A | 0.0000035 | FALSE | TRUE | TRUE | TRUE | MISSENSE | FALSE |
| 5:96400052:A:G | 0.0000065 | FALSE | TRUE | TRUE | TRUE | MISSENSE | FALSE |
| 5:96400061:A:T | 0.0000035 | FALSE | TRUE | FALSE | TRUE | MISSENSE | FALSE |
| 5:96400070:C:T | 0.0000065 | FALSE | TRUE | FALSE | TRUE | MISSENSE | FALSE |
| 5:96400071:G:A | 0.0000070 | TRUE | TRUE | TRUE | TRUE | STOP_GAINED | TRUE |
| 5:96400091:G:T | 0.0000035 | FALSE | TRUE | TRUE | TRUE | MISSENSE | FALSE |
| 5:96400096:A:T | 0.0000259 | FALSE | TRUE | TRUE | TRUE | MISSENSE | FALSE |
| 5:96400100:T:C | 0.0000085 | FALSE | TRUE | FALSE | TRUE | MISSENSE | FALSE |
| 5:96400106:C:T | 0.0000130 | TRUE | TRUE | TRUE | TRUE | STOP_GAINED | TRUE |
| 5:96400118:T:C | 0.0000085 | FALSE | TRUE | FALSE | FALSE | MISSENSE | FALSE |
| 5:96400128:G:A | 0.0000085 | FALSE | TRUE | TRUE | TRUE | MISSENSE | FALSE |
| 5:96400133:T:G | 0.0000175 | FALSE | TRUE | FALSE | TRUE | MISSENSE | FALSE |
| 5:96400142:G:C | 0.0000035 | FALSE | TRUE | FALSE | TRUE | MISSENSE | FALSE |
| 5:96400146:A:G | 0.0000070 | FALSE | TRUE | FALSE | TRUE | MISSENSE | FALSE |
| 5:96400156:G:C | 0.0000065 | FALSE | TRUE | TRUE | TRUE | MISSENSE | FALSE |
| 5:96400169:C:T | 0.0000035 | FALSE | TRUE | TRUE | TRUE | MISSENSE | FALSE |

TABLE 4-continued

| VARIANT | AAF | M1 | M2 | M3 | M4 | ANNOTATION | IS_LOF |
|---|---|---|---|---|---|---|---|
| 5:96400170:G:A | 0.0000175 | TRUE | TRUE | TRUE | TRUE | STOP_GAINED | TRUE |
| 5:96408221:A:C | 0.0000035 | TRUE | TRUE | TRUE | TRUE | SPLICE_DONOR | TRUE |
| 5:96408226:G:T | 0.0000280 | FALSE | TRUE | TRUE | TRUE | MISSENSE | FALSE |
| 5:96408232:A:G | 0.0000130 | FALSE | TRUE | TRUE | TRUE | MISSENSE | FALSE |
| 5:96408238:A:G | 0.0000035 | FALSE | TRUE | TRUE | TRUE | MISSENSE | FALSE |
| 5:96408242:C:G | 0.0000065 | FALSE | TRUE | TRUE | TRUE | MISSENSE | FALSE |
| 5:96408242:C:T | 0.0000070 | FALSE | TRUE | TRUE | TRUE | MISSENSE | FALSE |
| 5:96408244:A:G | 0.0000280 | FALSE | TRUE | TRUE | TRUE | MISSENSE | FALSE |
| 5:96408251:C:T | 0.0000035 | FALSE | TRUE | TRUE | TRUE | MISSENSE | FALSE |
| 5:96408254:C:T | 0.0000035 | FALSE | TRUE | TRUE | TRUE | MISSENSE | FALSE |
| 5:96408256:G:T | 0.0000065 | FALSE | TRUE | TRUE | TRUE | MISSENSE | FALSE |
| 5:96408271:G:A | 0.0000035 | FALSE | TRUE | FALSE | TRUE | MISSENSE | FALSE |
| 5:96408272:C:T | 0.0000065 | FALSE | TRUE | TRUE | TRUE | MISSENSE | FALSE |
| 5:96408274:G:A | 0.0000105 | FALSE | TRUE | TRUE | TRUE | MISSENSE | FALSE |
| 5:96408283:G:C | 0.0000194 | FALSE | TRUE | TRUE | TRUE | MISSENSE | FALSE |
| 5:96408285:G:T | 0.0000085 | FALSE | TRUE | TRUE | TRUE | MISSENSE | FALSE |
| 5:96408288:C:CA | 0.0000065 | TRUE | TRUE | TRUE | TRUE | FRAMESHIFT | TRUE |
| 5:96408289:G:A | 0.0000666 | FALSE | TRUE | FALSE | TRUE | MISSENSE | FALSE |
| 5:96408292:T:A | 0.0000065 | FALSE | TRUE | FALSE | TRUE | MISSENSE | FALSE |
| 5:96408293:C:T | 0.0000065 | FALSE | TRUE | FALSE | FALSE | MISSENSE | FALSE |
| 5:96408295:G:A | 0.0000035 | FALSE | TRUE | TRUE | TRUE | MISSENSE | FALSE |
| 5:96408296:T:A | 0.0000065 | FALSE | TRUE | TRUE | TRUE | MISSENSE | FALSE |
| 5:96408299:A:AG | 0.0000065 | TRUE | TRUE | TRUE | TRUE | FRAMESHIFT | TRUE |
| 5:96408303:A:T | 0.0000085 | FALSE | TRUE | FALSE | TRUE | MISSENSE | FALSE |
| 5:96408310:A:AG | 0.0000035 | TRUE | TRUE | TRUE | TRUE | FRAMESHIFT | TRUE |
| 5:96408312:G:C | 0.0000085 | FALSE | TRUE | TRUE | TRUE | MISSENSE | FALSE |
| 5:96408313:T:C | 0.0000065 | FALSE | TRUE | TRUE | TRUE | MISSENSE | FALSE |
| 5:96408316:G:A | 0.0000175 | FALSE | TRUE | FALSE | TRUE | MISSENSE | FALSE |
| 5:96408322:G:A | 0.0000070 | FALSE | TRUE | FALSE | TRUE | MISSENSE | FALSE |
| 5:96408323:T:C | 0.0001401 | FALSE | TRUE | FALSE | TRUE | MISSENSE | FALSE |
| 5:96408324:C:G | 0.0000035 | TRUE | TRUE | TRUE | TRUE | SPLICE_ACCEPTOR | TRUE |
| 5:96410771:T:TA | 0.0000105 | TRUE | TRUE | TRUE | TRUE | SPLICE_DONOR | TRUE |
| 5:96410773:C:T | 0.0000065 | TRUE | TRUE | TRUE | TRUE | SPLICE_DONOR | TRUE |
| 5:96410776:T:C | 0.0000035 | FALSE | TRUE | FALSE | TRUE | MISSENSE | FALSE |
| 5:96410785:C:T | 0.0000035 | FALSE | TRUE | TRUE | TRUE | MISSENSE | FALSE |
| 5:96410794:C:G | 0.0000070 | FALSE | TRUE | FALSE | TRUE | MISSENSE | FALSE |
| 5:96410797:C:A | 0.0000070 | TRUE | TRUE | TRUE | TRUE | STOP_GAINED | TRUE |
| 5:96410797:C:T | 0.0000035 | FALSE | TRUE | TRUE | TRUE | MISSENSE | FALSE |
| 5:96410808:G:C | 0.0000035 | FALSE | TRUE | TRUE | TRUE | MISSENSE | FALSE |
| 5:96410814:G:A | 0.0000035 | FALSE | TRUE | TRUE | TRUE | MISSENSE | FALSE |
| 5:96410818:G:T | 0.0000065 | FALSE | TRUE | TRUE | TRUE | MISSENSE | FALSE |
| 5:96410826:G:A | 0.0000035 | FALSE | TRUE | TRUE | TRUE | MISSENSE | FALSE |
| 5:96410839:C:A | 0.0000085 | FALSE | TRUE | FALSE | TRUE | MISSENSE | FALSE |
| 5:96410839:C:T | 0.0000105 | FALSE | TRUE | FALSE | TRUE | MISSENSE | FALSE |
| 5:96410840:G:C | 0.0000280 | TRUE | TRUE | TRUE | TRUE | STOP_GAINED | TRUE |
| 5:96410840:G:T | 0.0000065 | TRUE | TRUE | TRUE | TRUE | STOP_GAINED | TRUE |
| 5:96410842:A:G | 0.0000085 | FALSE | TRUE | TRUE | TRUE | MISSENSE | FALSE |
| 5:96410844:CAGGGGGAT:C | 0.0000070 | TRUE | TRUE | TRUE | TRUE | FRAMESHIFT | TRUE |
| 5:96410845:A:C | 0.0000210 | FALSE | TRUE | TRUE | TRUE | MISSENSE | FALSE |
| 5:96410856:C:A | 0.0000140 | FALSE | TRUE | TRUE | TRUE | MISSENSE | FALSE |
| 5:96410856:C:T | 0.0000070 | FALSE | TRUE | TRUE | TRUE | MISSENSE | FALSE |
| 5:96410857:C:A | 0.0000065 | FALSE | TRUE | TRUE | TRUE | MISSENSE | FALSE |
| 5:96410875:T:C | 0.0000035 | FALSE | TRUE | FALSE | TRUE | MISSENSE | FALSE |
| 5:96410878:T:A | 0.0000070 | FALSE | TRUE | TRUE | TRUE | MISSENSE | FALSE |
| 5:96410883:A:G | 0.0000105 | FALSE | TRUE | TRUE | TRUE | MISSENSE | FALSE |
| 5:96410887:T:C | 0.0000065 | FALSE | TRUE | TRUE | TRUE | MISSENSE | FALSE |
| 5:96410895:C:A | 0.0000065 | FALSE | TRUE | TRUE | TRUE | MISSENSE | FALSE |
| 5:96410901:G:A | 0.0000035 | FALSE | TRUE | TRUE | TRUE | MISSENSE | FALSE |
| 5:96410907:C:A | 0.0000035 | FALSE | TRUE | TRUE | TRUE | MISSENSE | FALSE |
| 5:96410907:C:T | 0.0000035 | FALSE | TRUE | TRUE | TRUE | MISSENSE | FALSE |
| 5:96410910:T:TC | 0.0000130 | TRUE | TRUE | TRUE | TRUE | FRAMESHIFT | TRUE |
| 5:96410913:C:T | 0.0000065 | FALSE | TRUE | TRUE | TRUE | MISSENSE | FALSE |
| 5:96410929:C:T | 0.0000453 | FALSE | TRUE | FALSE | TRUE | MISSENSE | FALSE |
| 5:96410934:C:T | 0.0000035 | FALSE | TRUE | FALSE | TRUE | MISSENSE | FALSE |
| 5:96410935:G:A | 0.0000035 | FALSE | TRUE | TRUE | TRUE | MISSENSE | FALSE |
| 5:96410935:G:GC | 0.0000035 | TRUE | TRUE | TRUE | TRUE | FRAMESHIFT | TRUE |
| 5:96410940:C:A | 0.0000035 | FALSE | TRUE | TRUE | TRUE | MISSENSE | FALSE |
| 5:96410941:C:T | 0.0000085 | FALSE | TRUE | TRUE | TRUE | MISSENSE | FALSE |
| 5:96410946:C:T | 0.0000105 | FALSE | TRUE | TRUE | TRUE | MISSENSE | FALSE |
| 5:96410949:G:A | 0.0000175 | FALSE | TRUE | FALSE | TRUE | MISSENSE | FALSE |
| 5:96410959:C:T | 0.0000525 | FALSE | TRUE | FALSE | TRUE | MISSENSE | FALSE |
| 5:96410965:T:G | 0.0000070 | FALSE | TRUE | FALSE | TRUE | MISSENSE | FALSE |
| 5:96410970:C:T | 0.0000035 | FALSE | TRUE | TRUE | TRUE | MISSENSE | FALSE |
| 5:96410974:TC:T | 0.0000712 | TRUE | TRUE | TRUE | TRUE | FRAMESHIFT | TRUE |
| 5:96410976:C:G | 0.0000065 | FALSE | TRUE | TRUE | TRUE | MISSENSE | FALSE |
| 5:96410983:T:TC | 0.0000035 | TRUE | TRUE | TRUE | TRUE | FRAMESHIFT | TRUE |
| 5:96410985:C:T | 0.0000065 | FALSE | TRUE | TRUE | TRUE | MISSENSE | FALSE |
| 5:96412322:T:C | 0.0000130 | FALSE | TRUE | FALSE | TRUE | MISSENSE | FALSE |

TABLE 4-continued

| VARIANT | AAF | M1 | M2 | M3 | M4 | ANNOTATION | IS_LOF |
|---|---|---|---|---|---|---|---|
| 5:96412328:C:T | 0.0000035 | FALSE | TRUE | TRUE | TRUE | MISSENSE | FALSE |
| 5:96412332:A:G | 0.0000130 | FALSE | TRUE | FALSE | TRUE | MISSENSE | FALSE |
| 5:96412355:C:T | 0.0000065 | FALSE | TRUE | FALSE | TRUE | MISSENSE | FALSE |
| 5:96412356:G:A | 0.0000175 | FALSE | TRUE | TRUE | TRUE | MISSENSE | FALSE |
| 5:96412362:G:A | 0.0000130 | FALSE | TRUE | TRUE | TRUE | MISSENSE | FALSE |
| 5:96412362:G:T | 0.0000035 | FALSE | TRUE | TRUE | TRUE | MISSENSE | FALSE |
| 5:96412364:C:G | 0.0000169 | FALSE | TRUE | TRUE | TRUE | MISSENSE | FALSE |
| 5:96412379:C:G | 0.0000070 | FALSE | TRUE | TRUE | TRUE | MISSENSE | FALSE |
| 5:96412382:T:C | 0.0000065 | FALSE | TRUE | TRUE | TRUE | MISSENSE | FALSE |
| 5:96412385:T:C | 0.0000169 | FALSE | TRUE | TRUE | TRUE | MISSENSE | FALSE |
| 5:96412395:C:T | 0.0000065 | FALSE | TRUE | TRUE | TRUE | MISSENSE | FALSE |
| 5:96412400:C:T | 0.0000085 | FALSE | TRUE | TRUE | TRUE | MISSENSE | FALSE |
| 5:96412416:C:T | 0.0000130 | FALSE | TRUE | TRUE | TRUE | MISSENSE | FALSE |
| 5:96412418:A:G | 0.0000140 | FALSE | TRUE | TRUE | TRUE | MISSENSE | FALSE |
| 5:96412419:C:T | 0.0000070 | FALSE | TRUE | TRUE | TRUE | MISSENSE | FALSE |
| 5:96412420:G:T | 0.0000105 | FALSE | TRUE | TRUE | TRUE | MISSENSE | FALSE |
| 5:96412425:C:T | 0.0000085 | FALSE | TRUE | FALSE | TRUE | MISSENSE | FALSE |
| 5:96412436:C:G | 0.0000065 | FALSE | TRUE | TRUE | TRUE | MISSENSE | FALSE |
| 5:96412436:C:T | 0.0000070 | FALSE | TRUE | TRUE | TRUE | MISSENSE | FALSE |
| 5:96412437:C:CA | 0.0000065 | TRUE | TRUE | TRUE | TRUE | FRAMESHIFT | TRUE |
| 5:96412437:C:T | 0.0000035 | FALSE | TRUE | TRUE | TRUE | MISSENSE | FALSE |
| 5:96412439:A:G | 0.0000085 | FALSE | TRUE | TRUE | TRUE | MISSENSE | FALSE |
| 5:96412440:T:C | 0.0000065 | FALSE | TRUE | FALSE | TRUE | MISSENSE | FALSE |
| 5:96412443:A:T | 0.0000065 | FALSE | TRUE | TRUE | TRUE | MISSENSE | FALSE |
| 5:96412445:C:T | 0.0000035 | FALSE | TRUE | FALSE | TRUE | MISSENSE | FALSE |
| 5:96412448:G:A | 0.0000070 | FALSE | TRUE | TRUE | TRUE | MISSENSE | FALSE |
| 5:96412452:C:A | 0.0000105 | TRUE | TRUE | TRUE | TRUE | STOP_GAINED | TRUE |
| 5:96412454:A:AT | 0.0000065 | TRUE | TRUE | TRUE | TRUE | FRAMESHIFT | TRUE |
| 5:96412454:A:G | 0.0000035 | FALSE | TRUE | TRUE | TRUE | MISSENSE | FALSE |
| 5:96412455:T:C | 0.0000712 | FALSE | TRUE | FALSE | TRUE | MISSENSE | FALSE |
| 5:96412463:G:A | 0.0000140 | FALSE | TRUE | TRUE | TRUE | MISSENSE | FALSE |
| 5:96412464:T:A | 0.0000035 | FALSE | TRUE | TRUE | TRUE | MISSENSE | FALSE |
| 5:96412480:C:G | 0.0000035 | FALSE | TRUE | TRUE | TRUE | MISSENSE | FALSE |
| 5:96412484:C:A | 0.0000085 | FALSE | TRUE | TRUE | TRUE | MISSENSE | FALSE |
| 5:96412488:T:C | 0.0000035 | FALSE | TRUE | FALSE | TRUE | MISSENSE | FALSE |
| 5:96416041:T:A | 0.0001296 | FALSE | TRUE | TRUE | TRUE | MISSENSE | FALSE |
| 5:96416041:T:G | 0.0000065 | FALSE | TRUE | TRUE | TRUE | MISSENSE | FALSE |
| 5:96416047:T:C | 0.0000070 | FALSE | TRUE | FALSE | TRUE | MISSENSE | FALSE |
| 5:96416050:T:C | 0.0000130 | FALSE | TRUE | TRUE | TRUE | MISSENSE | FALSE |
| 5:96416051:A:G | 0.0000070 | FALSE | TRUE | TRUE | TRUE | MISSENSE | FALSE |
| 5:96416053:G:A | 0.0000194 | FALSE | TRUE | TRUE | TRUE | MISSENSE | FALSE |
| 5:96416054:C:A | 0.0000035 | FALSE | TRUE | TRUE | TRUE | MISSENSE | FALSE |
| 5:96416054:C:G | 0.0000065 | FALSE | TRUE | TRUE | TRUE | MISSENSE | FALSE |
| 5:96416057:C:T | 0.0000194 | FALSE | TRUE | FALSE | TRUE | MISSENSE | FALSE |
| 5:96416059:C:A | 0.0000105 | FALSE | TRUE | TRUE | TRUE | MISSENSE | FALSE |
| 5:96416062:A:G | 0.0000070 | FALSE | TRUE | FALSE | TRUE | MISSENSE | FALSE |
| 5:96416063:C:T | 0.0000070 | FALSE | TRUE | TRUE | TRUE | MISSENSE | FALSE |
| 5:96416066:C:G | 0.0000035 | FALSE | TRUE | TRUE | TRUE | MISSENSE | FALSE |
| 5:96416066:C:T | 0.0000210 | FALSE | TRUE | TRUE | TRUE | MISSENSE | FALSE |
| 5:96416067:G:T | 0.0000035 | TRUE | TRUE | TRUE | TRUE | STOP_GAINED | TRUE |
| 5:96416068:C:T | 0.0000035 | FALSE | TRUE | TRUE | TRUE | MISSENSE | FALSE |
| 5:96416069:A:G | 0.0000035 | FALSE | TRUE | TRUE | TRUE | MISSENSE | FALSE |
| 5:96416072:T:A | 0.0000035 | TRUE | TRUE | TRUE | TRUE | STOP_GAINED | TRUE |
| 5:96416075:G:A | 0.0000035 | FALSE | TRUE | FALSE | TRUE | MISSENSE | FALSE |
| 5:96416092:G:A | 0.0001787 | FALSE | TRUE | TRUE | TRUE | MISSENSE | FALSE |
| 5:96416105:C:A | 0.0000035 | FALSE | TRUE | TRUE | TRUE | MISSENSE | FALSE |
| 5:96416105:C:T | 0.0000035 | FALSE | TRUE | TRUE | TRUE | MISSENSE | FALSE |
| 5:96416117:C:T | 0.0000035 | FALSE | TRUE | TRUE | TRUE | MISSENSE | FALSE |
| 5:96421879:CT:C | 0.0000035 | TRUE | TRUE | TRUE | TRUE | FRAMESHIFT | TRUE |
| 5:96421881:T:A | 0.0000035 | TRUE | TRUE | TRUE | TRUE | STOP_GAINED | TRUE |
| 5:96421882:G:T | 0.0000105 | FALSE | TRUE | TRUE | TRUE | MISSENSE | FALSE |
| 5:96421887:C:T | 0.0000105 | FALSE | TRUE | FALSE | TRUE | MISSENSE | FALSE |
| 5:96421893:TG:T | 0.0000065 | TRUE | TRUE | TRUE | TRUE | FRAMESHIFT | TRUE |
| 5:96421896:G:A | 0.0000070 | FALSE | TRUE | FALSE | TRUE | MISSENSE | FALSE |
| 5:96421898:T:A | 0.0000070 | FALSE | TRUE | TRUE | TRUE | MISSENSE | FALSE |
| 5:96421902:A:T | 0.0000035 | FALSE | TRUE | TRUE | TRUE | MISSENSE | FALSE |
| 5:96421904:C:T | 0.0000105 | FALSE | TRUE | TRUE | TRUE | MISSENSE | FALSE |
| 5:96421905:G:A | 0.0000194 | TRUE | TRUE | TRUE | TRUE | STOP_GAINED | TRUE |
| 5:96421908:G:A | 0.0000065 | FALSE | TRUE | TRUE | TRUE | MISSENSE | FALSE |
| 5:96421914:G:A | 0.0000194 | FALSE | TRUE | TRUE | TRUE | MISSENSE | FALSE |
| 5:96421916:T:C | 0.0000070 | FALSE | TRUE | TRUE | TRUE | MISSENSE | FALSE |
| 5:96421916:T:G | 0.0000105 | FALSE | TRUE | TRUE | TRUE | MISSENSE | FALSE |
| 5:96421922:T:C | 0.0000035 | FALSE | TRUE | TRUE | TRUE | MISSENSE | FALSE |
| 5:96421932:T:A | 0.0000065 | FALSE | TRUE | TRUE | TRUE | MISSENSE | FALSE |
| 5:96421934:A:C | 0.0000169 | FALSE | TRUE | FALSE | TRUE | MISSENSE | FALSE |
| 5:96421940:TA:T | 0.0000065 | TRUE | TRUE | TRUE | TRUE | FRAMESHIFT | TRUE |
| 5:96421941:A:G | 0.0000350 | FALSE | TRUE | TRUE | TRUE | MISSENSE | FALSE |
| 5:96421946:G:C | 0.0000210 | FALSE | TRUE | TRUE | TRUE | MISSENSE | FALSE |

TABLE 4-continued

| VARIANT | AAF | M1 | M2 | M3 | M4 | ANNOTATION | IS_LOF |
|---|---|---|---|---|---|---|---|
| 5:96421950:C:G | 0.0000035 | FALSE | TRUE | FALSE | TRUE | MISSENSE | FALSE |
| 5:96421951:TG:T | 0.0000065 | TRUE | TRUE | TRUE | TRUE | FRAMESHIFT | TRUE |
| 5:96421954:AT:A | 0.0000065 | TRUE | TRUE | TRUE | TRUE | FRAMESHIFT | TRUE |
| 5:96423315:A:G | 0.0003818 | FALSE | TRUE | TRUE | TRUE | MISSENSE | FALSE |
| 5:96423317:T:C | 0.0000806 | FALSE | TRUE | TRUE | TRUE | MISSENSE | FALSE |
| 5:96423320:G:A | 0.0000035 | FALSE | TRUE | FALSE | TRUE | MISSENSE | FALSE |
| 5:96423326:A:T | 0.0000169 | FALSE | TRUE | TRUE | TRUE | MISSENSE | FALSE |
| 5:96423332:G:A | 0.0000455 | FALSE | TRUE | TRUE | TRUE | MISSENSE | FALSE |
| 5:96423336:G:A | 0.0000105 | FALSE | TRUE | TRUE | TRUE | MISSENSE | FALSE |
| 5:96423337:A:T | 0.0000085 | FALSE | TRUE | TRUE | TRUE | MISSENSE | FALSE |
| 5:96423338:T:A | 0.0000085 | FALSE | TRUE | TRUE | TRUE | MISSENSE | FALSE |
| 5:96423354:CA:C | 0.0000065 | TRUE | TRUE | TRUE | TRUE | FRAMESHIFT | TRUE |
| 5:96423356:T:A | 0.0000085 | FALSE | TRUE | TRUE | TRUE | MISSENSE | FALSE |
| 5:96423363:C:T | 0.0000175 | FALSE | TRUE | FALSE | TRUE | MISSENSE | FALSE |
| 5:96423375:C:T | 0.0000035 | FALSE | TRUE | FALSE | TRUE | MISSENSE | FALSE |
| 5:96423377:C:T | 0.0000085 | FALSE | TRUE | TRUE | TRUE | MISSENSE | FALSE |
| 5:96423386:G:A | 0.0000070 | FALSE | TRUE | TRUE | TRUE | MISSENSE | FALSE |
| 5:96423387:T:A | 0.0000035 | FALSE | TRUE | FALSE | TRUE | MISSENSE | FALSE |
| 5:96423392:C:T | 0.0000065 | FALSE | TRUE | TRUE | TRUE | MISSENSE | FALSE |
| 5:96423393:C:T | 0.0000385 | FALSE | TRUE | TRUE | TRUE | MISSENSE | FALSE |
| 5:96423401:CAA:C | 0.0000035 | TRUE | TRUE | TRUE | TRUE | FRAMESHIFT | TRUE |
| 5:96423409:T:C | 0.0000065 | FALSE | TRUE | FALSE | TRUE | MISSENSE | FALSE |
| 5:96423410:A:G | 0.0000070 | FALSE | TRUE | FALSE | TRUE | MISSENSE | FALSE |
| 5:96423411:T:A | 0.0000105 | FALSE | TRUE | FALSE | TRUE | MISSENSE | FALSE |
| 5:96423416:T:G | 0.0000085 | FALSE | TRUE | TRUE | TRUE | MISSENSE | FALSE |
| 5:96423431:G:A | 0.0000065 | FALSE | TRUE | TRUE | TRUE | MISSENSE | FALSE |
| 5:96423443:G:A | 0.0000245 | FALSE | TRUE | FALSE | TRUE | MISSENSE | FALSE |
| 5:96423452:G:T | 0.0000245 | FALSE | TRUE | TRUE | TRUE | MISSENSE | FALSE |
| 5:96425819:C:G | 0.0000035 | TRUE | TRUE | TRUE | TRUE | SPLICE_DONOR | TRUE |
| 5:96425827:C:G | 0.0000035 | FALSE | TRUE | TRUE | TRUE | MISSENSE | FALSE |
| 5:96425827:C:T | 0.0000105 | TRUE | TRUE | TRUE | TRUE | STOP_GAINED | TRUE |
| 5:96425836:T:A | 0.0000070 | FALSE | TRUE | FALSE | TRUE | MISSENSE | FALSE |
| 5:96425836:T:C | 0.0000085 | FALSE | TRUE | FALSE | TRUE | MISSENSE | FALSE |
| 5:96425837:T:G | 0.0000175 | FALSE | TRUE | TRUE | TRUE | MISSENSE | FALSE |
| 5:96425841:C:T | 0.0002347 | FALSE | TRUE | FALSE | TRUE | MISSENSE | FALSE |
| 5:96425842:A:T | 0.0000175 | FALSE | TRUE | FALSE | TRUE | MISSENSE | FALSE |
| 5:96425843:TG:T | 0.0000130 | TRUE | TRUE | TRUE | TRUE | FRAMESHIFT | TRUE |
| 5:96425845:G:A | 0.0000065 | FALSE | TRUE | TRUE | TRUE | MISSENSE | FALSE |
| 5:96425851:T:C | 0.0000194 | FALSE | TRUE | FALSE | TRUE | MISSENSE | FALSE |
| 5:96425855:A:C | 0.0000175 | FALSE | TRUE | TRUE | TRUE | MISSENSE | FALSE |
| 5:96425881:G:A | 0.0000085 | FALSE | TRUE | FALSE | FALSE | MISSENSE | FALSE |
| 5:96425887:C:G | 0.0000065 | FALSE | TRUE | TRUE | TRUE | MISSENSE | FALSE |
| 5:96425887:C:T | 0.0000140 | FALSE | TRUE | TRUE | TRUE | MISSENSE | FALSE |
| 5:96425888:G:A | 0.0000140 | FALSE | TRUE | TRUE | TRUE | MISSENSE | FALSE |
| 5:96425891:T:A | 0.0000035 | TRUE | TRUE | TRUE | TRUE | STOP_GAINED | TRUE |
| 5:96425892:AC:A | 0.0000070 | TRUE | TRUE | TRUE | TRUE | FRAMESHIFT | TRUE |
| 5:96425893:C:G | 0.0000035 | FALSE | TRUE | FALSE | FALSE | MISSENSE | FALSE |
| 5:96425899:T:A | 0.0000035 | FALSE | TRUE | FALSE | TRUE | MISSENSE | FALSE |
| 5:96425920:G:A | 0.0000259 | FALSE | TRUE | FALSE | TRUE | MISSENSE | FALSE |
| 5:96425925:T:C | 0.0000070 | FALSE | TRUE | FALSE | FALSE | MISSENSE | FALSE |
| 5:96425929:A:G | 0.0000065 | FALSE | TRUE | TRUE | TRUE | MISSENSE | FALSE |
| 5:96429214:C:T | 0.0000035 | FALSE | TRUE | TRUE | TRUE | MISSENSE | FALSE |
| 5:96429215:G:A | 0.0000583 | FALSE | TRUE | TRUE | TRUE | MISSENSE | FALSE |
| 5:96429215:G:C | 0.0000035 | FALSE | TRUE | FALSE | TRUE | MISSENSE | FALSE |
| 5:96429217:T:C | 0.0000105 | FALSE | TRUE | FALSE | TRUE | MISSENSE | FALSE |
| 5:96429220:T:C | 0.0000070 | FALSE | TRUE | FALSE | TRUE | MISSENSE | FALSE |
| 5:96429228:T:A | 0.0000035 | FALSE | TRUE | TRUE | TRUE | MISSENSE | FALSE |
| 5:96429238:G:A | 0.0000085 | FALSE | TRUE | TRUE | TRUE | MISSENSE | FALSE |
| 5:96429242:T:C | 0.0000085 | FALSE | TRUE | FALSE | TRUE | MISSENSE | FALSE |
| 5:96429243:A:T | 0.0000035 | FALSE | TRUE | FALSE | TRUE | MISSENSE | FALSE |
| 5:96429244:T:C | 0.0000070 | FALSE | TRUE | FALSE | TRUE | MISSENSE | FALSE |
| 5:96429252:A:C | 0.0000035 | FALSE | TRUE | FALSE | TRUE | MISSENSE | FALSE |
| 5:96429253:C:G | 0.0000035 | FALSE | TRUE | FALSE | TRUE | MISSENSE | FALSE |
| 5:96429255:C:A | 0.0000035 | FALSE | TRUE | TRUE | TRUE | MISSENSE | FALSE |
| 5:96429256:CT:C | 0.0000065 | TRUE | TRUE | TRUE | TRUE | FRAMESHIFT | TRUE |
| 5:96429259:C:T | 0.0000065 | FALSE | TRUE | TRUE | TRUE | MISSENSE | FALSE |
| 5:96429260:G:A | 0.0000065 | TRUE | TRUE | TRUE | TRUE | STOP_GAINED | TRUE |
| 5:96429262:G:C | 0.0000245 | FALSE | TRUE | TRUE | TRUE | MISSENSE | FALSE |
| 5:96429264:C:A | 0.0000130 | FALSE | TRUE | FALSE | TRUE | MISSENSE | FALSE |
| 5:96429265:C:T | 0.0000085 | FALSE | TRUE | FALSE | TRUE | MISSENSE | FALSE |
| 5:96429269:TG:T | 0.0000130 | TRUE | TRUE | TRUE | TRUE | FRAMESHIFT | TRUE |
| 5:96429272:G:A | 0.0000035 | FALSE | TRUE | FALSE | TRUE | MISSENSE | FALSE |
| 5:96429283:T:C | 0.0000035 | FALSE | TRUE | FALSE | TRUE | MISSENSE | FALSE |
| 5:96429287:T:G | 0.0000035 | FALSE | TRUE | FALSE | TRUE | MISSENSE | FALSE |
| 5:96429290:A:G | 0.0000035 | FALSE | TRUE | FALSE | TRUE | MISSENSE | FALSE |
| 5:96429299:G:T | 0.0000070 | FALSE | TRUE | TRUE | TRUE | MISSENSE | FALSE |
| 5:96429310:G:A | 0.0000389 | FALSE | TRUE | FALSE | TRUE | MISSENSE | FALSE |
| 5:96429310:G:T | 0.0000070 | TRUE | TRUE | TRUE | TRUE | STOP_GAINED | TRUE |

TABLE 4-continued

| VARIANT | AAF | M1 | M2 | M3 | M4 | ANNOTATION | IS_LOF |
|---|---|---|---|---|---|---|---|
| 5:96429319:T:C | 0.0000070 | TRUE | TRUE | TRUE | TRUE | SPLICE_ACCEPTOR | TRUE |
| 5:96432082:C:T | 0.0000035 | TRUE | TRUE | TRUE | TRUE | SPLICE_DONOR | TRUE |
| 5:96432094:A:G | 0.0000490 | FALSE | TRUE | FALSE | FALSE | MISSENSE | FALSE |
| 5:96432105:A:T | 0.0000140 | FALSE | TRUE | FALSE | TRUE | MISSENSE | FALSE |
| 5:96432106:T:C | 0.0000035 | FALSE | TRUE | FALSE | FALSE | MISSENSE | FALSE |
| 5:96432108:G:A | 0.0000035 | FALSE | TRUE | FALSE | TRUE | MISSENSE | FALSE |
| 5:96432109:A:G | 0.0000035 | FALSE | TRUE | FALSE | FALSE | MISSENSE | FALSE |
| 5:96432113:C:G | 0.0000194 | FALSE | TRUE | FALSE | TRUE | MISSENSE | FALSE |
| 5:96432115:T:C | 0.0000065 | FALSE | TRUE | FALSE | TRUE | MISSENSE | FALSE |
| 5:96432118:C:G | 0.0000065 | FALSE | TRUE | FALSE | TRUE | MISSENSE | FALSE |
| 5:96432861:A:C | 0.0000065 | TRUE | TRUE | TRUE | TRUE | SPLICE_DONOR | TRUE |
| 5:96432869:CA:C | 0.0000085 | TRUE | TRUE | TRUE | TRUE | FRAMESHIFT | TRUE |
| 5:96432870:A:G | 0.0000070 | FALSE | TRUE | FALSE | TRUE | MISSENSE | FALSE |
| 5:96432874:G:A | 0.0000070 | FALSE | TRUE | FALSE | TRUE | MISSENSE | FALSE |
| 5:96432876:T:C | 0.0000130 | FALSE | TRUE | FALSE | TRUE | MISSENSE | FALSE |
| 5:96432877:C:T | 0.0000035 | FALSE | TRUE | FALSE | TRUE | MISSENSE | FALSE |
| 5:96432886:G:C | 0.0000070 | FALSE | TRUE | FALSE | TRUE | MISSENSE | FALSE |
| 5:96432888:T:G | 0.0001166 | FALSE | TRUE | FALSE | TRUE | MISSENSE | FALSE |
| 5:96432889:C:T | 0.0000085 | FALSE | TRUE | FALSE | TRUE | MISSENSE | FALSE |
| 5:96432894:G:T | 0.0000085 | FALSE | TRUE | FALSE | TRUE | MISSENSE | FALSE |
| 5:96432895:C:A | 0.0000105 | FALSE | TRUE | FALSE | TRUE | MISSENSE | FALSE |
| 5:96432896:G:C | 0.0001878 | FALSE | TRUE | FALSE | TRUE | MISSENSE | FALSE |
| 5:96432897:A:T | 0.0000130 | FALSE | TRUE | FALSE | TRUE | MISSENSE | FALSE |
| 5:96432903:G:A | 0.0000140 | FALSE | TRUE | FALSE | FALSE | MISSENSE | FALSE |
| 5:96432909:G:T | 0.0000105 | FALSE | TRUE | FALSE | TRUE | MISSENSE | FALSE |
| 5:96432913:C:A | 0.0000035 | TRUE | TRUE | TRUE | TRUE | STOP_GAINED | TRUE |
| 5:96432915:G:C | 0.0000105 | FALSE | TRUE | FALSE | FALSE | MISSENSE | FALSE |
| 5:96432918:C:T | 0.0000490 | FALSE | TRUE | TRUE | TRUE | MISSENSE | FALSE |
| 5:96432921:C:G | 0.0000065 | FALSE | TRUE | FALSE | TRUE | MISSENSE | FALSE |
| 5:96432922:C:T | 0.0000140 | FALSE | TRUE | TRUE | TRUE | MISSENSE | FALSE |
| 5:96432927:A:G | 0.0000035 | FALSE | TRUE | FALSE | TRUE | MISSENSE | FALSE |
| 5:96432948:A:G | 0.0000085 | FALSE | TRUE | FALSE | TRUE | MISSENSE | FALSE |
| 5:96432952:A:G | 0.0000035 | FALSE | TRUE | FALSE | TRUE | MISSENSE | FALSE |
| 5:96432957:CT:C | 0.0000065 | TRUE | TRUE | TRUE | TRUE | FRAMESHIFT | TRUE |
| 5:96432961:T:C | 0.0000254 | FALSE | TRUE | FALSE | FALSE | MISSENSE | FALSE |
| 5:96432963:G:A | 0.0000911 | FALSE | TRUE | FALSE | FALSE | MISSENSE | FALSE |
| 5:96432965:T:G | 0.0000070 | FALSE | TRUE | FALSE | FALSE | MISSENSE | FALSE |
| 5:96432967:T:C | 0.0000596 | FALSE | TRUE | FALSE | FALSE | MISSENSE | FALSE |
| 5:96432967:T:G | 0.0001036 | FALSE | TRUE | FALSE | FALSE | MISSENSE | FALSE |
| 5:96432971:AC:A | 0.0000259 | TRUE | TRUE | TRUE | TRUE | FRAMESHIFT | TRUE |
| 5:96432972:C:T | 0.0000130 | FALSE | TRUE | FALSE | FALSE | MISSENSE | FALSE |
| 5:96432975:T:A | 0.0002720 | FALSE | TRUE | FALSE | FALSE | MISSENSE | FALSE |
| 5:96432975:T:C | 0.0000035 | FALSE | TRUE | FALSE | FALSE | MISSENSE | FALSE |
| 5:96432976:T:A | 0.0002720 | FALSE | TRUE | FALSE | FALSE | MISSENSE | FALSE |
| 5:96432978:A:G | 0.0000065 | FALSE | TRUE | FALSE | FALSE | MISSENSE | FALSE |
| 5:96432979:G:T | 0.0000035 | FALSE | TRUE | FALSE | FALSE | MISSENSE | FALSE |
| 5:96432981:G:GCA | 0.0000035 | TRUE | TRUE | TRUE | TRUE | FRAMESHIFT | TRUE |
| 5:96432981:G:T | 0.0000140 | FALSE | TRUE | FALSE | TRUE | MISSENSE | FALSE |
| 5:96432985:A:G | 0.0000070 | FALSE | TRUE | FALSE | TRUE | MISSENSE | FALSE |
| 5:96432991:C:A | 0.0000339 | FALSE | TRUE | FALSE | FALSE | MISSENSE | FALSE |
| 5:96432993:CAA:C | 0.0000065 | TRUE | TRUE | TRUE | TRUE | FRAMESHIFT | TRUE |
| 5:96433000:G:A | 0.0000070 | FALSE | TRUE | FALSE | FALSE | MISSENSE | FALSE |
| 5:96433004:G:T | 0.0000035 | FALSE | TRUE | FALSE | FALSE | MISSENSE | FALSE |
| 5:96433008:G:A | 0.0000065 | FALSE | TRUE | FALSE | TRUE | MISSENSE | FALSE |
| 5:96433016:C:G | 0.0000065 | FALSE | TRUE | FALSE | FALSE | MISSENSE | FALSE |
| 5:96433017:T:A | 0.0000070 | FALSE | TRUE | FALSE | FALSE | MISSENSE | FALSE |
| 5:96433017:T:C | 0.0000130 | FALSE | TRUE | FALSE | FALSE | MISSENSE | FALSE |
| 5:96433032:C:T | 0.0000065 | FALSE | TRUE | FALSE | FALSE | MISSENSE | FALSE |
| 5:96433040:C:T | 0.0000065 | TRUE | TRUE | TRUE | TRUE | START_LOST | TRUE |
| 5:96433041:A:G | 0.0000035 | TRUE | TRUE | TRUE | TRUE | START_LOST | TRUE |

TABLE 5

| VARIANT | AAF | M1 | M2 | M3 | M4 | ANNOTATION | IS_LOF |
|---|---|---|---|---|---|---|---|
| 5:96393044:C:T | 0.0000245 | FALSE | TRUE | TRUE | TRUE | MISSENSE | FALSE |
| 5:96393045:G:A | 0.0002452 | FALSE | TRUE | TRUE | TRUE | MISSENSE | FALSE |
| 5:96393048:C:T | 0.0000420 | FALSE | TRUE | TRUE | TRUE | MISSENSE | FALSE |
| 5:96393050:T:C | 0.0000070 | FALSE | TRUE | TRUE | TRUE | MISSENSE | FALSE |
| 5:96393053:C:T | 0.0000035 | FALSE | TRUE | TRUE | TRUE | MISSENSE | FALSE |
| 5:96393057:G:T | 0.0000065 | FALSE | TRUE | TRUE | TRUE | MISSENSE | FALSE |
| 5:96393065:G:A | 0.0000194 | FALSE | TRUE | TRUE | TRUE | MISSENSE | FALSE |
| 5:96393077:T:C | 0.0000035 | FALSE | TRUE | TRUE | TRUE | MISSENSE | FALSE |
| 5:96393078:A:G | 0.0000035 | FALSE | TRUE | TRUE | TRUE | MISSENSE | FALSE |
| 5:96393101:T:C | 0.0000070 | FALSE | TRUE | TRUE | TRUE | MISSENSE | FALSE |

TABLE 5-continued

| VARIANT | AAF | M1 | M2 | M3 | M4 | ANNOTATION | IS_LOF |
|---|---|---|---|---|---|---|---|
| 5:96393104:A:C | 0.0000035 | FALSE | TRUE | TRUE | TRUE | MISSENSE | FALSE |
| 5:96393105:G:T | 0.0000035 | FALSE | TRUE | TRUE | TRUE | MISSENSE | FALSE |
| 5:96393155:G:A | 0.0000035 | FALSE | TRUE | TRUE | TRUE | MISSENSE | FALSE |
| 5:96393156:C:T | 0.0000035 | FALSE | TRUE | TRUE | TRUE | MISSENSE | FALSE |
| 5:96393172:A:C | 0.0000085 | TRUE | TRUE | TRUE | TRUE | STOP_GAINED | TRUE |
| 5:96393239:A:G | 0.0000140 | FALSE | TRUE | TRUE | TRUE | MISSENSE | FALSE |
| 5:96393258:G:A | 0.0000070 | TRUE | TRUE | TRUE | TRUE | STOP_GAINED | TRUE |
| 5:96393366:G:A | 0.0000194 | TRUE | TRUE | TRUE | TRUE | STOP_GAINED | TRUE |
| 5:96394925:G:A | 0.0000175 | FALSE | TRUE | TRUE | TRUE | MISSENSE | FALSE |
| 5:96394934:C:T | 0.0000175 | FALSE | TRUE | TRUE | TRUE | MISSENSE | FALSE |
| 5:96394935:G:A | 0.0000035 | FALSE | TRUE | TRUE | TRUE | MISSENSE | FALSE |
| 5:96394941:G:A | 0.0000035 | TRUE | TRUE | TRUE | TRUE | STOP_GAINED | TRUE |
| 5:96394973:T:C | 0.0000035 | FALSE | TRUE | TRUE | TRUE | MISSENSE | FALSE |
| 5:96394988:C:T | 0.0000065 | TRUE | TRUE | TRUE | TRUE | STOP_GAINED | TRUE |
| 5:96394997:A:G | 0.0000035 | FALSE | TRUE | TRUE | TRUE | MISSENSE | FALSE |
| 5:96395003:C:T | 0.0000065 | FALSE | TRUE | TRUE | TRUE | MISSENSE | FALSE |
| 5:96395024:G:C | 0.0000065 | FALSE | TRUE | TRUE | TRUE | MISSENSE | FALSE |
| 5:96397346:A:T | 0.0000105 | FALSE | TRUE | TRUE | TRUE | MISSENSE | FALSE |
| 5:96397351:CAA:C | 0.0000194 | TRUE | TRUE | TRUE | TRUE | FRAMESHIFT | TRUE |
| 5:96397351:C:G | 0.0000254 | FALSE | TRUE | TRUE | TRUE | MISSENSE | FALSE |
| 5:96397357:C:G | 0.0000065 | FALSE | TRUE | TRUE | TRUE | MISSENSE | FALSE |
| 5:96397358:C:T | 0.0000085 | TRUE | TRUE | TRUE | TRUE | STOP_GAINED | TRUE |
| 5:96397364:C:A | 0.0000065 | FALSE | TRUE | TRUE | TRUE | MISSENSE | FALSE |
| 5:96397377:C:A | 0.0000065 | TRUE | TRUE | TRUE | TRUE | STOP_GAINED | TRUE |
| 5:96397380:C:T | 0.0000065 | FALSE | TRUE | TRUE | TRUE | MISSENSE | FALSE |
| 5:96397382:C:T | 0.0000035 | TRUE | TRUE | TRUE | TRUE | STOP_GAINED | TRUE |
| 5:96397390:AAC:A | 0.0000065 | TRUE | TRUE | TRUE | TRUE | FRAMESHIFT | TRUE |
| 5:96397397:A:G | 0.0000065 | FALSE | TRUE | TRUE | TRUE | MISSENSE | FALSE |
| 5:96397432:A:T | 0.0000035 | FALSE | TRUE | TRUE | TRUE | MISSENSE | FALSE |
| 5:96397433:T:C | 0.0000070 | FALSE | TRUE | TRUE | TRUE | MISSENSE | FALSE |
| 5:96397440:C:A | 0.0000065 | TRUE | TRUE | TRUE | TRUE | STOP_GAINED | TRUE |
| 5:96397451:A:G | 0.0000035 | FALSE | TRUE | TRUE | TRUE | MISSENSE | FALSE |
| 5:96398877:A:G | 0.0000065 | TRUE | TRUE | TRUE | TRUE | SPLICE_DONOR | TRUE |
| 5:96398887:GAAGT:G | 0.0000085 | TRUE | TRUE | TRUE | TRUE | FRAMESHIFT | TRUE |
| 5:96398911:C:A | 0.0000130 | FALSE | TRUE | TRUE | TRUE | MISSENSE | FALSE |
| 5:96398917:C:T | 0.0002172 | FALSE | TRUE | TRUE | TRUE | MISSENSE | FALSE |
| 5:96398922:A:C | 0.0000035 | TRUE | TRUE | TRUE | TRUE | STOP_GAINED | TRUE |
| 5:96398929:A:G | 0.0000035 | FALSE | TRUE | TRUE | TRUE | MISSENSE | FALSE |
| 5:96399952:C:A | 0.0000065 | TRUE | TRUE | TRUE | TRUE | SPLICE_DONOR | TRUE |
| 5:96399993:T:A | 0.0000105 | TRUE | TRUE | TRUE | TRUE | STOP_GAINED | TRUE |
| 5:96399999:G:T | 0.0000175 | FALSE | TRUE | TRUE | TRUE | MISSENSE | FALSE |
| 5:96400002:C:T | 0.0000596 | FALSE | TRUE | TRUE | TRUE | MISSENSE | FALSE |
| 5:96400010:C:G | 0.0000085 | FALSE | TRUE | TRUE | TRUE | MISSENSE | FALSE |
| 5:96400028:A:G | 0.0000065 | FALSE | TRUE | TRUE | TRUE | MISSENSE | FALSE |
| 5:96400038:G:C | 0.0000070 | FALSE | TRUE | TRUE | TRUE | MISSENSE | FALSE |
| 5:96400047:C:A | 0.0000035 | FALSE | TRUE | TRUE | TRUE | MISSENSE | FALSE |
| 5:96400049:T:A | 0.0000035 | FALSE | TRUE | TRUE | TRUE | MISSENSE | FALSE |
| 5:96400052:A:G | 0.0000065 | FALSE | TRUE | TRUE | TRUE | MISSENSE | FALSE |
| 5:96400071:G:A | 0.0000070 | TRUE | TRUE | TRUE | TRUE | STOP_GAINED | TRUE |
| 5:96400091:G:T | 0.0000035 | FALSE | TRUE | TRUE | TRUE | MISSENSE | FALSE |
| 5:96400096:A:T | 0.0000259 | FALSE | TRUE | TRUE | TRUE | MISSENSE | FALSE |
| 5:96400106:C:T | 0.0000130 | TRUE | TRUE | TRUE | TRUE | STOP_GAINED | TRUE |
| 5:96400156:G:C | 0.0000065 | FALSE | TRUE | TRUE | TRUE | MISSENSE | FALSE |
| 5:96400169:C:T | 0.0000035 | FALSE | TRUE | TRUE | TRUE | MISSENSE | FALSE |
| 5:96400170:G:A | 0.0000175 | TRUE | TRUE | TRUE | TRUE | STOP_GAINED | TRUE |
| 5:96408221:A:C | 0.0000035 | TRUE | TRUE | TRUE | TRUE | SPLICE_DONOR | TRUE |
| 5:96408226:G:T | 0.0000280 | FALSE | TRUE | TRUE | TRUE | MISSENSE | FALSE |
| 5:96408232:A:G | 0.0000130 | FALSE | TRUE | TRUE | TRUE | MISSENSE | FALSE |
| 5:96408238:A:G | 0.0000035 | FALSE | TRUE | TRUE | TRUE | MISSENSE | FALSE |
| 5:96408242:C:G | 0.0000065 | FALSE | TRUE | TRUE | TRUE | MISSENSE | FALSE |
| 5:96408242:C:T | 0.0000070 | FALSE | TRUE | TRUE | TRUE | MISSENSE | FALSE |
| 5:96408244:A:G | 0.0000280 | FALSE | TRUE | TRUE | TRUE | MISSENSE | FALSE |
| 5:96408251:C:T | 0.0000035 | FALSE | TRUE | TRUE | TRUE | MISSENSE | FALSE |
| 5:96408254:C:T | 0.0000035 | FALSE | TRUE | TRUE | TRUE | MISSENSE | FALSE |
| 5:96408256:G:T | 0.0000065 | FALSE | TRUE | TRUE | TRUE | MISSENSE | FALSE |
| 5:96408272:C:T | 0.0000065 | FALSE | TRUE | TRUE | TRUE | MISSENSE | FALSE |
| 5:96408274:G:A | 0.0000105 | FALSE | TRUE | TRUE | TRUE | MISSENSE | FALSE |
| 5:96408283:G:C | 0.0000194 | FALSE | TRUE | TRUE | TRUE | MISSENSE | FALSE |
| 5:96408285:G:T | 0.0000085 | FALSE | TRUE | TRUE | TRUE | MISSENSE | FALSE |
| 5:96408288:C:CA | 0.0000065 | TRUE | TRUE | TRUE | TRUE | FRAMESHIFT | TRUE |
| 5:96408295:G:A | 0.0000035 | FALSE | TRUE | TRUE | TRUE | MISSENSE | FALSE |
| 5:96408296:T:A | 0.0000065 | FALSE | TRUE | TRUE | TRUE | MISSENSE | FALSE |
| 5:96408299:A:AG | 0.0000065 | TRUE | TRUE | TRUE | TRUE | FRAMESHIFT | TRUE |
| 5:96408310:A:AG | 0.0000035 | TRUE | TRUE | TRUE | TRUE | FRAMESHIFT | TRUE |
| 5:96408312:G:C | 0.0000085 | FALSE | TRUE | TRUE | TRUE | MISSENSE | FALSE |
| 5:96408313:T:C | 0.0000065 | FALSE | TRUE | TRUE | TRUE | MISSENSE | FALSE |
| 5:96408324:C:G | 0.0000035 | TRUE | TRUE | TRUE | TRUE | SPLICE_ACCEPTOR | TRUE |
| 5:96410771:T:TA | 0.0000105 | TRUE | TRUE | TRUE | TRUE | SPLICE_DONOR | TRUE |

TABLE 5-continued

| VARIANT | AAF | M1 | M2 | M3 | M4 | ANNOTATION | IS_LOF |
|---|---|---|---|---|---|---|---|
| 5:96410773:C:T | 0.0000065 | TRUE | TRUE | TRUE | TRUE | SPLICE_DONOR | TRUE |
| 5:96410785:C:T | 0.0000035 | FALSE | TRUE | TRUE | TRUE | MISSENSE | FALSE |
| 5:96410797:C:A | 0.0000070 | TRUE | TRUE | TRUE | TRUE | STOP_GAINED | TRUE |
| 5:96410797:C:T | 0.0000035 | FALSE | TRUE | TRUE | TRUE | MISSENSE | FALSE |
| 5:96410808:G:C | 0.0000035 | FALSE | TRUE | TRUE | TRUE | MISSENSE | FALSE |
| 5:96410814:G:A | 0.0000035 | FALSE | TRUE | TRUE | TRUE | MISSENSE | FALSE |
| 5:96410818:G:T | 0.0000065 | FALSE | TRUE | TRUE | TRUE | MISSENSE | FALSE |
| 5:96410826:G:A | 0.0000035 | FALSE | TRUE | TRUE | TRUE | MISSENSE | FALSE |
| 5:96410840:G:C | 0.0000280 | TRUE | TRUE | TRUE | TRUE | STOP_GAINED | TRUE |
| 5:96410840:G:T | 0.0000065 | TRUE | TRUE | TRUE | TRUE | STOP_GAINED | TRUE |
| 5:96410842:A:G | 0.0000085 | FALSE | TRUE | TRUE | TRUE | MISSENSE | FALSE |
| 5:96410844:CAGGGGGAT:C | 0.0000070 | TRUE | TRUE | TRUE | TRUE | FRAMESHIFT | TRUE |
| 5:96410845:A:C | 0.0000210 | FALSE | TRUE | TRUE | TRUE | MISSENSE | FALSE |
| 5:96410856:C:A | 0.0000140 | FALSE | TRUE | TRUE | TRUE | MISSENSE | FALSE |
| 5:96410856:C:T | 0.0000070 | FALSE | TRUE | TRUE | TRUE | MISSENSE | FALSE |
| 5:96410857:C:A | 0.0000065 | FALSE | TRUE | TRUE | TRUE | MISSENSE | FALSE |
| 5:96410878:T:A | 0.0000070 | FALSE | TRUE | TRUE | TRUE | MISSENSE | FALSE |
| 5:96410883:A:G | 0.0000105 | FALSE | TRUE | TRUE | TRUE | MISSENSE | FALSE |
| 5:96410887:T:C | 0.0000065 | FALSE | TRUE | TRUE | TRUE | MISSENSE | FALSE |
| 5:96410895:C:A | 0.0000065 | FALSE | TRUE | TRUE | TRUE | MISSENSE | FALSE |
| 5:96410901:G:A | 0.0000035 | FALSE | TRUE | TRUE | TRUE | MISSENSE | FALSE |
| 5:96410907:C:A | 0.0000035 | FALSE | TRUE | TRUE | TRUE | MISSENSE | FALSE |
| 5:96410907:C:T | 0.0000035 | FALSE | TRUE | TRUE | TRUE | MISSENSE | FALSE |
| 5:96410910:T:TC | 0.0000130 | TRUE | TRUE | TRUE | TRUE | FRAMESHIFT | TRUE |
| 5:96410913:C:T | 0.0000065 | FALSE | TRUE | TRUE | TRUE | MISSENSE | FALSE |
| 5:96410935:G:A | 0.0000035 | FALSE | TRUE | TRUE | TRUE | MISSENSE | FALSE |
| 5:96410935:G:GC | 0.0000035 | TRUE | TRUE | TRUE | TRUE | FRAMESHIFT | TRUE |
| 5:96410940:C:A | 0.0000035 | FALSE | TRUE | TRUE | TRUE | MISSENSE | FALSE |
| 5:96410941:C:T | 0.0000085 | FALSE | TRUE | TRUE | TRUE | MISSENSE | FALSE |
| 5:96410946:C:T | 0.0000105 | FALSE | TRUE | TRUE | TRUE | MISSENSE | FALSE |
| 5:96410970:C:T | 0.0000035 | FALSE | TRUE | TRUE | TRUE | MISSENSE | FALSE |
| 5:96410974:TC:T | 0.0000712 | TRUE | TRUE | TRUE | TRUE | FRAMESHIFT | TRUE |
| 5:96410976:C:G | 0.0000065 | FALSE | TRUE | TRUE | TRUE | MISSENSE | FALSE |
| 5:96410983:T:TC | 0.0000035 | TRUE | TRUE | TRUE | TRUE | FRAMESHIFT | TRUE |
| 5:96410985:C:T | 0.0000065 | FALSE | TRUE | TRUE | TRUE | MISSENSE | FALSE |
| 5:96412328:C:T | 0.0000035 | FALSE | TRUE | TRUE | TRUE | MISSENSE | FALSE |
| 5:96412356:G:A | 0.0000175 | FALSE | TRUE | TRUE | TRUE | MISSENSE | FALSE |
| 5:96412362:G:A | 0.0000130 | FALSE | TRUE | TRUE | TRUE | MISSENSE | FALSE |
| 5:96412362:G:T | 0.0000035 | FALSE | TRUE | TRUE | TRUE | MISSENSE | FALSE |
| 5:96412364:C:G | 0.0000169 | FALSE | TRUE | TRUE | TRUE | MISSENSE | FALSE |
| 5:96412379:C:G | 0.0000070 | FALSE | TRUE | TRUE | TRUE | MISSENSE | FALSE |
| 5:96412382:T:C | 0.0000065 | FALSE | TRUE | TRUE | TRUE | MISSENSE | FALSE |
| 5:96412385:T:C | 0.0000169 | FALSE | TRUE | TRUE | TRUE | MISSENSE | FALSE |
| 5:96412395:C:T | 0.0000065 | FALSE | TRUE | TRUE | TRUE | MISSENSE | FALSE |
| 5:96412400:C:T | 0.0000085 | FALSE | TRUE | TRUE | TRUE | MISSENSE | FALSE |
| 5:96412416:C:T | 0.0000130 | FALSE | TRUE | TRUE | TRUE | MISSENSE | FALSE |
| 5:96412418:A:G | 0.0000140 | FALSE | TRUE | TRUE | TRUE | MISSENSE | FALSE |
| 5:96412419:C:T | 0.0000070 | FALSE | TRUE | TRUE | TRUE | MISSENSE | FALSE |
| 5:96412420:G:T | 0.0000105 | FALSE | TRUE | TRUE | TRUE | MISSENSE | FALSE |
| 5:96412436:C:G | 0.0000065 | FALSE | TRUE | TRUE | TRUE | MISSENSE | FALSE |
| 5:96412436:C:T | 0.0000070 | FALSE | TRUE | TRUE | TRUE | MISSENSE | FALSE |
| 5:96412437:C:CA | 0.0000065 | TRUE | TRUE | TRUE | TRUE | FRAMESHIFT | TRUE |
| 5:96412437:C:T | 0.0000035 | FALSE | TRUE | TRUE | TRUE | MISSENSE | FALSE |
| 5:96412439:A:G | 0.0000085 | FALSE | TRUE | TRUE | TRUE | MISSENSE | FALSE |
| 5:96412443:A:T | 0.0000065 | FALSE | TRUE | TRUE | TRUE | MISSENSE | FALSE |
| 5:96412448:G:A | 0.0000070 | FALSE | TRUE | TRUE | TRUE | MISSENSE | FALSE |
| 5:96412452:C:A | 0.0000105 | TRUE | TRUE | TRUE | TRUE | STOP_GAINED | TRUE |
| 5:96412454:A:AT | 0.0000065 | TRUE | TRUE | TRUE | TRUE | FRAMESHIFT | TRUE |
| 5:96412454:A:G | 0.0000035 | FALSE | TRUE | TRUE | TRUE | MISSENSE | FALSE |
| 5:96412463:G:A | 0.0000140 | FALSE | TRUE | TRUE | TRUE | MISSENSE | FALSE |
| 5:96412464:T:A | 0.0000035 | FALSE | TRUE | TRUE | TRUE | MISSENSE | FALSE |
| 5:96412480:C:G | 0.0000035 | FALSE | TRUE | TRUE | TRUE | MISSENSE | FALSE |
| 5:96412484:C:A | 0.0000085 | FALSE | TRUE | TRUE | TRUE | MISSENSE | FALSE |
| 5:96416041:T:A | 0.0001296 | FALSE | TRUE | TRUE | TRUE | MISSENSE | FALSE |
| 5:96416041:T:G | 0.0000065 | FALSE | TRUE | TRUE | TRUE | MISSENSE | FALSE |
| 5:96416050:T:C | 0.0000130 | FALSE | TRUE | TRUE | TRUE | MISSENSE | FALSE |
| 5:96416051:A:G | 0.0000070 | FALSE | TRUE | TRUE | TRUE | MISSENSE | FALSE |
| 5:96416053:G:A | 0.0000194 | FALSE | TRUE | TRUE | TRUE | MISSENSE | FALSE |
| 5:96416054:C:A | 0.0000035 | FALSE | TRUE | TRUE | TRUE | MISSENSE | FALSE |
| 5:96416054:C:G | 0.0000065 | FALSE | TRUE | TRUE | TRUE | MISSENSE | FALSE |
| 5:96416059:C:A | 0.0000105 | FALSE | TRUE | TRUE | TRUE | MISSENSE | FALSE |
| 5:96416063:C:T | 0.0000070 | FALSE | TRUE | TRUE | TRUE | MISSENSE | FALSE |
| 5:96416066:C:G | 0.0000035 | FALSE | TRUE | TRUE | TRUE | MISSENSE | FALSE |
| 5:96416066:C:T | 0.0000210 | FALSE | TRUE | TRUE | TRUE | MISSENSE | FALSE |
| 5:96416067:G:T | 0.0000035 | TRUE | TRUE | TRUE | TRUE | STOP_GAINED | TRUE |
| 5:96416068:C:T | 0.0000035 | FALSE | TRUE | TRUE | TRUE | MISSENSE | FALSE |
| 5:96416069:A:G | 0.0000035 | FALSE | TRUE | TRUE | TRUE | MISSENSE | FALSE |
| 5:96416072:T:A | 0.0000035 | TRUE | TRUE | TRUE | TRUE | STOP_GAINED | TRUE |

TABLE 5-continued

| VARIANT | AAF | M1 | M2 | M3 | M4 | ANNOTATION | IS_LOF |
|---|---|---|---|---|---|---|---|
| 5:96416092:G:A | 0.0001787 | FALSE | TRUE | TRUE | TRUE | MISSENSE | FALSE |
| 5:96416105:C:A | 0.0000035 | FALSE | TRUE | TRUE | TRUE | MISSENSE | FALSE |
| 5:96416105:C:T | 0.0000035 | FALSE | TRUE | TRUE | TRUE | MISSENSE | FALSE |
| 5:96416117:C:T | 0.0000035 | FALSE | TRUE | TRUE | TRUE | MISSENSE | FALSE |
| 5:96421879:CT:C | 0.0000035 | TRUE | TRUE | TRUE | TRUE | FRAMESHIFT | TRUE |
| 5:96421881:T:A | 0.0000035 | TRUE | TRUE | TRUE | TRUE | STOP_GAINED | TRUE |
| 5:96421882:G:T | 0.000010 | FALSE | TRUE | TRUE | TRUE | MISSENSE | FALSE |
| 5:96421893:TG:T | 0.0000065 | TRUE | TRUE | TRUE | TRUE | FRAMESHIFT | TRUE |
| 5:96421898:T:A | 0.0000070 | FALSE | TRUE | TRUE | TRUE | MISSENSE | FALSE |
| 5:96421902:A:T | 0.0000035 | FALSE | TRUE | TRUE | TRUE | MISSENSE | FALSE |
| 5:96421904:C:T | 0.0000105 | FALSE | TRUE | TRUE | TRUE | MISSENSE | FALSE |
| 5:96421905:G:A | 0.0000194 | TRUE | TRUE | TRUE | TRUE | STOP_GAINED | TRUE |
| 5:96421908:G:A | 0.0000065 | FALSE | TRUE | TRUE | TRUE | MISSENSE | FALSE |
| 5:96421914:G:A | 0.0000194 | FALSE | TRUE | TRUE | TRUE | MISSENSE | FALSE |
| 5:96421916:T:C | 0.0000070 | FALSE | TRUE | TRUE | TRUE | MISSENSE | FALSE |
| 5:96421916:T:G | 0.0000105 | FALSE | TRUE | TRUE | TRUE | MISSENSE | FALSE |
| 5:96421922:T:C | 0.0000035 | FALSE | TRUE | TRUE | TRUE | MISSENSE | FALSE |
| 5:96421932:T:A | 0.0000065 | FALSE | TRUE | TRUE | TRUE | MISSENSE | FALSE |
| 5:96421940:TA:T | 0.0000065 | TRUE | TRUE | TRUE | TRUE | FRAMESHIFT | TRUE |
| 5:96421941:A:G | 0.0000350 | FALSE | TRUE | TRUE | TRUE | MISSENSE | FALSE |
| 5:96421946:G:C | 0.0000210 | FALSE | TRUE | TRUE | TRUE | MISSENSE | FALSE |
| 5:96421951:TG:T | 0.0000065 | TRUE | TRUE | TRUE | TRUE | FRAMESHIFT | TRUE |
| 5:96421954:AT:A | 0.0000065 | TRUE | TRUE | TRUE | TRUE | FRAMESHIFT | TRUE |
| 5:96423315:A:G | 0.0003818 | FALSE | TRUE | TRUE | TRUE | MISSENSE | FALSE |
| 5:96423317:T:C | 0.0000806 | FALSE | TRUE | TRUE | TRUE | MISSENSE | FALSE |
| 5:96423326:A:T | 0.0000169 | FALSE | TRUE | TRUE | TRUE | MISSENSE | FALSE |
| 5:96423332:G:A | 0.0000455 | FALSE | TRUE | TRUE | TRUE | MISSENSE | FALSE |
| 5:96423336:G:A | 0.0000105 | FALSE | TRUE | TRUE | TRUE | MISSENSE | FALSE |
| 5:96423337:A:T | 0.0000085 | FALSE | TRUE | TRUE | TRUE | MISSENSE | FALSE |
| 5:96423338:T:A | 0.0000085 | FALSE | TRUE | TRUE | TRUE | MISSENSE | FALSE |
| 5:96423354:CA:C | 0.0000065 | TRUE | TRUE | TRUE | TRUE | FRAMESHIFT | TRUE |
| 5:96423356:T:A | 0.0000085 | FALSE | TRUE | TRUE | TRUE | MISSENSE | FALSE |
| 5:96423377:C:T | 0.0000085 | FALSE | TRUE | TRUE | TRUE | MISSENSE | FALSE |
| 5:96423386:G:A | 0.0000070 | FALSE | TRUE | TRUE | TRUE | MISSENSE | FALSE |
| 5:96423392:C:T | 0.0000065 | FALSE | TRUE | TRUE | TRUE | MISSENSE | FALSE |
| 5:96423393:C:T | 0.0000385 | FALSE | TRUE | TRUE | TRUE | MISSENSE | FALSE |
| 5:96423401:CAA:C | 0.0000035 | TRUE | TRUE | TRUE | TRUE | FRAMESHIFT | TRUE |
| 5:96423416:T:G | 0.0000085 | FALSE | TRUE | TRUE | TRUE | MISSENSE | FALSE |
| 5:96423431:G:A | 0.0000065 | FALSE | TRUE | TRUE | TRUE | MISSENSE | FALSE |
| 5:96423452:G:T | 0.0000245 | FALSE | TRUE | TRUE | TRUE | MISSENSE | FALSE |
| 5:96425819:C:G | 0.0000035 | TRUE | TRUE | TRUE | TRUE | SPLICE_DONOR | TRUE |
| 5:96425827:C:G | 0.0000035 | FALSE | TRUE | TRUE | TRUE | MISSENSE | FALSE |
| 5:96425827:C:T | 0.0000105 | TRUE | TRUE | TRUE | TRUE | STOP_GAINED | TRUE |
| 5:96425837:T:G | 0.0000175 | FALSE | TRUE | TRUE | TRUE | MISSENSE | FALSE |
| 5:96425843:TG:T | 0.0000130 | TRUE | TRUE | TRUE | TRUE | FRAMESHIFT | TRUE |
| 5:96425845:G:A | 0.0000065 | FALSE | TRUE | TRUE | TRUE | MISSENSE | FALSE |
| 5:96425855:A:C | 0.0000175 | FALSE | TRUE | TRUE | TRUE | MISSENSE | FALSE |
| 5:96425887:C:G | 0.0000065 | FALSE | TRUE | TRUE | TRUE | MISSENSE | FALSE |
| 5:96425887:C:T | 0.0000140 | FALSE | TRUE | TRUE | TRUE | MISSENSE | FALSE |
| 5:96425888:G:A | 0.0000140 | FALSE | TRUE | TRUE | TRUE | MISSENSE | FALSE |
| 5:96425891:T:A | 0.0000035 | TRUE | TRUE | TRUE | TRUE | STOP_GAINED | TRUE |
| 5:96425892:AC:A | 0.0000070 | TRUE | TRUE | TRUE | TRUE | FRAMESHIFT | TRUE |
| 5:96425929:A:G | 0.0000065 | FALSE | TRUE | TRUE | TRUE | MISSENSE | FALSE |
| 5:96429214:C:T | 0.0000035 | FALSE | TRUE | TRUE | TRUE | MISSENSE | FALSE |
| 5:96429215:G:A | 0.0000583 | FALSE | TRUE | TRUE | TRUE | MISSENSE | FALSE |
| 5:96429228:T:A | 0.0000035 | FALSE | TRUE | TRUE | TRUE | MISSENSE | FALSE |
| 5:96429238:G:A | 0.0000085 | FALSE | TRUE | TRUE | TRUE | MISSENSE | FALSE |
| 5:96429255:C:A | 0.0000035 | FALSE | TRUE | TRUE | TRUE | MISSENSE | FALSE |
| 5:96429256:CT:C | 0.0000065 | TRUE | TRUE | TRUE | TRUE | FRAMESHIFT | TRUE |
| 5:96429259:C:T | 0.0000065 | FALSE | TRUE | TRUE | TRUE | MISSENSE | FALSE |
| 5:96429260:G:A | 0.0000065 | TRUE | TRUE | TRUE | TRUE | STOP_GAINED | TRUE |
| 5:96429262:G:C | 0.0000245 | FALSE | TRUE | TRUE | TRUE | MISSENSE | FALSE |
| 5:96429269:TG:T | 0.0000130 | TRUE | TRUE | TRUE | TRUE | FRAMESHIFT | TRUE |
| 5:96429299:G:T | 0.0000070 | FALSE | TRUE | TRUE | TRUE | MISSENSE | FALSE |
| 5:96429310:G:T | 0.0000070 | TRUE | TRUE | TRUE | TRUE | STOP_GAINED | TRUE |
| 5:96429319:T:C | 0.0000070 | TRUE | TRUE | TRUE | TRUE | SPLICE_ACCEPTOR | TRUE |
| 5:96432082:C:T | 0.0000035 | TRUE | TRUE | TRUE | TRUE | SPLICE_DONOR | TRUE |
| 5:96432861:A:C | 0.0000065 | TRUE | TRUE | TRUE | TRUE | SPLICE_DONOR | TRUE |
| 5:96432869:CA:C | 0.0000085 | TRUE | TRUE | TRUE | TRUE | FRAMESHIFT | TRUE |
| 5:96432913:C:A | 0.0000035 | TRUE | TRUE | TRUE | TRUE | STOP_GAINED | TRUE |
| 5:96432918:C:T | 0.0000490 | FALSE | TRUE | TRUE | TRUE | MISSENSE | FALSE |
| 5:96432922:C:T | 0.0000140 | FALSE | TRUE | TRUE | TRUE | MISSENSE | FALSE |
| 5:96432957:CT:C | 0.0000065 | TRUE | TRUE | TRUE | TRUE | FRAMESHIFT | TRUE |

TABLE 5-continued

| VARIANT | AAF | M1 | M2 | M3 | M4 | ANNOTATION | IS_LOF |
|---|---|---|---|---|---|---|---|
| 5:96432971:AC:A | 0.0000259 | TRUE | TRUE | TRUE | TRUE | FRAMESHIFT | TRUE |
| 5:96432981:G:GCA | 0.0000035 | TRUE | TRUE | TRUE | TRUE | FRAMESHIFT | TRUE |
| 5:96432993:CAA:C | 0.0000065 | TRUE | TRUE | TRUE | TRUE | FRAMESHIFT | TRUE |
| 5:96433040:C:T | 0.0000065 | TRUE | TRUE | TRUE | TRUE | START_LOST | TRUE |
| 5:96433041:A:G | 0.0000035 | TRUE | TRUE | TRUE | TRUE | START_LOST | TRUE |

TABLE 6

| VARIANT | AAF | M1 | M2 | M3 | M4 | ANNOTATION | IS_LOF |
|---|---|---|---|---|---|---|---|
| 5:96393012:C:T | 0.0000175 | FALSE | TRUE | FALSE | TRUE | MISSENSE | FALSE |
| 5:96393026:A:C | 0.0000035 | FALSE | TRUE | FALSE | TRUE | MISSENSE | FALSE |
| 5:96393027:C:T | 0.0000175 | FALSE | TRUE | FALSE | TRUE | MISSENSE | FALSE |
| 5:96393044:C:T | 0.0000245 | FALSE | TRUE | TRUE | TRUE | MISSENSE | FALSE |
| 5:96393045:G:A | 0.0002452 | FALSE | TRUE | TRUE | TRUE | MISSENSE | FALSE |
| 5:96393048:C:T | 0.0000420 | FALSE | TRUE | TRUE | TRUE | MISSENSE | FALSE |
| 5:96393050:T:C | 0.0000070 | FALSE | TRUE | TRUE | TRUE | MISSENSE | FALSE |
| 5:96393053:C:T | 0.0000035 | FALSE | TRUE | TRUE | TRUE | MISSENSE | FALSE |
| 5:96393057:G:T | 0.0000065 | FALSE | TRUE | TRUE | TRUE | MISSENSE | FALSE |
| 5:96393065:G:A | 0.0000194 | FALSE | TRUE | TRUE | TRUE | MISSENSE | FALSE |
| 5:96393077:T:C | 0.0000035 | FALSE | TRUE | TRUE | TRUE | MISSENSE | FALSE |
| 5:96393078:A:G | 0.0000035 | FALSE | TRUE | TRUE | TRUE | MISSENSE | FALSE |
| 5:96393083:A:C | 0.0000035 | FALSE | TRUE | FALSE | TRUE | MISSENSE | FALSE |
| 5:96393101:T:C | 0.0000070 | FALSE | TRUE | TRUE | TRUE | MISSENSE | FALSE |
| 5:96393104:A:C | 0.0000035 | FALSE | TRUE | TRUE | TRUE | MISSENSE | FALSE |
| 5:96393105:G:C | 0.0000035 | FALSE | TRUE | FALSE | TRUE | MISSENSE | FALSE |
| 5:96393105:G:T | 0.0000035 | FALSE | TRUE | TRUE | TRUE | MISSENSE | FALSE |
| 5:96393134:G:C | 0.0000085 | FALSE | TRUE | FALSE | TRUE | MISSENSE | FALSE |
| 5:96393155:G:A | 0.0000035 | FALSE | TRUE | TRUE | TRUE | MISSENSE | FALSE |
| 5:96393156:C:T | 0.0000035 | FALSE | TRUE | TRUE | TRUE | MISSENSE | FALSE |
| 5:96393159:C:T | 0.0000140 | FALSE | TRUE | FALSE | TRUE | MISSENSE | FALSE |
| 5:96393169:T:G | 0.0000035 | FALSE | TRUE | FALSE | TRUE | MISSENSE | FALSE |
| 5:96393172:A:C | 0.0000085 | TRUE | TRUE | TRUE | TRUE | STOP_GAINED | TRUE |
| 5:96393179:A:C | 0.0000105 | FALSE | TRUE | FALSE | TRUE | MISSENSE | FALSE |
| 5:96393186:G:A | 0.0000085 | FALSE | TRUE | FALSE | TRUE | MISSENSE | FALSE |
| 5:96393187:C:G | 0.0000035 | FALSE | TRUE | FALSE | TRUE | MISSENSE | FALSE |
| 5:96393210:G:A | 0.0000035 | FALSE | TRUE | FALSE | TRUE | MISSENSE | FALSE |
| 5:96393239:A:G | 0.0000140 | FALSE | TRUE | TRUE | TRUE | MISSENSE | FALSE |
| 5:96393257:C:A | 0.0000065 | FALSE | TRUE | FALSE | TRUE | MISSENSE | FALSE |
| 5:96393257:C:T | 0.0000140 | FALSE | TRUE | FALSE | TRUE | MISSENSE | FALSE |
| 5:96393258:G:A | 0.0000070 | TRUE | TRUE | TRUE | TRUE | STOP_GAINED | TRUE |
| 5:96393272:G:A | 0.0000035 | FALSE | TRUE | FALSE | TRUE | MISSENSE | FALSE |
| 5:96393284:T:C | 0.0000065 | FALSE | TRUE | FALSE | TRUE | MISSENSE | FALSE |
| 5:96393285:C:T | 0.0000130 | FALSE | TRUE | FALSE | TRUE | MISSENSE | FALSE |
| 5:96393300:T:A | 0.0000065 | FALSE | TRUE | FALSE | TRUE | MISSENSE | FALSE |
| 5:96393303:G:A | 0.0000140 | FALSE | TRUE | FALSE | TRUE | MISSENSE | FALSE |
| 5:96393308:C:A | 0.0000453 | FALSE | TRUE | FALSE | TRUE | MISSENSE | FALSE |
| 5:96393366:G:A | 0.0000194 | TRUE | TRUE | TRUE | TRUE | STOP_GAINED | TRUE |
| 5:96393378:C:G | 0.0000035 | FALSE | TRUE | FALSE | TRUE | MISSENSE | FALSE |
| 5:96394878:C:A | 0.0000070 | FALSE | TRUE | FALSE | TRUE | MISSENSE | FALSE |
| 5:96394882:C:G | 0.0000035 | FALSE | TRUE | FALSE | TRUE | MISSENSE | FALSE |
| 5:96394890:C:A | 0.0000035 | FALSE | TRUE | FALSE | TRUE | MISSENSE | FALSE |
| 5:96394893:C:T | 0.0000035 | FALSE | TRUE | FALSE | TRUE | MISSENSE | FALSE |
| 5:96394901:T:G | 0.0000035 | FALSE | TRUE | FALSE | TRUE | MISSENSE | FALSE |
| 5:96394911:C:T | 0.0000175 | FALSE | TRUE | FALSE | TRUE | MISSENSE | FALSE |
| 5:96394925:G:A | 0.0000175 | FALSE | TRUE | TRUE | TRUE | MISSENSE | FALSE |
| 5:96394934:C:T | 0.0000175 | FALSE | TRUE | TRUE | TRUE | MISSENSE | FALSE |
| 5:96394935:G:A | 0.0000035 | FALSE | TRUE | TRUE | TRUE | MISSENSE | FALSE |
| 5:96394941:G:A | 0.0000035 | TRUE | TRUE | TRUE | TRUE | STOP_GAINED | TRUE |
| 5:96394947:T:C | 0.0000065 | FALSE | TRUE | FALSE | TRUE | MISSENSE | FALSE |
| 5:96394964:G:T | 0.0000065 | FALSE | TRUE | FALSE | TRUE | MISSENSE | FALSE |
| 5:96394973:T:C | 0.0000035 | FALSE | TRUE | TRUE | TRUE | MISSENSE | FALSE |
| 5:96394988:C:T | 0.0000065 | TRUE | TRUE | TRUE | TRUE | STOP_GAINED | TRUE |
| 5:96394997:A:G | 0.0000035 | FALSE | TRUE | TRUE | TRUE | MISSENSE | FALSE |
| 5:96395003:C:T | 0.0000065 | FALSE | TRUE | TRUE | TRUE | MISSENSE | FALSE |
| 5:96395024:G:C | 0.0000065 | FALSE | TRUE | TRUE | TRUE | MISSENSE | FALSE |
| 5:96397344:T:C | 0.0000085 | FALSE | TRUE | FALSE | TRUE | MISSENSE | FALSE |
| 5:96397346:A:T | 0.0000105 | FALSE | TRUE | TRUE | TRUE | MISSENSE | FALSE |
| 5:96397347:T:A | 0.0000455 | FALSE | TRUE | FALSE | TRUE | MISSENSE | FALSE |
| 5:96397351:CAA:C | 0.0000194 | TRUE | TRUE | TRUE | TRUE | FRAMESHIFT | TRUE |
| 5:96397351:C:G | 0.0000254 | FALSE | TRUE | TRUE | TRUE | MISSENSE | FALSE |
| 5:96397357:C:G | 0.0000065 | FALSE | TRUE | TRUE | TRUE | MISSENSE | FALSE |
| 5:96397358:C:T | 0.0000085 | TRUE | TRUE | TRUE | TRUE | STOP_GAINED | TRUE |
| 5:96397362:T:C | 0.0000035 | FALSE | TRUE | FALSE | TRUE | MISSENSE | FALSE |
| 5:96397364:C:A | 0.0000065 | FALSE | TRUE | TRUE | TRUE | MISSENSE | FALSE |

TABLE 6-continued

| VARIANT | AAF | M1 | M2 | M3 | M4 | ANNOTATION | IS_LOF |
|---|---|---|---|---|---|---|---|
| 5:96397372:G:T | 0.0000035 | FALSE | TRUE | FALSE | TRUE | MISSENSE | FALSE |
| 5:96397377:C:A | 0.0000065 | TRUE | TRUE | TRUE | TRUE | STOP_GAINED | TRUE |
| 5:96397380:C:T | 0.0000065 | FALSE | TRUE | TRUE | TRUE | MISSENSE | FALSE |
| 5:96397382:C:T | 0.0000035 | TRUE | TRUE | TRUE | TRUE | STOP_GAINED | TRUE |
| 5:96397390:AAC:A | 0.0000065 | TRUE | TRUE | TRUE | TRUE | FRAMESHIFT | TRUE |
| 5:96397392:C:T | 0.0000701 | FALSE | TRUE | FALSE | TRUE | MISSENSE | FALSE |
| 5:96397397:A:G | 0.0000065 | FALSE | TRUE | TRUE | TRUE | MISSENSE | FALSE |
| 5:96397424:G:C | 0.0000210 | FALSE | TRUE | FALSE | TRUE | MISSENSE | FALSE |
| 5:96397431:T:A | 0.0000035 | FALSE | TRUE | FALSE | TRUE | MISSENSE | FALSE |
| 5:96397432:A:T | 0.0000035 | FALSE | TRUE | TRUE | TRUE | MISSENSE | FALSE |
| 5:96397433:T:C | 0.0000070 | FALSE | TRUE | TRUE | TRUE | MISSENSE | FALSE |
| 5:96397436:C:G | 0.0000194 | FALSE | TRUE | FALSE | TRUE | MISSENSE | FALSE |
| 5:96397437:G:A | 0.0000315 | FALSE | TRUE | FALSE | TRUE | MISSENSE | FALSE |
| 5:96397439:T:C | 0.0000035 | FALSE | TRUE | FALSE | TRUE | MISSENSE | FALSE |
| 5:96397440:C:A | 0.0000065 | TRUE | TRUE | TRUE | TRUE | STOP_GAINED | TRUE |
| 5:96397451:A:G | 0.0000035 | FALSE | TRUE | TRUE | TRUE | MISSENSE | FALSE |
| 5:96397461:T:C | 0.0000035 | FALSE | TRUE | FALSE | TRUE | MISSENSE | FALSE |
| 5:96397463:C:T | 0.0000035 | FALSE | TRUE | FALSE | TRUE | MISSENSE | FALSE |
| 5:96398877:A:G | 0.0000065 | TRUE | TRUE | TRUE | TRUE | SPLICE_DONOR | TRUE |
| 5:96398887:GAAGT:G | 0.0000085 | TRUE | TRUE | TRUE | TRUE | FRAMESHIFT | TRUE |
| 5:96398897:T:C | 0.0000035 | FALSE | TRUE | FALSE | TRUE | MISSENSE | FALSE |
| 5:96398902:T:C | 0.0000035 | FALSE | TRUE | FALSE | TRUE | MISSENSE | FALSE |
| 5:96398911:C:A | 0.0000130 | FALSE | TRUE | TRUE | TRUE | MISSENSE | FALSE |
| 5:96398917:C:T | 0.0002172 | FALSE | TRUE | TRUE | TRUE | MISSENSE | FALSE |
| 5:96398920:G:A | 0.0000035 | FALSE | TRUE | FALSE | TRUE | MISSENSE | FALSE |
| 5:96398922:A:C | 0.0000035 | TRUE | TRUE | TRUE | TRUE | STOP_GAINED | TRUE |
| 5:96398929:A:G | 0.0000035 | FALSE | TRUE | TRUE | TRUE | MISSENSE | FALSE |
| 5:96398945:G:T | 0.0000085 | FALSE | TRUE | FALSE | TRUE | MISSENSE | FALSE |
| 5:96398966:T:G | 0.0000070 | FALSE | TRUE | FALSE | TRUE | MISSENSE | FALSE |
| 5:96398980:C:T | 0.0000035 | FALSE | TRUE | FALSE | TRUE | MISSENSE | FALSE |
| 5:96398983:T:A | 0.0000085 | FALSE | TRUE | FALSE | TRUE | MISSENSE | FALSE |
| 5:96399007:A:G | 0.0000035 | FALSE | TRUE | FALSE | TRUE | MISSENSE | FALSE |
| 5:96399008:T:C | 0.0000065 | FALSE | TRUE | FALSE | TRUE | MISSENSE | FALSE |
| 5:96399952:C:A | 0.0000065 | TRUE | TRUE | TRUE | TRUE | SPLICE_DONOR | TRUE |
| 5:96399958:C:G | 0.0000070 | FALSE | TRUE | FALSE | TRUE | MISSENSE | FALSE |
| 5:96399969:T:C | 0.0000035 | FALSE | TRUE | FALSE | TRUE | MISSENSE | FALSE |
| 5:96399978:C:T | 0.0000245 | FALSE | TRUE | FALSE | TRUE | MISSENSE | FALSE |
| 5:96399980:A:G | 0.0000453 | FALSE | TRUE | FALSE | TRUE | MISSENSE | FALSE |
| 5:96399993:T:A | 0.0000105 | TRUE | TRUE | TRUE | TRUE | STOP_GAINED | TRUE |
| 5:96399994:C:G | 0.0000070 | FALSE | TRUE | FALSE | TRUE | MISSENSE | FALSE |
| 5:96399996:C:T | 0.0000070 | FALSE | TRUE | FALSE | TRUE | MISSENSE | FALSE |
| 5:96399999:G:T | 0.0000175 | FALSE | TRUE | TRUE | TRUE | MISSENSE | FALSE |
| 5:96400002:C:G | 0.0000070 | FALSE | TRUE | FALSE | TRUE | MISSENSE | FALSE |
| 5:96400002:C:T | 0.0000596 | FALSE | TRUE | TRUE | TRUE | MISSENSE | FALSE |
| 5:96400010:C:G | 0.0000085 | FALSE | TRUE | TRUE | TRUE | MISSENSE | FALSE |
| 5:96400028:A:G | 0.0000065 | FALSE | TRUE | TRUE | TRUE | MISSENSE | FALSE |
| 5:96400032:C:T | 0.0000035 | FALSE | TRUE | FALSE | TRUE | MISSENSE | FALSE |
| 5:96400038:G:C | 0.0000070 | FALSE | TRUE | TRUE | TRUE | MISSENSE | FALSE |
| 5:96400047:C:A | 0.0000035 | FALSE | TRUE | TRUE | TRUE | MISSENSE | FALSE |
| 5:96400049:T:A | 0.0000035 | FALSE | TRUE | TRUE | TRUE | MISSENSE | FALSE |
| 5:96400052:A:G | 0.0000065 | FALSE | TRUE | TRUE | TRUE | MISSENSE | FALSE |
| 5:96400061:A:T | 0.0000035 | FALSE | TRUE | FALSE | TRUE | MISSENSE | FALSE |
| 5:96400070:C:T | 0.0000065 | FALSE | TRUE | FALSE | TRUE | MISSENSE | FALSE |
| 5:96400071:G:A | 0.0000070 | TRUE | TRUE | TRUE | TRUE | STOP_GAINED | TRUE |
| 5:96400091:G:T | 0.0000035 | FALSE | TRUE | TRUE | TRUE | MISSENSE | FALSE |
| 5:96400096:A:T | 0.0000259 | FALSE | TRUE | TRUE | TRUE | MISSENSE | FALSE |
| 5:96400100:T:C | 0.0000085 | FALSE | TRUE | FALSE | TRUE | MISSENSE | FALSE |
| 5:96400106:C:T | 0.0000130 | TRUE | TRUE | TRUE | TRUE | STOP_GAINED | TRUE |
| 5:96400128:G:A | 0.0000085 | FALSE | TRUE | FALSE | TRUE | MISSENSE | FALSE |
| 5:96400133:T:G | 0.0000175 | FALSE | TRUE | FALSE | TRUE | MISSENSE | FALSE |
| 5:96400142:G:C | 0.0000035 | FALSE | TRUE | FALSE | TRUE | MISSENSE | FALSE |
| 5:96400146:A:G | 0.0000070 | FALSE | TRUE | FALSE | TRUE | MISSENSE | FALSE |
| 5:96400156:G:C | 0.0000065 | FALSE | TRUE | TRUE | TRUE | MISSENSE | FALSE |
| 5:96400169:C:T | 0.0000035 | FALSE | TRUE | TRUE | TRUE | MISSENSE | FALSE |
| 5:96400170:G:A | 0.0000175 | TRUE | TRUE | TRUE | TRUE | STOP_GAINED | TRUE |
| 5:96408221:A:C | 0.0000035 | TRUE | TRUE | TRUE | TRUE | SPLICE_DONOR | TRUE |
| 5:96408226:G:T | 0.0000280 | FALSE | TRUE | TRUE | TRUE | MISSENSE | FALSE |
| 5:96408232:A:G | 0.0000130 | FALSE | TRUE | TRUE | TRUE | MISSENSE | FALSE |
| 5:96408238:A:G | 0.0000035 | FALSE | TRUE | TRUE | TRUE | MISSENSE | FALSE |
| 5:96408242:C:G | 0.0000065 | FALSE | TRUE | TRUE | TRUE | MISSENSE | FALSE |
| 5:96408242:C:T | 0.0000070 | FALSE | TRUE | TRUE | TRUE | MISSENSE | FALSE |
| 5:96408244:A:G | 0.0000280 | FALSE | TRUE | TRUE | TRUE | MISSENSE | FALSE |
| 5:96408251:C:T | 0.0000035 | FALSE | TRUE | TRUE | TRUE | MISSENSE | FALSE |
| 5:96408254:C:T | 0.0000035 | FALSE | TRUE | TRUE | TRUE | MISSENSE | FALSE |
| 5:96408256:G:T | 0.0000065 | FALSE | TRUE | TRUE | TRUE | MISSENSE | FALSE |
| 5:96408271:G:A | 0.0000035 | FALSE | TRUE | FALSE | TRUE | MISSENSE | FALSE |
| 5:96408272:C:T | 0.0000065 | FALSE | TRUE | TRUE | TRUE | MISSENSE | FALSE |
| 5:96408274:G:A | 0.0000105 | FALSE | TRUE | TRUE | TRUE | MISSENSE | FALSE |

TABLE 6-continued

| VARIANT | AAF | M1 | M2 | M3 | M4 | ANNOTATION | IS_LOF |
|---|---|---|---|---|---|---|---|
| 5:96408283:G:C | 0.0000194 | FALSE | TRUE | TRUE | TRUE | MISSENSE | FALSE |
| 5:96408285:G:T | 0.0000085 | FALSE | TRUE | TRUE | TRUE | MISSENSE | FALSE |
| 5:96408288:C:CA | 0.0000065 | TRUE | TRUE | TRUE | TRUE | FRAMESHIFT | TRUE |
| 5:96408289:G:A | 0.0000666 | FALSE | TRUE | FALSE | TRUE | MISSENSE | FALSE |
| 5:96408292:T:A | 0.0000065 | FALSE | TRUE | FALSE | TRUE | MISSENSE | FALSE |
| 5:96408295:G:A | 0.0000035 | FALSE | TRUE | TRUE | TRUE | MISSENSE | FALSE |
| 5:96408296:T:A | 0.0000065 | FALSE | TRUE | TRUE | TRUE | MISSENSE | FALSE |
| 5:96408299:A:AG | 0.0000065 | TRUE | TRUE | TRUE | TRUE | FRAMESHIFT | TRUE |
| 5:96408303:A:T | 0.0000085 | FALSE | TRUE | FALSE | TRUE | MISSENSE | FALSE |
| 5:96408310:A:AG | 0.0000035 | TRUE | TRUE | TRUE | TRUE | FRAMESHIFT | TRUE |
| 5:96408312:G:C | 0.0000085 | FALSE | TRUE | TRUE | TRUE | MISSENSE | FALSE |
| 5:96408313:T:C | 0.0000065 | FALSE | TRUE | TRUE | TRUE | MISSENSE | FALSE |
| 5:96408316:G:A | 0.0000175 | FALSE | TRUE | FALSE | TRUE | MISSENSE | FALSE |
| 5:96408322:G:A | 0.0000070 | FALSE | TRUE | FALSE | TRUE | MISSENSE | FALSE |
| 5:96408323:T:C | 0.0001401 | FALSE | TRUE | FALSE | TRUE | MISSENSE | FALSE |
| 5:96408324:C:G | 0.0000035 | TRUE | TRUE | TRUE | TRUE | SPLICE_ACCEPTOR | TRUE |
| 5:96410771:T:TA | 0.0000105 | TRUE | TRUE | TRUE | TRUE | SPLICE_DONOR | TRUE |
| 5:96410773:C:T | 0.0000065 | TRUE | TRUE | TRUE | TRUE | SPLICE_DONOR | TRUE |
| 5:96410776:T:C | 0.0000035 | FALSE | TRUE | FALSE | TRUE | MISSENSE | FALSE |
| 5:96410785:C:T | 0.0000035 | FALSE | TRUE | TRUE | TRUE | MISSENSE | FALSE |
| 5:96410794:C:G | 0.0000070 | FALSE | TRUE | FALSE | TRUE | MISSENSE | FALSE |
| 5:96410797:C:A | 0.0000070 | TRUE | TRUE | TRUE | TRUE | STOP_GAINED | TRUE |
| 5:96410797:C:T | 0.0000035 | FALSE | TRUE | TRUE | TRUE | MISSENSE | FALSE |
| 5:96410808:G:C | 0.0000035 | FALSE | TRUE | TRUE | TRUE | MISSENSE | FALSE |
| 5:96410814:G:A | 0.0000035 | FALSE | TRUE | TRUE | TRUE | MISSENSE | FALSE |
| 5:96410818:G:T | 0.0000065 | FALSE | TRUE | TRUE | TRUE | MISSENSE | FALSE |
| 5:96410826:G:A | 0.0000035 | FALSE | TRUE | TRUE | TRUE | MISSENSE | FALSE |
| 5:96410839:C:A | 0.0000085 | FALSE | TRUE | FALSE | TRUE | MISSENSE | FALSE |
| 5:96410839:C:T | 0.0000105 | FALSE | TRUE | FALSE | TRUE | MISSENSE | FALSE |
| 5:96410840:G:C | 0.0000280 | TRUE | TRUE | TRUE | TRUE | STOP_GAINED | TRUE |
| 5:96410840:G:T | 0.0000065 | TRUE | TRUE | TRUE | TRUE | STOP_GAINED | TRUE |
| 5:96410842:A:G | 0.0000085 | FALSE | TRUE | TRUE | TRUE | MISSENSE | FALSE |
| 5:96410844:CAGGGGGAT:C | 0.0000070 | TRUE | TRUE | TRUE | TRUE | FRAMESHIFT | TRUE |
| 5:96410845:A:C | 0.0000210 | FALSE | TRUE | TRUE | TRUE | MISSENSE | FALSE |
| 5:96410856:C:A | 0.0000140 | FALSE | TRUE | TRUE | TRUE | MISSENSE | FALSE |
| 5:96410856:C:T | 0.0000070 | FALSE | TRUE | TRUE | TRUE | MISSENSE | FALSE |
| 5:96410857:C:A | 0.0000065 | FALSE | TRUE | TRUE | TRUE | MISSENSE | FALSE |
| 5:96410875:T:C | 0.0000035 | FALSE | TRUE | FALSE | TRUE | MISSENSE | FALSE |
| 5:96410878:T:A | 0.0000070 | FALSE | TRUE | TRUE | TRUE | MISSENSE | FALSE |
| 5:96410883:A:G | 0.0000105 | FALSE | TRUE | TRUE | TRUE | MISSENSE | FALSE |
| 5:96410887:T:C | 0.0000065 | FALSE | TRUE | TRUE | TRUE | MISSENSE | FALSE |
| 5:96410895:C:A | 0.0000065 | FALSE | TRUE | TRUE | TRUE | MISSENSE | FALSE |
| 5:96410901:G:A | 0.0000035 | FALSE | TRUE | TRUE | TRUE | MISSENSE | FALSE |
| 5:96410907:C:A | 0.0000035 | FALSE | TRUE | TRUE | TRUE | MISSENSE | FALSE |
| 5:96410907:C:T | 0.0000035 | FALSE | TRUE | TRUE | TRUE | MISSENSE | FALSE |
| 5:96410910:T:TC | 0.0000130 | TRUE | TRUE | TRUE | TRUE | FRAMESHIFT | TRUE |
| 5:96410913:C:T | 0.0000065 | FALSE | TRUE | TRUE | TRUE | MISSENSE | FALSE |
| 5:96410929:C:T | 0.0000453 | FALSE | TRUE | FALSE | TRUE | MISSENSE | FALSE |
| 5:96410934:C:T | 0.0000035 | FALSE | TRUE | FALSE | TRUE | MISSENSE | FALSE |
| 5:96410935:G:A | 0.0000035 | FALSE | TRUE | TRUE | TRUE | MISSENSE | FALSE |
| 5:96410935:G:GC | 0.0000035 | TRUE | TRUE | TRUE | TRUE | FRAMESHIFT | TRUE |
| 5:96410940:C:A | 0.0000035 | FALSE | TRUE | TRUE | TRUE | MISSENSE | FALSE |
| 5:96410941:C:T | 0.0000085 | FALSE | TRUE | TRUE | TRUE | MISSENSE | FALSE |
| 5:96410946:C:T | 0.0000105 | FALSE | TRUE | TRUE | TRUE | MISSENSE | FALSE |
| 5:96410949:G:A | 0.0000175 | FALSE | TRUE | FALSE | TRUE | MISSENSE | FALSE |
| 5:96410959:C:T | 0.0000525 | FALSE | TRUE | FALSE | TRUE | MISSENSE | FALSE |
| 5:96410965:T:G | 0.0000070 | FALSE | TRUE | FALSE | TRUE | MISSENSE | FALSE |
| 5:96410970:C:T | 0.0000035 | FALSE | TRUE | TRUE | TRUE | MISSENSE | FALSE |
| 5:96410974:TC:T | 0.0000712 | TRUE | TRUE | TRUE | TRUE | FRAMESHIFT | TRUE |
| 5:96410976:C:G | 0.0000065 | FALSE | TRUE | TRUE | TRUE | MISSENSE | FALSE |
| 5:96410983:T:TC | 0.0000035 | TRUE | TRUE | TRUE | TRUE | FRAMESHIFT | TRUE |
| 5:96410985:C:T | 0.0000065 | FALSE | TRUE | TRUE | TRUE | MISSENSE | FALSE |
| 5:96412322:T:C | 0.0000130 | FALSE | TRUE | FALSE | TRUE | MISSENSE | FALSE |
| 5:96412328:C:T | 0.0000035 | FALSE | TRUE | TRUE | TRUE | MISSENSE | FALSE |
| 5:96412332:A:G | 0.0000130 | FALSE | TRUE | FALSE | TRUE | MISSENSE | FALSE |
| 5:96412355:C:T | 0.0000065 | FALSE | TRUE | FALSE | TRUE | MISSENSE | FALSE |
| 5:96412356:G:A | 0.0000175 | FALSE | TRUE | TRUE | TRUE | MISSENSE | FALSE |
| 5:96412362:G:A | 0.0000130 | FALSE | TRUE | TRUE | TRUE | MISSENSE | FALSE |
| 5:96412362:G:T | 0.0000035 | FALSE | TRUE | TRUE | TRUE | MISSENSE | FALSE |
| 5:96412364:C:G | 0.0000169 | FALSE | TRUE | TRUE | TRUE | MISSENSE | FALSE |
| 5:96412379:C:G | 0.0000070 | FALSE | TRUE | TRUE | TRUE | MISSENSE | FALSE |
| 5:96412382:T:C | 0.0000065 | FALSE | TRUE | TRUE | TRUE | MISSENSE | FALSE |
| 5:96412385:T:C | 0.0000169 | FALSE | TRUE | TRUE | TRUE | MISSENSE | FALSE |
| 5:96412395:C:T | 0.0000065 | FALSE | TRUE | TRUE | TRUE | MISSENSE | FALSE |
| 5:96412400:C:T | 0.0000085 | FALSE | TRUE | TRUE | TRUE | MISSENSE | FALSE |
| 5:96412416:C:T | 0.0000130 | FALSE | TRUE | TRUE | TRUE | MISSENSE | FALSE |
| 5:96412418:A:G | 0.0000140 | FALSE | TRUE | TRUE | TRUE | MISSENSE | FALSE |
| 5:96412419:C:T | 0.0000070 | FALSE | TRUE | TRUE | TRUE | MISSENSE | FALSE |

TABLE 6-continued

| VARIANT | AAF | M1 | M2 | M3 | M4 | ANNOTATION | IS_LOF |
|---|---|---|---|---|---|---|---|
| 5:96412420:G:T | 0.0000105 | FALSE | TRUE | TRUE | TRUE | MISSENSE | FALSE |
| 5:96412425:C:T | 0.0000085 | FALSE | TRUE | FALSE | TRUE | MISSENSE | FALSE |
| 5:96412436:C:G | 0.0000065 | FALSE | TRUE | TRUE | TRUE | MISSENSE | FALSE |
| 5:96412436:C:T | 0.0000070 | FALSE | TRUE | TRUE | TRUE | MISSENSE | FALSE |
| 5:96412437:C:CA | 0.0000065 | TRUE | TRUE | TRUE | TRUE | FRAMESHIFT | TRUE |
| 5:96412437:C:T | 0.0000035 | FALSE | TRUE | TRUE | TRUE | MISSENSE | FALSE |
| 5:96412439:A:G | 0.0000085 | FALSE | TRUE | TRUE | TRUE | MISSENSE | FALSE |
| 5:96412440:T:C | 0.0000065 | FALSE | TRUE | FALSE | TRUE | MISSENSE | FALSE |
| 5:96412443:A:T | 0.0000065 | FALSE | TRUE | TRUE | TRUE | MISSENSE | FALSE |
| 5:96412445:C:T | 0.0000035 | FALSE | TRUE | FALSE | TRUE | MISSENSE | FALSE |
| 5:96412448:G:A | 0.0000070 | FALSE | TRUE | TRUE | TRUE | MISSENSE | FALSE |
| 5:96412452:C:A | 0.0000105 | TRUE | TRUE | TRUE | TRUE | STOP_GAINED | TRUE |
| 5:96412454:A:AT | 0.0000065 | TRUE | TRUE | TRUE | TRUE | FRAMESHIFT | TRUE |
| 5:96412454:A:G | 0.0000035 | FALSE | TRUE | TRUE | TRUE | MISSENSE | FALSE |
| 5:96412455:T:C | 0.0000712 | FALSE | TRUE | FALSE | TRUE | MISSENSE | FALSE |
| 5:96412463:G:A | 0.0000140 | FALSE | TRUE | TRUE | TRUE | MISSENSE | FALSE |
| 5:96412464:T:A | 0.0000035 | FALSE | TRUE | TRUE | TRUE | MISSENSE | FALSE |
| 5:96412480:C:G | 0.0000035 | FALSE | TRUE | TRUE | TRUE | MISSENSE | FALSE |
| 5:96412484:C:A | 0.0000085 | FALSE | TRUE | TRUE | TRUE | MISSENSE | FALSE |
| 5:96412488:T:C | 0.0000035 | FALSE | TRUE | FALSE | TRUE | MISSENSE | FALSE |
| 5:96416041:T:A | 0.0001296 | FALSE | TRUE | TRUE | TRUE | MISSENSE | FALSE |
| 5:96416041:T:G | 0.0000065 | FALSE | TRUE | TRUE | TRUE | MISSENSE | FALSE |
| 5:96416047:T:C | 0.0000070 | FALSE | TRUE | FALSE | TRUE | MISSENSE | FALSE |
| 5:96416050:T:C | 0.0000130 | FALSE | TRUE | TRUE | TRUE | MISSENSE | FALSE |
| 5:96416051:A:G | 0.0000070 | FALSE | TRUE | TRUE | TRUE | MISSENSE | FALSE |
| 5:96416053:G:A | 0.0000194 | FALSE | TRUE | TRUE | TRUE | MISSENSE | FALSE |
| 5:96416054:C:A | 0.0000035 | FALSE | TRUE | TRUE | TRUE | MISSENSE | FALSE |
| 5:96416054:C:G | 0.0000065 | FALSE | TRUE | TRUE | TRUE | MISSENSE | FALSE |
| 5:96416057:C:T | 0.0000194 | FALSE | TRUE | FALSE | TRUE | MISSENSE | FALSE |
| 5:96416059:C:A | 0.0000105 | FALSE | TRUE | TRUE | TRUE | MISSENSE | FALSE |
| 5:96416062:A:G | 0.0000070 | FALSE | TRUE | FALSE | TRUE | MISSENSE | FALSE |
| 5:96416063:C:T | 0.0000070 | FALSE | TRUE | TRUE | TRUE | MISSENSE | FALSE |
| 5:96416066:C:G | 0.0000035 | FALSE | TRUE | TRUE | TRUE | MISSENSE | FALSE |
| 5:96416066:C:T | 0.0000210 | FALSE | TRUE | TRUE | TRUE | MISSENSE | FALSE |
| 5:96416067:G:T | 0.0000035 | TRUE | TRUE | TRUE | TRUE | STOP_GAINED | TRUE |
| 5:96416068:C:T | 0.0000035 | FALSE | TRUE | TRUE | TRUE | MISSENSE | FALSE |
| 5:96416069:A:G | 0.0000035 | FALSE | TRUE | TRUE | TRUE | MISSENSE | FALSE |
| 5:96416072:T:A | 0.0000035 | TRUE | TRUE | TRUE | TRUE | STOP_GAINED | TRUE |
| 5:96416075:G:A | 0.0000035 | FALSE | TRUE | FALSE | TRUE | MISSENSE | FALSE |
| 5:96416092:G:A | 0.0001787 | FALSE | TRUE | TRUE | TRUE | MISSENSE | FALSE |
| 5:96416105:C:A | 0.0000035 | FALSE | TRUE | TRUE | TRUE | MISSENSE | FALSE |
| 5:96416105:C:T | 0.0000035 | FALSE | TRUE | TRUE | TRUE | MISSENSE | FALSE |
| 5:96416117:C:T | 0.0000035 | FALSE | TRUE | TRUE | TRUE | MISSENSE | FALSE |
| 5:96421879:CT:C | 0.0000035 | TRUE | TRUE | TRUE | TRUE | FRAMESHIFT | TRUE |
| 5:96421881:T:A | 0.0000035 | TRUE | TRUE | TRUE | TRUE | STOP_GAINED | TRUE |
| 5:96421882:G:T | 0.0000105 | FALSE | TRUE | TRUE | TRUE | MISSENSE | FALSE |
| 5:96421887:C:T | 0.0000105 | FALSE | TRUE | FALSE | TRUE | MISSENSE | FALSE |
| 5:96421893:TG:T | 0.0000065 | TRUE | TRUE | TRUE | TRUE | FRAMESHIFT | TRUE |
| 5:96421896:G:A | 0.0000070 | FALSE | TRUE | FALSE | TRUE | MISSENSE | FALSE |
| 5:96421898:T:A | 0.0000070 | FALSE | TRUE | TRUE | TRUE | MISSENSE | FALSE |
| 5:96421902:A:T | 0.0000035 | FALSE | TRUE | TRUE | TRUE | MISSENSE | FALSE |
| 5:96421904:C:T | 0.0000105 | FALSE | TRUE | TRUE | TRUE | MISSENSE | FALSE |
| 5:96421905:G:A | 0.0000194 | TRUE | TRUE | TRUE | TRUE | STOP_GAINED | TRUE |
| 5:96421908:G:A | 0.0000065 | FALSE | TRUE | TRUE | TRUE | MISSENSE | FALSE |
| 5:96421914:G:A | 0.0000194 | FALSE | TRUE | TRUE | TRUE | MISSENSE | FALSE |
| 5:96421916:T:C | 0.0000070 | FALSE | TRUE | TRUE | TRUE | MISSENSE | FALSE |
| 5:96421916:T:G | 0.0000105 | FALSE | TRUE | TRUE | TRUE | MISSENSE | FALSE |
| 5:96421922:T:C | 0.0000035 | FALSE | TRUE | TRUE | TRUE | MISSENSE | FALSE |
| 5:96421932:T:A | 0.0000065 | FALSE | TRUE | TRUE | TRUE | MISSENSE | FALSE |
| 5:96421934:A:C | 0.0000169 | FALSE | TRUE | FALSE | TRUE | MISSENSE | FALSE |
| 5:96421940:TA:T | 0.0000065 | TRUE | TRUE | TRUE | TRUE | FRAMESHIFT | TRUE |
| 5:96421941:A:G | 0.0000350 | FALSE | TRUE | TRUE | TRUE | MISSENSE | FALSE |
| 5:96421946:G:C | 0.0000210 | FALSE | TRUE | TRUE | TRUE | MISSENSE | FALSE |
| 5:96421950:C:G | 0.0000035 | FALSE | TRUE | FALSE | TRUE | MISSENSE | FALSE |
| 5:96421951:TG:T | 0.0000065 | TRUE | TRUE | TRUE | TRUE | FRAMESHIFT | TRUE |
| 5:96421954:AT:A | 0.0000065 | TRUE | TRUE | TRUE | TRUE | FRAMESHIFT | TRUE |
| 5:96423315:A:G | 0.0003818 | FALSE | TRUE | TRUE | TRUE | MISSENSE | FALSE |
| 5:96423317:T:C | 0.0000806 | FALSE | TRUE | TRUE | TRUE | MISSENSE | FALSE |
| 5:96423320:G:A | 0.0000035 | FALSE | TRUE | FALSE | TRUE | MISSENSE | FALSE |
| 5:96423326:A:T | 0.0000169 | FALSE | TRUE | TRUE | TRUE | MISSENSE | FALSE |
| 5:96423332:G:A | 0.0000455 | FALSE | TRUE | TRUE | TRUE | MISSENSE | FALSE |
| 5:96423336:G:A | 0.0000105 | FALSE | TRUE | TRUE | TRUE | MISSENSE | FALSE |
| 5:96423337:A:T | 0.0000085 | FALSE | TRUE | TRUE | TRUE | MISSENSE | FALSE |
| 5:96423338:T:A | 0.0000085 | FALSE | TRUE | TRUE | TRUE | MISSENSE | FALSE |
| 5:96423354:CA:C | 0.0000065 | TRUE | TRUE | TRUE | TRUE | FRAMESHIFT | TRUE |
| 5:96423356:T:A | 0.0000085 | FALSE | TRUE | TRUE | TRUE | MISSENSE | FALSE |
| 5:96423363:C:T | 0.0000175 | FALSE | TRUE | FALSE | TRUE | MISSENSE | FALSE |
| 5:96423375:C:T | 0.0000035 | FALSE | TRUE | FALSE | TRUE | MISSENSE | FALSE |

TABLE 6-continued

| VARIANT | AAF | M1 | M2 | M3 | M4 | ANNOTATION | IS_LOF |
|---|---|---|---|---|---|---|---|
| 5:96423377:C:T | 0.0000085 | FALSE | TRUE | TRUE | TRUE | MISSENSE | FALSE |
| 5:96423386:G:A | 0.0000070 | FALSE | TRUE | TRUE | TRUE | MISSENSE | FALSE |
| 5:96423387:T:A | 0.0000035 | FALSE | TRUE | FALSE | TRUE | MISSENSE | FALSE |
| 5:96423392:C:T | 0.0000065 | FALSE | TRUE | TRUE | TRUE | MISSENSE | FALSE |
| 5:96423393:C:T | 0.0000385 | FALSE | TRUE | TRUE | TRUE | MISSENSE | FALSE |
| 5:96423401:CAA:C | 0.0000035 | TRUE | TRUE | TRUE | TRUE | FRAMESHIFT | TRUE |
| 5:96423409:T:C | 0.0000065 | FALSE | TRUE | FALSE | TRUE | MISSENSE | FALSE |
| 5:96423410:A:G | 0.0000070 | FALSE | TRUE | FALSE | TRUE | MISSENSE | FALSE |
| 5:96423411:T:A | 0.0000105 | FALSE | TRUE | FALSE | TRUE | MISSENSE | FALSE |
| 5:96423416:T:G | 0.0000085 | FALSE | TRUE | TRUE | TRUE | MISSENSE | FALSE |
| 5:96423431:G:A | 0.0000065 | FALSE | TRUE | TRUE | TRUE | MISSENSE | FALSE |
| 5:96423443:G:A | 0.0000245 | FALSE | TRUE | FALSE | TRUE | MISSENSE | FALSE |
| 5:96423452:G:T | 0.0000245 | FALSE | TRUE | TRUE | TRUE | MISSENSE | FALSE |
| 5:96425819:C:G | 0.0000035 | TRUE | TRUE | TRUE | TRUE | SPLICE_DONOR | TRUE |
| 5:96425827:C:G | 0.0000035 | FALSE | TRUE | TRUE | TRUE | MISSENSE | FALSE |
| 5:96425827:C:T | 0.0000105 | TRUE | TRUE | TRUE | TRUE | STOP_GAINED | TRUE |
| 5:96425836:T:A | 0.0000070 | FALSE | TRUE | FALSE | TRUE | MISSENSE | FALSE |
| 5:96425836:T:C | 0.0000085 | FALSE | TRUE | FALSE | TRUE | MISSENSE | FALSE |
| 5:96425837:T:G | 0.0000175 | FALSE | TRUE | TRUE | TRUE | MISSENSE | FALSE |
| 5:96425841:C:T | 0.0002347 | FALSE | TRUE | FALSE | TRUE | MISSENSE | FALSE |
| 5:96425842:A:T | 0.0000175 | FALSE | TRUE | FALSE | TRUE | MISSENSE | FALSE |
| 5:96425843:TG:T | 0.0000130 | TRUE | TRUE | TRUE | TRUE | FRAMESHIFT | TRUE |
| 5:96425845:G:A | 0.0000065 | FALSE | TRUE | TRUE | TRUE | MISSENSE | FALSE |
| 5:96425851:T:C | 0.0000194 | FALSE | TRUE | FALSE | TRUE | MISSENSE | FALSE |
| 5:96425855:A:C | 0.0000175 | FALSE | TRUE | TRUE | TRUE | MISSENSE | FALSE |
| 5:96425887:C:G | 0.0000065 | FALSE | TRUE | TRUE | TRUE | MISSENSE | FALSE |
| 5:96425887:C:T | 0.0000140 | FALSE | TRUE | TRUE | TRUE | MISSENSE | FALSE |
| 5:96425888:G:A | 0.0000140 | FALSE | TRUE | TRUE | TRUE | MISSENSE | FALSE |
| 5:96425891:T:A | 0.0000035 | TRUE | TRUE | TRUE | TRUE | STOP_GAINED | TRUE |
| 5:96425892:AC:A | 0.0000070 | TRUE | TRUE | TRUE | TRUE | FRAMESHIFT | TRUE |
| 5:96425899:T:A | 0.0000035 | FALSE | TRUE | FALSE | TRUE | MISSENSE | FALSE |
| 5:96425920:G:A | 0.0000259 | FALSE | TRUE | FALSE | TRUE | MISSENSE | FALSE |
| 5:96425929:A:G | 0.0000065 | FALSE | TRUE | TRUE | TRUE | MISSENSE | FALSE |
| 5:96429214:C:T | 0.0000035 | FALSE | TRUE | TRUE | TRUE | MISSENSE | FALSE |
| 5:96429215:G:A | 0.0000583 | FALSE | TRUE | TRUE | TRUE | MISSENSE | FALSE |
| 5:96429215:G:C | 0.0000035 | FALSE | TRUE | FALSE | TRUE | MISSENSE | FALSE |
| 5:96429217:T:C | 0.0000105 | FALSE | TRUE | FALSE | TRUE | MISSENSE | FALSE |
| 5:96429220:T:C | 0.0000070 | FALSE | TRUE | FALSE | TRUE | MISSENSE | FALSE |
| 5:96429228:T:A | 0.0000035 | FALSE | TRUE | TRUE | TRUE | MISSENSE | FALSE |
| 5:96429238:G:A | 0.0000085 | FALSE | TRUE | TRUE | TRUE | MISSENSE | FALSE |
| 5:96429242:T:C | 0.0000085 | FALSE | TRUE | FALSE | TRUE | MISSENSE | FALSE |
| 5:96429243:A:T | 0.0000035 | FALSE | TRUE | FALSE | TRUE | MISSENSE | FALSE |
| 5:96429244:T:C | 0.0000070 | FALSE | TRUE | FALSE | TRUE | MISSENSE | FALSE |
| 5:96429252:A:C | 0.0000035 | FALSE | TRUE | FALSE | TRUE | MISSENSE | FALSE |
| 5:96429253:C:G | 0.0000035 | FALSE | TRUE | FALSE | TRUE | MISSENSE | FALSE |
| 5:96429255:C:A | 0.0000035 | FALSE | TRUE | TRUE | TRUE | MISSENSE | FALSE |
| 5:96429256:CT:C | 0.0000065 | TRUE | TRUE | TRUE | TRUE | FRAMESHIFT | TRUE |
| 5:96429259:C:T | 0.0000065 | FALSE | TRUE | TRUE | TRUE | MISSENSE | FALSE |
| 5:96429260:G:A | 0.0000065 | TRUE | TRUE | TRUE | TRUE | STOP_GAINED | TRUE |
| 5:96429262:G:C | 0.0000245 | FALSE | TRUE | TRUE | TRUE | MISSENSE | FALSE |
| 5:96429264:C:A | 0.0000130 | FALSE | TRUE | FALSE | TRUE | MISSENSE | FALSE |
| 5:96429265:C:T | 0.0000085 | FALSE | TRUE | FALSE | TRUE | MISSENSE | FALSE |
| 5:96429269:TG:T | 0.0000130 | TRUE | TRUE | TRUE | TRUE | FRAMESHIFT | TRUE |
| 5:96429272:G:A | 0.0000035 | FALSE | TRUE | FALSE | TRUE | MISSENSE | FALSE |
| 5:96429283:T:C | 0.0000035 | FALSE | TRUE | FALSE | TRUE | MISSENSE | FALSE |
| 5:96429287:T:G | 0.0000035 | FALSE | TRUE | FALSE | TRUE | MISSENSE | FALSE |
| 5:96429290:A:G | 0.0000035 | FALSE | TRUE | FALSE | TRUE | MISSENSE | FALSE |
| 5:96429299:G:T | 0.0000070 | FALSE | TRUE | TRUE | TRUE | MISSENSE | FALSE |
| 5:96429310:G:A | 0.0000389 | FALSE | TRUE | FALSE | TRUE | MISSENSE | FALSE |
| 5:96429310:G:T | 0.0000070 | TRUE | TRUE | TRUE | TRUE | STOP_GAINED | TRUE |
| 5:96429319:T:C | 0.0000070 | TRUE | TRUE | TRUE | TRUE | SPLICE_ACCEPTOR | TRUE |
| 5:96432082:C:T | 0.0000035 | TRUE | TRUE | TRUE | TRUE | SPLICE_DONOR | TRUE |
| 5:96432105:A:T | 0.0000140 | FALSE | TRUE | FALSE | TRUE | MISSENSE | FALSE |
| 5:96432108:G:A | 0.0000035 | FALSE | TRUE | FALSE | TRUE | MISSENSE | FALSE |
| 5:96432113:C:G | 0.0000194 | FALSE | TRUE | FALSE | TRUE | MISSENSE | FALSE |
| 5:96432115:T:C | 0.0000065 | FALSE | TRUE | FALSE | TRUE | MISSENSE | FALSE |
| 5:96432118:C:G | 0.0000065 | FALSE | TRUE | FALSE | TRUE | MISSENSE | FALSE |
| 5:96432861:A:C | 0.0000065 | TRUE | TRUE | TRUE | TRUE | SPLICE_DONOR | TRUE |
| 5:96432869:CA:C | 0.0000085 | TRUE | TRUE | TRUE | TRUE | FRAMESHIFT | TRUE |
| 5:96432870:A:G | 0.0000070 | FALSE | TRUE | FALSE | TRUE | MISSENSE | FALSE |
| 5:96432874:G:A | 0.0000070 | FALSE | TRUE | FALSE | TRUE | MISSENSE | FALSE |
| 5:96432876:T:C | 0.0000130 | FALSE | TRUE | FALSE | TRUE | MISSENSE | FALSE |
| 5:96432877:C:T | 0.0000035 | FALSE | TRUE | FALSE | TRUE | MISSENSE | FALSE |
| 5:96432886:G:C | 0.0000070 | FALSE | TRUE | FALSE | TRUE | MISSENSE | FALSE |
| 5:96432888:T:G | 0.0001166 | FALSE | TRUE | FALSE | TRUE | MISSENSE | FALSE |
| 5:96432889:C:T | 0.0000085 | FALSE | TRUE | FALSE | TRUE | MISSENSE | FALSE |
| 5:96432894:G:T | 0.0000085 | FALSE | TRUE | FALSE | TRUE | MISSENSE | FALSE |
| 5:96432895:C:A | 0.0000105 | FALSE | TRUE | FALSE | TRUE | MISSENSE | FALSE |

TABLE 6-continued

| VARIANT | AAF | M1 | M2 | M3 | M4 | ANNOTATION | IS_LOF |
|---|---|---|---|---|---|---|---|
| 5:96432896:G:C | 0.0001878 | FALSE | TRUE | FALSE | TRUE | MISSENSE | FALSE |
| 5:96432897:A:T | 0.0000130 | FALSE | TRUE | FALSE | TRUE | MISSENSE | FALSE |
| 5:96432909:G:T | 0.0000105 | FALSE | TRUE | FALSE | TRUE | MISSENSE | FALSE |
| 5:96432913:C:A | 0.0000035 | TRUE | TRUE | TRUE | TRUE | STOP_GAINED | TRUE |
| 5:96432918:C:T | 0.0000490 | FALSE | TRUE | TRUE | TRUE | MISSENSE | FALSE |
| 5:96432921:C:G | 0.0000065 | FALSE | TRUE | FALSE | TRUE | MISSENSE | FALSE |
| 5:96432922:C:T | 0.0000140 | FALSE | TRUE | TRUE | TRUE | MISSENSE | FALSE |
| 5:96432927:A:G | 0.0000035 | FALSE | TRUE | FALSE | TRUE | MISSENSE | FALSE |
| 5:96432948:A:G | 0.0000085 | FALSE | TRUE | FALSE | TRUE | MISSENSE | FALSE |
| 5:96432952:A:G | 0.0000035 | FALSE | TRUE | FALSE | TRUE | MISSENSE | FALSE |
| 5:96432957:CT:C | 0.0000065 | TRUE | TRUE | TRUE | TRUE | FRAMESHIFT | TRUE |
| 5:96432971:AC:A | 0.0000259 | TRUE | TRUE | TRUE | TRUE | FRAMESHIFT | TRUE |
| 5:96432981:G:GCA | 0.0000035 | TRUE | TRUE | TRUE | TRUE | FRAMESHIFT | TRUE |
| 5:96432981:G:T | 0.0000140 | FALSE | TRUE | FALSE | TRUE | MISSENSE | FALSE |
| 5:96432985:A:G | 0.0000070 | FALSE | TRUE | FALSE | TRUE | MISSENSE | FALSE |
| 5:96432993:CAA:C | 0.0000065 | TRUE | TRUE | TRUE | TRUE | FRAMESHIFT | TRUE |
| 5:96433008:G:A | 0.0000065 | FALSE | TRUE | FALSE | TRUE | MISSENSE | FALSE |
| 5:96433040:C:T | 0.0000065 | TRUE | TRUE | TRUE | TRUE | START_LOST | TRUE |
| 5:96433041:A:G | 0.0000035 | TRUE | TRUE | TRUE | TRUE | START_LOST | TRUE |

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having obesity and/or elevated body mass index (BMI), wherein the subject is heterozygous for a proprotein convertase subtilisin/kexin type 1 (PCSK1) variant genomic nucleic acid molecule associated with an increased risk of developing obesity and/or elevated BMI, the method comprising:
   detecting the presence of a PCSK1 variant genomic nucleic acid molecule associated with an increased risk of developing obesity and/or elevated BMI in a biological sample from the subject; and
   administering an MC4R agonist to the subject that is heterozygous for the PCSK1 variant genomic nucleic acid molecule associated with an increased risk of developing obesity and/or elevated BMI,
   wherein the PCSK1 variant genomic nucleic acid molecule comprises 5:96393172:A:C, 5:96393258:G:A, 5:96393366:G:A, 5:96394941:G:A, 5:96394988: C:T, 5:96397351:CAA:C, 5:96397358:C:T, 5:96397377:C:A, 5:96397382:C:T, 5:96397390:AAC:A, 5:96397440: C:A, 5:96398887:GAAGT:G, 5:96398922:A:C, 5:96399952:C:A, 5:96399993:T:A, 5:96400071:G:A, 5:96400106:C:T, 5:96408221:A:C, 5:96408288:C:CA, 5:96408299:A:AG, 5:96408310:A:AG, 5:96408324:C:G, 5:96410771:T:TA, 5:96410797:C:A, 5:96410840:G:T, 5:96410844:CAGGGGGAT:C, 5:96410910:T:TC, 5:96410935:G:GC, 5:96410974:TC:T, 5:96410983:T:TC, 5:96412437:C:CA, 5:96412454:A:AT, 5:96416067:G:T, 5:96416072:T:A, 5:96421879:CT:C, 5:96421881:T:A, 5:96421893:TG:T, 5:96421940:TA:T, 5:96421951:TG:T, 5:96421954:AT:A, 5:96423354:CA:C, 5:96423401:CAA:C, 5:96425819:C:G, 5:96425827:C:T, 5:96425843:TG:T, 5:96425891:T:A, 5:96425892:AC:A, 5:96429256:CT:C, 5:96429260:G:A, 5:96429269:TG:T, 5:96429310:G:T, 5:96429319:T:C, 5:96432082:C:T, 5:96432861:A:C, 5:96432869:CA:C, 5:96432913:C:A, 5:96432957:CT:C, 5:96432971:AC:A, 5:96432981:G:GCA, 5:96432993:CAA:C, and/or 5:96433040:C:T according to the GRCh38/hg38 human genome assembly; and
   wherein the MC4R agonist is setmelanotide, a peptide comprising the amino acid sequence His-Phe-Arg-Trp (SEQ ID NO:32), 1,2,3R,4-tetrahydroisoquinoline-3-carboxylic acid, or ALB-127158(a).

2. The method of claim 1, wherein the MC4R agonist is setmelanotide.

3. The method of claim 1, wherein the MC4R agonist is a peptide comprising the amino acid sequence His-Phe-Arg-Trp (SEQ ID NO:32).

4. The method of claim 1, wherein the MC4R agonist is 1,2,3R,4-tetrahydroisoquinoline-3-carboxylic acid.

5. The method of claim 1, wherein the MC4R agonist is ALB-127158(a).

6. The method of claim 1, wherein the subject has obesity.

7. The method of claim 1, wherein the subject has elevated body mass index (BMI).

* * * * *

SEQUENCE LISTING

<160> NUMBER OF SEQ ID NOS: 32

<210> SEQ ID NO 1
<211> LENGTH: 42916
<212> TYPE: DNA
<213> ORGANISM: homo sapien

<400> SEQUENCE: 1

```
actcagcctg gagaccgaag cgcttcactg agcgctcgcc gccgcccagc ctctcctctc      60
gcgcctccta gctcttcgca gagcaaccag gagccaggag tggtctagag cccgagggtg     120
ggaaggggga gtctgtctgg cttttctcct atcttgcttc ttttccctct tcccttccca     180
ctcttgttca agcgagtgtg tgagctatgg agcgaagagc ctggagtctg cagtgcactg     240
ctttcgtcct cttttgcgct tggtgtgcac tgaacagtgc aaaagcgaaa aggcaatttg     300
tcaatgaatg ggcagcggag atccccgggg gcccggaagc agcctcggcc atcgccgagg     360
agctgggcta tgacctttg ggtcaggtaa gagtttccac tttcaagaaa ctttctgggg      420 ccccaggga ctggcgggac tggagcgcgg tcttccaagt gggagcccca ggttgcactc      480
tccagagccc agagtagcaa agagcaagga gctgctccag ccctcgcccc tgtcgcgctt     540
ggagagagag aaagcttgca ttatttactg tttaggctgg gcgcagccaa gcagaaggaa     600
gccgctgcag ctgggtaggg cttatgctta ctgttggccg ctctagaatt gaaatccgtt     660
cccgcgcggt ttggaagaaa aatccctcca cgcttgttca gggaacttga gatacactca     720
agctcttacc aaccaagcgc ccccgggaga agcagtgcgc tccatccccc gggactgagg     780
cggtctgcgt caggagccgg ctgttgcctt cttttcaata tggcagcatc agatccaagt     840
cctgatgcaa gggctaagc aggcttgggg ctgtccgccc tggcagcctg taagggcacg      900
cccagggcat tggaagagtg ccagctgctg ggactcgcga ccaggaggtt ggaggccgc      960 ggagtagcct gggaagctgg ggggagaaat ggtgggtgaa agacacggga ccatctatcc    1020
ccgcgactct ctagggagct ccggcttttc actgggaact tataaagtcc aagcttcata    1080
```

```
actttgcccg gccagtccca ctgcagggtc gagatgccga actgactatg gggaagggat    1140
ctatttcttt cttgttcttc agccaagtac gtaatcgttt tcccgggaat ttcagcttat    1200
tgttgcctgt ccaagtgaag cttggtcga taggtagctg gttggaggtg ggtgggcgtc     1260
aagacattaa gtgggagact gcttatagct gagcgattcc gaggggaccc tagggagtgt    1320
gacttctagt ctagagcttt cctttccttg gctcggaatc aagccctcgc ccctgcttg     1380
ggaagttggt ctgcattgaa gcgtgggagg aggcagttgt aaaacatttt ggcgcgtttt    1440
ttctggaggt ggtggttgag acgccgctgg agtcacggat gagtaatcgg cggggcgtt    1500
ggcgattctg tagaccgaac cctctgggga attcgcctgc tcttgctaga ggcttcattc    1560
tcaactttat aaaccaaatt gtctttgaaa tgcccgaaag gaaaatcaat gcagattggc    1620
ttcctggtgt cccagcagca gatgagtctt ttgcttttgg ccagcccttg ccctcgtgcc    1680
aggctccgtg ttaggggctg aggaataaga ggagggaaag aaacgctctc aagtaatcaa    1740
gaatctagag gagactagct tagagataaa tgattgcaac tgattgtaat ttgtgtaatc    1800
atagaagttg tacttgaagt ctcaatattc attggttgaa ggaatgaaag tagtagggaa    1860
ttcgggaggg gtgaatgaaa actgcccaaa ggagaaaaca tttgctccgg gaacagaagt    1920
caaaggttgc caggagcaca taatgagatc ggagaagaca gtctaggcat agaaaacagc    1980
ttgtgggaaa acagtgagac ataatacagt ttagtagtaa gtctgggaat tgcacgcaat    2040
tattaggaat ttttgagacc caagagggt atgagtagca gaggaaattg tgctggtggg    2100
tactgtggac atcatacaaa tcatgtatga cctatggggg tggacactgg ggatttaatt    2160
gtgtattcct tgagcagcta ctgaaaggct aaatagcact ggtaaccgtg taggaggaga    2220
ctggggaaga cagcaaaaac taaatctctc ttctttttcc cacctgttag ctctaggcat    2280
gcatctaaac ctagaccatt caatgtgaaa actgcttttc aaaataaata aacataaatc    2340
ttaatagtaa aaaacaatac atcatcattc ttgggaggat ctttgagtaa gggatagcat    2400
agtcacaaaa gcattaacaa atagtggggg aaaaccatct atatttatat atgatttaca    2460
atactatctt tcctctaacc attttagtt aagatggcat tactaacaaa gttttaaaa     2520
caaacttaac aaaattattt tattagaata ataattcttt gtagaaggct gatagcacgt    2580
tcctggttct gcttatttct cttttgttt aatattacta aaattacact aatttagcat     2640
tactatattg ggtaccttat tgcctcagga taaagcttgg attaaggtag tgacaagaag    2700
aaaaaccagt tgacagcaga gaaaacagag ctaagcactg gtgatctttt tctgcggctg    2760
ctgatttctc tccccagttc catccacagc ttataggaag attcactgag attcaggctt    2820
ggagcagggc ctaagcttct ctattttaaa attctctggg cgatgagaat caccaattta    2880
aagaacacgt ttcttctgta atatactgtt gtcaactgtt tgtttcttaa ttttaaaaat    2940
gcagggttac ctagaggatt tggtagcctc aaatttagta ctgagtaaag ggagactagc    3000
tcaaaagaat aatgaatata gtcctaaatg aaccaaagat gtcaatagat acccggagaa    3060
gtacaaaccc tctaaagtgg gacaactgcc ctaaatgtag catgttcttt tctgaaagcc    3120
ttgaattagt ggaaaatcaa acgatcacta atagtggcta atagcaattt atcactatga    3180
attcaatggc tacattttat aacaacgata atttatttta gtggaaagtg gcactgacca    3240
tagatagtat cccaggtgtt tgcctgctta ccacaaataa ttgttctttg aacagatata    3300
tttgattaaa tgagcatttt aatatgatat tgtcacacat gaaaacatg tatttcctcc     3360
aatgtgtgta aaatagaagc atcactagcc tcctactgtg agctaatgaa tatactgtga    3420
actcaagcaa taatattctg agggtcatct taagacctct atcagtgcct tcttcatgaa    3480
```

```
gaatgtggat ggagctggag gccattattg ttggcaaact aacacaggaa cagaaaaccg    3540
aataccgcat gttctcactc acaagtgaga gctaaatgat gagaacacgt aaatacatag    3600 agggaacaa catatactgg ggccttttgg agggtggagg gtgggagaag agaagggatc     3660
agaaaaaaat aactaatggg tattgggctt aatacctggg tgatgaaata atctgtacaa    3720
aaataccccg tgacacaagt ttacctatgt aacaaacctg tacttgtact gctgaactta    3780 aaagttttaaa aaagaaaaa aaatattaat ttcagatacc aggaatgggc ttaataaaag    3840
ttgcctatct ctaagttagc tgagttttaa actagtccat atatacttgt ttgggaacgt    3900
ggatatttat tttatttctt tccttttata gattggttca cttgaaaatc actacttatt    3960
caaacataaa aaccacccca gaaggtctcg aaggagtgcc tttcatatca ctaagagatt    4020
atctgatgat gatcgtgtaa gtgttgtaca tttgtcttca aaccaatact ctagcttatc    4080
tgctttcttt atgatttcta ataaaaacag aagcattttg caaatgtggt ttttttttta    4140
ttgtgaccaa gattgtttat ctgtattatt tctaatttct ttccataaaa ttataatggc    4200
acataataat aacaagattg ggttgaattg gttgagccaa agttaattt acacatatat      4260 acgcagttta attatataat tacatatata tctaaagtta atttatatg tacactcaca    4320 aattcagtct aagagcatga aagtgaatat ttaaaatgag agggcagcac taataaaaat    4380
gtttgacaat acagtcaatc aacaaccttt tattaggtac ctattatgta ccaaacactt    4440
taataccaat gtgggctcaa agaaatacat gggccttact ttcaataaca tttcagtata    4500
actgaaaaaa aagtctatta tttctattg gttttgctgt ataaggagct agtgtttatg      4560
agagaactgt aaatccatgt cttcatgagg caaatgtttc cataagtaat ctattgttgg    4620
atccaaacca tctgatctct tttcatccta gtttgtatct tggttcaatg attaggttac     4680
agcagaaata aatataggta aataaggtag aggcagtttg aatagatagc taatgtacct    4740 attgatttg aagtctattt tcaaggtcaa caaacatatt agaaaatgtt tactatgttg     4800
ggagtattgt aattttcata cagtgttgcc ttttctcaaa gaaatgccat actggaagaa    4860
atttatcctg attcgcctga tatctgtgta cataattttt gttacctagg acaacctgga    4920
gaattagaat gagagatcct cttggtgaga ggattaaaaa catcctttca acttcccagg    4980
gggaaaatat atatatatgt atgtgacaga aaggtgatag aactgttgaa agtagacgaa    5040
attcatgagg actgtaagat aatttgcccct tttattcatt ctgaaactga tagaattttt    5100
aaaagaagaa gaaaaagaca aattatgagg gtagggaatg ggaatggcct gggtcaccag    5160
tgttcgaatg taaagaaac aacaacatcc tgacaatgct gtattaggac cacggacagt     5220
gaccgtatag ctcatctaca cccactgcta gctcttttt gtcaagttat tgcttgatgt     5280
gggagaccaa atcagaggcc ctggaccta ttacagaagt ttcttgtcca ctgaggtctt      5340
cccttactca cttcaaggga gagggctcat cgtgtgtggg ctctgaaaag cagaataact    5400
tctagcactc tggctaggct tagtccccgg gctaagcaga agagagattt ccttctttgc    5460
ctaaatgcat gcccaaactg catgcccatt aatgcacata gaactcaaac tgacctgcct    5520
tctcactttc ataggagaaa attggacaga atagagcata cctaactgtt attcttactc    5580
aaagtatctc atgacaatga agatggccca ttctactctt tatacatccc cttgatagct    5640
gatttggtgg gggagggtg gaatctcaag acattatgaa aaaatgctaa gaattccttc      5700
tccagcacag gtataacttt gtaaaaaatt agcccaagaa taattttatt ttaggaaaca    5760
ttctggaacc atagaaactt gcattggaag gttgaattag atgatcttca atgctctttc    5820
```

-continued

```
cagatcaaaa gtattattta taattaagta catgatacct ataatgcata atagaaagac    5880
actaccaatt ttcctctata ccattcagcc tgctcttcta gagattaata catgattctg    5940
agttaatgac attaatcata acactgtttt ctacaattgg atgtttatct gatcagacgg    6000
cagagtgcct cctcttatat cccatttcca aaaaattgct cttggttttc attttattgc    6060
tcttttttga tggaggataa tattctttca aatcagccct gtgaaatgca gcaacagtct    6120
atctttacaa gtctgttaat aaaatctcca agtgtaagtg accctctacc tcaaagatta    6180
gtacttattc cctagcagtc agcttccaga gatcaactca gatgataggc agcattccaa    6240
gcattgaggt attttaagcc aaaacaatta agcttgaaaa tacaagcact ttaaaaataa    6300
atcatagtga ctaatttcta gctttcaggt tcttcccatt attttttaata ggtttgcagt    6360
atatttttaa ttgaaaattg agggcagtct tagtggatgg ttttatcctt cagttgcaaa    6420
ttattttcg gttttatttt ttggagctga ttcatgagta ctctcacatt aacaatattc    6480
caccacacac tgaattgtca tcatgcatac agcagaaaag atgtgtttgg ggtaggaaat    6540
agtcatattg ccaagaaaaa taagagtata gaattatctc ataatgaata taactacaag    6600
gcagcccctc actctctcag ggcttcaagt ataatagtat tatgctgtaa atatggggca    6660
ggtaattttc gtattgtcag atctctttgc ataatacatg agactgaatt aatggtaagt    6720
gtgcgtggtc agtagtgctc attcatcacc caggatctgt gtctcatatt aaatacttt    6780
aagcagaggt cgaagcacag gggagggagt ttcaaatttg catggataca gcaccattct    6840
tactttataa aatatttgca atttctacct gttgtatgta aagacagaga aattaatcta    6900
taaaagcatt ataacagcag tctcttggct tgttgactca atccataaaa gcagacaaat    6960
tttcagccat ggagccctga aacctcaata taaaaatgag tattatggtc catttgctga    7020
tgaaagcaga ctgaactttt gcttccactg taaccacaat gtaaataatt tagggaatta    7080
tcatttcact gactgcttct cctcccccta aaggtgcact ttactgtaat agaggaaata    7140
ttcatctccc cagtgggcaa tcccttcttc tcactgaggt gccagtttaa tctgtagtca    7200
aatgaaaata ttgcagagct gcctgaactc tgatgggaag ggtactggag atagttagag    7260
gaagtataca gaggtagata tttgactttt gattttcttg ctataaaaat ccttgtaggt    7320
gatatgggct gaacaacagt atgaaaaaga aagaagtaaa cgttcagctc taagggactc    7380
agcactaaat ctcttcaatg atcccatgtg gaatcagcaa tggtacttgg taagtaccta    7440
cagaaggact atgtgggtgg gacctgggac ctggcttctt tatgttgtta catttgcaac    7500
atggattttt ttttttttt atgatggaga atttcatagg gagctatatt gtctggagat    7560
tagggctgat gggatcttct tgatctgcct cttctgtttt gctgagtaag gatgttggaa    7620
acagatatct ttagctgctg tgaaaaaaat aggttgtatt ttttgtcttc ttaagtttat    7680
ttgggataaa tgcagaaaaa taatatcttg caggttaggg tttccaaaaa cagtacttgt    7740
ggcaaaaatc tcatttggtt aaagttattc ttcagaaccc tttaaagcac tcacagagta    7800
tagtgaacat aatttggcat atacaacccct gaatgacaat tcttatatga cacagatgag    7860
aatctctgaa agaggttaaa agaaggaaca caagaaaagt ctattgcaaa tgtctagact    7920
tgcaaaccat tctaccttta agatagttac caaatccttg agcgaagaaa ttgttaagtg    7980
ttgctgtcta cctgcagggt gtcctctctt ctgtttaatg ttacgtctgt atggtagtag    8040
tataggctaa tagaaggatt tgttgttgag aattttataa agattatttt ctcttgaaaa    8100
acacaagcta agactttgat actcttgttg cataaggggt agaaaagggg atcagtttct    8160
cttgacccta cgttttcttt ctttctttct ttctttcttt ctttctttct ttctttcttt    8220
```

```
ctttctttct ttctttcttt tctttcttto tctttcttto tttctttcta tctttctttt      8280 ttttttgac   agagttttgc  tcttgttgcc  caggctggag  tgcaatggca  tgatctcagc   8340
tcactgcaat  ctctgtctcc  tggcttcaag  cgattctcct  gcctcagcct  ctggagtagc   8400
ttggattaca  gatgcccgcc  accatgccca  gctaattttt  gtattttaa   tagagatggg   8460 gttttgtcac  attggtcagt  ctggtctcga  actcctgacc  tcaggtgatc  cacccgcctt   8520
ggcctcccaa  agtgctggga  ttacaggcat  gagccaccgc  accgggcctc  ttgccactat   8580
cttaagtatt  tgctcattgc  agcagaagag  acttatcagt  taacacttgt  gcatttcctg   8640
tgtgacaaac  actattctaa  aatgtttgat  atgaattaat  tcattttgtt  ctcatgattg   8700
tctgtgttgt  agaaatagta  attatgccca  tttaacagat  ggaaaacag   agatattgga   8760 aagtagaata  atttgccaaa  atccatggct  gctagtggtg  ggactataat  tcacgactcc   8820
agagtccata  ctcttaacaa  ctacagtcta  aaattgttcc  tgcaactgac  atagaggcct   8880
tcttctctga  ctttggccaa  caatctgtgt  acagttccag  cctcctgtga  ttcagcttca   8940
taccagcctg  gcaaatactt  gtcaccccac  cccccaacct  ctttatgggg  aggagggcac   9000
aaaagcaaga  gggcagctcc  ttcactgaca  cttttgattg  tggttattta  tagatttctt   9060 attgacccctt  tcaccgggta  cctggcattc  ttttactgtc  tctgtctcac  atgcttagaa   9120
atgtgcttat  atctgtgttc  ccttgctacc  ctgtacttat  ctcctgtaca  gtcccacact   9180
ctgactatca  gaaaatgtat  tttaaaagga  aaaccctgaa  tctcctctca  cagacactta   9240 cccctaaat   cactcatact  taaaaatagg  caatcacatt  gcaattcctg  aggcaatcac   9300
agtctcctga  gcattccagg  ttctgctttt  tcctttagaa  taaaaattct  aaaacattca   9360
tgaatgacta  tgcaccaggc  aatataatga  gagctcaatg  tggcaatgga  gaatcaggat   9420 ttgggggag   atgaaaacat  cgactatcaa  atagagcttc  catagatgaa  agggttgagc   9480
atgttattat  aaatgaaaga  aatttaggga  taaaattctt  caaagccatg  tagttcaaag   9540
agaaggagca  caggtgattc  atcttttcaa  gtgatgtcca  tttgggacaa  tcgggagaag   9600
agcagcactc  tgggggttca  tttgccctta  ctctcaactt  tgttttctca  tttcactgaa   9660
ttggcttctt  ctaaagagta  gagtgaccca  aggaaaaaga  aagatgggtc  tccaggttgg   9720
aactgaagtg  cccatttttgt agcaagcaaa  tgataatttt  atcaatgctt  cgttgttttt   9780
ctttaccagc  aagataccag  gatgacggca  gccctgccca  agctggacct  tcatgtgata   9840
cctgtttggc  aaaaaggcat  tacgggcaaa  ggagttgtta  tcaccgtact  ggatgatggt   9900
ttggagtgga  atcacacgga  catttatgcc  aactatgtaa  gtgtgtgcct  tctcatgact   9960
gtgacttagg  gagctgtctg  tgcagacaca  cagttagggc  tttccttctt  ttcaagggga  10020
tgctgctctg  tgtcagtcc   ctgggattat  gggccaaggt  tatgtccctt  ctcccacttc  10080
ccactagctt  atatgaattt  attttgtacc  agtgggcatt  gaaataattc  agtgggatca  10140
aaaattgtac  aaaagtatat  gtgttgggag  aagaaggggc  agtgcctaca  ccaattaagt  10200
taccaaaatc  tgatgacttt  gagttgctca  gtgtttgggg  cattaaagta  atcaaatcaa  10260
gccccttgcc  tgagatcatt  gtcacagttt  ccctcctcac  ctcttttatg  agtctatatc  10320
cctgacattg  taaaattata  tgaatgtgat  tccttccatg  caaatccaaa  gtgaatacca  10380
cacaatgcac  ctatgccaag  ctgagaaagg  aaaagttttc  tagaaatggg  aaaataaata  10440
aataaaaaca  atttgcttca  ttgttttatta agtttataat  ataatatgaa  caccatcata  10500
tatcttaggt  ctttagatca  ggaggctggt  gtttcatctt  tcagattatc  ccttgttttt  10560
```

```
ctctcatcct ttccacctat caaacattcc ccagctataa caccaagcta aagagccaag  10620
gaaaagagaa ggaaaaatag tagcacagag tagaaattag gaatgattga aatatacgga  10680
aagcattgaa aagtaacagt aagggtatgc gggaggcgtt taagtgtagc tattgggttg  10740
gaaaagggag tggagcctgg aagcttgtct tgaatttcaa gcaccctctc tcaaattaaa  10800
ttacatgttt atttagtgtg cctgggaggc tgaaggagag caccatggac ctgagtccca  10860
ccctcagcca cttctttgca cctatattca taagagagat gagtgtcaaa gtgtcactaa  10920
ctagctttat ggccttaggg aagtcattta acttctctgg gcctcaattt tctcatctga  10980
aaactgagat gactgaacta agtaaactaa ttccttccaa ctccaatatc ccatgagtgc  11040
ctgtgaacca taggcttggt aacattcact gagaattgaa tgctggctca cctggctgtg  11100
ttcatcatct ctgcctggtt tgtgagtaaa ataaatattc agtgactcgg ccagaaactc  11160
taaaatgcag gcttttgagc tatcagccag gatgggaagg catagggtaa gaggcttggg  11220
aagtgatgct tttttttttt tttttttttt tttttaatgc tgccacagtg ttatattttg  11280
ttgtctcttt aggatccaga ggctagctat gattttaatg ataatgacca tgatccattt  11340
ccccgatatg atcccacaaa cgagaacaag tgagtaaata tgcatttgtg tgaaataaag  11400
tactttacaa tgcttttatc ttgtttgaga aaattatacc atatatttca tccacattcc  11460
agtgctcagg aaatgttaat gcacaacatc cataccacaa tattttgttg cttttaaaac  11520 agaaccaaa gttctatttt ttatattccc tttggtttat agaaccatat tttcattaaa  11580
cttcttacat tatgaaattc tcctctcaaa tgttactgaa ctgttgtagc tttagaaaga  11640
atgtttgaga cataaagagt acacactttg agcccatccc tcccctcaat tcctctatga  11700
atcttttact cttagcaaca tgctttatgt tagtcatgaa agaaaatata tgtaaagaaa  11760
tggatatgaa caatgcccac aacttctgac ggtggctaca gtcaccttca ccagttctct  11820
cagaagagca tggccaaact ccagacagag aaatgcctct gaggtctggc ccctgaatcc  11880
aacacagtct ccagggcatt gagccagccg gaagtctcct ccagagttcc tgctgctata  11940
aggccatagg aaagagagag gagacagcac ccgactccca gattaactct ctgtcccttg  12000
aagccacatt atggtgagag aggccaagag ccacagaggc caagagcaag atcttctaaa  12060
gggagaggtg aaagaaagac ccagaggcaa gagactttca acttctctcc tagccccaaa  12120
gaaacttcac gctctaggca tgtggaccct caaagtgtcc atgcccatgg gagagaccat  12180
ctttgctcat accgatgttc tcacagacat caaggagaca ctcaaacttt ccttttcatt  12240
ttctctacac agaagagact tgcaccaaaa tgatcaaagc caaggtcaaa attagggctt  12300
gttgctacaa gtgaggatgg aaaaagccaa gcatctaaca gctcttggta tatgtcacat  12360
gaagcgcttc tttattctct ctggatggca ctgtctcttg gactgttacc caacttgggt  12420
cagacaagtc tgtctctgtc tctctctctc tctctctctc tttctctctc tctctccctc  12480
tcttccttcc tccctccctc cctccctccc ttccttattc tccctcagaa ctcccaagtg  12540
gctggtgcag taatactgat ctaaagttat ttctttcttt ggatagtctt ccctccagaa  12600
agccaacaaa ccccaggatg ggaggctggg gtacatggac ttggcctcaa cttctgggtg  12660
tttatttctt cctggggaa aatgggaggc ttgtggatag ttcagggata tgacttcttt  12720
ccgtaccatt tatttctttg agggtgacta aaggggttaa ccgcaaatat cccttagagg  12780
tgaaaacatt ccagtaaaaa cacaatagga accactggca agggtaccct tggagcaaag  12840
tgggagtgtt tcgagagctt acagcagacc ctcagacaaa cttttgcta tatgtctgaa  12900 gcaggataat gcaggaccag taaggacatc tactcttttg gggcacagcc ttgcaatgta  12960
```

```
gttatggctt tgccaattcc cagagtaaag ggtgaccttg gagaaatcac ttacctctct    13020
ctgcctctat tccattttct tccctaaac tgggtgacaa cgtaccttct ccctatgttt    13080
cttaaatgaa cttcctgagg aaatggctaa taagcacttg gaataataag ccttcttaga    13140
gtggagtaga aacaactttc attccacccc cttggttaag actacgggaa atctgttccc    13200
agacacttga ggagacttag atggaggcac tggctccttc ctaggcagta tacggtcctt    13260
ccaggcagat cctgggtctg gccccaggat ccagtgtggg tgataacttg tacgatggct    13320
gcatagtggg cgaattcttg atgaaatgac attctctgga gttttccag tcaggagatg     13380 gaacactcag accttcctca aaacaaaggg gatctcacag cacagcattt ataatagttg    13440
ttttatatat atgaatataa taattaaaat aaaatataat ttccctgact cagggagtta    13500
cctgcaaagg ccctagggaa gcagcccata taatgctatt tgttttgtgc ctgaaagccc    13560
tgagcttcca gatcatagcc tgctgtgaat cttccacaca gcattgagag agcatgtcat    13620
agcccaacag ttaagagcag acttgggagc caaatttagg tcaaattta gatctgccac      13680 ttagtagttg ggtgatcttg aggaaattat ttaacttctt tgtgcttaag ttttatcatc    13740
ttttgaaaaa gaatctctac ttccttgagt tagaggtatt aagtgagtgt atatatatat    13800
agagagagag agggagagag agagagagag agaggtatta agtgagttta tatatatata    13860
tataataagt attatataac atatataata cttcattgag ttaggggtta aagtgaggtt    13920
ttatatatat atatatatct cacttaatat atatatacat ataaactcat ttaatacctc    13980
taacttaatg aggtagatta tttatctata tctatatctg tatatctggc atttaaacaa    14040
attgatttgt ttaaaaatta ttccacaaga tatttaaata ctacccttat tctggttaaa    14100
atattcttgt cacacttgtt atttaagcca tatgtgtata tgtgtgcata tgtatatata    14160
tggcttaaat aacatgtgtg acaaggatat ttggcttgga catacacata tatatggctt    14220
ggacactggt acacaaaaaa gttaagtaag tgtttgctgt ggtgatgatg atgatgataa    14280
tgatcacagc ttctcattta gtaactgagg tagaccttct ttcagtgaga aatcaacatg    14340
acaagaataa tatcatccga tgggagcagc agagacaagt caattttctg agccaattca    14400
gaatctgcta tttggaaatg acataatgag caactctctc tcaggatcct cttgactatc    14460
aaccaaaaag gtggcatcct tatcatttat cagaaggtat aataaaaagt agatttgcct    14520
tctagcatgt tgtcagacat aaagccctta ggtttagaaa atgaatggct ccattttgtc    14580
ttggccttta cagcaattgg agaggtatta taccccaatt ccaaggttat tatctcttca    14640
aactatcagt attgctgttg ttctttatta ccacgtaaat gagattaata gaagctacat    14700
ttgaatgcta ctctgaaagt caaaagagga atcactaaat aataaaatct taacagtgca    14760
ggtaatgctt accattaagc tggcataaat ctgtattcat tatttcaaca ccaattacag    14820 attgttttc tagttaaata acaaatgtga caaggatatt ttaaccagaa taagggtagt     14880
atttaaacta tctcatggaa taatttttaa acaaatcatt ttgtttaaat gccagttact    14940
accattgttc taagataata gaaagttctt tactgcagca cctcacttag aaaagaaaaa    15000
gagctgcggc ctataaagaa tgacatagga acacttttct ttctctcaac gtttggaggt    15060
ggaacctgag gataagagga ggaaaacatg tcaatgcata tttgtaccat gatcctcctg    15120
cagctctcac tagagaatag tcgtccatat acaaggagag ataaataata ggtgctgtca    15180
cactgcatca tttttagga caaaggcaca aacctgggga tgtctgtcag cagattgatt     15240
ctgttggctc aggctgaaga cctgcactgg attcttttgc tgacctgagc cttgtctccc    15300
```

```
atcctgtata catggaaata tataagaagg cagtggtgac ttctggaagt acatttctca    15360
gagatgacaa ctgaattact ccttctacta aggcaaagag cgttcatcca tccacaaagc    15420
ataagttgcc ttctgtatgt tcagatgtgt gcacttttct cagagaatgg tgtggtcagg    15480
acagcttcag ttgcaaatga aagaatccta actcaaagat taagtaacaa agggatttta    15540
aaaatattca cccaagtgat gttctagttt ctgatgtttc aagatccaag agctcaaaca    15600
atatgttctc aggacaccaa gcactctgtt tccatctcta gtgctgctcg cctctgcttg    15660
gcttcacttt caagagaatc ctgcctggca gagcaagacc catatgactc acatggaact    15720
taaagctcat aattctcaag aaagagtggg gtttcttccc tataatctac atcagtcctt    15780
gaaagttgtc tgagaggagg ggccccatga ttgaaaaaaa tcacaaaaag tcaggagggc    15840
tgcttcccca acaggaaaaa tgctagcata cataaaagaa gcaggtgttt gctgcatcag    15900
gaaagatctt gaattaaaga taattatatt gtcctgactt agaattccta gccaggatta    15960
acatgaagga gcaggaatct tattttgtgg aaggagacca ggaaatcatc tttgctactt    16020
caggaaaaag agaagttgaa caattcttct tgatggccag tcaatttagg aattttatat    16080
tccatgctat gctgaattaa tagatggcca gtatagtaga attgaaatgt aactggccaa    16140
cattattgct ccgagctaac ccttcctctc tttcactcta tgttggtata tctgtaggc    16200 tcctccaagc caccaacagc cttcacactc ttacaggttg tttccacaat agaataaaat    16260
cacgaaataa atgaattcac attaatgtgc ttttggcttg ttggccctcc tgagtcagga    16320
tggtggtggg aaaagacaat tatcatcctc agaatttcag aatagatgct ttagtggtgg    16380
aatttggtgt ttggaagacg catttttctt ccaaatactc tgaaatcata aattaccctc    16440
tttgcttgac tgcaaaacca atcatgttca ggcttctggc cccagttggg atttcaggag    16500
catcttggct ttccaattag ctggtaatgt cttgcaaata tctcaagctc ctcttggtac    16560
cagataatct tcagacattt tagtgtggca tatatttaga ggagaggagg agggcttaat    16620 agggacttg ttctaggata tcctactaag gctgatcaag gataatctaa tccaaggcag    16680
tcactaggga gaaaagtgag gagccacttt gctaccaaaa agtacaaagc agaagccatt    16740
tctctgaaat tgtttctgaa tgtcagagtt cttataatag tatcaatagt taacactcac    16800
tgtgttctta ctatctgcca tccactgctc taagtgtttt acatataatt tgtcatgtga    16860
ccaagccttt gcagacaagt aacttaccca aggtcacacc cttagtgaat ggcagaagcc    16920
agaatttgaa atcacatact ttgtctctaa tacttgtgcc cttcatctga acataagttt    16980
tatgttatac taatttaaaa caaacaaaca aaaacagtaa caaggccgac aaaaagttaa    17040
tatacctatg ccccattaat tcattcatat gcaaaacaaa tgtttgttct tctgtatgtt    17100
ttataattct tatttttcaa tcctcagaca cgggaccaga tgtgcaggag aaattgccat    17160
gcaagcaaat aatcacaaat gcggggttgg agttgcatac aattccaaag ttggaggtaa    17220
aacagaggat tgtccctata gcttggcatt ttaatgtgaa gcttacatca cccattgtaa    17280 atggggagg ggagcttttc tttttaacaa ctggaggaac aaattagttc catgccaaag    17340
ttgctacagg acttgaatat gatttgccag cgagtcaata gatatggatt cctagaaaat    17400
ggatagttga atatagccta tacatctttg caggaaaaaa aaatgtggaa atgttgaata    17460
gcatttgaac caaatctaat tttctctatg ttctgattta gaatggtttg ttattgagtg    17520
cttgctaagg aaacagaagg aggaggtaaa tttaggcaaa gacttttcct gcctctcaat    17580
tctgtagaag ttcttcactt tatagagaag aacagcttca aaatttaaaa aaagtacata    17640
cttattatat taaatagcca aattttatct tttatagcaa ggatgtagga tttaattgtt    17700
```

```
ttcatcagtg tccttatggg gaaacacatg gtaagttgca ttagggcaac tgtggacatt    17760
ttaataaaga aacgatttac aagaattaga gaaaaccaac aagggggctaa gaagtggtag    17820 gcagatgtta tcacctttag cctcaaggag caaagggaag aagtcagcag aaaatagaga    17880
gggaaagctg tggtcacagg agagagccac tggataggcc ttgagtacaa caacagagcc    17940
acttctaggc aaaggggatt caggggtata ggcacctcat tctcctcttg attcccaccc    18000
tcttgctggt gtcttcagtt ggctgaaccc aatgggaaga cagagcccat tgatgcagtc    18060
catgttctaa tggagaagag tggaaagtgt atctgcaggg gccaagagaa aagaaaaaac    18120
tgtctctcct ctttatgcta tcccaacctc aggctttcat gttatgttat aagcttcaag    18180
tttagtttgg ttttcaaaaa ccataatcac aaaaagaatc aattgtagaa catttcaatt    18240
acaataaaac cccattaaac tctacatgag tataccttgc atttggttat gcatttcttt    18300
ttagaaacca aataaatata catcgtgaca tgtaatgcat cttttcatgaa tatagggcac    18360 tcttagaatt ttaagtgtca ttcctgattc ctttgatact aacatcttca aagtgttctg    18420 ttaatttta aaaaaaatga agggagaagc acaaattatg taattagcta gtaaaagaat    18480
tcactctttt agtcataatg aacgaaacag ctatagtttg tgaaagaatc atctgatccc    18540
ttcattttgt agagaaagaa tcagaagcaa gctgctcaag gtaatgaaag caagtttgtg    18600
gcagtgtaga actgaaacac aagattccaa gcctactgat gttttccatt actccatcct    18660
ttgatggtct ggccccaaat gcattttta ccaataatct tcatttatta ggcacctatt    18720
gtatgtcagt tactctacaa atattatagg cagtgtatcc tggtggttaa cagatttagg    18780
ggctagattt gtagggttca aattctggct ccccagtttc aagctatgtg gccttgagca    18840
agtcactatc ccttcctggc ctcaatctct ccatttataa agtgaggaga attacggcac    18900
ccacctcaaa tggtggttgt aaggtttaga tgagtttata catgtaaagc ctgtggattg    18960
gtggctgcat atagactatc atgaatgcac atgagctgtt attatcatcc ctatttaca    19020 gttgaagaaa ctgaggcaca gagggttaac tggcttgccc aagattccac agctggtaag    19080
agcagaactg ggattttttt tttttttttt tagacagagt ctcactctgt cgcccaggct    19140
ggagtgcagt ggcgcgatct cggctcactg caagctccgc ctcccgggtt catgccattc    19200
tcctgcctca gcctcctgag tagctaggac tacaggaacc cgccactacg cccggctaat    19260
tttttttttt tttttttttt tttttgtatt tttagtggag acagggtttc atcatgttag    19320
ccaggatggt ctcgatctct tgacctcgtg atccgcccgc ctcggcctcc caaagtgctg    19380
ggattacagg cgtgagccac cgcacctggc cgatttttt tctaaatgca ttttttttt    19440 ttttttttga cagagtct tgctctgttg cccaggctgg agtgcagtgg ttgcaatctt    19500
agctcactgc aacctctgcc tcccaggttc aagcatttct tgtgcctcag cctcctgagt    19560
agctgggatt ataggtgcgt gccagcatgc ctgactaatt tttgtatttt tagtaaagat    19620
ggggtttctc catgttggcc aggctggtct tgaactcctg gcctcaagtg atccaccccac    19680 ctcggcctcc caaagtgttg gtattaaagg catgagccac tgcgcctggc tctaaatgca    19740
tttttgaaca attctttttt tacaaataca actttcactg atcatatcaa tttcatatca    19800
ttttaccttt gctccatagt aaataagtgt gaaaatctaa ggctgtgcac tttattgtat    19860
tatgagcctg aagccagaaa taaccaggta gctgcctgta atctgtccag attgtttttg    19920
ccttcctggc tcttgaattc ataagtctga tgacgggtga cagcctgttg gaaagcacaa    19980
agagctaccg cacctacatt gtcctgatga aaaatgattc cccttggggg tgaaatccat    20040
```

```
ggcaatgatt tcatccttga gattatttag aagaatagga agcatgttcc ttgaaaatgt    20100
ttcttagcaa acacatgaaa ggatggcctc tgggttattt ttaatcaggg cttagaaaca    20160
aaagtgcttt ccctatttgt tagtttcctg ttgtgactag atcttttgaa gctacatgtt    20220
tcctgtccag agtccttgtg tggcgtagac tgggccacag ccatttgtgg gacagccatg    20280
aggaggtgca tcaccagagg gctgcttgga gggtctttct gaaagctggt ctgtcattta    20340
gttggggtgg gagggagggc aaacattttg taattgacaa caatcacggc cacttcctct    20400
catccaagga tgctgctcca cttcagactc aatgcccaga gcttttgctg ggaagagagc    20460
cttgagtggg accaaaaaaa aaaaaaaaa aaaaacatc acagctgcct acacagtgca    20520
tggtattgca tagtattatc tctaaagtgc gacaaaaaag cttatggggg cagcaacatg    20580
ttccttcctt ctgtggtgtc agtagctggg ttacagaaat tggggacatc tatctagtag    20640
ttacctggtt tttgactctt aaaatccttt aaaaatacaa atagtaagag tattgggctt    20700
ttgtccatgt acatactgac atcaaccttt gtgtgtcttt gtttattttg tttctcaggc    20760
ataagaatgc tggatggcat tgtgacggat gctattgagg ccagttcaat tggattcaat    20820
cctggacacg tggatattta cagtgcaagc tggggcccta atgatgatgg gaaaactgtg    20880
gaggggcctg gccggctagc ccagaaggct tttgaatatg gtgtcaaaca ggtaagatgc    20940
tttacacaga cccacatgaa atgaaacctg accatctgga tatgaggaga aggaagaac    21000 acttaggtta catggaataa cattgttgtg gatttcttaa caaagtcctt tacaatttta    21060
aatgcactta gagggccaaa tcattcttca gagggatggg agttaaggct taagaaagtt    21120
ttccctattt gtggccaggc gcgatggcca agggaggcag atcaattgag gccaggagtg    21180
gccaatatgg agaaacccca cctctactaa aaacacaaaa attagccagg tgtaactagg    21240
ttgcactgtt ctgcaaccta gtttagacag tgaaactgtg gtctcaactt agatgcctat    21300
agtcccagct actcgggagg ctgaggcaca agaattgctt gaacccagaa ggcggaggta    21360
gcagtgagct gagattgcag cattgcactc cagcctgggt gacagagtga gaccctgcct    21420
caaaactaaa tataaataaa taaaatgaat tttccctatt tgggtctgag gttgaatgga    21480
aatttattac ttttagcata tttatttttaa aagtgcttct ggacatttct ttctccttac    21540
tcattttcct gctgcttttg ggtttttaca ctagtaaaaa actactcagt cttcttccaa    21600
gcgcggaaat gcttttcaaa tatagaaacg tgttgcctttc tgctctgcac gtgcctgttg    21660
aatacctgtg ccttggttgg attgctctgt cacttgggtt tactgtattc ttgcacagat    21720
tctaaagcct tgtgctccat aagatgaaac aaaagtagaa actctggaga gcacaaattg    21780
aaaaatcata gaaagggcgg ctttgacgag ttccattcaa ttgaagagtc ccttttaatg    21840
cagctgcaag gcagatctga ataattccta attttgtcat tctatcagtc agccagaaga    21900
ttgaagcaga aagaaagaga ggaagttcaa agatttaagt gcagtgacat aaactaagag    21960
aagggtggaa aaatatgagc aagtgcaaaa cgctagatta tgaatctgca taagaaagaa    22020
aagcgtgtgc tcagccctac cccaggaggg cccagagact ggcagggcca gagtccagtg    22080
gcttataata cacagccttg tgagatttcc aatatcgaag ccaaaagatc tggaattgaa    22140
aatagatccc aaatagctgt ctctgagaat tcacacatg tagtcgttgg ggattttatt    22200
gggatataac aatgacccca atagatgata acagataata tgcattctgg cttttccttt    22260
aggggagaca ggggaagggg tccatcttcg tctgggcttc gggaaacggg gggcgtcagg    22320
gagataattg tgactgtgat ggctacacag acagcatcta caccatctcc atcagcagtg    22380
cctcccagca aggcctatcc ccctggtacg ctgagaagtg ctcctccaca ctggccacct    22440
```

```
cttacagcag cggagattac accgaccaga gaatcgtatg ttgcttttgt ctaattctct    22500
ctgcttagtt aggagagcgt ggcatgcatg tgaaatgatt cccctaactg acctttggta    22560
cgactgattc gcttaagctt gatgtctcag ttgggagaac tcacacttac tcacttgaaa    22620
ggctggcatc catcagaaag ttttctctcc agggataatg acacttctgc caagatgatc    22680
ttcccctctg tcatttttaa acccagcctt gagaagccac caaacctgtc attacacaca    22740
gcggagactc caaatgtctt ttctgcttgt ctgatgcctc cctggaaaca gccttaaagg    22800
agatctcagg gttgtagggg ctttatcacc cttgtacttg ctgatccttt aacagcaggg    22860
atatagtctg acctgccctg tcgcagatga taaaaataca gagtctacac cagctatgtc    22920
tcctaagaat ggatgacctg caggaaaata gcagtttcag tgtcccctga ggtgaactgc    22980
tcagcatctg ggtaagcagc tcggggaggt cgtatgctca gagagctcct ccagcccacg    23040
cttgcctgcg cctttgcttc catgagtcag acggccaagg gcaattactg gatttcccct    23100
caagggcatg acgatggagg ggcatttagg ggctttgaga acaaagggag acacctttaa    23160
tttaaaaaat gtaaggcccc caatttaact cctgacacag aaaggaccaa ctagctaaag    23220
tatatagatc ctatctcagt gaaatagcag gtcatgatct aattagaggg tgggtgaacc    23280
ctataataat gaccttggaa tgcgtgcaag attcctatta atggcatctc aacaaaattg    23340
tcaacacgaa catcttcttc atacaggatc acttctgcaa gctagtttag acagtaaagc    23400
tgtggtctca acttagaagt gtgggcctgc ttctcacgcg catctcttca gctactcaag    23460
taatagacag tggcattcta ccgaggggtt ttatggcagg cacattttaa agggtttgaa    23520
aggggcatat cagacatctg ccccacttgt cttcagagcc cctggctgtt gtcatttccc    23580
tgggtgtcca gagctgcctt tagaaaatgg cctgttgggc atttcagaat caccatttca    23640
cagactgttc cttatcttgg gtaacctgca ctgaagcaga agaaagattt tctatctttg    23700
taaaactccc tccttaagaa agccagcctt aggagagaca gctggtggat tctatttgag    23760
acagtctcag taacataacc ttttcttac gcaaaccttt tcctcagcat agtcatctct    23820
gggggcttgc ttgcgtcaac aggtaaaaag ggcaaccttg cttccgcagc cctctgagga    23880
gcagagccat cataacttga gaaattcagc aactccaagc aggaagccaa tggaggtgat    23940
aatagaacaa attatttttt tacacctccc tcccacacat cgaaatctcg agctagaact    24000
tcggtgctgg agcctgggtg ggtgtcttgt tagtaatccc ttggcccaac cagcagcgcc    24060
gtggtcctta aggcagacag gaagtctttt cagtttcttc ccttcatctc agcaatctct    24120
tcattaccct aaagttagcc agggtaattc cttacttgca agaaaattat gtaaaactac    24180
tttcacagag aacatctcgg gtaagtctcg catatgagtc agaaaatata aatcgcattt    24240
tacagatggg gagccaaatg acttgcccga ggacaaatct attaagtagc agttagaaa    24300 tttgaaccca gaactaagtc cagcacactt tccattttaa agacccatcg ttttcctcaa    24360
agtgtaaatg tggacaccaa ctcacaggta tcaaatctag ttcaacagtg agtgcaaact    24420
acatattaag cattttttgt gcaagtagtt caaatggcta aggccaggat gtcttcatat    24480
ccttgggctg aagaggcagc caaatgtcaa tctgaaggca aagggaatt ttgtatgaga    24540 cagaatttct aaatatgcca gaccaaacac aatggacccg atgattaatg ggccagcatg    24600
attcacagtg attttgaaac tttgtttttt atagacagca tttcgtttgg gaatctcaga    24660
aaagaaaata ttcgtagtgg gagtacttca tccccagaaa aggcatcttg ctgccagaat    24720
tatagagaag ttgcatatag agggtgaact aaaatatcag cagatggcaa acatccgcct    24780
```

-continued

| | | | | | |
|---|---|---|---|---|---|
| gtggtttaga | ggagaaagta | ggcaatcgaa | tcagctgagt | ttcctggtca | tagcagatgc | 24840 |
| agcctttggt | acagttaacc | cccaagacag | gcccacactc | ctcacgtgtt | ctccctgcct | 24900 |
| ttctctcctt | cctgacgtca | tccagacgag | cgctgacctg | cacaatgact | gcacggagac | 24960 |
| gcacacaggc | acctcggcct | ctgcacctct | ggctgctggc | atcttcgctc | tggccctgga | 25020 |
| agcaaagtaa | ggcccagaaa | gcttctaatc | acctttacaa | aggctgattc | tccttatttt | 25080 |
| taataacact | ttttttttctg | aatacatggt | tacaggagaa | attttggaat | actgcaaata | 25140 |
| aagataagct | ctttcctgcc | acttcgaggt | cactaaccat | agttaacatc | tcaatgtaga | 25200 |
| tttaatacac | acacatctta | caaaattggg | atcttaatat | agacgttatt | ttgtaatctg | 25260 |
| tttttaaaac | ccattctaca | atatattaaa | catactttct | cctgtctaaa | tcaatatgct | 25320 |
| ttgacccttta | aaactcatgc | tatccctcaa | atcttcttcc | cactcagcta | caacgccttt | 25380 |
| tgtttattct | cttccagcag | gattttgttt | aaatagtttc | cagtgggcag | tattaggaac | 25440 |
| aagtttaaaa | aactccttct | tttgaatatg | taagcctagt | cctggagctg | atataaccac | 25500 |
| atcagggggac | atgagattta | aaggcaggag | ttttatattt | tcacagtgtt | ccattgtata | 25560 |
| aacacaaatt | tccttaaagt | catctaatca | tgcttaaaca | ccattgtcag | taaatattag | 25620 |
| ttgtcatctc | tgacaatttc | ctcaggataa | acactcagaa | ttggaatttc | tgggtcaaag | 25680 |
| ggcaagcatg | ttttaatgat | ttttatatat | attgacaaga | tgctgccttg | aatgactata | 25740 |
| ccattttata | ttccctccag | gaatatatgt | gtgaaagtgc | cagtttccaa | acccttgtc | 25800 |
| aaaactactt | ttattatctt | ttaaaatatt | tgctatgttg | ataggtgaaa | atggtatctc | 25860 |
| attttaatat | gcttgtattt | aattactaat | gaagctcaat | atttcatacc | cttcagctct | 25920 |
| ttgtcttctg | gggttgcttc | tttatggcct | tagttttgtt | ttatggcctt | ggttcacaaa | 25980 |
| agctagatgc | tttataagtt | tgacatttac | ctttttaattt | gtttctatgt | aattttttaat | 26040 |
| gaaatgtagt | taatatgtat | gtagttatgt | ttgtcagtct | gtttctttaa | ggcttcttcc | 26100 |
| tttgcttttta | tgctcagaaa | aaatcttcac | aaccccaaat | tagataaaca | ttaattatat | 26160 |
| gtcttttatt | atggtttctt | taccatatt | aaattctaaa | tccctctgga | attttatttta | 26220 |
| gtgtatgatg | ttaaaaaaag | atttaactttt | tttttttctca | taattaccca | atagtccaat | 26280 |
| acttaacaca | gaggaaaaaa | attgaactgt | ctcacactgc | acatcacagc | ttttttatgtg | 26340 |
| tcctcattcc | tgcttttctga | tgtgtggtga | cagtgaatct | tgaaatgtca | agtcaggtgc | 26400 |
| tatggttgca | tattagaaga | agtgattaaa | cttgtaaatt | actattatcc | ttcctaataa | 26460 |
| ggagattatc | ctagaataaa | ttacatattc | tctagagaga | gaacaaagca | gtgtccttat | 26520 |
| gtcatattca | gtagactcag | ttcgtaataa | cagaaaggaa | aaatatcttg | gcctttgcca | 26580 |
| tgactggaaa | agccctgagg | ttcctgagcc | tttgtccagg | agagtccagt | ttatctctag | 26640 |
| gatccctggg | gcttcctatg | gagatggggt | atattcctgg | gtatctcggc | tgtgagatgg | 26700 |
| ctacagtggc | taagcaagga | agtctagcaa | ggctcttacc | aagagtccac | ctacttggag | 26760 |
| gggctggcaa | gatgtttggt | aagggaagaa | gtaaattcag | gtgctcaatt | agaaatagat | 26820 |
| attgggccct | ccagaaaagc | tatgttcaga | atctaagttc | acttataata | ggaagtagat | 26880 |
| ggacaaaaga | caaaaatcta | tgaacacaag | ctgagactgg | catcagcaga | tccaaattaa | 26940 |
| ccgagaaata | attgtccaag | cagtgaaaat | tgcaaggaac | acctggcttc | aagttctagc | 27000 |
| tctaccacta | gctatgtggc | cttcggcaag | ttaatttact | tgtggggttc | agtctttcca | 27060 |
| tctataaaat | gaaggggtca | aacgagacct | tttttttacaa | acttcttctc | ttcctaagat | 27120 |
| tctcagagtt | gagattgaaa | atgtcagcct | gcataggtaa | tccaacatga | attgttgggg | 27180 |

```
tcagtgatga ggggtctgga ctggaagaaa atagggtcct atggattata ggatcctgtg    27240
caacagactt attatattta agatttcaaa acacagacta ctaccccagg gagctgttaa    27300
aagaaagcaa tcttaaaatt ttatgtctag agcctttctt ctctatccaa cacctgtcag    27360
atgcatgtaa atataactag ccgtgcctag cccatccttg tatagtgacc aatatagtag    27420
aaatatccat ctgctgaaca gaagtaatgc caattttatg taagagctga aattgtaaaa    27480
gtgcaatcct tggtttctaa aacctcaagg cttcttttc tgtatagtgg aaaatgatcc    27540
tatacagaaa ataatccttt ccttttcttt ttcttttgga cagtgtct cactccgtca       27600 cccaggctgg agtgcagtgg caagatctcg gctcactgca acctcaaccc ctccggttca    27660
agaaattctt atgcctcagc ctcctgagta gctgggatta caggcatgtg ccaccatgcc    27720
tggctaattt gatccttctt ttttctatgt aggagaaaat gatctaggaa tgatctagcc    27780
tcattaatct cagtctctga tggacagtct ctaaagcagg tgtttcattt ctgtgaaaca    27840
ctcagatggg ttccaagggg tccatgaatc tctttgcaac taaatgcaga attgcttata    27900
aatgtatgta tggcatattt ctggggaatg gcttataggt ttcaccagat tctcagtgtt    27960
cgtgatttaa gagatattaa gagtctatga tctcccaggt gcttatcata agaatttaat    28020
tcccttcatt ttgactcaat tcatcagtaa gataagtatg actgatctat cttaacattt    28080
atatccttac tgccaaggta catagaggtt attaagattt ctgttctcaa ttgaacattt    28140
ttctgaactc tattcaattg tctataccaa agctgaatgc cagaatttct agacatgtga    28200
ccaagcttta tcccaaggca ctcaagaatg agaaaatcat ttaatcatgt gccatcccac    28260
aggaacaact atggagactg aagagccctt gcctaaactt atcaagaata atggcaccca    28320
atattgatta ggttcttact gtagaccaga cacagctggc ctctttatat acaatattaa    28380
ttataacgct tacaacattc ttatgacata gaaattatta atttcaccta taaatgggaa    28440
aaaataaggc ttagagaggt tgagatatat aaccaagatc ccacaaagaa attcaaactc    28500
aagtctctct gactgcaaag tctgtgctat cagcaaccac accttgcagc ctcccacagc    28560
cctgtgaggg agaggcaatg ttgaatggca gcctatcatc tcctcaaata aggagggtt    28620 cggaagattg aggctgataa atgaacatgc atttatgagt ttcttataag ttttctgtca    28680
caagcagact actcaatatg ctgtgttaaa tgttatatag ccagagtatt ggggaatggg    28740
aggagaaaag gaaggagaa ggaatggttt ctggctgaat atgcacaaag aaatactttc     28800
cttccccaaa gcgatgtttc tcaagtacca gcatatatag tcatcacctg gggagtttat    28860
ttaacatgca ggttcccagg tcattttgcc agcaactatt cagaccttgt atctgcctag    28920
gagtttctgg tattcaacct aggaattcct ttttaacaa atctcccagg cacttttaa      28980 tgctagtaat accttaacca gttttgaga aacaaatgct ataaagagtt acttttacca     29040
ctgtgttttc ctacaacctc atccacctgt gtttgtgtag aaacccatta gggtagttag    29100
taggtgtatc ttggagataa atatactaag agaagaagga attccttgca taatgtttg     29160 tggcactatt attattatgt agtgagtata cctaagaaag ctgtagaaaa tagcctcagc    29220
cttctgagga gagatcaaaa gaatcagaat aattttaat aggtgaggaa aattctgaag     29280
tgaaccattg aatcccttca caccttgga aatattaaac aaacagataa gccaaacttc     29340
tggtcttatt aaaacctgga gaaagagaaa tggactttca atgctgcatg aaacctttgg    29400
aaaaaaatca caacaaaaaa gtcttgactt agtgggttgt gaaatgttag aaagtccaag    29460
ttagaaaaat tttaagatct aggctaattt aggtatgatt agaggctgaa ccagatagct    29520
```

```
cctaagactt ttcactctgg aattttgtct ccaaattaca ttacctacat ctcttctaat    29580
tagaagcaat gcttaattcg gtgtttaatt ccatacccttt attttctgta aacatatctt    29640
tgattagcca ctcaatgcag tgtttaaaaa tttaattatc gtggatgtca ttgagcacaa    29700
attaacaaag gaaggctgtc aggaatgagt tgcactgttg ttagcagctc cttttcattt    29760
atgaaataca agcacacgaa tgaacaataa ctctgttaga aaatacacc ggggcctgtc     29820 atggggtggg gtgagtggag agggatagca ttaggagata tacctaatgt aaatgacgag    29880
ttaacgggtg cagcacacca acatggcaca tgtgtacata tgtaacaaaa ctgcacgttg    29940
tgcacatgta ccctagaact taagtataa aataataaaa aaaagaaaaa taggtttttc     30000
taattgcatg acaatgaagc tccttaatat tttgcagaga ctagataaag gaaatttta    30060 aaacaaaata acctgcaact gcatataaaa taaatgctct actacagaaa cataggacac    30120
acatgctata tgtgataatc atgattatca gcaccttgcc ttaagcctcc tcagtacgct    30180
tcctccttcc tgcctccaca catgcacctg cacatactga tgatccaaac ggaaaactgg    30240
tgtgttgccc attgactgcc ttgataagag gcttttacct aaaactcctt ttaaaagact    30300
ggaaggaagc aagcatttca ataaaatgtc ctattctatt tacaagtgta ccaggtgatc    30360
atgaggcaag cattctggga ctcactgagg atccctaaac tggtgtcctt ccaaggcctc    30420
tctgtcagtc actctccagg gtaaagtggt atgtttgtcg ggagctcagc tcaggtgagc    30480
tgagctgtca ggtgtggagt agcctattaa ttcaacaagc caaaaatgaa agcattgagc    30540
ctttagtcac ttactgctat gacataagca agagtctgaa accggagaaa acacttactc    30600
gccctgttcc tggcatactg gttgagtggc tcagcacaga cttgagggtc atctcactgc    30660
tgagggagcc ccgaacaaaa ggctctggca attttatgga ctctgaggtg tgaggcgggg    30720
agggaccaag agagtacggg agtggagaag caccaggcac tgagtctgag tgaggaaagt    30780
gtctagatgt ttcccctcct ctctccacga ggaggcctga ccaagggacc taggaaggaa    30840
agctctcacc agctaggaat gtcaatatgg aaagaacatg aggggccagg gggcctgcgg    30900
ccttcatgga aactcctctc agaggctgcg agccacaaac tgcacactgt gtctgcatgg    30960
ggagggcagc ttccccgtgt gtcgtgccag gtaagacctt tgaaatcgcc tatggtcagg    31020
cctgaaaaat cacacacggt ttttaactag gagccggact cttcagtgtt taggaatgtc    31080
cactgcctct ttcttgtcac aggggattac tgagccagta catgatgggc tctggggaga    31140
aggcagcaaa gtgagccaga ctcccctgat gattgttctc caaccgagtg ctgagacagg    31200
aaccttgagg agtaaaaact gggcatctac ttattacata atgcttgatt ggcttcaggg    31260
aacaatacag gtctcaaagt cgaggaaaag tttgagaatc tgactgatga ctaggagcaa    31320
tatgttttaa aattatattt ggggctagtt agcacttagg catgttcagt ctctgaacca    31380
accatatctg ctgagcatat ataccctgtg cccagcattc ttctgggtgc tacacatcag    31440
agaacaagat ggataaagat ctcaccactt ctcatggtta aattagaacc agggagagag    31500
acatcaacaa aacacaatac aaatgagttt cccgcatgtt agaagccat aagtgcaatg     31560 gaaggagaat atgcacatat agcagaataa aagagctcgg gaccatgtgg gagagtggaa    31620
attttaaata ggctgatcaa ggaaggcctc atcatagtat aatagatcca acaatccctt    31680
atatctctga tttatcttta tagtgttgct aaattaatct tactaagact tatgatttta    31740
ctatttcctt actcaaaaat tctcactgat tcccactgcc caaaagataa agtataagct    31800 cccttctctgg catgccaggt tctcatcgct ctggcccaat actcctcact gcctctccc    31860 tgccccagca aaccaggctg tcatctggcc acacctgtac tgtcccactt tggtgctttt   31920
```

-continued

| | |
|---|---|
| gctccagtgg ccttcttctc tatctccact tcttaacact ctaccccctg tcaaagtcca | 31980 |
| gctcaaatat ttctccccca caaagttttc ctagatcttt ctattccatg gaaattcttt | 32040 |
| ctactctaaa ctcccacaat gcgttaagct atgaatatag cactcaccag atagaattat | 32100 |
| aaaagcctta attctttta ctggattgta aacttcttt tttttttttt tttttttttt | 32160 |
| ttgagacgga gtcccgctct ttagcccagg ccggattgca gtggcacaat cttggctcac | 32220 |
| tgcaagctcc gcctcccagg ttcacgccat tctcctgcct cagcctcccg agtagctggg | 32280 |
| actacaggcg cccgccaccg cgcccggcta atttttgta tttttagtag agacggggtt | 32340 |
| tcaccgtgtt agccaagatg gtctcgatct cctgaccttg tgatccgccc gcctcggcct | 32400 |
| cccaaagtgc tgggattaca ggcgtgagcc accgcgccca gcctggattg taaacttcta | 32460 |
| aaagacaaga accacatcct tgaatatccc catggtatta gcatagtgcc ttgcaagagt | 32520 |
| gagctcaaat agctaagagt ttcttgacgc ttttgataga taaagaaaaa ggcaatacat | 32580 |
| gtttacagca ggtagccagt ctgtgtcttt aacatctcac tcttcctaag aaggaagtca | 32640 |
| aggcctcgtc tgtgggttca taatgctgaa agtgctaagg cttttaatgg acagcatgag | 32700 |
| actggagggc ataagaaaag tgttaccatt taaaatgttt gctcagttaa atggaagcaa | 32760 |
| ttagaaatta aggacaaagt tttatacttc tatattgctg aggactgaat tttactcata | 32820 |
| gtaaaagctt atatgctctg gagagaagtc ataacttata tgttacaggg agaagttttc | 32880 |
| agctctgtat tctgaattct gaatgaaaag atatatgaac agtaatagac actagaataa | 32940 |
| cataactaca atagcaaaag gcacttcata atccctgaat ggagatgctt attgttagca | 33000 |
| cttgcttttg caaggaaact tcattttct ctgaaagaca ctttgggtca cttcccctcc | 33060 |
| agcccaaatc tcacctggcg agatatgcag cacctggttg tctggacctc tgagtatgac | 33120 |
| ccgctggcca ataaccctgg atggaaaaag aatggagcag gcttgatggt gaatagtcga | 33180 |
| tttggatttg gcttgctaaa tgccaaagct ctggtggatt tagctgaccc caggacctgg | 33240 |
| aggagcgtgc ctgagaagaa agagtgtgtt gtaaaggaca atgactttga gcccaggtaa | 33300 |
| gtatctcctg gaattttaaa cacatgtgtg cccatggcat aatttcatta ctatgtttgc | 33360 |
| cattctgcct gattttttg tatctaccct tctgaagtag atggaggtgg aattttctag | 33420 |
| tgttctctgt gggtatccat ggggactaac taagagacca aagctctaga accatgtta | 33480 |
| accatttgca tgttcctctt gtagtccacc taccacatag cacccagtct aagatgcacc | 33540 |
| attgttttat tgtcaattaa actgtgatca accacccatc agttttaaga ttcattctaa | 33600 |
| attcaatgtt taactatttt tttaaaatgc atcttagggt tgatgaaatg cagtacttgc | 33660 |
| caaccagttt tacccaaaat ctgcttgcaa aatagccttg cttcatgcca cagtgctgtg | 33720 |
| tgattcatgg cttttcttcc atgagggatt ctttatcata cacttactta gactccctct | 33780 |
| agcacaccac atcttgtcac agaagaaatt tctactagga gtgttttgta atttctatca | 33840 |
| aagcaatcaa aataatactg aagacctgct cacacaaaat atccaaggat gggaggcttg | 33900 |
| gggcatgcct tcagaaggcc ttctagataa aatcattttt ttcttaagag gggcttttg | 33960 |
| atgggtctac aataaatctg cctgaatttg actccacagc aaatagcatt gtatttaagt | 34020 |
| attagtgccc cttaccattt tcttatgcat taaaattcat gtatacataa ttctgaatta | 34080 |
| ggttctacac atcacaggga gtgacaaaaa gcttagttga gcatctagtc aagattgatg | 34140 |
| catgcagata tgcataaaat gcaaggaagt ttggatatac tttattcaat gctgattctt | 34200 |
| taatgtatt agagccctga aagctaatgg agaagttatc attgaaattc caacaagagc | 34260 |

```
ttgtgaagga caagaaaatg ctatcaagtc cctggagcat gtacaatttg aagcaacaat    34320
tgaatattcc cgaagaggag accttcatgt cacacttact tctgctgctg gtaaattaaa    34380
aaagttctaa gccatttata ttttttaagtg taagttgaat gattcaaata actgattgct    34440
tttgtttatt catagaacaa agtctcctaa tagatatttt caggtcttaa aaaacatgct    34500 tatttttttcc tttttcttgg tgttagatct ccctctgccc tgcccatttc cactgatcct    34560
ttgataagca gagaatgagg cccattcaaa taatgctaat taatacactt ttctgaagtc    34620
atgcattttc aaactgttta cttttccatt ttactgacct atcacttttc tcttagatag    34680
caaattagtg aaagttactc tgataattaa ccaaactcac agatatatcc gaaacataca    34740
aggagtccat tgaaaactgg gaattcagat cgattagagg agattgagaa gattaacaaa    34800
tttatcatag taacatgaat aaggccattt tatatgatgt atgaacattt gctttttcct    34860
gcgagggcac taattcagat aagatagtgg atgggaaaga gctcgtgaac cataagccat    34920
aatctaacca ggaggagcag tcccaatact cctttatgtt ttagcaggac tcaactgact    34980
aaatttggtt tctgtgggtg atatgtgagg aaagatgagc tatctctatg atcttcctcc    35040
tgaatattaa ttcttagagg tttggaatag gctctgttaa ttttgaagtt atgctttcta    35100
gatgtattgg aattaacctg aaatattggt ggaatgcttt tttaattgat agacctgcag    35160
ttatttaacc cttccacata gaactattat caattgatct agaaagggct gggacttaaa    35220
aatttacagg taacctgtct tttaatataa gagattgtta aattaatata tctttaagaa    35280
attaatacat taattaaata attatgatta ttaatgattg cataataaat taaataataa    35340
tttttatgtt taaatcatta tggagtcagg cacctactaa attttcaaga tttcctctca    35400
cacttcagaa atgatagttt cattaaaata ttttttagatt tttgactctc taattcaatt    35460
tgtaaatgta gttcgccgag ttttccttat ttaaataaac cttagtcaac attttcattc    35520
attcattcat tattttttcc acaatattta ttgaggcaaa taatattatt cattattata    35580
tatgccaggc aatgtgctaa gcactataga taaaaacatc atattttttc cttgtgagtg    35640
tctctatcct ggtcttatac taaaagagaa aattaggaga actcatcttt ttcagctttt    35700 atttcagtt atcagatgct agagtgtatc ctactatcag agctattagg acattcatta    35760 acttgtatt gtttcatagg aactagcact gtgctcttgg ctgaaagaga acgggataca    35820
tctcctaatg gctttaagaa ttgggactttc atgtctgttc acacatgggg agagaaccct    35880
ataggtactt ggactttgag aattacagac atggtaagtg tgaatgagag gatgaaaaaa    35940
cacaagctta cttttaaaca ttttgaagca cttttaaggt tgatttcatc attaattagg    36000
gccctaaaga attgtacccc ttcttagtag aagtaaggga aaagtagagt gtttcaagcc    36060
ctgaccactt ggttacgtag ataatattca aaaagaaaga ttaggcttca gccatactat    36120
aagaggggga aaaacactta tataaacaat gtgacagact gtgggacaaa tccaggtgtt    36180
cccatgtctg catgcagcca gccatctaac ctattcagcc aacaaaatca atcatattca    36240
caaagatact taaatgctca gaccaacttt ggtgtgacat tctgccagag tcacatctta    36300
aaggcatgct tatgattatt ctgcaatagc tatttagatg tagcttaatg tttggagaga    36360
tatcttattt aatatgactt ttttaaacag ttttagtcat gaaacaaacc gaaagcattt    36420
ctcatttctt tttcattctg tttactaaca ttctttgaca tccttctgta attttaacac    36480
acagtcacaa aaatgcaagt acagagcaaa agttagaaaa aagccaaata tagcttaatt    36540
atttattttt gcatcatttc tccaacattc tctgtaggtg agaatataaa tgaataatgt    36600
tttggctctg agttcttctg tgacaaaagt gtaataaata tcagcagtgt agaattatac    36660
```

```
gcctaaataa cttttttttt tttttttgag acggagtctt gctctgtcac ccaggctgga    36720
gttgcagtgg cacagtctcg gctcactgca acctctgcct cctgggttca agcgcttctc    36780
ctgcctcagc ctcccgacta gctggaatta caggtaccca ccaccaagcc tggctaattt    36840
ttgtattttt agtagaaatg gggtttcacc atgttggtca ggctggtctc gagctcctta    36900
cctcaggtga tttacccacc tcggcctccc aaagtggtgg gattacaggt gtaagccacc    36960
acacccggcc tagataactt tttgaaaata aatcatttaa agttcttgga gatgtcaatt    37020
aaattaatac aaattctata gtcgtttgtt acatttttt ctctgaggat agctttctcc    37080
taaagactgc taaaattgtg atttagaaat ggaagttgta aaatgtcctt ctctcataga    37140
gcaaaaaaag aatgttctta gcatctgggc ctgttcttga atttggcctc tattcttcaa    37200
ctcaatttca ccatcaggaa actaagaaaa tctatttacc aaggtgggat ttatttcatg    37260
tcaagtctgc aaaatctgac cttacacttc taaatttta aagatatttt agattttaac    37320
acattattta taattgttga gccttgaaaa ttatgactat tcccccaaat atgcaacttt    37380
ttgtaactga atttatagac ctcttattta tttatttttt gtcattgaac tttatagacc    37440
tcttttattt agtttttat tatactttaa gttctggagt acatgtacag agtgtgcagg    37500
tttgttacat aggtatacac atgccatggt ggtttgctgc acccatcaac ccatcatcta    37560
cattagatat ttctcctaat gctatccctc cccttgcccc ctactccctg acaggcccat    37620
tgtgtgatgt tcccctccct gtgcccatat gttcccactg ttcaactccc acttatgagt    37680
gagaacattc agtgtttggt tttctgttcc tgtgttggtt tgctgagaat gatggtttcc    37740
agctttatcc atgtccctgc agaggacatg aactcactct ttttatggc tgcatagtat    37800 tccacagtgc atatgtgcca cacaattttt aagggcttat taatgctaga ggttgtttat    37860
aatactccat agaggctgac tttttccca gtggaatgtt tctataagtt gataattggg    37920
aaatatattt atagaaggta cagtcagctt tccaagaaca catccaatat ggaaaagaag    37980
acttacatag agatttctga tttttaaatt aaatgtttga ttatgaagca atcagtttct    38040
aaactgttga acctacaaat tgtcaatttt tatagcaaga gtggatccaa tggtttcttt    38100
cacatgaaat gcacagaatc ttaaaatgag attttaacaa tgaaatcctt tttagctatt    38160
ttgaatgagt ttgttttata ttatctaaaa cacatactaa atgtaggtat gcttatttgt    38220
tagtctggaa gaattcaaaa tgaaggaaga attgtgaact ggaagctgat tttgcacggg    38280
acctcttctc agccagagca tatgaagcag cctcgtgtgt acacgtccta caacactgtt    38340
cagaatgaca aagaggggt ggagaagatg gtggatccag gggaggtctg tgtggctctg    38400
ttcttggcat gctctctttt gaactggggt agacaatgta gtcagtgaag ctgtacccaa    38460
cttccaagca ggaaataagt caaacatgga tggggaggaa aagaagtgat agtggtaaac    38520
tattcttttc cataggataa aactgtatt ttttcattca atattttatc cagaacttag    38580
aaatcacaat taatgaattc aaaagtatta aatttcctaa catgaatttt ctccacttat    38640
gacagataac aaatggaaaa aaaagttatc tttatgccca atcacatata tctaacattt    38700
gtactgtact ttgtttttaa gcattttcca cattgtctca ttaacctata atccctataa    38760
cctaggaagg atagacattc gtgtatccat tttgcagaaa gaaaaacaag gctcaaatgg    38820
ccaaatcatg taggcttctt tttattaatt cattaactga cacttcttgg caacaccaag    38880
gggagcgata gatcacactt tttctcaaaa aatttcagag gatagctaaa ataagtcgtt    38940
cacattcctg ggtttcagcc tgctatggct cctggcttcc ttctatcaga tggtgagaaa    39000
```

```
agcccacatt ttctttatct ctgtatccca gcatctagca cagtgcctca ggtgtaatag   39060
gtaggttttc agaattttca gaacgccctg ctctgaatag gtccagctct gagctgggtg   39120
ttttggaaga tacagaggca aagtacatat tcaagaaact tacacatgaa ctgtgaaggc   39180
ctcagcttga attctagttc catttatatt cttcaaagca gcttccctcc aggacctgag   39240
tcctgagtac ttttcttcac agtctgggaa gcaggttaac cttgtcagtg ttggaatatt   39300
gaaacacttc cacagcagtt ggccaaggtt ggcttctctg agctctccag ctccctcctc   39360
cccagcctag cacctcagtc tctcccctga ccacttctta cagctcagtg gctaaaaggg   39420
tagttctgaa agccagtgcc tccaggaagg cacacccatg ctaccgcaac cagtgggtgc   39480
cttctatatg acttgttaga tattttgata tcctctgctt cccaaaatgg attccatgac   39540
agcaggctga caagtaaaga aaaccaccat gtactgagta cttacctata cagtctcatc   39600
tagtcttcaa aaccaccaca aatggaggta ctcttattcc acctgacagg tgaagttgag   39660
ggagattaaa aaggttgtta aaggtacccc agagggtagg caaatgaggg ttgaagccca   39720
agtccatgtg gctcccagtc ttgaactctc tcccctcccc tcattgcctc tcaagcggca   39780
ggcagcgttc ctgtggtagg gttgcaacta gcttgcctgg ccataaataa tgaaccttct   39840
tccctttgtg gatggcattc tatgttttag gagcagccca cacaagagaa ccctaaggag   39900
aacaccctgg tgtccaaaag ccccagcagc agcagcgtag ggggccggag ggatgagttg   39960
gaggagggag ccccttccca ggccatgctg cgactcctgc aaagtgcttt cagtaaaaac   40020
tcaccgccaa agcaatcacc aaagaagtcc ccaagtgcaa agctcaacat cccttatgaa   40080
aacttctacg aagccctgga aaagctgaac aaaccttccc agcttaaaga ctctgaagac   40140
agtctgtata atgactatgt tgatgttttt tataacacta aaccttacaa gcacagagac   40200
gaccggctgc ttcaagctct ggtggacatt ctgaatgagg aaaattaaaa taagtgtgtg   40260
gtcccaagtt ggaaatattc atgcttcttc cttaccctgc gattttgcct gtgtctgaag   40320
tggttgtttt gtcatgaatt cttatgctta taatatcctt tgtggcacct tttctttttc   40380
tccctaaact gtacatgtga aggggatgag ctcaagcagg aagttcaact tccagaattg   40440
atcataggta tttcaaaaca catctttcct gtctgcacaa gtgaagtgtt ttgttctttc   40500
tggagtcaca gttgacaaaa agctcttaca ctacattaga acactgcatt agagcccatt   40560
tcaattctca aaagaaaagg caaaacctgg gatatcaatt aatttgaaaa cataatctgc   40620
aaagaatgag aaggagtcag aaactgtttc tgtagcttgt tccctgtctt gtccatgtgg   40680
ttcttcaaat tttgatgcca agaaagtatt tggtaggcct aatgaaggag ttcactgtaa   40740
gactcattcc ctagatcttt ctattccaaa gtgccactca ttcctgtagt caaaatctgg   40800
tcatgttggt caaaagctgg attatttaga tctagaaaca gatcttgaaa tctgaatgct   40860
ctggtttgag caattttcga acattctttg cctggtgcac tgtgtctgtg gtgccagagg   40920
cgtccgtgga tccagaggtg gttatgactc gtgctgcatg cctggtcttt cctctgtttc   40980
tccttctgaa agttttctat acctgtctcc tttctcagcc acaaaataaa tgttgggaga   41040
aatgatatat accactttcc cagaaaaaaa aaaacttaca cttgggactt ggcaaattcc   41100
tagtcacaat ttttttcagc agtaacagga aaccacttat cacatggaga cctaatgtaa   41160
taatagaaaa atactcataa tagggagaaa ccaagagaag ttttgttttt gttttttcc    41220 aactgtgttc attagaacag cgtgttctaa gtatttgaaa ctgaatgttt attccttgat   41280
actaaaagtt cttctccaat cctatcactg atagtgtcca aattctcacc aaattgctcc   41340
taagcttcaa atcagaagca gaaactggca ggccatggac cttaattgtc cctcaggtag   41400
```

```
attttgtttg gtatgcagaa tgttttaaa atatgagtgg ttattgaaaa tatgatgttt    41460
cacataaaac ctcattctcg gacccatctt tgctcatggc aacagttagc tggagctgag    41520
tagcagctgc ctgattagat gactctcagt ccccatggca ccctgctcca tgttacctag    41580
agcaggcact tgattccttg ctgggcagta tccaataggc atttgatttt gcccactcct    41640
acactaagcg aatgtgtaca aagtgtaaat gcattaggaa aaacaaacta cccgcatctt    41700
ctgttaggca ggatctgtac aataataatt atgagtttgc ttatgtaatc tcacctcacc    41760
tggatgatca ctaatactaa ttcatttatt actaacctttc tggcttcctt ctctcaatat    41820
gcttacaaag tctccagtca cctacaatgc tggctttctc ccactgagtt tgctgtttgc    41880 aattttttcca tgaagtttga acttcataag gtaattcatg gcattgaact ggttcatgaa    41940
aagaacacta gagtctgtca tttgctttgg cttgaagtat ggttggtaac acaaattttc    42000
acctgctctt ctaccatttg aatttgtgta gagggtgttt gcagagcaat gcccgtaatg    42060
cttagagaat gttctcctaa aagacttgcg gaatcactct gtccttggaa gtttcatata    42120
ttgtttgata tgaagtgtta gatagaattt ccaatattgg agcatatcaa aaagtattaa    42180
aactaaaaag gaccagagaa ttcttagatt ggcccggaaa ggccaataaa gagttagaat    42240
gaaaactcat tacttttcca ttcccaatct agtgctagat gtataaatct ttcttttgat    42300
tcttcctaac aaaatatttt ctgggttaaa accccagcca actcattggg ttgtagccaa    42360
aggttcactc tcaagaagct ttaatattta aataaaatca tattgaatgt ttccaacctg    42420
gagtataata ttcagatata aaacagtttt gtcagtcttt cttagtgcct gtgtggattt    42480
ttgtgaaaat gtcaaagaga aacttatat actatttccc ttgaaatttt aaactatatt    42540
ttctttacag gtatttataa tataccaatg cttttatcaa acagaatttt aaagagcata    42600
ataaattata ttaaagaacc aaaagttttc ctgagaataa gaaagtttca cccaataaaa    42660 tattttgaa aggcatgttc ctctgtcaat gaaaaaagt acatgtatgt gttgtgatat    42720
taaaagtgac atttgtctaa tagcctaata caacatgtag ctgagtttaa catgtgtggt    42780
cttggtattc ttaagggaac ttccacatta tacatttgat gtattgacca gaatatgtaa    42840
aatatgctta taaatcagaa aaataaattg tttctcacta agtcaaaaga aaaaaagctc    42900
atgtttccac cacaaa                                                    42916
```

<210> SEQ ID NO 2
<211> LENGTH: 2394
<212> TYPE: DNA
<213> ORGANISM: homo sapien

<400> SEQUENCE: 2

```
guucguugca acaaauugau gagcaaugcu uuuuauaau gccaacuuug uacaaaaaag     60
uuggcaccau ggagcgaaga gccuggaguc ugcagugcac ugcuuucguc cucuuuugcg    120
cuuggugugc acugaacagu gcaaaagcga aaggcaauu ugucaaugaa ugggcagcgg    180
agauccccgg gggcccggaa gcagccucgg ccaucgccga ggagcugggc uaugaccuuu    240
ugggucagau ugguucacuu gaaaaucacu acuuauucaa acauaaaaac caccccagaa    300
ggucucgaag gagugccuuu cauaucacua agagauuauc ugaugaugau cgugugauau    360
gggcugaaca acaguaugaa aaagaaagaa guaaacguuc agcucuaagg gacucagcac    420
uaaaucucuu caaugauccc auguggaauc agcaauggua cuugcaagau accaggauga    480
cggcagcccu gcccaagcug gaccuucaug ugauaccugu uuggcaaaaa ggcauuacgg    540
```

-continued

```
gcaaaggagu uguuaucacc guacuggaug augguuugga guggaaucac acggacauuu    600
augccaacua ugauccagag gcuagcuaug auuuuaauga uaaugaccau gauccauuuc    660
cccgauauga ucccacaaac gagaacaaac acgggaccag augugcagga gaaauugcca    720
ugcaagcaaa uaaucacaaa ugcggggu ug gaguugcaua caauuccaaa guuggaggca    780
uaagaaugcu ggauggcauu gugacggaug cuauugaggc caguucaauu ggauucaauc    840
cuggacacgu ggauauuuac agugcaagcu ggggcccuaa ugaugauggg aaaacuguggg   900 aggggccugg ccggcuagcc cagaaggcuu uugaauaugg ugucaaacag gggagacagg    960 ggaaggg guc caucuucguc ugggcuucgg gaaacgggg g cgucaggga gauaauugug    1020 acgugaugg cuacacagac agcaucuaca ccaucuccau cagcagugcc ucccagcaag     1080 gccuauccc c cugguacgcu gagaagugcc ccuccacacu ggccaccucu uacagcagcg    1140
gagauuacac cgaccagaga aucacgagcg cugaccugca caaugacugc acggagacgc    1200
acacaggcac cucggccucu gcaccucugg cugcuggcau cuucgcucug gcccuggaag    1260
caaacccaaa ucucaccugg cgagauaugc agcaccuggu ugucuggacc ucugaguaug    1320
acccgcuggc caauaacccu ggauggaaaa agaauggagc aggcuugaug gugaauaguc    1380
gauuuggauu uggcuugcua aaugccaaag cucugguaga uuuagcugac ccaggaccu     1440 ggaggagcgu gccugagaag aaagagugug uguaaagga caaugacuuu gagcccagag     1500
cccugaaagc uaauggagaa guuaucauug aaauuccaac aagagcuugu gaaggacaag    1560
aaaaugcuau caaguccccug gagcauguac aauuugaagc aacaauugaa uaucccgaa    1620 gaggagaccu ucaugucaca cuacuucug cugcuggaac uagcacgugg ucucugcgcu     1680
aaagagaacg ggauacaucu ccuaauggcu uuaagaauug ggacuucau g ucuguucaca    1740 cauggggaga gaacccuaua gguacuugga cuuugagaau uacagacaug ucuggaagaa    1800
uucaaaauga aggagaauu gugaacugga agcugauuuu gcacgggac ucuucucagc      1860 cagagcauau gaagcagccu cgugucguaca cguccacau cacuguucag aaugacagaa    1920
gaggggugga aagaugguug gauccagggg aggagcagcc cacacaagag aaccccuaagg   1980 agaacacccu gguguccaaa agccccaacga gcagcagcgu agggggccgg agggaugagu   2040
uggaggaggg agcccccuucc gaggccaugc ugcgacuccu gcaaagugcu uucaguaaaa   2100
acucaccgcc aaagcaauca ccaaaagaagu ccccaacgc aaagcucaac aucccuuaug    2160 aaacuucua cgaagcccug gaaaagcuga acaaaccuuc ccagcuuaaa gacucugaag     2220
acagucugua uaaugacuau guugauguuu uuuauaacac uaaaccuuac aagcacagag    2280
acgaccggcu gcuucaagcu cugguggaca uucugaauga ggaaaauuug ccaacuuucu    2340
uguacaaagu uggcauuaua agaaagcauu gcuuaucaau uguugcaac gaac           2394
```

<210> SEQ ID NO 3
<211> LENGTH: 2394
<212> TYPE: DNA
<213> ORGANISM: homo sapien

<400> SEQUENCE: 3

```
guucguugca acaaauugau gagcaaugcu uuuuuauaau gccaacuuug uacaaaaaag     60
uuggcaccau ggagcgaaga gccuggaguc ugcagugcac ugcuuucguc cucuuuugcg    120
cuuggugugc acugaacagu gcaaaagcga aaaggcaauu ugucaaugaa ugggcagcgg    180 agaucccc gg gggcccggaa gcagccucgg ccaucgccga ggagcugggc uaugaccuuu    240 uggguucagau ugguucacuu gaaaaucacu acuuauucaa acauaaaaac caccccagaa   300
```

```
ggucucgaag gagugccuuu cauaucacua agagauuauc ugaugaugau cgugugauau    360
gggcugaaca acaguaugaa aaagaaagaa guaaacguuc agcucuaagg gacucagcac    420
uaaaucucuu caaugauccc auguggaauc agcaauggua cuugcaagau accaggauga   480
cggcagcccu gcccaagcug gaccuucaug ugauaccugu uuggcaaaaa ggcauuacgg    540
gcaaaggagu guuaucacc guacuggaug augguuugga guggaaucac acggacauuu    600
augccaacua ugauccagag gcuagcuaug auuuuaauga uaaugaccau gauccauuuc    660
cccgauauga ucccacaaac gagaacaaac acgggaccag augugcagga gaaauugcca    720
ugcaagcaga uaaucacaaa ugcggggug gaguugcaua caauuccaaa guuggaggca    780
uaagaaugcu ggauggcauu gugacggaug cuauugaggc caguucaauu ggauucaauc    840
cuggacacgu ggauauuuac agugcaagcu ggggcccuaa ugaugauggg aaaacugugg    900 agggggccugg ccggcuagcc cagaaggcuu uugaauaugg ugucaaacag gggagacagg    960
ggaagggguc caucuucguc uggggcuucgg gaaacggggg cgucaggga gauaauugug   1020 acugugaugg cuacacagac agcaucuaca ccaucuccau cagcagugcc ucccagcaag   1080
gccuaucccc cugguacgcu gagaagugcc ccuccacacu ggccaccucu uacagcagcg   1140
gagauuacac cgaccagaga aucacgagcg cugaccugca caaugacugc acggagacgc   1200
acacaggcac cucggccucu gcaccucugg cugcuggcau cuucgcucug gcccuggaag   1260
caaacccaaa ucucaccugg cgagauaugc agcaccuggu ugucuggacc ucugaguaug   1320
acccgcuggc caauaacccu ggauggaaaa agaauggagc aggccuugau gugaauaguc   1380
gauuuggauu uggcuugcua aaugccaaag cucuggugga uuuagcugac cccaggaccu   1440
ggaggagcgu gccugagaag aaagagugug uuguaaagga caaugacuuu gagcccagag   1500
cccugaaagc uaauggagaa guuaucauug aaauccaac aagagcuugu gaaggacaag   1560
aaaaugcuau caagucccug gagcauguac aauuugaagc aacaauugaa uauucccgaa   1620
gaggagaccu ucaugucaca cuuacuucug cugcuggaac uagcacugug ucuuggcug    1680 aaagagaacg ggauacaucu ccuaauggcu uuaagaauug ggacuucaug ucuguucaca   1740
caugggagga gaacccuaua gguacuugga cuuugagaau uacagacaug ucuggaagaa   1800
uucaaaauga aggaagaauu gugaacugga agcugauuuu gcacgggacc ucuucucagc   1860
cagagcauau gaagcagccu cgugguaca cguccuacaa cacuguucag aaugacagaa   1920
gaggggugga aagauggug gauccagggg aggagcagcc cacacaagag aacccuaagg   1980
agaacacccu ggugucccaaa agccccagca gcagcagcgu aggggggccgg agggaugagu   2040 uggaggaggg agccccuucc gaggccaugc ucgacuccu gcaaagugcu uucaguaaaa   2100
acucaccgcc aaagcaauca ccaaagaagu ccccaacugc aaagcucaac aucccuuaug   2160
aaaacuucua cgaagcccug gaaaagcuga acaaaccuuc ccagcuuaaa gacucugaag   2220
acagucugua uaaugacuau guugauguuu uuuauaacac uaaaccuuac aagcacagag   2280
acgaccggcu gcuucaagcu cugguggaca uucugaauga ggaaaauuug ccaacuuucu   2340
uguacaaagu uggcauuaua agaaagcauu gcuuaucaau uguugcaac gaac           2394
```

<210> SEQ ID NO 4
<211> LENGTH: 2394
<212> TYPE: DNA
<213> ORGANISM: homo sapien

<400> SEQUENCE: 4

-continued

```
guucguugca acaaauugau gagcaaugcu uuuuuauaau gccaacuuug uacaaaaaag    60
uuggcaccau ggagcgaaga gccuggaguc ugcagugcac ugcuuucguc cucuuuugcg   120
cuuggugugc acugaacagu gcaaaagcga aaggcaauu ugucaaugaa ugggcagcgg    180
agauccccgg gggcccggaa gcagccucgg ccaucgccga ggagcugggc uaugaccuuu   240
ugggucagau ugguucacuu gaaaaucacu acuuauucaa acauaaaaac caccccagaa   300
ggucucgaag gagugccuuu cauaucacua agagauuauc ugaugaugau cgugugauau   360
gggcugaaca acaguaugaa aagaaagaa guaaacguuc agcucuaagg gacucagcac    420
uaaaucucuu caaugauccc auguggaauc agcaauggua cuugcaagau accaggauga   480
cggcagcccu gcccaagcug gaccuucaug ugauaccugu uuggcaaaaa ggcauuacgg   540
gcaaaggagu uguuaucacc guacuggaug augguuugga guggaaucac acggacauuu   600
augccaacua ugauccagag gcuagcuaug auuuuaauga uaaugaccau gauccauuuc   660
cccgauauga ucccacaaac gagaacaaac acgggaccag augcagga gaaauugcca    720 ugcaagcaaa uaaucacaaa ugcggggulg gagulgcaua caauuccaaa guuggaggca   780
uaagaaugcu ggauggcauu gugacgga u cuauugagc caguucaauu ggauucaauc    840
cuggacacgu ggauauuuac agugcaagcu ggggcccuaa ugaugaugg aaaacugugg   900 agggccugg ccgccuagcc cagaaggcuu uugaauaugg ugucaaacag gggagacagg    960 ggaaggguc caucuucguc ugggcuuugg gaaacgggg cgucaggga gauaauugug    1020 acugugaugg cuacacagac agcaucuaca ccaucuccau cagcagugcc ucccagcaag   1080
gccuaucccc cugguacgcu gagaagugcc ccuccacacu ggccaccucu uacagcagcg   1140
gagauuacac cgaccagaga aucacgagcg cugaccugca caugacugc acggagacgc    1200 acacaggcac cucggccucu gcaccucugg cugcuggcau cuucgcucug gcccuggaag   1260
caaacccaaa ucucaccugg cgagauaugc agcaccuggu ugucuggacc ucugaguaug   1320
acccgcuggc caauaacccu ggauggaaaa agaauggagc aggcuugaug gugaauagcc   1380
gauuuggauu uggcuugcua aaugccaaag cucuggugga uuuagcugac cccaggaccu   1440
ggaggagcgu gccugagaag aaagaguguu uguaaagga caaugacuuu gagcccagag   1500
cccugaaagc uaauggagaa guuaucauug aaauccaac aagagcuugu gaaggacaag   1560
aaaaugcuau caagcccug gagcauguac aauuugaagc aacaauugaa uaucccgaa    1620 gaggagaccu ucaugucaca cuuacuucug cugcuggaac uagcacugug cucuuggcug   1680
aaagagaacg ggauacaucu ccuaauggcu uuaagaauug ggacuucaug ucuguucaca   1740
caugggagaa gaacccuaua gguacuugga cuuugagaau uacagacaug ucuggaagaa   1800
uucaaaauga aggaagaauu gugaacugga agcugauuu gcacgggacc ucuucagc    1860 cagagcauau gaagcagccu cgugugaca cguccuacaa cacuguucag aaugacagaa   1920
gaggggugga aagauggugg gauccagggg aggagcagcc cacacaagag aacccuaagg   1980
agaacacccu ggguccaaa agccccagca gcagcagcgu agggggccgg agggaugagu   2040
uggaggaggg agcccuuucc gaggccaugc ugcgacuccu gcaaagugcu uucaguaaaa   2100
acucaccgcc aaagcaauca ccaaagaagu cccaacugc aaagcucaac aucccuuaug   2160
aaaacuucua cgaagcccug gaaaagcuga caaaccuuc ccagcuuaaa gacucugaag   2220
acagucugua uaaugacuau guugauguuu uuauaacac uaaaccuuac aagcacagag   2280
acgaccggcu gcuucaagcu cuggugggaca uucugauga ggaaauuug ccaacuuucu   2340 uguacaaagu uggcauuaua agaaagcauu gcuuaucaau uuguugcaac gaac        2394
```

<210> SEQ ID NO 5
<211> LENGTH: 2394
<212> TYPE: DNA
<213> ORGANISM: homo sapien

<400> SEQUENCE: 5

| | | | | | |
|---|---|---|---|---|---|
| guucguugca | acaaauugau | gagcaaugcu | uuuuauaau | gccaacuuug | uacaaaaaag | 60 |
| uuggcaccau | ggagcgaaga | gccuggaguc | ugcagugcac | ugcuuucguc | cucuuuugcg | 120 |
| cuuggugugc | acugaacagu | gcaaaagcga | aaaggcaauu | ugucaaugaa | ugggcagcgg | 180 |
| agauccccgg | gggcccggaa | gcagccucgg | ccaucgccga | ggagcugggc | uaugaccuuu | 240 |
| ugggucagau | ugguucacuu | gaaaaucacu | acuuauucaa | acauaaaaac | caccccagaa | 300 |
| ggucucgaag | gagugccuuu | cauaucacua | agagauuauc | ugaugaugau | cgugugauau | 360 |
| gggcugaaca | acaguaugaa | aaagaaagaa | guaaacguuc | agcucuaagg | gacucagcac | 420 |
| uaaaucucuu | caaugauccc | auguggaauc | agcaauggua | cuugcaagau | accaggauga | 480 |
| cggcagcccu | gcccaagcug | gaccuucaug | ugauaccugu | uuggcaaaaa | ggcauuacgg | 540 |
| gcaaaggagu | guuauacacc | guacuggaug | augguuugga | guggaaucac | acggacauuu | 600 |
| augccaacua | ugauccagag | gcuagcuaug | auuuuaauga | uaaugaccau | gauccauuuc | 660 |
| cccgauauga | ucccacaaac | gagaacaaac | acgggaccag | augugcagga | gaaauugcca | 720 |
| ugcaagcaaa | uaaucacaaa | ugcggggung | gaguugcaua | caauuccaaa | guuggaggca | 780 |
| uaagaaugcu | ggauggcauu | ugacggaug | cuauugaggc | caguucaauu | ggauucaauc | 840 |
| cuggacacgu | ggauauuuac | agugcaagcu | ggggcccuaa | ugaugauggg | aaaacugugg | 900 |
| agggccuggg | ccggcuagcc | cagaaggcuu | uugaauaugg | ugucaaacag | gggagacagg | 960 |
| ggaagggguc | caucuucguc | ugggcuucgg | gaaacggggg | gcgucaggga | gauaauugug | 1020 |
| acugugaugg | cuacacagac | agcaucuaca | ccaucuccau | cagcagugcc | ucccagcaag | 1080 |
| gccuauccc | cugguacgcu | gagaagugcu | ccuccacacu | ggccaccucu | uacagcagcg | 1140 |
| gagauuacac | cgaccagaga | aucacgagcg | cugaccugca | caaugacugc | acggagacgc | 1200 |
| acacaggcac | cucggccucu | gcaccucugg | cugcuggcau | cuucgcucug | ccccuggaag | 1260 |
| caaacccaaa | ucucaccugg | cgagauaugc | agcaccuggu | ugucggacc | ucugaguaug | 1320 |
| acccgcuggc | caauaacccu | ggauggaaaa | agaauggagc | aggcuugaug | ugaauagac | 1380 |
| gauuuggauu | uggcuugcua | aaugccaaag | cucggugga | uuuagcugac | cccaggaccu | 1440 |
| ggaggagcgu | gccugagaag | aaagagugug | uuguaaagga | caaugacuuu | gagcccagag | 1500 |
| cccugaaagc | uaauggagaa | guuaucauug | aaauuccaac | aagagcuugu | gaaggacaag | 1560 |
| aaaaugcuau | caagucccug | gagcauguac | aauuugaagc | aacaauugaa | uauuccegaa | 1620 |
| gaggagaccu | ucaugucaca | cuuacuucug | cugcuggaac | uagcacugug | ucucuuggcug | 1680 |
| aaagagaacg | ggauacaucu | ccuaauggcu | uuaagaauug | ggacuucaug | ucuguucaca | 1740 |
| cauggggaga | gaacccuaua | gguacuugga | cuuugagaau | uacagacaug | ucuggaagaa | 1800 |
| uucaaaauga | aggaagaauu | ugaaacugga | agcugauuuu | gcacaggacc | ucuucucagc | 1860 |
| cagagcauau | gaagcagccu | cguguacaca | cguccuacaa | cacuguucag | aaugacgaaa | 1920 |
| gagggguggua | gaagaugguug | gauccagggg | aggagcagcc | cacacaagag | aacccuaagg | 1980 |
| agaacacccu | ggugccaaa | agccccagca | gcagcagcgu | agggggccgg | agggaugagu | 2040 |
| uggaggaggg | agccccuucc | gaggccaugc | ugcgacuccu | gcaaagugcu | uucaguaaaa | 2100 |

| | |
|---|---|
| acucaccgcc aaagcaauca ccaaagaagu ccccaacugc aaagcucaac aucccuuaug | 2160 |
| aaaacuucua cgaagcccug gaaaagcuga acaaaccuuc ccagcuuaaa gacucugaag | 2220 |
| acagucugua uaaugacuau guugauguuu uuuauaacac uaaaccuuac aagcacagag | 2280 |
| acgaccggcu gcuucaagcu cugguggaca uucugaauga ggaaaauuug ccaacuuucu | 2340 |
| uguacaaagu uggcauuaua agaaagcauu gcuuaucaau uguugcaac gaac | 2394 |

<210> SEQ ID NO 6
<211> LENGTH: 4815
<212> TYPE: DNA
<213> ORGANISM: homo sapien

<400> SEQUENCE: 6

| | |
|---|---|
| ggcaauuugu caaugaaugg gcagcggaga uccccggggg cccggaagca gccucggcca | 60 |
| ucgccgagga gcugggcuau gaccuuuugg gucagauugg uucacuugaa aaucacuacu | 120 |
| uauucaaaca uaaaaaccac cccagaaggu cucgaaggag ugccuuucau ucacuaaga | 180 |
| gauuaucuga ugaugaucgu gugauauggg cugaacaaca guaugaaaaa gaaagaagua | 240 |
| aacguucagc ucuaagggac ucagcacuaa aucucuucaa ugaucccaug uggaaucagc | 300 |
| aaugguacuu gcaagauacc aggagacgg cagcccugcc caagcuggac cuucaugugu | 360 |
| uaccuguuug gcaaaaaggc auuacgggca aaggaguugu uauccgcgua cuggaugaug | 420 |
| guuuggagug gaaucacacg gacauuuaug ccaacauga uccagaggcu agcuaugauu | 480 |
| uuaaugauaa ugaccaugau ccauucccc gauaugaucc cacaaacgag aacaaacacg | 540 |
| ggaccagaug ugcaggagaa auugccaugc aagcaaauaa ucacaaagc gggguuggag | 600 |
| uugcauacaa uuccaaaguu ggaggcauaa gaaugcugga uggcauugug acggaugcua | 660 |
| uugaggccag uucaauugga uucaauccug gacacgugga uauuuacagu gcaagcuggg | 720 |
| gcccuaauga ugaugggaaa acuguggagg ggccuggccg gcuagcccag aaggcuuuug | 780 |
| aauaugugu caaacagggg agacagggga aggguccau cuucgucugg gcuucgggaa | 840 |
| acgggggggcg ucaggagau aauugugacu gugauggcua cacagacagc aucuacacca | 900 |
| ucuccaucag cagugccucc cagcaaggcc uaucccccug uacgcugag aagugcuccu | 960 |
| ccacacuggc caccucuuac agcagcggag auuacaccga ccagagaauc acgagcgcug | 1020 |
| accugcacaa ugacugcacg gagacgcaca caggcaccuc ggccucugca ccucuggcug | 1080 |
| cuggcaucuu cgcucuggcc cuggaagcaa acccaaaucu caccuggcga gauaugcagc | 1140 |
| accuggguug cuggaccucu gaguaugacc cgcuggccaa uaccccugga uggaaaaga | 1200 |
| auggagcagg cuugauggug aauagucgaa uuggauuugg cuugcuaaau gccaaagcuc | 1260 |
| ugguggauuu agcugacccc aggaccugga ggagcgugcc ugagaagaaa gagugugu ug | 1320 |
| uaaaggacaa ugacuuugag cccagagccc ugaaagcuaa uggagaaguu aucauugaaa | 1380 |
| uuccaacaag agcuugugaa ggacaagaaa augcuaucaa gucccuggag cauguacaau | 1440 |
| uugaagcaac aauugaauau ucccgaagag gagaccuuca uguacacuu acuucugcug | 1500 |
| cuggaacuag cacugugcuc uuggcugaaa agaacgggga uacaucccu aauggcuuua | 1560 |
| agaauuggga cuucaugucu guucacacau ggggagagaa cccuauaggu acuuggacuu | 1620 |
| ugagaauuac agacauguc ggaagaauuc aaaaugaagg aagaauugug aacuggaagc | 1680 |
| ugauuuugca cgggaccucu ucucagccag agcaugaa gcagcccgu guguacacgu | 1740 |
| ccuacaacac uguucagaau gacagaagag ggugggagaa gaugguggau ccaggggagg | 1800 |
| agcagcccac acaagagaac ccuaaggaga cacccuggu guccaaaagc cccagcagca | 1860 |

```
gcagcguagg gggccggagg gaugaguugg aggagggagc cccuuccgag gccaugcugc    1920
gacuccugca aagugcuuuc aguaaaaacu caccgccaaa gcaaucacca aagaagcccc    1980
caacugcaaa gcucaacauc ccuuaugaaa acuucuacga agcccuggaa agcugaaca     2040 aaccuuccca gcuuaaagac ucugaagaca gucuguauaa ugacuauguu gauguuuuu    2100 auaacacuaa accuuacaag cacagagacg accggcugcu ucaagcucug guggacauuc    2160
ugaaugagga aaauuaaaau aagugugugg ucccaaguug gaaauauuca ugcuucuucc    2220
uuaccccgcg auuuugccug ugucugaagu gguuguuuug caugaauuc uuaugcuuau     2280 aauauccuuu guggcaccuu uucuuuucu cccuaaacug uacaugugaa ggggaugagc     2340
ucaagcagga aguucaacuu ccagaauuga ucauagguau ucaaaacac aucuuuccug     2400 ucugcacaag ugaaguguuu uguucuucu ggagucacag uugacaaaaa gcucuuacac     2460
uacauuagaa cacugcauua gagcccauuu caauucucaa agaaaaggc aaaaccuggg     2520 auaucaauua auugaaaac auaaucugca agaaugaga aggagucaga acuguuucu       2580 guagcuuguu cccgucuug uccauguggu ucuuucaaauu ugaugccaa gaaaguauuu     2640 gguaggccua augaaggagu cacuguaag acucauucccc uagaucuuuc uauuccaaag    2700
ugccacucau uccuguaguc aaaaucuggu cauguuqquc aaaagcugga uuauuuagau    2760
cuagaaacag aucuugaaau cugaaugcuc uggguugagc aauuuucgaa cauucuuugc    2820
cuggugcacu gugucugugg ugccagaggc guccguggau ccagaggugg uuaugacucg    2880
ugcugcaugc cuggcuuuuc cucuguuucu ccuucuucug aaaguuucu auaccugucu     2940 ccuuucucag ccacaaaaua aauguuggga gaaaugauau auaccacuuu cccagaaaaa    3000
aaaaacuuac acugggacu uggcaaauuc cuagucacaa uuuuuucag caguaacagg     3060 aaaccacuua ucauggag accuaaugua auaagaaa aauacucua auagggagaa         3120 accaagagaa guuguuuu uguuuuuuc caacugguguu cauuagaaca gcguguucua     3180 aguauugaa acgaauguu uauuccuga uacuaaaga ucuucccaa uccuaucacu        3240 gauagugucc aaauucucac caaauugcuc cuaagcuuca aaucagaagc agaaacuggc    3300
aggccaugga ccuuaauugu cccucaggua gauuugguu gguaugcaga auguuuuaa     3360 aauaugagug guuauugaaa auaugauguu ucacauaaaa ccucauucuc ggacccaucu    3420
uugcucaugg caacaguuag cuggagcuga guagcagcug ccugauuaga ugacucucag    3480
uccccauggc acccugcucc auguuaccua gagcaggcac uugauuccuu gcugggcagu    3540
auccaauagg cauuugauuu ugcccacucc uacacuaagc gaauguguac aaagguuaaa    3600
ugcauuagga aaacaaacu acccgcaucu ucuguuaggc aggaucugua caauaauaau    3660
uaugaguuug cuuauguaau cucaccucac cuggaugauc acuaauacca auucauuau     3720 uacuaaccuu cuggcuuccu cucucaauau gcuuacaaa gucccagucuc accuacaaug    3780 cuggcuuucu cccacugagu uugcuguuug caauuuuucc augaaguuug aacuucauaa   3840
gguaauucau ggcauugaac ugguucauga aagaacacu agagucuguc auugcuuug     3900 gcuugaagua ugguugguaa cacaaauuuu caccugcucu ucuaccauuu gaauugugu    3960 agagggugu ugcagagcaa ugcccguaau gcuagagaa uguucccua aaagacugc       4020 ggaaucacuc uguccuugga aguuucauau auuguuugau augaaguguu agauagaauu    4080
uccaauauug gagcauauca aaaaguauua aaacuaaaaa ggaccagaga auucuuagau    4140
uggcccggaa aggccaauaa agaguuagaa ugaaaacuca uuacuuuccc auucccaauc    4200
```

| | | | | |
|---|---|---|---|---|
| uagugcuaga | uguauaaauc | uuucuuuuga | uucuuccuaa | caaaauauuu ucugggUuaa | 4260 |
| aaccccagcc | aacucauugg | guuguagcca | aagguucacu | cucaagaagc uuuaauauuu | 4320 |
| aaauaaaauc | auauugaaug | uuccaaccu | ggaguauaau | auucagauau aaaacaguuu | 4380 |
| ugucagucuu | ucuuagugcc | uguguggauu | uuugugaaaa | ugucaaagag aaaacuuaua | 4440 |
| uacuauuucc | cuugaaauuu | uaaacuauau | uuucuuuaca | gguauuuaua auauaccaau | 4500 |
| gcuuuuauca | aacagaauuu | uaagagcau | aauaaauuau | auuaaagaac caaaaguuuu | 4560 |
| ccugagaaua | agaaaguuuc | acccaauaaa | auauuuuga | aaggcauguu ccucugucaa | 4620 |
| ugaaaaaaag | uacauguaug | uguugugaua | uuaaaaguga | cauuugucua auagccuaau | 4680 |
| acaacaugua | gcugaguuua | acaugugugg | ucuugguauu | cuuaagggaa cuuccacauu | 4740 |
| auacauuuga | uguauugacc | agaauaugua | aaauaugcuu | auaaaucaga aaauaaauu | 4800 |
| guuucucacu | aaguc | | | | 4815 |

<210> SEQ ID NO 7
<211> LENGTH: 5037
<212> TYPE: DNA
<213> ORGANISM: homo sapien

<400> SEQUENCE: 7

| | | | | |
|---|---|---|---|---|
| aagcgcuuca | cugagcgcuc | gccgccgccc | agccucuccu | cucgcgccuc cuagcucuuc | 60 |
| gcagagcaac | caggagccag | gaguggucua | gagcccgagg | gugggaaggg ggagucuguc | 120 |
| uggcuuuucu | ccuaucuugc | uucuuuuucc | ucuucccuuc | ccacucuugu ucaagcgagu | 180 |
| gugugagcua | uggagcgaag | agccuggagu | cugcagugca | cugcuuucgu ccucuuuugc | 240 |
| gcuuggugug | cacugaacag | ugcaaaagcg | aaaaggcaau | uugucaauga augggcagcg | 300 |
| gagauccccg | ggggcccgga | agcagccucg | gccaucgccg | aggagcuggg cuaugaccuu | 360 |
| uugggucaga | uugguucacu | ugaaaaucac | uacuuauuca | aacauaaaaa ccaccccaga | 420 |
| aggucucgaa | ggagugccuu | ucauaucacu | aagagauuau | cugaugauga ucgugugaua | 480 |
| ugggcugaac | aacaguauga | aaaagaaaga | aguaaacguu | cagcucuaag ggacucagca | 540 |
| cuaaaucucu | ucaaugaucc | caugugggau | cagcaauggu | acuugcaaga uaccaggaug | 600 |
| acggcagccc | ugcccaagcu | ggaccuucau | gugauaccug | uuuggcaaaa aggcauuacg | 660 |
| ggcaaaggag | uuguuaucac | cguacuggau | gaugguuugg | aguggaauca cacgacauu | 720 |
| uaugccaacu | augauccaga | ggcuagcuau | gauuuuaaug | auaaugacca ugauccauuu | 780 |
| ccccgauaug | aucccacaaa | cgagaacaaa | cacgggacca | gaugugcagg agaaauugcc | 840 |
| augcaagcaa | auaucacaa | augcggguu | ggaguugcau | acaauccaa aguuggaggc | 900 |
| auaagaaugc | uggauggcau | ugugacggau | gcauugagg | ccaguucaau uggauucaau | 960 |
| ccuggacacg | uggauauuua | cagugcaagc | uggggcccua | ugaugaugg aaaacugug | 1020 |
| gaggggccug | gccggcuagc | ccagaaggcu | uuugaauaug | gugucaaaca ggggagacag | 1080 |
| gggaaggggu | ccaucuucgu | cugggcuucg | ggaaacgggg | ggcgucaggg agauaauugu | 1140 |
| gacugugaug | gcuacacaga | cagcaucuac | accaucucca | ucagcagugc cucccagcaa | 1200 |
| ggccuauccc | ccuggacgc | ugagaagugc | uccccacac | uggccaccuc uuacagcggc | 1260 |
| ggagauuaca | ccgaccagag | aaucacgagc | gcugaccugc | acaaugacug cacggagacg | 1320 |
| cacacaggca | cccugccucu | gccaccucug | cgcucuggca | ucuucgcucu ggcccuggaa | 1380 |
| gcaaacccaa | aucucaccug | gcgagauaug | cagcaccugg | uugucggac cucugaguau | 1440 |
| gacccgcugg | ccaauaaccc | uggauggaaa | aagaauggag | caggcuugau ggugaauagu | 1500 |

-continued

```
cgauuuggau uuggcuugcu aaaugccaaa gcucuggugg auuuagcuga ccccaggacc   1560
uggaggagcg ugccugagaa gaaagagugu guuguaaagg acaaugacuu ugagcccaga   1620
gcccugaaag cuaauggaga aguuaucauu gaaauuccaa caagagcuug ugaaggacaa   1680
gaaaaugcua ucaagccccu ggagcaugua caauuugaag caacaauuga auauucccga   1740
agaggagacc uucaugucac acuuacuucu gcugcuggaa cuagcacugu gcucuuggcu   1800
gaaagagaac gggauacauc uccuaauggc uuuaagaacu gggacuucau gucuguucac   1860
acauggggag agaacccuau agguacuugg acuuugagaa uuacagacau gucuggaaga   1920
auucaaaaug aaggaagaau ugugaacugg aagcugauuu ugcacgggac ucuucucag    1980 ccagagcaua ugaagcagcc ucgugugua  acguccuaca acacuguuca gaaugacaga   2040
agaggggugg agaagauggu ggauccaggg gaggagcagc ccacacaaga gaacccuaag   2100
gagaacaccc uggguguccaa aagccccagc agcagcagcg uagggggccg gagggaugag   2160
uuggaggagg gagccccuuc ccaggccaug cugcgacucc ugcaaagugc uuucaguaaa   2220
aacucaccgc caaagcaauc accaaagaag uccccaagug caaagcucaa caucccuuau   2280
gaaaacuucu acgaagcccu ggaaaagcug aacaaaccuu cccagcuuaa agacucugaa   2340
gacagucugu auaaugacua guugauguu uuuuauaaca cuaaaccuua caagcacaga    2400
gacgaccggc ugcuucaagc ucugguggac auucugaaug aggaaaauua aaauaagugu   2460 gugguccccaa guuggaaaua uucaugcuuc uuccuuaccc ugcgauuuug ccugugucug   2520 aaguгguугu uuugucauga auucuuaugc uuauaauauc cuuuguggca ccuuucuuu    2580 uucucccuaa acuguacaug ugaaggggau gagcucaagc aggaaguuca acuuccagaa   2640
uugaucauag guauuucaaa acacaucuuu ccugucugca caagugaagu guuuuguucu   2700
uucuggaguc acaguugaca aaaagcucuu acacuacauu agaacacugc auuagagccc   2760
auuucaauuc ucaaaagaaa aggcaaaacc ugggauauca auuaauuuga aaacauaauc   2820
ugcaaagaau gagaaggagu cagaaacugu ucugагсu ugucccugu cuugcccaug     2880 ugguucuuca aauuuugaug ccaagaaagu auuugguagg ccuaaugaag gaguucacug   2940
uaagacucau ucccuagauc uuucuauucc aaagugccac ucauuccugu agucaaaauc   3000
uggucauguu ggucaaaagc uggauuauuu agaucuagaa acagaucuug aaaucugaau   3060
gcucugguuu gagcaauuuu cgaacauucu ugccgguug cacugugucu guggugccag    3120
aggcguccgu ggauccagag gugguuauga cucgugcugc augccugguc uuuccucugu   3180
uucuccuucu gaaaguuuuc uauaccuguc uccuuucuca gccacaaaau aaauguuggg   3240
agaaaugaua uauccacuu uccccagaaaa aaaaaacuu acacuuggga cuuggcaaau    3300
uccuagucac aauuuuuuuc agcaguaaca ggaaaccacu uaucacaugg agaccuaaug   3360
uaauaauaga aaauacuca uaauagggag aaaccaagag aaguuugugu uuuguuuuuu    3420
uccaacugug uucauuagaa cagcguguuc uaaguauuug aaacgaaaug uuuauuccuu   3480
gauacuaaaa guucuucucc aauccuauca cugauagugu ccaaauucuc accaaauugc   3540
uccuaagcuu caaaucagaa gcagaaacug gcaggccaug gaccuuaauu gcccucagg    3600 uagauuuugu uggцaugca gaauguuuuu aaaauaugag ugguuauga aaauaugaug    3660 uuucacauaa aaccucauuc ucggacccau cuuugcucau ggcaacaguu agcuggagcu   3720
gaguagcagc ugccgauuua gaugcacucu agcccuaug gcacccugcu ccauguuacc    3780
uagagcaggc acuugauucc uugcugggca guauccaaua ggcauuugau uugcccacu    3840
```

| | |
|---|---|
| ccuacacuaa gcgaugugu acaaagugua aaugcauuag gaaaaacaaa cuacccgcau | 3900 |
| cuucuguuag gcaggaucug uacaauaaua auuaugaguu ugcuuaugua aucucaccuc | 3960 |
| accuggauga ucacuaauac uaauucauuu auuacuaacc uucuggcuuc cuucucucaa | 4020 |
| uaugcuuaca aagucccag ucaccuacaa ugcuggcuuu ucccacuga guuugcuguu | 4080 |
| ugcaauuuuu ccaugaaguu ugaacuucau aagguaauuc auggcauuga acugguucau | 4140 |
| gaaaagaaca cuagagucug ucauuugcuu uggcuugaag uaugguuggu aacacaaauu | 4200 |
| uucaccugcu cuucuaccau uugaauuugu guagagggug uuugcagagc aaugcccgua | 4260 |
| augcuuagag aauguucccc uaaaagacuu gcggaaucac ucuguccuug gaaguuucau | 4320 |
| auauuguuug uaugaagug uuagauagaa uuuccaauau uggagcauau caaaaaguau | 4380 |
| uaaaacuaaa aaggaccaga gaauucuuag auuggcccgg aaaggccaau aaagaguuag | 4440 |
| aaugaaaacu cauuacuuuu ccauucccaa ucuagcucua gauguauaaa ucuuucuuuu | 4500 |
| gauucuuccu aacaaaauau uuucgggguu aaaaccccag ccaacucauu ggguuguagc | 4560 |
| caaagguuca cucucaagaa gcuuuaauau uuaaauaaaa ucauuugaa uguuccaac | 4620 |
| cuggaguaua auauucagau auaaaacagu uuugucaguc uuucuuagug ccugugugga | 4680 |
| uuuuugugaa aaugucaaag agaaaacuua uauacuauuu cccuugaaau uuaaacuau | 4740 |
| auuuucuuua cagguauuua uaauauacca augcuuuuau caaacagaau uuuaaagagc | 4800 |
| auaauaaauu auauuaaaga accaaaaguu uccugagaa uaagaaaguu ucacccaaua | 4860 |
| aaauauuuuu gaaaggcaug uuccucuguc aaugaaaaaa aguacaugua uguuguga | 4920 |
| uauuaaaagu gacauuuguc uaauagccua auacaacaug uagcgaguu uaacaugugu | 4980 |
| ggucuuggua uucuuaaggg aacuuccaca uuauacauuu gauguauuga ccagaau | 5037 |

<210> SEQ ID NO 8
<211> LENGTH: 3298
<212> TYPE: DNA
<213> ORGANISM: homo sapien

<400> SEQUENCE: 8

| | |
|---|---|
| guugucgacu ucaggaccg aagcgcuuca cugagcgcuc gccgccgccc agccucuccu | 60 |
| cucgcgccuc cuagcucuuc gcagagcaac caggagccag gaguggucua gagcccgagg | 120 |
| gugggaaggg ggagucuguc uggcuuuucu ccuaucuugc uucuuuucc ucuucccuuc | 180 |
| ccacucuugu ucaagcgagu gugugagcua uggagcgaag agccuggagu cugcagugca | 240 |
| cugcuuucgu ccucuuuugc gcuuggugug cacugaacag ugcaaaagcg aaaaggcaau | 300 |
| uugucaauga auggggcagcg agaucccccg gggcccggga agcagccucg gccaucgccg | 360 |
| aggagcuggg cuaugaccuu uggggucaga auggguucacu ugaaaaucac uacuuauuca | 420 |
| aacauaaaaa ccaccccaga aggucucgaa ggagugccuu ucauaucacu aagagauuau | 480 |
| cugaugauga ucgugugaua uggggcugaac aacagaauga aaaagaaaga aguaaacguu | 540 |
| cagcucuaag ggacucagca cuaaaucucu ucaaugaucc caugguggaau cagcaauggu | 600 |
| acuugcaaga uaccaggaug acggcagccc ugcccaagcu ggaccuucau gugauaccug | 660 |
| uuuggcaaaa aggcauuacg ggcaaaggag uguuaucac cguacuggau gaugguuugg | 720 |
| aguggaauca cacggacauu uaugccaacu augauccaga ggcuagcuau gauuuuaaug | 780 |
| auaaugacca uguccauuu ccccgauaug aucccacaaa cgagaacaaa cacgggacca | 840 |
| gaugugcagg agaaauugcc augcaagcaa uaaucacaa augcggggu ggaguugcau | 900 |
| acaauuccaa aguuggaggc auaagaaugc uggauggcau ugugacggau gcuauugagg | 960 |

-continued

```
ccaguucaau uggauucaau ccuggacacg uggauauuua cagugcaagc uggggcccua    1020
augaugaugg gaaaacugug gagggggccug gccggcuagc ccagaaggcu uuugaauaug   1080
gugucaaaca ggggagacag gggaaggggu ccaucuucgu cugggcuucg ggaaacgggg   1140
ggcgucaggg agauaauugu gacugugaug gcuacacaga cagcaucuac accaucucca   1200
ucagcagugc ucccagcaa ggccuauccc ccugguacgc ugagaagugc uccuccacac    1260
uggccaccuc uuacagcagc ggagauuaca ccgaccagag aaucacgagc gcugaccugc   1320
acaaugacug cacggagacg cacacaggca ccucggccuc ugcaccucug gcugcuggca   1380
ucuucgcucu ggcccuggaa gcaaacccaa aucucaccug gcgagauaug cagcaccugg   1440
uugucuggac cucugaguau gacccgcugg ccaauacccc uggauggaaa aagaauggag   1500 cagggcuugau ggugaauagu cgauuuggau uggcuugcu aaaugccaaa gcucggugg   1560 auuuagcuga ccccaggacc uggaggagcg ugccugagaa gaaagagugu uuguaaagg   1620 acaaugacuu ugagcccaga gcccugaaag cuaauggaga aguuaucauu gaaauuccaa   1680
caagagcuug ugaaggacaa gaaaaugcua ucaagucccu ggagcaugua caauuugaag   1740
caacaauuga auauucccga agaggagacc uucaugucac acuuacuucu gcugcuggaa   1800
cuagcacugu gcucuuggcu gaaagagaac gggauacauc uccuaauggc uuuaagaacu   1860
gggacuucau gucuguucac acauggggag agaacccuau agguacuugg acuuugagaa   1920
uuacagacau gucuggaaga auucaaaaug aaggaagaau ugugaacugg aagcugauuu   1980
ugcacgggac cucuucucag ccagagcaua ugaagcagcc ucguguguac acguccuaca   2040
acacuguuca gaaugacaga gaggggugg agaagauggu ggauccaggg gaggagcagc   2100
ccacacaaga gaacccuaag gagaacaccc uguguccaa aagccccagc agcagcagcg   2160 uaggggccg gagggaugag uuggaggagg gagcccuuc ccaggccaug cugcgacucc    2220
ugcaaagugc uucaguaaa acucaccgc caaagcaauc accaaagaag uccccaagug   2280
caaagcucaa caucccuuau gaaaacuucu acgaagcccu ggaaaagcug aacaaaccuu   2340
cccagcuuaa agacucugaa gacagucugu auaaugacua uuugaugguu uuuuauaaca   2400
cuaaaccuua caagcacaga gacgaccggc ugcuucaagc ucugguggac auucugaaug   2460
aggaaaauua aaauaagugu gugguccaa guuggaaaua ucaugccuuc uuccuuaccc    2520
ugcgauuuug ccugugucug aagugguugu uuugucauga auucuuaugc uuauaauauc   2580
cuuuguggca ccuuuucuuu uucucccuaa acuguacauu ugaaggggau gagcucaagc   2640
aggaaguuca acuuccagaa uugaucauag guauuucaaa acacaucuuu ccugucugca   2700
caagugaagu guuuguucu ucuggaguc acaguugaca aaaagcucuu acacuacauu     2760
agaacacugc auuagagccc auuucaauuc ucaaagaaa aggcaaaacc ugggauauca    2820
auuaauuuga aaacauaauc ugcaaagaau gagaaggagu cagaaacugu ucuguagcu    2880 uguucccugu cuuguccaug ugguucuuca aauuuugaug ccaagaaagu auuugguagg   2940
ccuaaugaag gaguucacug uaagacucau ucccuagauc uuucuauucc aaagugccac   3000
ucauuccugu agucaaaauc uggucaucuu ggucaaaagc cuggauuauu uagaucuaga   3060
aacagaucuu gaaaucugaa ugcucugguu ugagcaauuu cgaacauuc uuugccuggu    3120 gcacuguguc uguggugcca gaggcguccg uggauccaga gguguuaug acucgugcug    3180 caugccuggu cuuccucugu uuucccuuc ugaaaguuuu cuauaccugu ucccuuucuc    3240
agccacaaaa uaaauguugg gagaaaugau auauaccacu uucccaaaaa aaaaaaaa     3298
```

<210> SEQ ID NO 9
<211> LENGTH: 2233
<212> TYPE: DNA
<213> ORGANISM: homo sapien

<400> SEQUENCE: 9

| | | | | | |
|---|---|---|---|---|---|
| ggccaguccc | acugcagggu | cgagaugccg | aacugacuau | ggggaaggga | ucuauuucuu | 60 |
| ucuuguucuu | cagccaaauu | gguucacuug | aaaaucacua | cuuauucaaa | cauaaaaacc | 120 |
| accccagaag | gucucgaagg | agugccuuuc | auaucacuaa | gagauuaucu | gaugaugauc | 180 |
| gugugauaug | ggcugaacaa | caguaugaaa | agaaagaag | uaaacguuca | gcucuaaggg | 240 |
| acucagcacu | aaaucucuuc | aaugauccca | uguggaauca | gcaaugguac | uugcaagaua | 300 |
| ccaggaugac | ggcagcccug | cccaagcugg | accuucaugu | gauaccuguu | ggcaaaaag | 360 |
| gcauuacggg | caaaggaguu | guuauacaccg | uacuggauga | ugguuggag | uggaaucaca | 420 |
| cggacauuua | ugccaacuau | gauccagagg | cuagcuauga | uuuuaaugau | aaugaccaug | 480 |
| auccauuucc | ccgauaugau | cccacaaacg | agaacaaaca | cgggaccaga | ugugcaggag | 540 |
| aaauugccau | gcaagcaaau | aaucacaaau | gcggggguugg | agugcauac | aauuccaaag | 600 |
| uuggaggcau | aagaaugcug | gauggcauug | ugacggaugc | uauugaggcc | aguucaauug | 660 |
| gauucaaucc | uggacacgug | gauauuuaca | gugcaagcug | ggcccuaau | gaugauggga | 720 |
| aaacugugga | ggggccuggc | cggcuagccc | agaaggcuuu | ugaauauggu | ucaaacagg | 780 |
| ggagacaggg | gaaggggucc | aucuucgucu | gggcuucggg | aaacgggggg | cgucagggag | 840 |
| auaauuguga | cugugauggc | uacacagaca | gcaucuacac | caucuccauc | agcagugccu | 900 |
| cccagcaagg | ccuaucccc | ugguacgcug | agaagugcuc | cuccacacug | gccaccucuu | 960 |
| acagcagcgg | agauuacacc | gaccagagaa | ucacgagcgc | ugaccugcac | aaugacugca | 1020 |
| cggagacgca | cacaggcacc | ucggccucug | caccucuggc | ugcuggcauc | uucgcucugg | 1080 |
| cccuggaagc | aaacccaaau | cucaccuggc | gagauaugca | gcaccugguu | gucuggaccu | 1140 |
| cugaguauga | cccgcuggcc | aauaacccug | gauggaaaaa | gaauggagca | ggcuugaugg | 1200 |
| ugaauagucg | auuuggauuu | ggcuugcuaa | augccaaagc | ucugguggau | uuagcugacc | 1260 |
| ccaggaccug | gaggagcgug | ccugagaaga | agagugugu | uguaaaggac | aaugacuuug | 1320 |
| agcccagagc | ccugaaagcu | aauggagaag | uuaucauuga | aauccaaca | agagcuugug | 1380 |
| aaggacaaga | aaaugcuauc | aagucccugg | agcauguaca | auuugaagca | caauugaau | 1440 |
| auucccgaag | aggagaccuu | caugucacac | uuacuucgc | ugcuggaacu | agcacugugc | 1500 |
| ucuuggcuga | aagagaacgg | gauacaucuc | cuaauggcuu | uaagaacugg | gacuucaugu | 1560 |
| cguucacac | augggagag | aacccuauag | guacuuggac | uuugagaauu | acagacaugu | 1620 |
| cuggaagaau | ucaaaaugaa | ggaagaauug | ugaacuggaa | gcugauuuug | cacgggaccu | 1680 |
| cuucucagcc | agagcauaug | aagcagcccuc | guguguacac | guccuacaac | acuguucaga | 1740 |
| augacggaag | agggguggag | aagauggugg | auccagggga | ggagcagccc | acacaagaga | 1800 |
| acccuaagga | gaacacccug | guguccaaaa | gccccagcag | cagcagcgua | ggggccgga | 1860 |
| gggaugaguu | ggaggaggga | gccccuuccc | aggccaugcu | gcgacuccug | caaagugcuu | 1920 |
| ucaguaaaaa | cucaccgcca | agcaaucac | caaagaaguc | cccaagugca | agcucaaca | 1980 |
| ucccuuauga | aaacuucuac | gaagcccugg | aaaagcugaa | caaaccuucc | cagcuuaaag | 2040 |
| acucugaga | caguccuguau | aaugacuaug | uugauguuuu | uauaacacu | aaaccuuaca | 2100 |
| agcacagaga | cgaccggcug | cuucaagcuc | ugguggacau | ucgaaugag | gaaaauuaaa | 2160 |

| | |
|---|---|
| auaagugugu ggucccaagu uggaaauauu caugcuucuu ccuuacccug cgauuuugcc | 2220 |
| ugugucugaa gug | 2233 |

<210> SEQ ID NO 10
<211> LENGTH: 2450
<212> TYPE: DNA
<213> ORGANISM: homo sapien

<400> SEQUENCE: 10

| | |
|---|---|
| accaggagcc aggagugguc cagagcccga gggugggaag ggggagucug ucuggcuuuu | 60 |
| cuccuaucuu gcuucuuuuu ccucuuccccu ucccacucuu guucaagcga gugugugagc | 120 |
| uauggagcga agagccugga gucugcagug cacugcuuuc guccucuuuu gcgcuuggug | 180 |
| ugcacugaac agugcaaaag cgaaaaggca auuugucaau gaaugggcag cggagauccc | 240 |
| cgggggcccg gaagcagccu cggccaucgc cgaggagcug ggcuaugacc uuuggguca | 300 |
| gauugguuca cuugaaaauc acuacuuauu caaacauaaa aaccacccca gaaggucucg | 360 |
| aaggagugcc uucauauca cuaagagauu aucgaugau gaucguguga uagggcuga | 420 |
| acaacaguau gaaaagaaa gaaguaaacg uucagcucua agggacucag cacuaaaucu | 480 |
| cuucaaugau cccaugugga aucagcaaug guacuugcaa gauaccagga ugacggcagc | 540 |
| ccugcccaag cuggaccuuc augugauacc uguuugcaa aaaggcauua cgggcaaagg | 600 |
| aguuguuauc accguacugg augaugguuu ggaguggaau cacacggaca uuuaugccaa | 660 |
| cuaugaucca gaggcuagcu augauuuuaa ugauaaugac caugauccau uccccgaua | 720 |
| ugaucccaca aacgagaaca aacacgggac cagaugugca ggagaaauug ccaugcaagc | 780 |
| aaauaaucac aaaugcgggg uuggaguugc auacaauucc aaaguuggag gcauaagaau | 840 |
| gcuggauggc auugugacgg augcuauuga ggccaguuca auuggauuca auccuggaca | 900 |
| cguggauauu uacagugcaa gcuggggccc uaaugaugau gggaaaacug ugagggggcc | 960 |
| uggccggcua gcccagaagg cuuuugaaua uggugucaaa caggggagac aggggaaggg | 1020 |
| guccaucuuc gucugggcuu cgggaaacgg ggcgucag ggagauaauu ugacuguga | 1080 |
| uggcuacaca gacagcaucu acaccaucuc caucagcagu gccucccagc aaggccuauc | 1140 |
| ccccugguac gcugaaagu gcuccuccac acuggccacc ucuuacagca gcggagauua | 1200 |
| caccgaccag agaaucacga gcgcugaccu gcacaaugac ugcacggaga cgcacacagg | 1260 |
| cacccucggcc ucugcaccuc uggcugcugg caucuucgcu cuggcccugg aagcaaaccc | 1320 |
| aaaucucacc uggcgagaua ugcagcaccu gguugucugg accucugagu ugacccgcu | 1380 |
| ggccaauaac ccuggauggga aaagaaugg agcaggcuug augugaaua gucgauuugg | 1440 |
| auuuggcuug cuaaaugcca agcucugguu gauuuagcu gacccagga ccuggaggag | 1500 |
| cgugccugag aagaaagagu guguguaaa ggacaaugac uuugagccca gagcccugaa | 1560 |
| agcuaaugga gaaguuauca uugaaauucc aacaagagcu ugaaggac aagaaaaugc | 1620 |
| uaucaagucc cuggagcaug uacaauuuga agcaacaauu gaauauuccc gaagaggaga | 1680 |
| ccuucaugucc acacuuacuu cugcugcugg aacuagcacu gugcucuugg cugaaagaga | 1740 |
| acgggauaca ucuccaaaug gcuuuaagaa uuggacuuc augucuguuc acacaugggg | 1800 |
| agagaacccu auaggguacuu ggacuuugag aauuacagac augucuggaa gaauucaaaa | 1860 |
| ugaaggaaga auugugaacu ggaagcugau uuugcacggg accucuucuc agccagagca | 1920 |
| uaugaagcag ccucgugugu acacguccua caacacuguu cagaaugaca aagagggggu | 1980 |

| | |
|---|---|
| ggagaagaug guggauccag ggaggagca gcccacacaa gagaacccua aggagaacac | 2040 |
| ccugugucc aaaagcccca gcagcagcag cguaggggc cggagggaug aguuggagga | 2100 |
| gggagccccu uccgaggcca ugcugcgacu ccugcaaagu gcuucagua aaacucacc | 2160 |
| gccaaagcaa ucaccaaaga agucccaac ugcaaagcuc aacaucccuu augaaaacuu | 2220 |
| cuacgaagcc cuggaaaagc ugaacaaacc uucccagcuu aaagacucug aagacaqucu | 2280 |
| guauaaugac uauguugaug uuuuuauaa cauaaaccu acaagcaca gagacgaccg | 2340 |
| gcugcuucaa gcucuggugg acauucugaa ugaggaaaau aaaauaagu guguggaccc | 2400 |
| aaguuggaaa uauucaugcu ucuuccuuac ccugcgauuu ugccuguguc | 2450 |

<210> SEQ ID NO 11
<211> LENGTH: 2450
<212> TYPE: DNA
<213> ORGANISM: homo sapien

<400> SEQUENCE: 11

| | |
|---|---|
| accaggagcc aggagugguc cagagcccga ggugggaag ggggagucug ucuggcuuuu | 60 |
| cuccuaucuu gcuucuuuuu ccucuucccu uccacucuu guucaagcga gugugugagc | 120 |
| uauggagcga agagccugga gucugcagug cacugcuuuc guccucuuuu gcgcuuggug | 180 |
| ugcacugaac agugcaaaag cgaaaaggca auuugucaau gaaugggcag cggagauccc | 240 |
| cggggggcccg gaagcagccu cggccaucgc cgaggagcug ggcuaugacc uuuggguca | 300 |
| gauuggguuca cuugaaaauc acuacuuauu caaacauaaa aaccacccca gaaggucucg | 360 |
| aaggagugcc uuucauauca cuaagagauu aucugaugau gaucgugaga uaugggcuga | 420 |
| acaacaguau gaaaagaaa gaaguaaacg uucagcucua agggacucag cacuaaaucu | 480 |
| cuucaaugau cccaugugga aucagcaaug guacuugcaa gauaccagga ugacggcagc | 540 |
| ccugcccaag cuggaccuuc augugauacc uguuuggcaa aaaggcauua cgggcaaagg | 600 |
| aguuguuauc accgacugg augaugguuu ggagaguggaau cacacggaca uuuaugccaa | 660 |
| cuaugaucca gaggcuagcu augauuuuaa ugauaaugac caugauccau ucccccgaua | 720 |
| ugaucccaca aacgagaaca aacacggac cagaugugca ggagaaauug ccaugcaagc | 780 |
| aaauaaucac aaaugcgggg uuggaguugc auacaauucc aaaguuggag cauaagaau | 840 |
| gcuggauggc auugugacgg augcuauuga ggccaguuca auuggauuca auccuggaca | 900 |
| cguggauauu uacagugcaa gcuggggccc uaaugaugau gggaaaacug uggaggggcc | 960 |
| uggccggcua gcccagaagg cuuuugaaua uggugucaaa caggggagac aggggaaggg | 1020 |
| guccaucuuc gucugggcuu cgggaaacgg ggggcgucag ggagauaauu ugacugcuga | 1080 |
| uggcuacaca gacagcaucu acaccaucuc caucagcagu gccucccaac aaggccuauc | 1140 |
| ccccugguac gcugagaagu gcuccuccac acuggccacc ucuuacagca gcggagauua | 1200 |
| caccgaccag agaaucacga gcgcugaccu gcacaaugac ugcacggaga cgcacacagg | 1260 |
| caccucggcc ucugcaccuc uggcugcugg caucuucgcu cuggcccugg aagcaaaccc | 1320 |
| aaaucucacc uggcgagaua ugcagcaccu gguugucugg accucugagu augacccgcu | 1380 |
| ggccaauaac ccuggauggga aaagaaugg agcaggcuug augugaaua gucgauuugg | 1440 |
| auuggcuug cuaaaugcca aagcucuggu ggauuuagcu gaccccagga ccuggaggag | 1500 |
| cgugccugag aagaaagagu guguugaaaa ggacaaugac uuugagccca gagcccugaa | 1560 |
| agcuaaugga gaaguuauca uugaaauucc aacaagagcu ugugaaggac aagaaaaugc | 1620 |
| uaucaaguco cuggagcaug acaauuuga agcaacaauu gaauauuccc gaagaggaga | 1680 | ccuucauguc acacuuacuu cugcugcugg aacuagcacu gugcucuugg cugaaagaga    1740 acgggauaca ucuccuaaug gcuuuaagaa uugggacuuc augucuguuc acacauggggg   1800 agagaacccu auagguacuu ggacuuuugag aauuacagac augucuggaa gaauucaaaa   1860 ugaaggaaga auugugaacu ggaagcgauu uuugcacggg accucuucuc agccagagca    1920 uaugaagcag ccucgugugu acacguccua caacacuguu cagaaugaca aagagggggu    1980 ggagaagaug guggauccag ggaggagca gcccacacaa gagaacccua aggagaacac    2040 ccugguguvcc aaaagcccca gcagcagcag cguagggggc cggagggaug aguuggagga   2100 gggagcccccu uccgaggcca ugcugcgacu ccugcaaagu gcuuucagua aaaacucacc   2160 gccaaagcaa ucaccaaaga aguccccaac ugcaaagcuc aacaucccuu augaaaacuu    2220 cuacgaagcc cuggaaaagc ugaacaaacc uucccagcuu aaagacucug aagacagucu    2280 guauaaugac uauguugaug uuuuuuauaa cacuaaaccu uacaagcaca gagcgaccg    2340 gcugcuucaa gcucuggugg acauucgaa ugaggaaaau uaaaauaagu gugguccccc    2400 aaguuggaaa uauucaugcu ucuuccuuac ccugcgauuu ugccugugc                2450

<210> SEQ ID NO 12
<211> LENGTH: 2276
<212> TYPE: DNA
<213> ORGANISM: homo sapien

<400> SEQUENCE: 12
gcgaucgcca uggagcgaag agccuggagu cugcagugca cugcuuucgu ccucuuuugc    60
gcuuggugug cacugaacag ugcaaaagcg aaaaggcaau uugucaauga augggcagcg    120
gagauccccg ggggcccgga agcagccucg gccaucgccg aggagcuggg cuaugaccuu    180 uuggguccaga uuggauucacu ugaaaaucac uacuuauuca aacauaaaaa ccaccccaga   240
aggucucgaa ggagugcccuu ucauaucacu aagagauuau cugaugauga ucgugugaua   300 uggggcugaac aacaguauga aaaagaaaga aguaaacguu cagcucuaag ggacucagca   360
cuaaaucucu ucaaugaucc caugugggaau cagcaauggu acuugcaaga uaccaggaug   420
acggcagccc ugcccaagcu ggaccuucau gugauaccug uuuggcaaaa aggcauuacg    480
ggcaaaggag uuguuaucac cguacuggau gauggguugg aguggaauca cacggacauu    540
uaugccaacu augauccaga ggcuagcuau gauuuuaaug auaagaucca ugauccauuu    600
ccccgauaug aucccacaaa cgagaacaaa cacgggaacca gaugugcagg agaaauugcc    660
augcaagcaa auaaucacaa augcgggguu ggaguugcau acaauuccaa aguuggaggc    720
auaagaaugc uggauggcau ugugacggau gcuauugagg ccaguucaau uggauucaau    780
ccuggacacg uggauauuuua caguacaagc ugggggccua augaugaugg gaaaacugug    840 gaggggcccug gccgcucuagc ccagaaggcu uuugaauaug gugucaaaca ggggagacag    900
gggaaggggu ccaucuucgu cugggcuucg ggaaacgggg ggcgucaggg agauaauugu    960
gacugugaug gcuacacaga cagcaucuac accaucucca ucagcagugc cucccagcaa    1020 ggccuaucccc ccugguacgc ugagaagugc uccuccacac uggccacccu uuacagcagc    1080
ggagauuaca ccgaccagag aaucacgagc gcugaccugc acaaugacug cacggagacg    1140
cacacaggca cccggccccuu ugcaccucug cugcuggca cuucgcucu ggcccuggaa    1200 gcaaacccaa aucucaccug gcgagauaug cagcaccugg uuguggac cucugaguau    1260 gacccgcugg ccaauaaccc uggauggaaa aagaauggag caggcuugau ggugaauagu   1320

| | |
|---|---|
| cgauuuggau uuggcuugcu aaaugccaaa gcucuggugg auuuagcuga ccccaggacc | 1380 |
| uggaggagcg ugccugagaa gaaagagugu guuguaaagg acaaugacuu ugagcccaga | 1440 |
| gcccugaaag cuaauggaga aguuaucauu gaaauuccaa caagagcuug ugaaggacaa | 1500 |
| gaaaaugcua ucaagcccu ggagcaugua caauuugaag caacaauuga auauucccga | 1560 |
| agaggagacc uucaugucac acuuacuucu gcugcuggaa cuagcacugu gcucuuggcu | 1620 |
| gaaagagaac gggauacauc uccuaauggc uuuaagaauu gggacuucau gucuguucac | 1680 |
| acauggggag agaacccuau agguacuugg acuuugagaa uuacagacau gucuggaaga | 1740 |
| auucaaaaug aaggaagaau ugugaacugg aagcugauuu ugcacgggac ucuucucag | 1800 |
| ccagagcaua ugaagcagcc ucguguguac acguccuaca acacuguuca gaaugacaga | 1860 |
| agaggggugg agaagauggu ggauccaggg gaggagcagc ccacacaaga gaacccuaag | 1920 |
| gagaacaccc uggugccaa aagccccagc agcagcagcg uaggggccg gagggaugag | 1980 |
| uuggaggagg gagcccccuuc ccaggccaug cugcgacucc ugcaaagugc uuucaguaaa | 2040 |
| aacucaccgc caaagcaauc accaaagaag uccccaagug caaagcucaa cauccccuuau | 2100 |
| gaaaacuucu acgaagcccu ggaaaagcug aacaaaaccuu cccagcuuaa agacucugaa | 2160 |
| gacagucugu auaaugacua uguugauguu uuuuauaaca cuaaaccuua caagcacaga | 2220 |
| gacgaccggc ugcuucaagc ucugguggac auucugaaug aggaaaagu uuaaac | 2276 |

<210> SEQ ID NO 13
<211> LENGTH: 2394
<212> TYPE: DNA
<213> ORGANISM: homo sapien

<400> SEQUENCE: 13

| | |
|---|---|
| gttcgttgca acaaattgat gagcaatgct tttttataat gccaactttg tacaaaaaag | 60 |
| ttggcaccat ggagcgaaga gcctggagtc tgcagtgcac tgctttcgtc ctcttttgcg | 120 |
| cttggtgtgc actgaacagt gcaaaagcga aaaggcaatt tgtcaatgaa tgggcagcgg | 180 |
| agatccccgg gggcccggaa gcagcctcgg ccatcgccga ggagctgggc tatgaccttt | 240 |
| tgggtcagat tggttcactt gaaaatcact acttattcaa acataaaaac cacccccagaa | 300 |
| ggtctcgaag gagtgccttt catatcacta agagattatc tgatgatgat cgtgtgatat | 360 |
| gggctgaaca acagtatgaa aaagaaagaa gtaaacgttc agctctaagg gactcagcac | 420 |
| taaatctctt caatgatccc atgtggaatc agcaatggta cttgcaagat accaggatga | 480 |
| cggcagccct gccaagctg daccttcatg tgatacctgt ttggcaaaaa ggcattacgg | 540 |
| gcaaaggagt tgttatcacc gtactggatg atggtttgga gtggaatcac acggacattt | 600 |
| atgccaacta tgatccagag gctagctatg atttttaatga taatgaccat gatccatttc | 660 |
| cccgatatga tcccacaaac agaaacaaac acgggaccag atgtgcagga gaaattgcca | 720 |
| tgcaagcaaa taatcacaaa tgcggggttg gagttgcata caattccaaa gttggaggca | 780 |
| taagaatgct ggatggcatt gtgacggatg ctattgaggc cagttcaatt ggattcaatc | 840 |
| ctggacacgt ggatatttac agtgcaagct ggggccctaa tgatgatggg aaaactgtgg | 900 |
| aggggcctgg ccggctagcc cagaaggctt tgaatatgg tgtcaaacag ggagacagg | 960 |
| ggaaggggtc catcttcgtc tgggcttcgg gaaacggggg gcgtcaggga gataattgtg | 1020 |
| actgtgatgg ctacacagac agcatctaca ccatctccat cagcagtgcc tcccagcaag | 1080 |
| gcctatcccc ctggtacgct gagaagtgct cctccacact ggccaccctc tacagcagcg | 1140 |
| gagattacac cgaccagaga atcacgagcg ctgacctgca caatgactgc acggagacgc | 1200 |

```
acacaggcac ctcggcctct gcacctctgg ctgctggcat cttcgctctg gccctggaag   1260
caaacccaaa tctcacctgg cgagatatgc agcacctggt tgtctggacc tctgagtatg   1320
acccgctggc caataaccct ggatggaaaa agaatggagc aggcttgatg gtgaatagtc   1380
gatttggatt tggcttgcta atgccaaag ctctggtgga tttagctgac cccaggacct   1440
ggaggagcgt gcctgagaag aaagagtgtg ttgtaaagga caatgacttt gagcccagag   1500
ccctgaaagc taatggagaa gttatcattg aaattccaac aagagcttgt gaaggacaag   1560
aaaatgctat caagtccctg gagcatgtac aatttgaagc aacaattgaa tattcccgaa   1620
gaggagacct tcatgtcaca cttacttctg ctgctggaac tagcactgtg ctcttggctg   1680
aaagagaacg ggatacatct cctaatggct ttaagaattg ggacttcatg tctgttcaca   1740
catgggagaa gaaccctata ggtacttgga cttttgagaat tacagacatg tctgaagaa   1800
ttcaaaatga aggaagaatt gtgaactgga agctgatttt gcacgggacc tcttctcagc   1860
cagagcatat gaagcagcct cgtgtgtaca cgtcctacaa cactgttcag aatgacagaa   1920
gaggggtgga agatggtg atccagggg aggagcagcc cacacaagag aaccctaagg   1980
agaacaccct ggtgtccaaa gccccagca gcagcagcgt aggggccgg agggatgagt   2040
tggaggaggg agcccttcc gaggccatgc tgcgactcct gcaaagtgct ttcagtaaaa   2100
actcaccgcc aaagcaatca ccaaagaagt ccccaactgc aaagctcaac atcccttatg   2160
aaaacttcta cgaagccctg aaaagctga acaaaccttc ccagcttaaa gactctgaag   2220
acagtctgta taatgactat gttgatgttt tttataacac taaaccttac aagcacagag   2280
acgaccggct gcttcaagct ctggtggaca ttctgaatga ggaaaatttg ccaactttct   2340
tgtacaaagt tggcattata agaaagcatt gcttatcaat ttgttgcaac gaac         2394
```

<210> SEQ ID NO 14
<211> LENGTH: 2394
<212> TYPE: DNA
<213> ORGANISM: homo sapien

<400> SEQUENCE: 14

```
gttcgttgca acaaattgat gagcaatgct tttttataat gccaactttg tacaaaaaag    60
ttggcaccat ggagcgaaga gcctggagtc tgcagtgcac tgctttcgtc ctcttttgcg   120
cttggtgtgc actgaacagt gcaaaagcga aaaggcaatt tgtcaatgaa tgggcagcgg   180
agatccccgg gggcccggaa gcagcctcgg ccatcgccga ggagctgggc tatgaccttt   240
tgggtcagat tggttcactt gaaaatcact acttattcaa acataaaaac cacccccagaa   300
ggtctcgaag gagtgccttt catatcacta agagattatc tgatgatgat cgtgtgatat   360
gggctgaaca acagtatgaa aaagaaagaa gtaaacgttc agctctaagg gactcagcac   420
taaatctctt caatgatccc atgtggaatc agcaatggta cttgcaagat accaggatga   480
cggcagccct gcccaagctg gaccttcatg tgatacctgt ttggcaaaaa ggcattacgg   540
gcaaaggagt tgttatcacc gtactggatg atggtttgga gtggaatcac acggacattt   600
atgccaacta tgatccagag gctagctatg attttaatga atgaccat gatccatttc    660
cccgatatga tcccacaaac gagaacaaac acgggaccag atgtgcagga gaaattgcca   720
tgcaagcaga taatcacaaa tgcgggggttg agttgcata caattccaaa gttggaggca   780
taagaatgct ggatggcatt gtgacggatg ctattgaggc cagttcaatt ggattcaatc   840
ctggacacgt ggatatttac agtgcaagct ggggcccctaa tgatgatggg aaaactgtgg   900
```

| | |
|---|---:|
| aggggcctgg ccggctagcc cagaaggctt ttgaatatgg tgtcaaacag gggagacagg | 960 |
| ggaagggtc catcttcgtc tgggcttcgg gaaacggggg gcgtcaggga gataattgtg | 1020 |
| actgtgatgg ctacacagac agcatctaca ccatctccat cagcagtgcc tcccagcaag | 1080 |
| gcctatcccc ctggtacgct gagaagtgct cctccacact ggccacctct tacagcagcg | 1140 |
| gagattacac cgaccagaga atcacgagcg ctgacctgca caatgactgc acggagacgc | 1200 |
| acacaggcac ctcggcctct gcacctctgg ctgctggcat cttcgctctg gcctggaag | 1260 |
| caaacccaaa tctcacctgg cgagatatgc agcacctggt tgtctggacc tctgagtatg | 1320 |
| acccgctggc caataaccct ggatggaaaa agaatggagc aggcttgatg gtgaatagtc | 1380 |
| gatttggatt tggcttgcta aatgccaaag ctctggtgga tttagctgac cccaggacct | 1440 |
| ggaggagcgt gcctgagaag aaagagtgtg ttgtaaagga caatgacttt gagcccagag | 1500 |
| ccctgaaagc taatggagaa gttatcattg aaattccaac aagagcttgt gaaggacaag | 1560 |
| aaaatgctat caagtccctg gagcatgtac aatttgaagc aacaattgaa tattcccgaa | 1620 |
| gaggagacct tcatgtcaca cttacttctg ctgctggaaac tagcactgtg ctcttggctg | 1680 |
| aaagagaacg ggatacatct cctaatggct ttaagaattg ggacttcatg tctgttcaca | 1740 |
| catggggaga gaaccctata ggtacttgga cttttgagaat tacagacatg tctggaagaa | 1800 |
| ttcaaaatga aggaagaatt gtgaactgga agctgatttt gcacgggacc tcttctcagc | 1860 |
| cagagcatat gaagcagcct cgtgtgtaca cgtcctacaa cactgttcag aatgacagaa | 1920 |
| gaggggtgga agatggtg gatccagggg aggagcagcc cacacaagag aaccctaagg | 1980 |
| agaacaccct ggtgtccaaa gccccagca gcagcagcgt agggggccgg agggatgagt | 2040 |
| tggaggaggg agcccttcc gaggccatgc tgcgactcct gcaaagtgct ttcagtaaaa | 2100 |
| actcaccgcc aaagcaatca ccaaagaagt ccccaactgc aaagctcaac atcccttatg | 2160 |
| aaaacttcta cgaagccctg gaaaagctga acaaaccttc ccagcttaaa gactctgaag | 2220 |
| acagtctgta taatgactat gttgatgttt tttataacac taaaccttac aagcacagag | 2280 |
| acgaccggct gcttcaagct ctggtggaca ttctgaatga ggaaaatttg ccaactttct | 2340 |
| tgtacaaagt tggcattata agaaaagcatt gcttatcaat ttgttgcaac gaac | 2394 |

<210> SEQ ID NO 15
<211> LENGTH: 2394
<212> TYPE: DNA
<213> ORGANISM: homo sapien

<400> SEQUENCE: 15

| | |
|---|---:|
| gttcgttgca acaaattgat gagcaatgct tttttataat gccaactttg tacaaaaaag | 60 |
| ttggcaccat ggagcgaaga gcctggagtc tgcagtgcac tgctttcgtc tctcttttgcg | 120 |
| cttggtgtgc actgaacagt gcaaaagcga aaggcaatt tgtcaatgaa tgggcagcgg | 180 |
| agatccccgg gggcccggaa gcagcctcgg ccatcgccga ggagctgggc tatgaccttt | 240 |
| tgggtcagat tggttcactt gaaaatcact acttattcaa acataaaaac cacccagaa | 300 |
| ggtctcgaag gagtgccttt catatcacta agagattatc tgatgatgat cgtgtgatat | 360 |
| gggctgaaca acagtatgaa aaagaaagaa gtaaacgttc agctctaagg gactcagcac | 420 |
| taaatctctt caatgatccc atgtggaatc agcaatggta cttgcaagat accaggatga | 480 |
| cggcagccct gcccaagctg gaccttcatg tgataccttg ttggcaaaaa ggcattacgg | 540 |
| gcaaaggagt tgttatcacc gtactggatg atggtttgga gtggaatcac acggacattt | 600 |
| atgccaacta tgatccagag gctagctatg atttttaatga taatgaccat gatccatttc | 660 |

```
cccgatatga tcccacaaac gagaacaaac acgggaccag atgtgcagga gaaattgcca      720
tgcaagcaaa taatcacaaa tgcggggttg gagttgcata caattccaaa gttggaggca      780
taagaatgct ggatggcatt gtgacggatg ctattgaggc cagttcaatt ggattcaatc      840
ctggacacgt ggatatttac agtgcaagct ggggccctaa tgatgatggg aaaactgtgg      900
aggggcctgg ccggctagcc cagaaggctt ttgaatatgg tgtcaaacag gggagacagg      960
ggaaggggtc catcttcgtc tgggctttgg gaaacggggg cgtcaggga gataattgtg     1020 actgtgatgg ctacacagac agcatctaca ccatctccat cagcagtgcc tcccagcaag     1080
gcctatcccc ctggtacgct gagaagtgct cctccacact ggccacctct tacagcagcg     1140
gagattacac cgaccagaga atcacgagcg ctgacctgca caatgactgc acggagacgc     1200
acacaggcac ctcggcctct gcacctctgg ctgctggcat cttcgctctg gcctggaag       1260 caaacccaaa tctcacctgg cgagatatgc agcacctggt tgtctggacc tctgagtatg     1320
acccgctggc caataaccct ggatggaaaa agaatggagc aggcttgatg gtgaatagtc     1380
gatttggatt tggcttgcta aatgccaaag ctctggtgga tttagctgac cccaggacct     1440
ggaggagcgt gcctgagaag aaagagtgtg ttgtaaagga caatgacttt gagcccagag     1500
ccctgaaagc taatggagaa gttatcattg aaattccaac aagagcttgt gaaggacaag     1560
aaaatgctat caagtccctg gagcatgtac aatttgaagc aacaattgaa tattcccgaa     1620
gaggagacct tcatgtcaca cttacttctg ctgctggaac tagcactgtg ctcttggctg     1680
aaagagaacg ggatacatct cctaatggct ttaagaattg ggacttcatg tctgttcaca     1740
catggggaga gaaccctata ggtacttgga cttttgagaat tacagacatg tctggaagaa     1800
ttcaaaatga aggaagaatt gtgaactgga agctgatttt gcacgggacc tcttctcagc     1860
cagagcatat gaagcagcct cgtgtgtaca cgtcctacaa cactgttcag aatgacagaa     1920 gagggggtgga aagatggtg gatccagggg aggagcagcc cacacaagag aaccctaagg     1980
agaacaccct ggtgtccaaa gccccagca gcagcagcgt agggggccgg agggatgagt     2040
tggaggaggg agccccttcc gaggccatgc tgcgactcct gcaaagtgct ttcagtaaaa     2100
actcaccgcc aaagcaatca ccaaagaagt ccccaactgc aaagctcaac atcccttatg     2160
aaaacttcta cgaagccctg gaaaagctga caaaaccttc ccagcttaaa gactctgaag     2220
acagtctgta taatgactat gttgatgttt tttataacac taaaccttac aagcacagag     2280
acgaccggct gcttcaagct ctggtggaca ttctgaatga ggaaaatttg ccaactttct     2340
tgtacaaagt tggcattata agaaagcatt gcttatcaat ttgttgcaac gaac         2394
```

<210> SEQ ID NO 16
<211> LENGTH: 2394
<212> TYPE: DNA
<213> ORGANISM: homo sapien

<400> SEQUENCE: 16

```
gttcgttgca acaaattgat gagcaatgct ttttataat gccaactttg tacaaaaaag        60
ttggcaccat ggagcgaaga gcctggagtc tgcagtgcac tgctttcgtc ctcttttgcg      120
cttggtgtgc actgaacagt gcaaaagcga aaggcaatt tgtcaatgaa tgggcagcgg      180
agatccccgg gggcccggaa gcagcctcgg ccatcgccga ggagctgggc tatgaccttt      240
tgggtcagat tggttcactt gaaaatcact acttattcaa acataaaaac cacccccagaa    300 ggtctcgaag gagtgccttt catatcacta agagattatc tgatgatgat cgtgtgatat     360
```

-continued

| | |
|---|---|
| gggctgaaca acagtatgaa aaagaaagaa gtaaacgttc agctctaagg gactcagcac | 420 |
| taaatctctt caatgatccc atgtggaatc agcaatggta cttgcaagat accaggatga | 480 |
| cggcagccct gcccaagctg accttcatg tgatacctgt ttggcaaaaa ggcattacgg | 540 |
| gcaaaggagt tgttatcacc gtactggatg atggtttgga gtggaatcac acggacattt | 600 |
| atgccaacta tgatccagag gctagctatg attttaatga taatgaccat gatccatttc | 660 |
| cccgatatga tcccacaaac gagaacaaac acgggaccag atgtgcagga gaaattgcca | 720 |
| tgcaagcaaa taatcacaaa tgcggggttg gagttgcata caattccaaa gttggaggca | 780 |
| taagaatgct ggatggcatt gtgacggatg ctattgaggc cagttcaatt ggattcaatc | 840 |
| ctggacacgt ggatatttac agtgcaagct ggggccctaa tgatgatggg aaaactgtgg | 900 |
| aggggcctgg ccggctagcc cagaaggctt ttgaatatgg tgtcaaacag gggagacagg | 960 |
| ggaaggggtc catcttcgtc tgggcttcgg gaaacggggg gcgtcaggga gataattgtg | 1020 |
| actgtgatgg ctacacagac agcatctaca ccatctccat cagcagtgcc tcccagcaag | 1080 |
| gcctatcccc ctggtacgct gagaagtgct cctccacact ggccacctct tacagcagcg | 1140 |
| gagattacac cgaccagaga atcacgagcc tgacctgca caatgactgc acggagacgc | 1200 |
| acacaggcac ctcggcctct gcacctctgg ctgctggcat cttcgctctg gccctggaag | 1260 |
| caaacccaaa tctcacctgg cgagatatgc agcacctggt tgtctggacc tctgagtatg | 1320 |
| acccgctggc caataaccct ggatggaaaa agaatggagc aggcttgatg gtgaatagtc | 1380 |
| gatttggatt tggcttgcta aatgccaaag ctctggtgga tttagctgac cccaggacct | 1440 |
| ggaggagcgt gcctgagaag aaagagtgtg ttgtaaagga caatgacttt gagcccagag | 1500 |
| ccctgaaagc taatggagaa gttatcattg aaattccaac aagagcttgt gaaggacaag | 1560 |
| aaaatgctat caagtccctg gagcatgtac aatttgaagc aacaattgaa tattcccgaa | 1620 |
| gaggagacct tcatgtcaca cttacttctg ctgctggaac tagcactgtg ctcttggctg | 1680 |
| aaagagaacg ggatacatct cctaatggct ttaagaattg ggacttcatg tctgttcaca | 1740 |
| catggggaga gaaccctata ggtacttgga ctttgagaat tacagacatg tctggaagaa | 1800 |
| ttcaaaatga aggaagaatt gtgaactgga agctgatttt gcacaggacc tcttctcagc | 1860 |
| cagagcatat gaagcagcct cgtgtgtaca cgtcctacaa cactgttcag aatgacagaa | 1920 |
| gaggggtgga gaagatggtg gatccagggg aggagcagcc cacacaagag aaccctaagg | 1980 |
| agaacaccct ggtgtccaaa gccccagca gcagcagcgt aggggccgg agggatgagt | 2040 |
| tggaggaggg agcccctcc gaggccatgc tgcgactcct gcaaagtgct ttcagtaaaa | 2100 |
| actcaccgcc aaagcaatca ccaaagaagt ccccaactgc aaagctcaac atcccttatg | 2160 |
| aaaacttcta cgaagccctg gaaaagctga acaaaccttc ccagcttaaa gactctgaag | 2220 |
| acagtctgta taatgactat gttgatgttt tttataacac taaaccttac aagcacagag | 2280 |
| acgaccggct gcttcaagct ctggtggaca ttctgaatga ggaaaatttg ccaactttct | 2340 |
| tgtacaaagt tggcattata agaaagcatt gcttatcaat ttgttgcaac gaac | 2394 |

<210> SEQ ID NO 17
<211> LENGTH: 4815
<212> TYPE: DNA
<213> ORGANISM: homo sapien

<400> SEQUENCE: 17

| | |
|---|---|
| ggcaatttgt caatgaatgg gcagcggaga tccccggggg cccggaagca gcctcggcca | 60 |
| tcgccgagga gctgggctat gacctttggg gtcagattgg ttcacttgaa aatcactact | 120 |

```
tattcaaaca taaaaaccac cccagaaggt ctcgaaggag tgcctttcat atcactaaga      180
gattatctga tgatgatcgt gtgatatggg ctgaacaaca gtatgaaaaa gaaagaagta      240
aacgttcagc tctaagggac tcagcactaa atctcttcaa tgatcccatg tggaatcagc      300
aatggtactt gcaagatacc aggatgacgg cagccctgcc caagctggac cttcatgtga      360
tacctgtttg gcaaaaggc attacgggca aggagttgt tatcaccgta ctggatgatg        420
gtttggagtg gaatcacacg gacatttatg ccaactatga tccagaggct agctatgatt      480
ttaatgataa tgaccatgat ccatttcccc gatatgatcc cacaaacgag aacaaacacg      540
ggaccagatg tgcaggagaa attgccatgc aagcaaataa tcacaaatgc ggggttggag      600
ttgcatacaa ttccaaagtt ggaggcataa gaatgctgga tggcattgtg acggatgcta      660
ttgaggccta ttcaattgga ttcaatcctg gacacgtgga tatttacagt gcaagctggg      720
gccctaatga tgatgggaaa actgtggagg ggcctggccg gctagcccag aaggcttttg      780
aatatggtgt caaacagggg agacagggga aggggtccat cttcgtctgg gcttcgggaa      840
acggggggcg tcagggagat aattgtgact gtgatggcta cacagacagc atctacacca      900
tctccatcag cagtgcctcc cagcaaggcc tatcccctg gtacgctgag aagtgctcct       960
ccacactggc cacctcttac agcagcggag attacaccga ccagagaatc acgagcgctg     1020
acctgcacaa tgactgcacg gagacgcaca caggcacctc ggcctctgca cctctggctg     1080
ctggcatctt cgctctggcc ctggaagcaa acccaaatct cacctggcga gatatgcagc     1140
acctggttgt ctggacctct gagtatgacc cgctggccaa taaccctgga tggaaaaaga     1200
atggagcagg cttgatggtg aatagtcgaa ttggatttgg cttgctaaat gccaaagctc     1260
tggtggattt agctgacccc aggacctgga ggagcgtgcc tgagaagaaa gagtgtgttg     1320
taaaggacaa tgactttgag cccagagccc tgaaagctaa tggagaagtt atcattgaaa     1380
ttccaacaag agcttgtgaa ggacaagaaa atgctatcaa gtccctggag catgtacaat     1440
ttgaagcaac aattgaatat tcccgaagag gagaccttca tgtcacactt acttctgctg     1500
ctggaactag cactgtgctc ttggctgaaa gagaacggga tacatctcct aatggcttta     1560
agaattggga cttcatgtct gttcacacat ggggagagaa ccctataggt acttggactt     1620
tgagaattac agacatgtct ggaagaattc aaaatgaagg aagaattgtg aactggaagc     1680
tgattttgca cgggacctct tctcagccag agcatgaagc agcctcgt gtgtacacgt       1740 cctacaacac tgttcagaat gacagaagag gggtggagaa gatggtggat ccaggggagg     1800
agcagcccac acaagagaac cctaaggaga cacccctggt gtccaaaagc cccagcagca     1860
gcagcgtagg gggccggagg gatgagttgg aggagggagc ccttccgag gccatgctgc      1920 gactcctgca aagtgctttc agtaaaaact caccgccaaa gcaatcacca agaagtccc      1980 caactgcaaa gctcaacatc ccttatgaaa acttctacga agccctggaa aagctgaaca     2040
aaccttccca gctaaagac tctgaagaca gtctgtataa tgactatgtt gatgtttttt      2100
ataacactaa accttacaag cacagagacg accggctgct tcaagctctg gtggacattc     2160
tgaatgagga aaattaaaat aagtgtgtgg tcccaagttg gaaatattca tgcttcttcc     2220
ttaccccgcg attttgcctg tgtctgaagt ggttgttttg tcatgaattc ttatgcttat     2280
aatatccttt gtggcacctt ttcttttttct ccctaaactg tacatgtgaa ggggatgagc    2340
tcaagcagga agttcaactt ccagaattga tcataggtat ttcaaaacac atcttttcctg    2400 tctgcacaag tgaagtgttt tgttctttct ggagtcacag ttgacaaaaa gctcttacac     2460
```

```
tacattagaa cactgcatta gagcccattt caattctcaa agaaaaggc aaaacctggg      2520 atatcaatta atttgaaaac ataatctgca aagaatgaga aggagtcaga aactgtttct      2580
gtagcttgtt ccctgtcttg tccatgtggt tcttcaaatt ttgatgccaa gaaagtattt      2640
ggtaggccta atgaaggagt tcactgtaag actcattccc tagatctttc tattccaaag      2700
tgccactcat tcctgtagtc aaaatctggt catgttggtc aaaagctgga ttatttagat      2760
ctagaaacag atcttgaaat ctgaatgctc tggtttgagc aattttcgaa cattctttgc      2820
ctggtgcact gtgtctgtgg tgccagaggc gtccgtggat ccagaggtgg ttatgactcg      2880
tgctgcatgc ctggtctttc ctctgtttct ccttcttctg aaagttttct atacctgtct      2940
cctttctcag ccacaaaata aatgttggga gaaatgatat ataccacttt cccagaaaaa      3000
aaaaacttac acttgggact tggcaaattc ctagtcacaa ttttttttcag cagtaacagg      3060 aaaccactta tcacatggag acctaatgta ataatagaaa aatactcata atagggagaa      3120
accaagagaa gttttgtttt tgttttttc caactgtgtt cattagaaca gcgtgttcta      3180
agtatttgaa actgaatgtt tattccttga tactaaaaga tcttctccaa tcctatcact      3240
gatagtgtcc aaattctcac caaattgctc ctaagcttca aatcagaagc agaaactggc      3300
aggccatgga ccttaattgt ccctcaggta gattttgttt ggtatgcaga atgttttaa      3360 aatatgagtg gttattgaaa atatgatgtt tcacataaaa cctcattctc ggacccatct      3420
ttgctcatgg caacagttag ctggagctga gtagcagctg cctgattaga tgactctcag      3480
tccccatggc accctgctcc atgttaccta gagcaggcac ttgattcctt gctgggcagt      3540
atccaatagg catttgattt tgcccactcc tacactaagc gaatgtgtac aaagtgtaaa      3600
tgcattagga aaacaaaact acccgcatct tctgttaggc aggatctgta caataataat      3660
tatgagtttg cttatgtaat ctcacctcac ctggatgatc actaatacca attcatttat      3720
tactaacctt ctggcttcct tctctcaata tgcttacaaa gtctccagtc acctacaatg      3780 ctggcttttct cccactgagt ttgctgtttg caattttttcc atgaagtttg aacttcataa      3840
ggtaattcat ggcattgaac tggttcatga aaagaacact agagtctgtc atttgctttg      3900
gcttgaagta tggttggtaa cacaaatttt cacctgctct tctaccattt gaatttgtgt      3960
agagggtgtt tgcagagcaa tgcccgtaat gcttagagaa tgttctccta aaagacttgc      4020
ggaatcactc tgtccttgga agtttcatat attgtttgat atgaagtgtt agatagaatt      4080
tccaatattg gagcatatca aaagtatta aaactaaaaa ggaccagaga attcttagat      4140
tggcccggaa aggccaataa agagttagaa tgaaaactca ttacttttcc attcccaatc      4200
tagtgctaga tgtataaatc tttctttga ttcttcctaa caaaatattt tctgggttaa      4260
aaccccagcc aactcattgg gttgtagcca aaggttcact ctcaagaagc tttaatattt      4320
aaataaaatc atattgaatg tttccaacct ggagtataat attcagatat aaaacagttt      4380
tgtcagtctt tcttagtgcc tgtgtggatt tttgtgaaaa tgtcaaagag aaaacttata      4440
tactatttcc cttgaaattt taaactatat tttctttaca ggtatttata atataccaat      4500
gcttttatca aacagaattt taaagagcat aataaattat attaaagaac caaaagtttt      4560
cctgagaata agaagtttc acccaataaa atattttga aaggcatgtt cctctgtcaa      4620
tgaaaaaaag tacatgtatg tgttgtgata ttaaaagtga catttgtcta atagcctaat      4680
acaacatgta gctgagttta acatgtgtgg tcttggtatt cttaagggaa cttccacatt      4740
atacatttga tgtattgacc agaatatgta aaatatgctt ataaatcaga aaataaaatt      4800
gtttctcact aagtc                                                      4815
```

<210> SEQ ID NO 18
<211> LENGTH: 5037
<212> TYPE: DNA
<213> ORGANISM: homo sapien

<400> SEQUENCE: 18

```
aagcgcttca ctgagcgctc gccgccgccc agcctctcct ctcgcgcctc ctagctcttc      60
gcagagcaac caggagccag gagtggtcta gagcccgagg gtgggaaggg ggagtctgtc     120
tggcttttct cctatcttgc ttcttttttcc tcttcccttc ccactcttgt tcaagcgagt    180
gtgtgagcta tggagcgaag agcctggagt ctgcagtgca ctgctttcgt cctcttttgc    240
gcttggtgtg cactgaacag tgcaaaagcg aaaaggcaat ttgtcaatga atgggcagcg    300
gagatccccg ggggcccgga agcagcctcg gccatcgccg aggagctggg ctatgacctt    360
ttgggtcaga ttggttcact tgaaaatcac tacttattca aacataaaaa ccaccccaga    420
aggtctcgaa ggagtgcctt tcatatcact aagagattat ctgatgatga tcgtgtgata    480
tgggctgaac aacagtatga aaagaaaga agtaaacgtt cagctctaag ggactcagca    540
ctaaatctct tcaatgatcc catgtggaat cagcaatggt acttgcaaga taccaggatg    600
acggcagccc tgcccaagct ggaccttcat gtgatacctg tttggcaaaa aggcattacg    660
ggcaaaggag ttgttatcac cgtactggat gatggtttgg agtggaatca cacggacatt    720
tatgccaact atgatccaga ggctagctat gattttaatg ataatgacca tgatccattt    780
ccccgatatg atcccacaaa cgagaacaaa cacgggacca gatgtgcagg agaaattgcc    840
atgcaagcaa ataatcacaa atgcggggtt ggagttgcat acaattccaa agttggaggc    900
ataagaatgc tggatggcat tgtgacggat gctattgagg ccagttcaat tggattcaat    960
cctggacacg tggatattta cagtgcaagc tggggcccta atgatgatgg aaaaactgtg   1020
gaggggcctg gccggctagc ccagaaggct tttgaatatg tgtcaaaca ggggagacag    1080
gggaagggt ccatcttcgt ctgggcttcg ggaaacgggg ggcgtcaggg agataattgt    1140
gactgtgatg gctacacaga cagcatctac accatctcca tcagcagtgc ctcccagcaa   1200
ggcctatccc cctggtacgc tgagaagtgc tcctccacac tggccacctc ttacagcggc    1260
ggagattaca ccgaccagag aatcacgagc gctgacctgc acaatgactg cacggagacg    1320
cacacaggca ccctcggcct tgcacctctg gctgctggca tcttcgctct ggccctggaa    1380
gcaaacccaa atctccacctg gcgagatatg cagcacctgg ttgtctggac ctctgagtat    1440
gacccgctgg ccaataaccc tggatggaaa agaatggag caggcttgat ggtgaatagt   1500
cgatttggat ttggcttgct aaatgccaaa gctctggtgg atttagctga ccccaggacc    1560
tggaggagcg tgcctgagaa gaaagagtgt gttgtaaagg acaatgactt tgagcccaga    1620
gccctgaaag ctaatggaga agttatcatt gaaattccaa caagagcttg tgaaggacaa   1680
gaaaatgcta tcaagtccct ggagcatgta caatttgaag caacaattga atattcccga    1740
agaggagacc ttcatgtcac acttacttct gctgctggaa ctagcactgt gctcttggct    1800
gaaagagaac gggatacatc tcctaatggc tttaagaact gggacttcat gtctgttcac    1860
acatggggag agaaccctat aggtacttgg actttgaaa ttacagacat gtctggaaga    1920
attcaaaatg aaggaagaat tgtgaactgg aagctgattt tgcacgggac ctcttctcag    1980
ccagagcata tgaagcagcc tcgtgtgtac acgtcctaca acactgttca gaatgacaga    2040
agggggtgg agaagatggt ggatccaggg gaggagcagc ccacacaaga gaaccctaag    2100
```

```
gagaacaccc tggtgtccaa aagccccagc agcagcagcg tagggggccg gagggatgag    2160
ttggaggagg gagccccttc ccaggccatg ctgcgactcc tgcaaagtgc tttcagtaaa    2220
aactcaccgc caaagcaatc accaaagaag tccccaagtg caaagctcaa catcccttat    2280
gaaaacttct acgaagccct ggaaaagctg aacaaacctt cccagcttaa agactctgaa    2340
gacagtctgt ataatgacta tgttgatgtt ttttataaca ctaaaccctta caagcacaga   2400 gacgaccggt tgcttcaagc tctggtggac attctgaatg aggaaaatta aaataagtgt    2460
gtggtcccaa gttggaaata ttcatgcttc ttccttaccc tgcgattttg cctgtgtctg    2520
aagtggttgt tttgtcatga attcttatgc ttataatatc ctttgtggca cctttttcttt  2580 ttctccctaa actgtacatg tgaaggggat gagctcaagc aggaagttca acttccagaa    2640
ttgatcatag gtatttcaaa acacatcttt cctgtctgca caagtgaagt gttttgttct    2700
ttctggagtc acagttgaca aaaagctctt acactacatt agaacactgc attagagccc    2760
atttcaattc tcaaaagaaa aggcaaaacc tgggatatca attaatttga aaacataatc    2820
tgcaaagaat gagaaggagt cagaaactgt ttctgtagct tgttccctgt cttgtccatg    2880
tggttcttca aattttgatg ccaagaaagt atttggtagg cctaatgaag gagttcactg    2940
taagactcat tccctagatc tttctattcc aaagtgccac tcattcctgt agtcaaaatc    3000
tggtcatgtt ggtcaaaagc tggattattt agatctagaa acagatcttg aaatctgaat    3060
gctctggttt gagcaatttt cgaacattct ttgcctggtg cactgtgtct gtggtgccag    3120
aggcgtccgt ggatccagag gtggttatga ctcgtgctgc atgcctggtc tttcctctgt    3180
ttctccttct gaaagttttc tatacctgtc tcctttctca gccacaaaat aaatgttggg    3240
agaaatgata tataccactt tcccagaaaa aaaaaaactt acacttggga cttggcaaat    3300
tcctagtcac aatttttttc agcagtaaca ggaaaccact tatcacatgg agacctaatg    3360
taataataga aaaatactca taataggagg aaaccaagag aagttttgtt tttgttttttt    3420 tccaactgtg ttcattagaa cagcgtgttc taagtatttg aaactgaatg tttattcctt    3480
gatactaaaa gttcttctcc aatcctatca ctgatagtgt ccaaattctc accaaattgc    3540
tcctaagctt caaatcagaa gcagaaactg gcaggccatg gacctttaatt gtccctcagg   3600 tagattttgt ttggtatgca gaatgttttt aaaatatgag tggttattga aaatatgatg     3660
tttcacataa aacctcattc tcggacccat cttttgctcat ggcaacagtt agctggagct    3720
gagtagcagc tgcctgatta gatgactctc agtccccatg gcaccctgct ccatgttacc    3780
tagagcaggc acttgattcc ttgctgggca gtatccaata ggcatttgat tttgcccact    3840
cctacactaa gcgaatgtgt acaaagtgta aatgcattag gaaaaacaaa ctacccgcat    3900
cttctgttag gcaggatctg tacaataata attatgagtt tgcttatgta atctcacctc    3960
acctggatga tcactaatac taattcattt attactaacc ttctggcttc cttctctcaa    4020
tatgcttaca aagtctccag tcacctacaa tgctggcttt ctcccactga gtttgctgtt    4080 tgcaatttttt ccatgaagtt tgaacttcat aaggtaattc atggcattga actggttcat   4140
gaaaagaaca ctagagtctg tcatttgctt tggcttgaag tatggttggt aacacaaatt    4200
ttcacctgct cttctaccat ttgaatttgt gtagagggtg tttgcagagc aatgcccgta    4260
atgcttagag aatgttctcc taaaagactt gcggaatcac tctgtccttg gaagtttcat    4320
atattgtttg atatgaagtg ttagatagaa tttccaatat tggagcatat caaaaagtat    4380
taaaactaaa aaggaccaga gaattcttag attggcccgg aaaggccaat aaagagttag    4440
aatgaaaact cattactttt ccattcccaa tctagtgcta gatgtataaa tctttctttt    4500
```

```
gattcttcct aacaaaatat tttctgggtt aaaaccccag ccaactcatt gggttgtagc      4560
caaaggttca ctctcaagaa gctttaatat ttaaataaaa tcatattgaa tgtttccaac      4620
ctggagtata atattcagat ataaaacagt tttgtcagtc tttcttagtg cctgtgtgga      4680
tttttgtgaa aatgtcaaag agaaaactta tatactattt cccttgaaat tttaaactat      4740
attttcttta caggtattta taatatacca atgctttat caaacagaat tttaaagagc      4800
ataataaatt atattaaaga accaaaagtt tcctgagaa taagaaagtt tcacccaata      4860
aaatattttt gaaaggcatg ttcctctgtc aatgaaaaaa agtacatgta tgtgttgtga      4920
tattaaaagt gacatttgtc taatagccta atacaacatg tagctgagtt taacatgtgt      4980
ggtcttggta ttcttaaggg aacttccaca ttatacattt gatgtattga ccagaat        5037

<210> SEQ ID NO 19
<211> LENGTH: 3298
<212> TYPE: DNA
<213> ORGANISM: homo sapien

<400> SEQUENCE: 19
gttgtcgact gtcaggaccg aagcgcttca ctgagcgctc gccgccgccc agcctctcct        60
ctcgcgcctc ctagctcttc gcagagcaac caggagccag gagtggtcta gagcccgagg       120
gtgggaaggg ggagtctgtc tggcttttct cctatcttgc ttcttttcc tcttcccttc       180 ccactcttgt tcaagcgagt gtgtgagcta tggagcgaag agcctggagt ctgcagtgca       240
ctgctttcgt cctctttgc gcttggtgtg cactgaacag tgcaaaagcg aaaaggcaat       300
ttgtcaatga atgggcagcg gagatccccg ggggcccgga agcagcctcg gccatcgccg       360
aggagctggg ctatgacctt ttgggtcaga ttggttcact tgaaaatcac tacttattca       420
aacataaaaa ccaccccaga aggtctcgaa ggagtgcctt tcatatcact aagagattat       480
ctgatgatga tcgtgtgata tgggctgaac aacagtatga aaagaaaga agtaaacgtt       540 cagctctaag ggactcagca ctaaatctct tcaatgatcc catgtggaat cagcaatggt       600
acttgcaaga taccaggatg acggcagccc tgcccaagct ggaccttcat gtgatacctg       660
tttggcaaaa aggcattacg ggcaaaggag ttgttatcac cgtactggat gatggttgg       720 agtggaatca cacggacatt tatgccaact atgatccaga ggctagctat gattttaatg       780
ataatgacca tgatccattt ccccgatatg atcccacaaa cgagaacaaa cacgggacca       840
gatgtgcagg agaaattgcc atgcaagcaa ataatcacaa atgcgggtt ggagttgcat       900 acaattccaa agttggaggc ataagaatgc tggatggcat tgtgacggat gctattgagg       960
ccagttcaat tggattcaat cctggacacg tggatattta cagtgcaagc tggggcccta      1020
atgatgatgg gaaaactgtg gaggggcctg gccggctagc ccagaaggct tttgaatatg      1080
gtgtcaaaca ggggagacag gggaaggggt ccatcttcgt ctgggcttcg ggaaacgggg      1140
ggcgtcaggg agataattgt gactgtgatg gctacacaga cagcatctac accatctcca      1200
tcagcagtgc ctcccagcaa ggcctatccc cctggtacgc tgagaagtgc tcctccacac      1260
tggccacctc ttacagcagc ggagattaca ccgaccagag aatcacgagc gctgacctgc      1320
acaatgactg cacggagacg cacacaggca cctcggcctc tgcacctctg ctgctggca       1380 tcttcgctct ggccctggaa gcaaacccaa atctcacctg gcgagatatg cagcacctgg      1440
ttgtctggac ctctgagtat gacccgctgg ccaataaccc tggatggaaa agaatggag      1500 caggcttgat ggtgaatagt cgatttggat ttggcttgct aaatgccaaa gctctggtgg      1560
```

| | |
|---|---|
| atttagctga ccccaggacc tggaggagcg tgcctgagaa gaaagagtgt gttgtaaagg | 1620 |
| acaatgactt tgagcccaga gccctgaaag ctaatggaga agttatcatt gaaattccaa | 1680 |
| caagagcttg tgaaggacaa gaaaatgcta tcaagtccct ggagcatgta caatttgaag | 1740 |
| caacaattga atattcccga agaggagacc ttcatgtcac acttacttct gctgctggaa | 1800 |
| ctagcactgt gctcttggct gaaagagaac gggatacatc tcctaatggc tttaagaact | 1860 |
| gggacttcat gtctgttcac acatgggag agaaccctat aggtacttgg actttgagaa | 1920 |
| ttacagacat gtctggaaga attcaaaatg aaggaagaat tgtgaactgg aagctgattt | 1980 |
| tgcacgggac ctcttctcag ccagagcata tgaagcagcc tcgtgtgtac acgtcctaca | 2040 |
| acactgttca gaatgacaga gaggggtgg agaagatggt ggatccaggg gaggagcagc | 2100 |
| ccacacaaga gaaccctaag gagaacaccc tggtgtccaa agccccagc agcagcagcg | 2160 |
| tagggggccg gagggatgag ttggaggagg agcccccttc ccaggccatg ctgcgactcc | 2220 |
| tgcaaagtgc tttcagtaaa aactcaccgc caaagcaatc accaaagaag tccccaagtg | 2280 |
| caaagctcaa catcccttat gaaaacttct acgaagccct ggaaaagctg aacaaacctt | 2340 |
| cccagcttaa agactctgaa gacagtctgt ataatgacta tgttgatgtt ttttataaca | 2400 |
| ctaaaccttaa caagcacaga gacgaccggc tgcttcaagc tctggtggac attctgaatg | 2460 |
| aggaaaatta aaataagtgt gtggtcccaa gttggaaata ttcatgcttc ttccttaccc | 2520 |
| tgcgattttg cctgtgtctg aagtggttgt tttgtcatga attcttatgc ttataatatc | 2580 |
| ctttgtggca cctttttcttt ttctccctaa actgtacatg tgaaggggat gagctcaagc | 2640 |
| aggaagttca acttccagaa ttgatcatag gtatttcaaa acacatcttt cctgtctgca | 2700 |
| caagtgaagt gttttgttct ttctggagtc acagttgaca aaaagctctt acactacatt | 2760 |
| agaacactgc attagagccc atttcaattc tcaaaagaaa aggcaaaacc tgggatatca | 2820 |
| attaatttga aaacataatc tgcaaagaat gagaaggagt cagaaactgt ttctgtagct | 2880 |
| tgttccctgt cttgtccatg tggttcttca aatttttgatg ccaagaaagt atttggtagg | 2940 |
| cctaatgaag gagttcactg taagactcat tccctagatc tttctattcc aaagtgccac | 3000 |
| tcattcctgt agtcaaaatc tggtcatgtt ggtcaaaagc ctggattatt tagatctaga | 3060 |
| aacagatctt gaaatctgaa tgctctggtt tgagcaattt tcgaacattc tttgcctggt | 3120 |
| gcactgtgtc tgtggtgcca gaggcgtccg tggatccaga ggtggttatg actcgtgctg | 3180 |
| catgcctggt cttttcctctg tttctccttc tgaaagtttt ctataccgtgt ctcctttctc | 3240 |
| agccacaaaa taaatgttgg gagaaatgat atataccact ttcccaaaaa aaaaaaaa | 3298 |

<210> SEQ ID NO 20
<211> LENGTH: 2233
<212> TYPE: DNA
<213> ORGANISM: homo sapien

<400> SEQUENCE: 20

| | |
|---|---|
| ggccagtccc actgcagggt cgagatgccg aactgactat ggggaaggga tctatttctt | 60 |
| tcttgttctt cagccaaatt ggttcacttg aaaatcacta cttattcaaa cataaaaacc | 120 |
| accccagaag gtctcgaagg agtgcctttc atatcactaa gagattatct gatgatgatc | 180 |
| gtgtgatatg ggctgaacaa cagtatgaaa agaaagaag taaacgttca gctctaaggg | 240 |
| actcagcact aaatctcttc aatgatccca tgtggaatca gcaatggtac ttgcaagata | 300 |
| ccaggatgac ggcagccctg cccagctgg accttcatgt gatacctgtt tggcaaaaag | 360 |
| gcattacggg caaaggagtt gttatcaccg tactggatga tggtttggag tggaatcaca | 420 |

```
cggacattta tgccaactat gatccagagg ctagctatga ttttaatgat aatgaccatg    480
atccatttcc ccgatatgat cccacaaacg agaacaaaca cgggaccaga tgtgcaggag    540
aaattgccat gcaagcaaat aatcacaaat gcggggttgg agttgcatac aattccaaag    600
ttggaggcat aagaatgctg gatggcattg tgacggatgc tattgaggcc agttcaattg    660
gattcaatcc tggacacgtg gatatttaca gtgcaagctg gggccctaat gatgatggga    720
aaactgtgga ggggcctggc cggctagccc agaaggcttt tgaatatggt gtcaaacagg    780
ggagacaggg gaaggggtcc atcttcgtct gggcttcggg aaacgggggg cgtcagggag    840
ataattgtga ctgtgatggc tacacagaca gcatctacac catctccatc agcagtgcct    900
cccagcaagg cctatccccc tggtacgctg agaagtgctc ctccacactg gccacctctt    960
acagcagcgg agattacacc gaccagagaa tcacgagcgc tgacctgcac aatgactgca   1020
cggagacgca cacaggcacc tcggcctctg cacctctggc tgctggcatc ttcgctctgg   1080
ccctggaagc aaacccaaat ctcacctggc gagatatgca gcacctggtt gtctggacct   1140
ctgagtatga cccgctggcc aataaccctg gatggaaaaa gaatggagca ggcttgatgg   1200
tgaatagtcg atttggattt ggcttgctaa atgccaaagc tctggtggat ttagctgacc   1260
ccaggacctg gaggagcgtg cctgagaaga aagagtgtgt tgtaaaggac aatgactttg   1320
agcccagagc cctgaaagct aatggagaag ttatcattga aattccaaca agagcttgtg   1380
aaggacaaga aaatgctatc aagtccctgg agcatgtaca atttgaagca caattgaat   1440 attcccgaag aggagacctt catgtcacac ttacttctgc tgctggaact agcactgtgc   1500
tcttggctga aagagaacgg gatacatctc ctaatggctt taagaactgg gacttcatgt   1560
ctgttcacac atggggagag aaccctatag gtacttggac tttgagaatt acagacatgt   1620
ctggaagaat tcaaaatgaa ggaagaattg tgaactggaa gctgattttg cacgggacct   1680
cttctcagcc agagcatatg aagcagcctc gtgtgtacac gtcctacaac actgttcaga   1740
atgacggaag aggggtggag aagatggtgg atccagggga ggagcagccc acacaagaga   1800
accctaagga gaacaccctg gtgtccaaaa gccccagcag cagcagcgta ggggccgga   1860 gggatgagtt ggaggaggga gccccttccc aggccatgct gcgactcctg caaagtgctt   1920
tcagtaaaaa ctcaccgcca aagcaatcac caaagaagtc cccaagtgca agctcaaca   1980 tcccttatga aaacttctac gaagccctgg aaaagctgaa caaaccttcc cagcttaaag   2040
actctgaaga cagtctgtat aatgactatg ttgatgtttt ttataacact aaaccttaca   2100
agcacagaga cgaccggctg cttcaagctc tggtggacat tctgaatgag gaaaattaaa   2160
ataagtgtgt ggtcccaagt tggaaatatt catgcttctt ccttaccctg cgattttgcc   2220
tgtgtctgaa gtg                                                      2233
```

<210> SEQ ID NO 21
<211> LENGTH: 2450
<212> TYPE: DNA
<213> ORGANISM: homo sapien

<400> SEQUENCE: 21

```
accaggagcc aggagtggtc cagagcccga gggtgggaag ggggagtctg tctggctttt     60
ctcctatctt gcttcttttt cctcttccct tcccactctt gttcaagcga gtgtgtgagc    120
tatggagcga agagcctgga gtctgcagtg cactgctttc gtcctctttt gcgcttggtg    180
tgcactgaac agtgcaaaag cgaaaaggca atttgtcaat gaatgggcag cggagatccc    240
```

-continued

| | |
|---|---|
| cggggggcccg gaagcagcct cggccatcgc cgaggagctg ggctatgacc tttgggtca | 300 |
| gattggttca cttgaaaatc actacttatt caaacataaa aaccacccca gaaggtctcg | 360 |
| aaggagtgcc tttcatatca ctaagagatt atctgatgat gatcgtgtga tatgggctga | 420 |
| acaacagtat gaaaagaaa gaagtaaacg ttcagctcta agggactcag cactaaatct | 480 |
| cttcaatgat cccatgtgga atcagcaatg gtacttgcaa gataccagga tgacggcagc | 540 |
| cctgcccaag ctggacccttc atgtgatacc tgtttggcaa aaaggcatta cgggcaaagg | 600 |
| agttgttatc accgtactgg atgatggttt ggagtggaat cacacggaca tttatgccaa | 660 |
| ctatgatcca gaggctagct atgattttaa tgataatgac catgatccat ttccccgata | 720 |
| tgatcccaca aacgagaaca aacacgggac cagatgtgca ggagaaattg ccatgcaagc | 780 |
| aaataatcac aaatgcgggg ttggagttgc atacaattcc aaagttggag gcataagaat | 840 |
| gctggatggc attgtgacgg atgctattga ggccagttca attggattca atcctggaca | 900 |
| cgtggatatt tacagtgcaa gctggggccc taatgatgat gggaaaactg tggaggggcc | 960 |
| tggccggcta gcccagaagg cttttgaata tggtgtcaaa caggggagac aggggaaggg | 1020 |
| gtccatcttc gtctgggctt cgggaaacgg ggggcgtcag ggagataatt gtgactgtga | 1080 |
| tggctacaca gacagcatct acaccatctc catcagcagt gcctcccagc aaggcctatc | 1140 |
| cccctggtac gctgagaagt gctcctccac actggccacc tcttacagca gcggagatta | 1200 |
| caccgaccag agaatcacga gcgctgacct gcacaatgac tgcacggaga cgcacacagg | 1260 |
| cacctcggcc tctgcacctc tggctgctgg catcttcgct ctggccctgg aagcaaaccc | 1320 |
| aaatctcacc tggcgagata tgcagcacct ggttgtctgg acctctgagt atgacccgct | 1380 |
| ggccaataac cctggatgga aaagaatgg agcaggcttg atggtgaata gtcgatttgg | 1440 |
| atttggcttg ctaaatgcca aagctctggt ggatttagct gaccccagga cctggaggag | 1500 |
| cgtgcctgag aagaaagagt gtgttgtaaa ggacaatgac tttgagccca gagccctgaa | 1560 |
| agctaatgga gaagttatca ttgaaaattcc aacaagagct tgtgaaggac aagaaaatgc | 1620 |
| tatcaagtcc ctggagcatg tacaatttga agcaacaatt gaatattccc gaagaggaga | 1680 |
| ccttcatgtc acacttactt ctgctgctgg aactagcact gtgctcttgg ctgaaagaga | 1740 |
| acgggataca tctcctaatg gctttaagaa ttgggacttc atgtctgttc acacatgggg | 1800 |
| agagaaccct ataggtactt ggactttgag aattacagac atgtctggaa gaattcaaaa | 1860 |
| tgaaggaaga attgtgaact ggaagctgat tttgcacggg acctcttctc agccagagca | 1920 |
| tatgaagcag cctcgtgtgt acacgtccta caacactgtt cagaatgaca gaagaggggt | 1980 |
| ggagaagatg gtggatccag gggaggagca gcccacacaa gagaaccctaa aggagaacac | 2040 |
| cctggtgtcc aaaagcccca gcagcagcag cgtaggggc cggagggatg agttggagga | 2100 |
| gggagcccct tccgaggcca tgctgcgact cctgcaaagt gctttcagta aaaactcacc | 2160 |
| gccaaagcaa tcaccaaaga agtccccaac tgcaaagctc aacatccctt atgaaaactt | 2220 |
| ctacgaagcc ctggaaaagc tgaacaaacc ttcccagctt aaagactctg aagacagtct | 2280 |
| gtataatgac tatgttgatg ttttttataa cactaaacct tacaagcaca gagacgaccg | 2340 |
| gctgcttcaa gctctggtgg acattctgaa tgaggaaaat taaaataagt gtgtggtccc | 2400 |
| aagttggaaa tattcatgct tcttccttac cctgcgattt tgcctgtgtc | 2450 |

<210> SEQ ID NO 22
<211> LENGTH: 2450
<212> TYPE: DNA
<213> ORGANISM: homo sapien

<400> SEQUENCE: 22

```
accaggagcc aggagtggtc cagagcccga gggtgggaag ggggagtctg tctggctttt      60
ctcctatctt gcttcttttt cctcttccct tcccactctt gttcaagcga gtgtgtgagc     120
tatggagcga gagcctgga gtctgcagtg cactgctttc gtcctctttt gcgcttggtg     180
tgcactgaac agtgcaaaag cgaaaaggca atttgtcaat gaatgggcag cggagatccc     240
cgggggcccg gaagcagcct cggccatcgc cgaggagctg ggctatgacc ttttgggtca     300
gattggttca cttgaaaatc actacttatt caaacataaa aaccacccca gaaggtctcg     360
aaggagtgcc tttcatatca ctaagagatt atctgatgat gatcgtgtga tatgggctga     420
acaacagtat gaaaagaaa gaagtaaacg ttcagctcta agggactcag cactaaatct     480
cttcaatgat cccatgtgga atcagcaatg gtacttgcaa gataccagga tgacggcagc     540
cctgcccaag ctggaccttc atgtgatacc tgtttggcaa aaaggcatta cgggcaaagg     600
agttgttatc accgtactgg atgatggttt ggagtggaat cacacggaca tttatgccaa     660
ctatgatcca gaggctagct atgattttaa tgataatgac catgatccat tccccgata      720
tgatcccaca aacgagaaca aacacggac cagatgtgca ggagaaattg ccatgcaagc     780
aaataatcac aaatgcgggg ttggagttgc atacaattcc aaagttggag cataagaat      840
gctggatggc attgtgacgg atgctattga ggccagttca attggattca atcctggaca     900
cgtggatatt tacagtgcaa gctggggccc taatgatgat gggaaaactg tggaggggcc     960
tggccggcta gcccagaagg cttttgaata tggtgtcaaa caggggagac aggggaaggg    1020
gtccatcttc gtctgggctt cgggaaacgg ggggcgtcag ggagataatt gtgactgtga    1080
tggctacaca gacagcatct acaccatctc catcagcagt gcctcccaac aaggcctatc    1140
cccctggtac gctgagaagt gctcctccac actggccacc tcttacagca gcggagatta    1200
caccgaccag agaatcacga gcgctgacct gcacaatgac tgcacggaga cgcacacagg    1260
cacctcggcc tctgcacctc tggctgctgg catcttcgct ctggcctgg aagcaaaccc     1320
aaatctcacc tggcgagata tgcagcacct ggttgtctgg acctctgagt atgacccgct    1380
ggccaataac cctggatgga aaagaatgg agcaggcttg atggtgaata gtcgatttgg     1440
atttggcttg ctaaatgcca aagctctggt ggatttagct gaccccagga cctggaggag    1500
cgtgcctgag aagaaagagt gtgttgtaaa ggacaatgac tttgagccca gagccctgaa    1560
agctaatgga gaagttatca ttgaaattcc aacaagagct tgtgaaggac aagaaaatgc    1620
tatcaagtcc ctggagcatg tacaatttga agcaacaatt gaatattccc gaagaggaga    1680
ccttcatgtc acacttactt ctgctgctgg aactagcact gtgctcttgg ctgaaagaga    1740
acgggataca tctcctaatg gctttaagaa ttgggacttc atgtctgttc acacatgggg    1800
agagaaccct ataggtactt ggactttgag aattacagac atgtctggaa gaattcaaaa    1860
tgaaggaaga attgtgaact ggaagctgat tttgcacggg acctcttctc agccagagca    1920
tatgaagcag cctcgtgtgt acacgtccta caacactgtt cagaatgaca aagaggggt     1980
ggagaagatg gtggatccag gggaggagca gcccacacaa gagaaccct aggagaacac    2040
cctggtgtcc aaaagcccca gcagcagcag cgtaggggc cggagggatg agttggagga    2100
gggagcccct tccgaggcca tgctgcgact cctgcaaagt gctttcagta aaaactcacc    2160
gccaaagcaa tcaccaagaa agtccccaac tgcaaagctc aacatccctt atgaaaactt    2220
ctacgaagcc ctggaaaagc tgaacaaacc ttcccagctt aaagactctg aagacagtct    2280
```

-continued

| | |
|---|---|
| gtataatgac tatgttgatg ttttttataa cactaaacct tacaagcaca gagacgaccg | 2340 |
| gctgcttcaa gctctggtgg acattctgaa tgaggaaaat taaaataagt gtgtggtccc | 2400 |
| aagttggaaa tattcatgct tcttccttac cctgcgattt tgcctgtgtc | 2450 |

<210> SEQ ID NO 23
<211> LENGTH: 2276
<212> TYPE: DNA
<213> ORGANISM: homo sapien

<400> SEQUENCE: 23

| | |
|---|---|
| gcgatcgcca tggagcgaag agcctggagt ctgcagtgca ctgctttcgt cctcttttgc | 60 |
| gcttggtgtg cactgaacag tgcaaaagcg aaaaggcaat ttgtcaatga atgggcagcg | 120 |
| gagatccccg ggggcccgga agcagcctcg gccatcgccg aggagctggg ctatgacctt | 180 |
| ttgggtcaga ttggttcact tgaaaatcac tacttattca acataaaaa ccaccccaga | 240 |
| aggtctcgaa ggagtgcctt tcatatcact aagagattat ctgatgatga tcgtgtgata | 300 |
| tgggctgaac aacagtatga aaagaaaga agtaaacgtt cagctctaag ggactcagca | 360 |
| ctaaatctct tcaatgatcc catgtggaat cagcaatggt acttgcaaga taccaggatg | 420 |
| acggcagccc tgcccaagct ggaccttcat gtgatacctg tttggcaaaa aggcattacg | 480 |
| ggcaaaggag ttgttatcac cgtactggat gatggtttgg agtggaatca cacggacatt | 540 |
| tatgccaact atgatccaga ggctagctat gattttaatg ataatgacca tgatccattt | 600 |
| ccccgatatg atcccacaaa cgagaacaaa cacgggacca gatgtgcagg agaaattgcc | 660 |
| atgcaagcaa ataatcacaa atgcggggtt ggagttgcat acaattccaa agttggaggc | 720 |
| ataagaatgc tggatggcat tgtgacggat gctattgagg ccagttcaat tggattcaat | 780 |
| cctggacacg tggatattta cagtgcaagc tggggcccta atgatgatgg gaaaactgtg | 840 |
| gaggggcctg gccggctagc ccagaaggct tttgaatatg gtgtcaaaca ggggagacag | 900 |
| gggaaggggt ccatcttcgt ctgggcttcg ggaaacgggg ggcgtcaggg agataattgt | 960 |
| gactgtgatg gctacacaga cagcatctac accatctcca tcagcagtgc ctcccagcaa | 1020 |
| ggcctatccc cctggtacgc tgagaagtgc tcctccacac tggccacctc ttacagcagc | 1080 |
| ggagattaca ccgaccagag aatcacgagc gctgacctgc acaatgactg cacggagacg | 1140 |
| cacacaggca cctcggcctc tgcacctctg gctgctggca tcttcgctct ggccctggaa | 1200 |
| gcaaacccaa atctcacctg gcgagatatg cagcacctgg ttgtctggac tctgagtat | 1260 |
| gacccgctgg ccaataaccc tggatggaaa agaatggag caggcttgat ggtgaatagt | 1320 |
| cgatttggat ttggcttgct aaatgccaaa gctctggtgg atttagctga ccccaggacc | 1380 |
| tggaggagcg tgcctgagaa gaaagagtgt gttgtaaagg acaatgactt tgagcccaga | 1440 |
| gccctgaaag ctaatggaga agttatcatt gaaattccaa caagagcttg tgaaggacaa | 1500 |
| gaaaatgcta tcaagtccct ggagcatgta caatttgaag caacaattga atattcccga | 1560 |
| agaggagacc ttcatgtcac acttacttct gctgctggaa ctagcactgt gctcttggct | 1620 |
| gaaagagaac gggatacatc tcctaatggc tttaagaatt gggacttcat gtctgttcac | 1680 |
| acatggggag agaaccctat aggtacttgg acttttgagaa ttacagacat gtctggaaga | 1740 |
| attcaaaatg aaggaagaat tgtgaactgg aagctgattt tgcacgggac tcttctcag | 1800 |
| ccagagcata tgaagcagcc tcgtgtgtac acgtcctaca acactgttca gaatgacaga | 1860 |
| agaggggtgg agaagatggt ggatccaggg gaggagcagc ccacacaaga gaaccctaag | 1920 |
| gagaacaccc tggtgtccaa aagccccagc agcagcagcg tagggggccg gagggatgag | 1980 |

```
ttggaggagg gagcccctcc ccaggccatg ctgcgactcc tgcaaagtgc tttcagtaaa   2040
aactcaccgc caaagcaatc accaaagaag tccccaagtg caaagctcaa catcccttat   2100
gaaaacttct acgaagccct ggaaaagctg aacaaacctt cccagcttaa agactctgaa   2160
gacagtctgt ataatgacta tgttgatgtt ttttataaca ctaaaaccta caagcacaga   2220
gacgaccggc tgcttcaagc tctggtggac attctgaatg aggaaaatgt ttaaac      2276
```

<210> SEQ ID NO 24
<211> LENGTH: 753
<212> TYPE: PRT
<213> ORGANISM: homo sapien

<400> SEQUENCE: 24

```
Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
                20                  25                  30

Asn Glu Trp Ala Ala Glu Ile Pro Gly Gly Pro Glu Ala Ala Ser Ala
            35                  40                  45

Ile Ala Glu Glu Leu Gly Tyr Asp Leu Leu Gly Gln Ile Gly Ser Leu
        50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300

Trp Ala Ser Gly Asn Gly Gly Arg Gln Gly Asp Asn Cys Asp Cys Asp
305                 310                 315                 320
```

```
Gly Tyr Thr Asp Ser Ile Tyr Thr Ile Ser Ile Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
            355                 360                 365

Asp Leu His Asn Asp Cys Thr Glu Thr His Thr Gly Thr Ser Ala Ser
        370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
            420                 425                 430

Leu Met Val Asn Ser Arg Phe Gly Phe Gly Leu Leu Asn Ala Lys Ala
            435                 440                 445

Leu Val Asp Leu Ala Asp Pro Arg Thr Trp Arg Ser Val Pro Glu Lys
        450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
            515                 520                 525

Ala Gly Thr Ser Thr Val Leu Leu Ala Glu Arg Glu Arg Asp Thr Ser
        530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
        610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Val Gly Gly Arg Arg Asp
                645                 650                 655

Glu Leu Glu Glu Gly Ala Pro Ser Glu Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Thr Ala Lys Leu Asn Ile Pro Tyr Glu Asn Phe Tyr Glu Ala Leu
        690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
```

Asn

<210> SEQ ID NO 25
<211> LENGTH: 753
<212> TYPE: PRT
<213> ORGANISM: homo sapien

<400> SEQUENCE: 25

Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
            20                  25                  30

Asn Glu Trp Ala Ala Glu Ile Pro Gly Gly Pro Glu Ala Ala Ser Ala
        35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Arg Val
            85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
            115                 120                 125

Gln Trp Tyr Leu Gln Asp Thr Arg Met Thr Ala Ala Leu Pro Lys Leu
130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
            195                 200                 205

Gly Thr Arg Cys Ala Gly Glu Ile Ala Met Gln Ala Asp Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala

```
              355                 360                 365
Asp Leu His Asn Asp Cys Thr Glu Thr His Thr Gly Thr Ser Ala Ser
        370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
            420                 425                 430

Leu Met Val Asn Ser Arg Phe Gly Phe Gly Leu Leu Asn Ala Lys Ala
        435                 440                 445

Leu Val Asp Leu Ala Asp Pro Arg Thr Trp Arg Ser Val Pro Glu Lys
450                 455                 460

Lys Glu Cys Val Val Lys Asp Asn Asp Phe Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
        610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Val Gly Gly Arg Arg Asp
                645                 650                 655

Glu Leu Glu Glu Gly Ala Pro Ser Glu Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Thr Ala Lys Leu Asn Ile Pro Tyr Glu Asn Phe Tyr Glu Ala Leu
690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
            740                 745                 750

Asn

<210> SEQ ID NO 26
<211> LENGTH: 753
```

```
<212> TYPE: PRT
<213> ORGANISM: homo sapien

<400> SEQUENCE: 26

Met Glu Arg Arg Ala Trp Ser Leu Gln Cys Thr Ala Phe Val Leu Phe
1               5                   10                  15

Cys Ala Trp Cys Ala Leu Asn Ser Lys Ala Lys Arg Gln Phe Val
            20                  25                  30

Asn Glu Trp Ala Ala Glu Ile Pro Gly Gly Pro Glu Ala Ala Ser Ala
            35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300

Trp Ala Leu Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
        355                 360                 365

Asp Leu His Asn Asp Cys Thr Glu Thr His Thr Gly Thr Ser Ala Ser
    370                 375                 380

Ala Pro Leu Ala Ala Gly Ile Phe Ala Leu Ala Leu Glu Ala Asn Pro
385                 390                 395                 400
```

```
Asn Leu Thr Trp Arg Asp Met Gln His Leu Val Val Trp Thr Ser Glu
                405                 410                 415
Tyr Asp Pro Leu Ala Asn Asn Pro Gly Trp Lys Lys Asn Gly Ala Gly
            420                 425                 430
Leu Met Val Asn Ser Arg Phe Gly Phe Gly Leu Leu Asn Ala Lys Ala
        435                 440                 445
Leu Val Asp Leu Ala Asp Pro Arg Thr Trp Arg Ser Val Pro Glu Lys
    450                 455                 460
Lys Glu Cys Val Val Lys Asp Asn Asp Phe Glu Pro Arg Ala Leu Lys
465                 470                 475                 480
Ala Asn Gly Glu Val Ile Ile Glu Ile Pro Thr Arg Ala Cys Glu Gly
                485                 490                 495
Gln Glu Asn Ala Ile Lys Ser Leu Glu His Val Gln Phe Glu Ala Thr
            500                 505                 510
Ile Glu Tyr Ser Arg Arg Gly Asp Leu His Val Thr Leu Thr Ser Ala
        515                 520                 525
Ala Gly Thr Ser Thr Val Leu Leu Ala Glu Arg Glu Arg Asp Thr Ser
    530                 535                 540
Pro Asn Gly Phe Lys Asn Trp Asp Phe Met Ser Val His Thr Trp Gly
545                 550                 555                 560
Glu Asn Pro Ile Gly Thr Trp Thr Leu Arg Ile Thr Asp Met Ser Gly
                565                 570                 575
Arg Ile Gln Asn Glu Gly Arg Ile Val Asn Trp Lys Leu Ile Leu His
            580                 585                 590
Gly Thr Ser Ser Gln Pro Glu His Met Lys Gln Pro Arg Val Tyr Thr
        595                 600                 605
Ser Tyr Asn Thr Val Gln Asn Asp Arg Arg Gly Val Glu Lys Met Val
    610                 615                 620
Asp Pro Gly Glu Glu Gln Pro Thr Gln Glu Asn Pro Lys Glu Asn Thr
625                 630                 635                 640
Leu Val Ser Lys Ser Pro Ser Ser Ser Val Gly Gly Arg Arg Asp
                645                 650                 655
Glu Leu Glu Glu Gly Ala Pro Ser Glu Ala Met Leu Arg Leu Leu Gln
            660                 665                 670
Ser Ala Phe Ser Lys Asn Ser Pro Pro Lys Gln Ser Pro Lys Lys Ser
        675                 680                 685
Pro Thr Ala Lys Leu Asn Ile Pro Tyr Glu Asn Phe Tyr Glu Ala Leu
    690                 695                 700
Glu Lys Leu Asn Lys Pro Ser Gln Leu Lys Asp Ser Glu Asp Ser Leu
705                 710                 715                 720
Tyr Asn Asp Tyr Val Asp Val Phe Tyr Asn Thr Lys Pro Tyr Lys His
                725                 730                 735
Arg Asp Asp Arg Leu Leu Gln Ala Leu Val Asp Ile Leu Asn Glu Glu
            740                 745                 750
Asn

<210> SEQ ID NO 27
<211> LENGTH: 753
<212> TYPE: PRT
<213> ORGANISM: homo sapien

<400> SEQUENCE: 27

Met Glu Arg Arg Ala Trp Ser Leu Gln Cys Thr Ala Phe Val Leu Phe
1               5                   10                  15
```

-continued

Cys Ala Trp Cys Ala Leu Asn Ser Ala Lys Ala Lys Arg Gln Phe Val
                20                  25                  30

Asn Glu Trp Ala Ala Glu Ile Pro Gly Gly Pro Glu Ala Ala Ser Ala
            35                  40                  45

Ile Ala Glu Glu Leu Gly Tyr Asp Leu Leu Gly Gln Ile Gly Ser Leu
50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Arg Val
                85                  90                  95

Ile Trp Ala Glu Gln Gln Tyr Glu Lys Glu Arg Ser Lys Arg Ser Ala
                100                 105                 110

Leu Arg Asp Ser Ala Leu Asn Leu Phe Asn Asp Pro Met Trp Asn Gln
            115                 120                 125

Gln Trp Tyr Leu Gln Asp Thr Arg Met Thr Ala Ala Leu Pro Lys Leu
130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
                180                 185                 190

Asp His Asp Pro Phe Pro Arg Tyr Asp Pro Thr Asn Glu Asn Lys His
            195                 200                 205

Gly Thr Arg Cys Ala Gly Glu Ile Ala Met Gln Ala Asn Asn His Lys
            210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
            275                 280                 285

Glu Tyr Gly Val Lys Gln Gly Arg Gln Gly Lys Gly Ser Ile Phe Val
            290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
            355                 360                 365

Asp Leu His Asn Asp Cys Thr Glu Thr His Thr Gly Thr Ser Ala Ser
            370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
            420                 425                 430

```
Leu Met Val Asn Ser Arg Phe Gly Phe Gly Leu Leu Asn Ala Lys Ala
            435                 440                 445

Leu Val Asp Leu Ala Asp Pro Arg Thr Trp Arg Ser Val Pro Glu Lys
450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
    530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
            580                 585                 590

Arg Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
    610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Val Gly Gly Arg Arg Asp
                645                 650                 655

Glu Leu Glu Glu Gly Ala Pro Ser Glu Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Thr Ala Lys Leu Asn Ile Pro Tyr Glu Asn Phe Tyr Glu Ala Leu
690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
            740                 745                 750

Asn

<210> SEQ ID NO 28
<211> LENGTH: 724
<212> TYPE: PRT
<213> ORGANISM: homo sapien

<400> SEQUENCE: 28

Gln Phe Val Asn Glu Trp Ala Ala Glu Ile Pro Gly Gly Pro Glu Ala
1               5                   10                  15

Ala Ser Ala Ile Ala Glu Glu Leu Gly Tyr Asp Leu Leu Gly Gln Ile
                20                  25                  30

Gly Ser Leu Glu Asn His Tyr Leu Phe Lys His Lys Asn His Pro Arg
            35                  40                  45
```

```
Arg Ser Arg Arg Ser Ala Phe His Ile Thr Lys Arg Leu Ser Asp Asp
 50                  55                  60

Asp Arg Val Ile Trp Ala Glu Gln Gln Tyr Glu Lys Glu Arg Ser Lys
 65                      70                  75                  80

Arg Ser Ala Leu Arg Asp Ser Ala Leu Asn Leu Phe Asn Asp Pro Met
                     85                  90                  95

Trp Asn Gln Gln Trp Tyr Leu Gln Asp Thr Arg Met Thr Ala Ala Leu
                100                 105                 110

Pro Lys Leu Asp Leu His Val Ile Pro Val Trp Gln Lys Gly Ile Thr
                115                 120                 125

Gly Lys Gly Val Val Ile Thr Val Leu Asp Asp Gly Leu Glu Trp Asn
130                 135                 140

His Thr Asp Ile Tyr Ala Asn Tyr Asp Pro Glu Ala Ser Tyr Asp Phe
145                 150                 155                 160

Asn Asp Asn Asp His Asp Pro Phe Pro Arg Tyr Asp Pro Thr Asn Glu
                165                 170                 175

Asn Lys His Gly Thr Arg Cys Ala Gly Glu Ile Ala Met Gln Ala Asn
                180                 185                 190

Asn His Lys Cys Gly Val Gly Val Ala Tyr Asn Ser Lys Val Gly Gly
                195                 200                 205

Ile Arg Met Leu Asp Gly Ile Val Thr Asp Ala Ile Glu Ala Ser Ser
210                 215                 220

Ile Gly Phe Asn Pro Gly His Val Asp Ile Tyr Ser Ala Ser Trp Gly
225                 230                 235                 240

Pro Asn Asp Asp Gly Lys Thr Val Glu Gly Pro Gly Arg Leu Ala Gln
                245                 250                 255

Lys Ala Phe Glu Tyr Gly Val Lys Gln Gly Arg Gln Gly Lys Gly Ser
                260                 265                 270

Ile Phe Val Trp Ala Ser Gly Asn Gly Gly Arg Gln Gly Asp Asn Cys
                275                 280                 285

Asp Cys Asp Gly Tyr Thr Asp Ser Ile Tyr Thr Ile Ser Ile Ser Ser
                290                 295                 300

Ala Ser Gln Gln Gly Leu Ser Pro Trp Tyr Ala Glu Lys Cys Ser Ser
305                 310                 315                 320

Thr Leu Ala Thr Ser Tyr Ser Ser Gly Asp Tyr Thr Asp Gln Arg Ile
                325                 330                 335

Thr Ser Ala Asp Leu His Asn Asp Cys Thr Glu Thr His Thr Gly Thr
                340                 345                 350

Ser Ala Ser Ala Pro Leu Ala Ala Gly Ile Phe Ala Leu Ala Leu Glu
                355                 360                 365

Ala Asn Pro Asn Leu Thr Trp Arg Asp Met Gln His Leu Val Val Trp
370                 375                 380

Thr Ser Glu Tyr Asp Pro Leu Ala Asn Asn Pro Gly Trp Lys Lys Asn
385                 390                 395                 400

Gly Ala Gly Leu Met Val Asn Ser Arg Ile Gly Phe Gly Leu Leu Asn
                405                 410                 415

Ala Lys Ala Leu Val Asp Leu Ala Asp Pro Arg Thr Trp Arg Ser Val
                420                 425                 430

Pro Glu Lys Lys Glu Cys Val Val Lys Asp Asn Asp Phe Glu Pro Arg
                435                 440                 445

Ala Leu Lys Ala Asn Gly Glu Val Ile Glu Ile Pro Thr Arg Ala
450                 455                 460

Cys Glu Gly Gln Glu Asn Ala Ile Lys Ser Leu Glu His Val Gln Phe
```

```
                465                 470                 475                 480
        Glu Ala Thr Ile Glu Tyr Ser Arg Arg Gly Asp Leu His Val Thr Leu
                        485                 490                 495

Thr Ser Ala Ala Gly Thr Ser Thr Val Leu Ala Glu Arg Glu Arg
                    500                 505                 510

Asp Thr Ser Pro Asn Gly Phe Lys Asn Trp Asp Phe Met Ser Val His
                    515                 520                 525

Thr Trp Gly Glu Asn Pro Ile Gly Thr Trp Thr Leu Arg Ile Thr Asp
                    530                 535                 540

Met Ser Gly Arg Ile Gln Asn Glu Gly Arg Ile Val Asn Trp Lys Leu
        545                 550                 555                 560

Ile Leu His Gly Thr Ser Ser Gln Pro Glu His Met Lys Gln Pro Arg
                        565                 570                 575

Val Tyr Thr Ser Tyr Asn Thr Val Gln Asn Asp Arg Arg Gly Val Glu
                        580                 585                 590

Lys Met Val Asp Pro Gly Glu Glu Gln Pro Thr Gln Glu Asn Pro Lys
                        595                 600                 605

Glu Asn Thr Leu Val Ser Lys Ser Pro Ser Ser Ser Val Gly Gly
                    610                 615                 620

Arg Arg Asp Glu Leu Glu Gly Ala Pro Ser Glu Ala Met Leu Arg
        625                 630                 635                 640

Leu Leu Gln Ser Ala Phe Ser Lys Asn Ser Pro Pro Lys Gln Ser Pro
                        645                 650                 655

Lys Lys Ser Pro Thr Ala Lys Leu Asn Ile Pro Tyr Glu Asn Phe Tyr
                    660                 665                 670

Glu Ala Leu Glu Lys Leu Asn Lys Pro Ser Gln Leu Lys Asp Ser Glu
                    675                 680                 685

Asp Ser Leu Tyr Asn Asp Tyr Val Asp Val Phe Tyr Asn Thr Lys Pro
                    690                 695                 700

Tyr Lys His Arg Asp Asp Arg Leu Leu Gln Ala Leu Val Asp Ile Leu
        705                 710                 715                 720

Asn Glu Glu Asn

<210> SEQ ID NO 29
<211> LENGTH: 753
<212> TYPE: PRT
<213> ORGANISM: homo sapien

<400> SEQUENCE: 29

Met Glu Arg Arg Ala Trp Ser Leu Gln Cys Thr Ala Phe Val Leu Phe
        1               5                   10                  15

Cys Ala Trp Cys Ala Leu Asn Ser Ala Lys Ala Lys Arg Gln Phe Val
                    20                  25                  30

Asn Glu Trp Ala Ala Glu Ile Pro Gly Gly Pro Glu Ala Ala Ser Ala
                    35                  40                  45

Ile Ala Glu Glu Leu Gly Tyr Asp Leu Leu Gly Gln Ile Gly Ser Leu
                    50                  55                  60

Glu Asn His Tyr Leu Phe Lys His Lys Asn His Pro Arg Arg Ser Arg
        65                  70                  75                  80

Arg Ser Ala Phe His Ile Thr Lys Arg Leu Ser Asp Asp Arg Val
                        85                  90                  95

Ile Trp Ala Glu Gln Gln Tyr Glu Lys Glu Arg Ser Lys Arg Ser Ala
                    100                 105                 110

Leu Arg Asp Ser Ala Leu Asn Leu Phe Asn Asp Pro Met Trp Asn Gln
```

-continued

```
             115                 120                 125
Gln Trp Tyr Leu Gln Asp Thr Arg Met Thr Ala Ala Leu Pro Lys Leu
    130                 135                 140
Asp Leu His Val Ile Pro Val Trp Gln Lys Gly Ile Thr Gly Lys Gly
145                 150                 155                 160
Val Val Ile Thr Val Leu Asp Asp Gly Leu Glu Trp Asn His Thr Asp
                165                 170                 175
Ile Tyr Ala Asn Tyr Asp Pro Glu Ala Ser Tyr Asp Phe Asn Asp Asn
            180                 185                 190
Asp His Asp Pro Phe Pro Arg Tyr Asp Pro Thr Asn Glu Asn Lys His
        195                 200                 205
Gly Thr Arg Cys Ala Gly Glu Ile Ala Met Gln Ala Asn Asn His Lys
    210                 215                 220
Cys Gly Val Gly Val Ala Tyr Asn Ser Lys Val Gly Gly Ile Arg Met
225                 230                 235                 240
Leu Asp Gly Ile Val Thr Asp Ala Ile Glu Ala Ser Ser Ile Gly Phe
                245                 250                 255
Asn Pro Gly His Val Asp Ile Tyr Ser Ala Ser Trp Gly Pro Asn Asp
            260                 265                 270
Asp Gly Lys Thr Val Glu Gly Pro Gly Arg Leu Ala Gln Lys Ala Phe
        275                 280                 285
Glu Tyr Gly Val Lys Gln Gly Arg Gln Gly Lys Gly Ser Ile Phe Val
    290                 295                 300
Trp Ala Ser Gly Asn Gly Gly Arg Gln Gly Asp Asn Cys Asp Cys Asp
305                 310                 315                 320
Gly Tyr Thr Asp Ser Ile Tyr Thr Ile Ser Ile Ser Ser Ala Ser Gln
                325                 330                 335
Gln Gly Leu Ser Pro Trp Tyr Ala Glu Lys Cys Ser Ser Thr Leu Ala
            340                 345                 350
Thr Ser Tyr Ser Gly Gly Asp Tyr Thr Asp Gln Arg Ile Thr Ser Ala
        355                 360                 365
Asp Leu His Asn Asp Cys Thr Glu Thr His Thr Gly Thr Ser Ala Ser
    370                 375                 380
Ala Pro Leu Ala Ala Gly Ile Phe Ala Leu Ala Leu Glu Ala Asn Pro
385                 390                 395                 400
Asn Leu Thr Trp Arg Asp Met Gln His Leu Val Val Trp Thr Ser Glu
                405                 410                 415
Tyr Asp Pro Leu Ala Asn Asn Pro Gly Trp Lys Lys Asn Gly Ala Gly
            420                 425                 430
Leu Met Val Asn Ser Arg Phe Gly Phe Gly Leu Leu Asn Ala Lys Ala
        435                 440                 445
Leu Val Asp Leu Ala Asp Pro Arg Thr Trp Arg Ser Val Pro Glu Lys
    450                 455                 460
Lys Glu Cys Val Val Lys Asp Asn Asp Phe Glu Pro Arg Ala Leu Lys
465                 470                 475                 480
Ala Asn Gly Glu Val Ile Ile Glu Ile Pro Thr Arg Ala Cys Glu Gly
                485                 490                 495
Gln Glu Asn Ala Ile Lys Ser Leu Glu His Val Gln Phe Glu Ala Thr
            500                 505                 510
Ile Glu Tyr Ser Arg Arg Gly Asp Leu His Val Thr Leu Thr Ser Ala
        515                 520                 525
Ala Gly Thr Ser Thr Val Leu Leu Ala Glu Arg Glu Arg Asp Thr Ser
    530                 535                 540
```

-continued

```
Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
            565                 570                 575

Arg Ile Gln Asn Glu Gly Arg Ile Val Asn Trp Lys Leu Ile Leu His
        580                 585                 590

Gly Thr Ser Ser Gln Pro Glu His Met Lys Gln Pro Arg Val Tyr Thr
    595                 600                 605

Ser Tyr Asn Thr Val Gln Asn Asp Arg Arg Gly Val Glu Lys Met Val
610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Val Gly Gly Arg Arg Asp
            645                 650                 655

Glu Leu Glu Glu Gly Ala Pro Ser Gln Ala Met Leu Arg Leu Leu Gln
        660                 665                 670

Ser Ala Phe Ser Lys Asn Ser Pro Lys Gln Ser Pro Lys Lys Ser
        675                 680                 685

Pro Ser Ala Lys Leu Asn Ile Pro Tyr Glu Asn Phe Tyr Glu Ala Leu
    690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
                725                 730                 735

Arg Asp Asp Arg Leu Leu Gln Ala Leu Val Asp Ile Leu Asn Glu Glu
            740                 745                 750

Asn

<210> SEQ ID NO 30
<211> LENGTH: 753
<212> TYPE: PRT
<213> ORGANISM: homo sapien

<400> SEQUENCE: 30

Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
            20                  25                  30

Asn Glu Trp Ala Ala Glu Ile Pro Gly Gly Pro Glu Ala Ala Ser Ala
        35                  40                  45

Ile Ala Glu Glu Leu Gly Tyr Asp Leu Leu Gly Gln Ile Gly Ser Leu
50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Arg Val
            85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
130                 135                 140

Asp Leu His Val Ile Pro Val Trp Gln Lys Gly Ile Thr Gly Lys Gly
145                 150                 155                 160
```

-continued

```
Val Val Ile Thr Val Leu Asp Asp Gly Leu Glu Trp Asn His Thr Asp
            165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
            195                 200                 205

Gly Thr Arg Cys Ala Gly Glu Ile Ala Met Gln Ala Asn Asn His Lys
            210                 215                 220

Cys Gly Val Gly Val Ala Tyr Asn Ser Lys Val Gly Ile Arg Met
225                 230                 235                 240

Leu Asp Gly Ile Val Thr Asp Ala Ile Glu Ala Ser Ser Ile Gly Phe
            245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
            275                 280                 285

Glu Tyr Gly Val Lys Gln Gly Arg Gln Gly Lys Gly Ser Ile Phe Val
            290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
            325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
            355                 360                 365

Asp Leu His Asn Asp Cys Thr Glu Thr His Thr Gly Thr Ser Ala Ser
            370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
            405                 410                 415

Tyr Asp Pro Leu Ala Asn Asn Pro Gly Trp Lys Lys Asn Gly Ala Gly
            420                 425                 430

Leu Met Val Asn Ser Arg Phe Gly Phe Gly Leu Leu Asn Ala Lys Ala
            435                 440                 445

Leu Val Asp Leu Ala Asp Pro Arg Thr Trp Arg Ser Val Pro Glu Lys
            450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
            485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
            515                 520                 525

Ala Gly Thr Ser Thr Val Leu Leu Ala Glu Arg Glu Arg Asp Thr Ser
            530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
            565                 570                 575
```

-continued

```
Arg Ile Gln Asn Glu Gly Arg Ile Val Asn Trp Lys Leu Ile Leu His
                580                 585                 590
Gly Thr Ser Ser Gln Pro Glu His Met Lys Gln Pro Arg Val Tyr Thr
            595                 600                 605
Ser Tyr Asn Thr Val Gln Asn Asp Arg Arg Gly Val Glu Lys Met Val
        610                 615                 620
Asp Pro Gly Glu Glu Pro Thr Gln Glu Asn Pro Lys Glu Asn Thr
625                 630                 635                 640
Leu Val Ser Lys Ser Pro Ser Ser Ser Val Gly Gly Arg Arg Asp
                645                 650                 655
Glu Leu Glu Glu Gly Ala Pro Ser Gln Ala Met Leu Arg Leu Leu Gln
            660                 665                 670
Ser Ala Phe Ser Lys Asn Ser Pro Pro Lys Gln Ser Pro Lys Lys Ser
        675                 680                 685
Pro Ser Ala Lys Leu Asn Ile Pro Tyr Glu Asn Phe Tyr Glu Ala Leu
690                 695                 700
Glu Lys Leu Asn Lys Pro Ser Gln Leu Lys Asp Ser Glu Asp Ser Leu
705                 710                 715                 720
Tyr Asn Asp Tyr Val Asp Val Phe Tyr Asn Thr Lys Pro Tyr Lys His
                725                 730                 735
Arg Asp Asp Arg Leu Leu Gln Ala Leu Val Asp Ile Leu Asn Glu Glu
            740                 745                 750
Asn

<210> SEQ ID NO 31
<211> LENGTH: 706
<212> TYPE: PRT
<213> ORGANISM: homo sapien

<400> SEQUENCE: 31

Met Gly Lys Gly Ser Ile Ser Phe Leu Phe Ser Gln Ile Gly Ser
1               5                   10                  15
Leu Glu Asn His Tyr Leu Phe Lys His Lys Asn His Pro Arg Arg Ser
                20                  25                  30
Arg Arg Ser Ala Phe His Ile Thr Lys Arg Leu Ser Asp Asp Asp Arg
            35                  40                  45
Val Ile Trp Ala Glu Gln Gln Tyr Glu Lys Glu Arg Ser Lys Arg Ser
        50                  55                  60
Ala Leu Arg Asp Ser Ala Leu Asn Leu Phe Asn Asp Pro Met Trp Asn
65                  70                  75                  80
Gln Gln Trp Tyr Leu Gln Asp Thr Arg Met Thr Ala Ala Leu Pro Lys
                85                  90                  95
Leu Asp Leu His Val Ile Pro Val Trp Gln Lys Gly Ile Thr Gly Lys
            100                 105                 110
Gly Val Val Ile Thr Val Leu Asp Asp Gly Leu Glu Trp Asn His Thr
        115                 120                 125
Asp Ile Tyr Ala Asn Tyr Asp Pro Glu Ala Ser Tyr Asp Phe Asn Asp
130                 135                 140
Asn Asp His Asp Pro Phe Pro Arg Tyr Asp Pro Thr Asn Glu Asn Lys
145                 150                 155                 160
His Gly Thr Arg Cys Ala Gly Glu Ile Ala Met Gln Ala Asn Asn His
                165                 170                 175
Lys Cys Gly Val Gly Val Ala Tyr Asn Ser Lys Val Gly Gly Ile Arg
            180                 185                 190
```

```
Met Leu Asp Gly Ile Val Thr Asp Ala Ile Glu Ala Ser Ser Ile Gly
            195                 200                 205

Phe Asn Pro Gly His Val Asp Ile Tyr Ser Ala Ser Trp Gly Pro Asn
        210                 215                 220

Asp Asp Gly Lys Thr Val Glu Gly Pro Gly Arg Leu Ala Gln Lys Ala
225                 230                 235                 240

Phe Glu Tyr Gly Val Lys Gln Gly Arg Gln Gly Lys Gly Ser Ile Phe
                245                 250                 255

Val Trp Ala Ser Gly Asn Gly Gly Arg Gln Gly Asp Asn Cys Asp Cys
            260                 265                 270

Asp Gly Tyr Thr Asp Ser Ile Tyr Thr Ile Ser Ile Ser Ser Ala Ser
        275                 280                 285

Gln Gln Gly Leu Ser Pro Trp Tyr Ala Glu Lys Cys Ser Ser Thr Leu
    290                 295                 300

Ala Thr Ser Tyr Ser Ser Gly Asp Tyr Thr Asp Gln Arg Ile Thr Ser
305                 310                 315                 320

Ala Asp Leu His Asn Asp Cys Thr Glu Thr His Thr Gly Thr Ser Ala
                325                 330                 335

Ser Ala Pro Leu Ala Ala Gly Ile Phe Ala Leu Ala Leu Glu Ala Asn
            340                 345                 350

Pro Asn Leu Thr Trp Arg Asp Met Gln His Leu Val Val Trp Thr Ser
        355                 360                 365

Glu Tyr Asp Pro Leu Ala Asn Asn Pro Gly Trp Lys Lys Asn Gly Ala
    370                 375                 380

Gly Leu Met Val Asn Ser Arg Phe Gly Phe Gly Leu Leu Asn Ala Lys
385                 390                 395                 400

Ala Leu Val Asp Leu Ala Asp Pro Arg Thr Trp Arg Ser Val Pro Glu
                405                 410                 415

Lys Lys Glu Cys Val Val Lys Asp Asn Asp Phe Glu Pro Arg Ala Leu
            420                 425                 430

Lys Ala Asn Gly Glu Val Ile Ile Glu Ile Pro Thr Arg Ala Cys Glu
        435                 440                 445

Gly Gln Glu Asn Ala Ile Lys Ser Leu Glu His Val Gln Phe Glu Ala
    450                 455                 460

Thr Ile Glu Tyr Ser Arg Arg Gly Asp Leu His Val Thr Leu Thr Ser
465                 470                 475                 480

Ala Ala Gly Thr Ser Thr Val Leu Leu Ala Glu Arg Glu Arg Asp Thr
                485                 490                 495

Ser Pro Asn Gly Phe Lys Asn Trp Asp Phe Met Ser Val His Thr Trp
            500                 505                 510

Gly Glu Asn Pro Ile Gly Thr Trp Thr Leu Arg Ile Thr Asp Met Ser
        515                 520                 525

Gly Arg Ile Gln Asn Glu Gly Arg Ile Val Asn Trp Lys Leu Ile Leu
    530                 535                 540

His Gly Thr Ser Ser Gln Pro Glu His Met Lys Gln Pro Arg Val Tyr
545                 550                 555                 560

Thr Ser Tyr Asn Thr Val Gln Asn Asp Gly Arg Gly Val Glu Lys Met
                565                 570                 575

Val Asp Pro Gly Glu Glu Gln Pro Thr Gln Glu Asn Pro Lys Glu Asn
            580                 585                 590

Thr Leu Val Ser Lys Ser Pro Ser Ser Ser Val Gly Gly Arg Arg
        595                 600                 605

Asp Glu Leu Glu Glu Gly Ala Pro Ser Gln Ala Met Leu Arg Leu Leu
```

```
                610                 615                 620
Gln Ser Ala Phe Ser Lys Asn Ser Pro Pro Lys Gln Ser Pro Lys Lys
625                 630                 635                 640

Ser Pro Ser Ala Lys Leu Asn Ile Pro Tyr Glu Asn Phe Tyr Glu Ala
                645                 650                 655

Leu Glu Lys Leu Asn Lys Pro Ser Gln Leu Lys Asp Ser Glu Asp Ser
                660                 665                 670

Leu Tyr Asn Asp Tyr Val Asp Val Phe Tyr Asn Thr Lys Pro Tyr Lys
                675                 680                 685

His Arg Asp Asp Arg Leu Leu Gln Ala Leu Val Asp Ile Leu Asn Glu
                690                 695                 700

Glu Asn
705

<210> SEQ ID NO 32
<211> LENGTH: 4
<212> TYPE: PRT
<213> ORGANISM: Artificial Sequence
<220> FEATURE:
<223> OTHER INFORMATION: MC4R agonist

<400> SEQUENCE: 32

His Phe Arg Trp
1
```